United States Patent
Collins et al.

(10) Patent No.: US 11,739,371 B2
(45) Date of Patent: *Aug. 29, 2023

(54) ARRAYS FOR SINGLE MOLECULE DETECTION AND USE THEREOF

(71) Applicant: Invitae Corporation, San Francisco, CA (US)

(72) Inventors: Patrick James Collins, San Francisco, CA (US); Adrian Nielsen Fehr, San Francisco, CA (US); Jill Lyndon Herschleb, San Francisco, CA (US); Hywel Bowden Jones, San Francisco, CA (US)

(73) Assignee: Invitae Corporation, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/551,788

(22) PCT Filed: Feb. 18, 2016

(86) PCT No.: PCT/US2016/018549
§ 371 (c)(1),
(2) Date: Aug. 17, 2017

(87) PCT Pub. No.: WO2016/134191
PCT Pub. Date: Aug. 25, 2016

(65) Prior Publication Data
US 2018/0023124 A1    Jan. 25, 2018

Related U.S. Application Data

(60) Provisional application No. 62/117,942, filed on Feb. 18, 2015.

(51) Int. Cl.
*C12Q 1/68* (2018.01)
*C12Q 1/6827* (2018.01)
*C07H 21/04* (2006.01)

(52) U.S. Cl.
CPC ....... *C12Q 1/6827* (2013.01); *C12Q 2565/50* (2013.01)

(58) Field of Classification Search
None
See application file for complete search history.

(56) References Cited

U.S. PATENT DOCUMENTS

| | | | |
|---|---|---|---|
| 5,256,536 A | 10/1993 | Miyada et al. | |
| 5,547,839 A | 8/1996 | Dower et al. | |
| 5,670,330 A * | 9/1997 | Sonenberg | G01N 33/5011 435/15 |
| 5,681,943 A | 10/1997 | Letsinger et al. | |
| 5,800,984 A * | 9/1998 | Vary | C12Q 1/6839 435/6.12 |
| 6,028,189 A | 2/2000 | Blanchard | |
| 6,083,699 A | 7/2000 | Leushner et al. | |
| 6,103,463 A | 8/2000 | Chetverin et al. | |
| 6,268,146 B1 | 7/2001 | Shultz et al. | |
| 6,284,497 B1 | 9/2001 | Sabanayagam et al. | |
| 6,346,379 B1 | 2/2002 | Gelfand et al. | |
| 6,495,320 B1 | 12/2002 | Lockhart et al. | |
| 6,582,908 B2 * | 6/2003 | Fodor | B01J 19/0046 435/288.3 |
| 6,706,473 B1 | 3/2004 | Edman et al. | |
| 6,864,071 B2 * | 3/2005 | Carrino | C12Q 1/6825 435/6.11 |
| 6,890,741 B2 | 5/2005 | Fan et al. | |
| 6,913,884 B2 | 7/2005 | Stuelpnagel et al. | |
| 7,582,420 B2 | 9/2009 | Oliphant et al. | |
| 7,955,794 B2 | 6/2011 | Shen et al. | |
| 8,288,103 B2 | 10/2012 | Oliphant et al. | |
| 8,700,338 B2 | 4/2014 | Oliphant et al. | |
| 8,906,626 B2 | 12/2014 | Oliphant et al. | |
| 9,057,730 B2 | 6/2015 | Mir | |
| 9,212,394 B2 * | 12/2015 | Fehr | C12Q 1/6876 |
| 9,376,677 B2 | 6/2016 | Mir | |
| 9,481,883 B2 | 11/2016 | Mir | |
| 9,556,429 B2 | 1/2017 | Mir | |
| 9,758,814 B2 | 9/2017 | Fehr et al. | |
| 10,626,450 B2 | 4/2020 | Fehr et al. | |
| 11,326,204 B2 * | 5/2022 | Fehr | C12Q 1/6825 |
| 2001/0014448 A1 | 8/2001 | Chappa et al. | |
| 2002/0006617 A1 | 1/2002 | Fan et al. | |
| 2002/0086289 A1 * | 7/2002 | Straus | C12Q 1/6827 435/6.18 |
| 2002/0197630 A1 | 12/2002 | Knapp et al. | |
| 2003/0207323 A1 | 11/2003 | Bandaru et al. | |
| 2004/0121371 A1 * | 6/2004 | Andersen | C12Q 1/6827 435/6.14 |
| 2004/0225362 A1 | 11/2004 | Richelsoph | |
| 2004/0253625 A1 | 12/2004 | Barany et al. | |
| 2004/0259102 A1 | 12/2004 | Kool | |
| 2005/0003380 A1 * | 1/2005 | Cohen | C12Q 1/6811 435/91.2 |
| 2005/0042649 A1 * | 2/2005 | Balasubramanian | C12Q 1/6837 435/6.11 |
| 2005/0164241 A1 | 7/2005 | Hahn et al. | |
| 2005/0244863 A1 | 11/2005 | Mir | |
| 2005/0272075 A1 | 12/2005 | Jacobsen et al. | |

(Continued)

FOREIGN PATENT DOCUMENTS

| CA | 2850785 A1 | 4/2013 | |
|---|---|---|---|
| CA | 2894381 A1 * | 6/2014 | ........... C12Q 1/6827 |

(Continued)

OTHER PUBLICATIONS

"Viruses", Wikipedia.com, accessed Nov. 24, 2012. (Year: 2012).*

(Continued)

*Primary Examiner* — Bradley L. Sisson
(74) *Attorney, Agent, or Firm* — Wolf, Greenfield & Sacks, P.C.

(57) ABSTRACT

The invention relates to methods of detecting a genetic variation in a genetic sample from a subject using labeled probes and counting the number of labels in the probes. The invention also relates to manufacturing and using molecular arrays and analytical approaches based on single molecule detection techniques.

10 Claims, 62 Drawing Sheets

Specification includes a Sequence Listing.

(56) References Cited

U.S. PATENT DOCUMENTS

| | | | |
|---|---|---|---|
| 2006/0019304 A1 | 1/2006 | Hardenbol et al. | |
| 2006/0275782 A1 | 12/2006 | Gunderson et al. | |
| 2007/0026429 A1 | 2/2007 | Livak et al. | |
| 2007/0037152 A1 | 2/2007 | Drmanac | |
| 2008/0038733 A1* | 2/2008 | Bischoff | C12Q 1/6883 435/6.12 |
| 2008/0138809 A1 | 6/2008 | Kapur et al. | |
| 2009/0036316 A1 | 2/2009 | Drmanac | |
| 2009/0143243 A1 | 6/2009 | Gunning et al. | |
| 2009/0305230 A1* | 12/2009 | Beattie | G01N 33/54373 435/7.1 |
| 2010/0015626 A1 | 1/2010 | Oliphant et al. | |
| 2010/0267585 A1 | 10/2010 | Terbrueggen | |
| 2010/0273164 A1 | 10/2010 | Church et al. | |
| 2010/0279305 A1 | 11/2010 | Kuersten | |
| 2010/0297585 A1 | 11/2010 | Yarovesky | |
| 2010/0323361 A1 | 12/2010 | Pugh et al. | |
| 2011/0151453 A1 | 6/2011 | Bergeron et al. | |
| 2011/0159499 A1 | 6/2011 | Hindson et al. | |
| 2012/0003633 A1* | 1/2012 | Kuijpers | C12Q 1/6858 435/6.11 |
| 2012/0015842 A1 | 1/2012 | Scholl et al. | |
| 2012/0021919 A1 | 1/2012 | Scholl et al. | |
| 2012/0034603 A1 | 2/2012 | Oliphant et al. | |
| 2012/0034685 A1 | 2/2012 | Sparks et al. | |
| 2012/0040859 A1 | 2/2012 | Sparks et al. | |
| 2012/0077185 A1 | 3/2012 | Oliphant et al. | |
| 2012/0164646 A1 | 6/2012 | Song et al. | |
| 2012/0190020 A1 | 7/2012 | Oliphant et al. | |
| 2012/0190021 A1 | 7/2012 | Oliphant et al. | |
| 2012/0190557 A1 | 7/2012 | Oliphant et al. | |
| 2012/0219950 A1 | 8/2012 | Oliphant et al. | |
| 2012/0252015 A1 | 10/2012 | Hindson et al. | |
| 2012/0316075 A1* | 12/2012 | Buzby | C12Q 1/6869 506/6 |
| 2013/0004950 A1 | 1/2013 | Sparks et al. | |
| 2013/0040375 A1 | 2/2013 | Sparks et al. | |
| 2013/0072390 A1 | 3/2013 | Wang et al. | |
| 2013/0089863 A1 | 4/2013 | Oliphant et al. | |
| 2013/0090250 A1 | 4/2013 | Sparks et al. | |
| 2013/0122500 A1 | 5/2013 | Sparks et al. | |
| 2013/0143213 A1 | 6/2013 | Oliphant et al. | |
| 2013/0171641 A1 | 7/2013 | Jewell et al. | |
| 2013/0172211 A1 | 7/2013 | Oliphant et al. | |
| 2013/0172212 A1 | 7/2013 | Oliphant et al. | |
| 2013/0172213 A1 | 7/2013 | Oliphant et al. | |
| 2013/0172216 A1 | 7/2013 | Mir | |
| 2013/0178369 A1 | 7/2013 | Burns et al. | |
| 2013/0178371 A1 | 7/2013 | Oliphant et al. | |
| 2013/0210640 A1 | 8/2013 | Sparks et al. | |
| 2013/0261003 A1 | 10/2013 | Oliphant et al. | |
| 2013/0275103 A1 | 10/2013 | Struble et al. | |
| 2013/0288252 A1 | 10/2013 | Sparks et al. | |
| 2013/0310262 A1 | 11/2013 | Zahn et al. | |
| 2014/0024538 A1 | 1/2014 | Zahn et al. | |
| 2014/0186827 A1 | 7/2014 | Pieprzyk et al. | |
| 2014/0221217 A1* | 8/2014 | Van Eijk | C12Q 1/6874 506/2 |
| 2014/0235470 A1 | 8/2014 | Olivares et al. | |
| 2014/0242582 A1 | 8/2014 | Oliphant et al. | |
| 2014/0256572 A1 | 9/2014 | Struble et al. | |
| 2014/0287468 A1 | 9/2014 | Richard | |
| 2014/0302068 A1 | 10/2014 | Khoo et al. | |
| 2014/0315747 A1* | 10/2014 | Roth | C12Q 1/6823 506/9 |
| 2014/0342940 A1* | 11/2014 | Oliphant | C12Q 1/6827 506/9 |
| 2014/0349859 A1 | 11/2014 | Oliphant et al. | |
| 2015/0038336 A1* | 2/2015 | Barany | C12Q 1/6813 506/2 |
| 2015/0038373 A1* | 2/2015 | Banyai et al. | C12N 15/1096 506/16 |
| 2015/0167077 A1 | 6/2015 | Fehr et al. | |
| 2015/0203903 A1 | 7/2015 | Mir | |
| 2015/0337296 A1 | 11/2015 | Mir | |
| 2016/0076087 A1 | 3/2016 | Fehr et al. | |
| 2016/0122754 A1 | 5/2016 | Mir | |
| 2016/0160272 A1 | 6/2016 | Mir | |
| 2018/0023138 A1 | 1/2018 | Collins et al. | |
| 2018/0179586 A1 | 6/2018 | Fehr et al. | |
| 2020/0325528 A1 | 10/2020 | Fehr et al. | |

FOREIGN PATENT DOCUMENTS

| | | |
|---|---|---|
| CN | 1791682 A | 6/2006 |
| CN | 1824786 A | 8/2006 |
| CN | 101864482 A | 10/2010 |
| CN | 102936755 A | 2/2013 |
| CN | 103069005 A | 4/2013 |
| JP | 2009-232778 A | 10/2009 |
| WO | 89/10977 A1 | 11/1989 |
| WO | 92/10092 A1 | 6/1992 |
| WO | 96/27025 A1 | 9/1996 |
| WO | 98/44152 A1 | 10/1998 |
| WO | 00/06770 A1 | 2/2000 |
| WO | 00/36152 A1 | 6/2000 |
| WO | 00/79008 A2 | 12/2000 |
| WO | 01/23610 A2 | 4/2001 |
| WO | 01/57248 A3 | 8/2001 |
| WO | 01/57249 A1 | 8/2001 |
| WO | WO 2001/079548 A2 | 10/2001 |
| WO | 2005/026329 A3 | 3/2005 |
| WO | WO 2005/118847 A1 | 12/2005 |
| WO | 2011142836 A2 | 11/2011 |
| WO | WO 2011/156387 A2 | 12/2011 |
| WO | 2012/021749 A1 | 2/2012 |
| WO | WO 2014/089536 A1 | 6/2014 |
| WO | WO 2015/026873 A1 | 2/2015 |
| WO | WO 2016/018986 A1 | 2/2016 |
| WO | WO 2016/070164 A1 | 5/2016 |

OTHER PUBLICATIONS

"How many species of bacteria are there", wisegeek.com; accessed Jan. 21, 2014. (Year: 2014).*

"Fungi," Wikipedia.com; accessed Jun. 3, 2013. (Year: 2013).*

"Plant," Wikipedia.com; accessed Aug. 28, 2015. (Year: 2015).*

"Mammal," Wikipedia.com; accessed Sep. 22, 2011. (Year: 2011).*

"Murinae," Wikipedia.com, accessed Mar. 18, 2013. (Year: 2013).*

"Fish," Wikipedia.com, accessed Nov. 2, 2014. (Year: 2014).*

"Archaea," Wikipedia.com, accessed May 11, 2016. (Year: 2016).*

"Algae," Wikipedia.com, accessed Mar. 4, 2016. (Year: 2016).*

"Protozoa," Wikipedia.com, accessed May 11, 2016. (Year: 2016).*

"List of sequenced bacterial genomes", Wikipedia.com; accessed Jan. 24, 2014. (Year: 2014).*

Dolgova and Lao, "Evolutionary and Medical Consequences of Archaic Introgression into Modern Human Genomes", Genes, 2018, vol. 9, 358. (Year: 2018).*

Sharon Begley, "Psst, the human genome was never completely sequenced", StatNews.com, Jun. 20, 2017. (Year: 2017).*

Forster et al., "A human gut bacterial genome and culture collection for improved metagenomic analyses", Nature Biotechnology, vol. 37, Feb. 2019, 186-172. (Year: 2019).*

Froster et al., "A human gut bacterial genome and culture collection for improved metagenomic analyses", Nature Biotechnology, vol. 37, Feb. 2019, 186-192. (Year: 2019).*

Sah et al., "Complete Genome Sequence of a 2019 Novel Coronavirus (SARS-CoV-2) Strain Isolated in Nepal", Microbiology Resource Announcements, vol. 9, issue 11, Mar. 12, 2020, 1-3. (Year: 2020).*

International Search Report and the Written Opinion issued in related International Patent Application No. PCT/US2014/051763 dated Dec. 11, 2014.

Osborne et al., "Single-Molecule Analysis of DNA Immobilized on Microspheres," Analytical Chemistry, 72: 3678-3681 (2000).

Shalon et al., "A DNA Microarray System for Analyzing Complex DNA Samples Using Two-color Fluorescent Probe Hybridization," Genome Research, 6: 639-645 (1996).

Extended European Search Report issued in related European Patent Application No. 14172340.3 dated Oct. 14, 2014.

(56) References Cited

OTHER PUBLICATIONS

Liu et al., "Molecular Beacons for DNA Biosensors with Micrometer to Submicrometer Dimensions," Analytical Biochemistry, 283: 56-63 (2000).
Goodwin et al., "Single-Molecule Detection in Liquids by Laser-Induced Fluorescence," Accounts of Chemical Research, 29: 607-613 (1996).
International Preliminary Examination Report issued in related International Patent Application No. PCT/GB02/01245 dated Oct. 24, 2003.
Ampligase® Thermostable DNA Ligase, downloaded from internet (http://www.epibio.com/docs/default-source/protocols/ampligase-thermostable-dna-ligasepdf?sfvrsn=4) in Jun. 2015.
Batool et al., Ligase Chain Reaction, http://www.slideshare.net/SHBZaidi/ligase-chain-reactionlcr# (Dec. 2012).
Battistella et al., "Genotyping beta-globin gene mutations on copolymer-coated glass slides with the ligation detection reaction," Clinical Chemistry, 54: 1657-1663 (2008).
Cheng et al., "Multiplexed profiling of candidate genes for CpG island methylation status using a flexible PCR/LDR/Universal Array assay," Genome Research, 16:282-289 (2006).
Davis et al., "A comparison of ligase chain reaction to polymerase chain reaction in the detection of Chlamydia trachomatis endocervical infections," Infections Diseases in Obstetrics and Gynecology 6: 57-60 (1998).
Deng et al., "Oligonucleotide ligation assay-based DNA chip for multiplex detection of single nucleotide polymorphism," Biosensorsand Bioelectronics, 19:1277-1283 (2004).
Dille et al., "Amplification of Chlamydia trachomatis DNA by ligase chain reaction," Journal of Clinical Microbiology, 31: 729-731 (1993).
Eggerding, "A one-step coupled amplification and oligonucleotide ligation procedure for multiplex genetic typing," Genome Research, 4:337-345 (1995).
Fu et al., "Counting individual DNA molecules by the stochastic attachment of diverse labels," PNAS, 108: 9026-9031 (2011).
Grossman et al., "High-density multiplex detection of nucleic acid sequences: oligonucleotide ligation assay and sequence-coded separation," Nucleic Acids Research, 22: 4527-4534 (1994).
Hesse et al., "RNA expression profiling at the single molecule level," Genome Research, 16: 1041-1045 (2006).
Kuhn et al., "Template-independent ligation of single-stranded DNA by T4 DNA ligase," FEBS Journal, 272: 5991-6000 (2005).
Landergren, "A ligase mediated gene detection technique," Science, 241: 1077-1080 (1988).
Sullivan, Chapter 7: Nucleic Acid Amplification Techniques, downloaded from internet (http://www.austincc.edu/mlt/mdfund/mdfund_unit9Chapter7NucleicAcidAmplificationTechniques.ppt) in Jun. 2015.
Sample Protocol for Oligonucleotide Ligation Assay (OLA) and Hybridization to Magplex-Tag Microspheres—Washed Protocol, Luminex Corporation (Aug. 2010).
MacDonald, "Genotyping by Oligonucleotide Ligation Assay (OLA)," Cold Spring Harbor Protocols (2007).
Muresan et al., "Microarray analysis at single molecule resolution," IEEE Trans Nanobioscience, 9: 51-58 (2010).
Romppanen, "Oligonucleotide ligation assays for the diagnosis of inherited diseases," Chapter 4, Molecular Diagnostics, 31-40 (2005).
Stone et al., "Combined PCR-oligonucleotide ligation assay for rapid detection of *Salmonella serovars*," Journal of Clinical Microbiology, 33: 2888-2893 (1995).
Tobler et al., "Universal Detector Assay for Measuring DNA Copy Number Changes," American Society of Human Genetics (ASHG) Annual Meeting (2006).
Wiedmann et al., "Ligase chain reaction (LCR)-overview and applications," Genome Research, 3: S51-S64 (1994).
Supplementary European Search Report issued in related European Patent Application No. 14838189 dated Feb. 27, 2017.
International Search Report issued in corresponding International Patent Application No. PCT/US2016/018549 dated Apr. 29, 2016.
Written Opinion issued in corresponding International Patent Application No. PCT/US2016/018549 dated Apr. 29, 2016.
International Preliminary Report on Patentability for Application No. PCT/US2016/018549, dated Aug. 31, 2017.
International Preliminary Report on Patentability for Application No. PCT/US2014/051763, dated Mar. 3, 2016.
International Search Report and Written Opinion for Application No. PCT/US2015/058529, dated Mar. 30, 2016.
International Preliminary Report on Patentability for Application No. PCT/US2015/058529, dated May 11, 2017.
[No Author Listed], List of sequenced animal genomes. Wikipedia. Retrieved from www.wikipedia.com. Accessed on Jan. 19, 2018. 29 pages.
Office Action, dated Sep. 5, 2017 for Chinese Application No. 201480057266.8.

\* cited by examiner

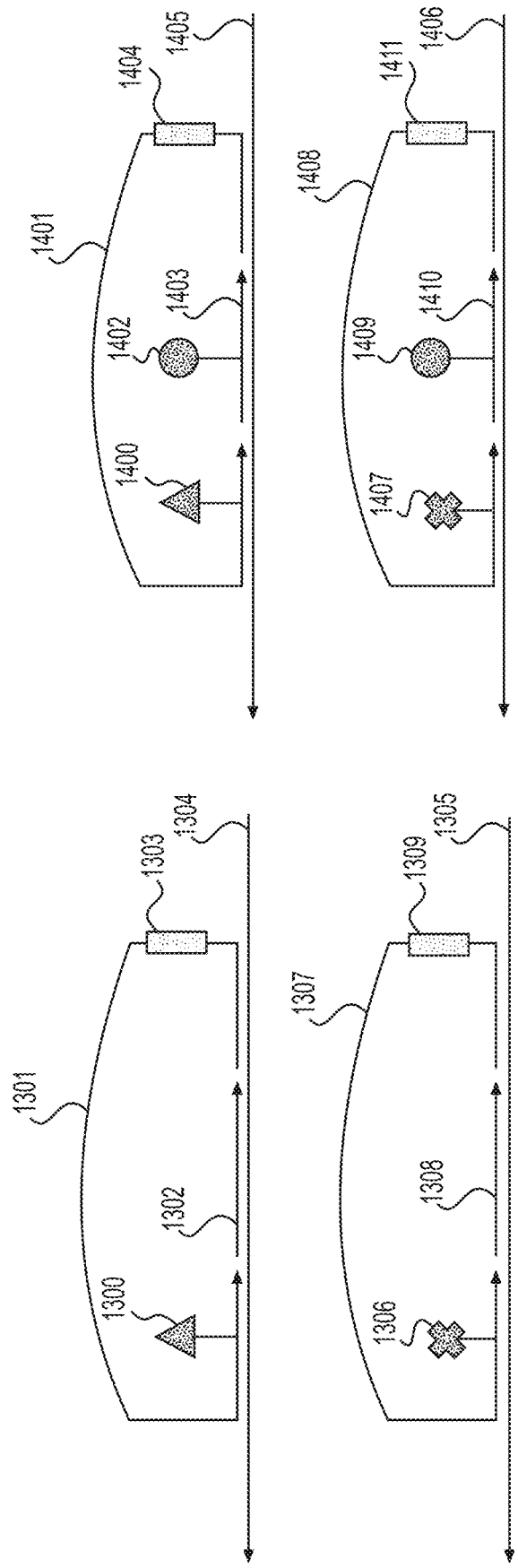

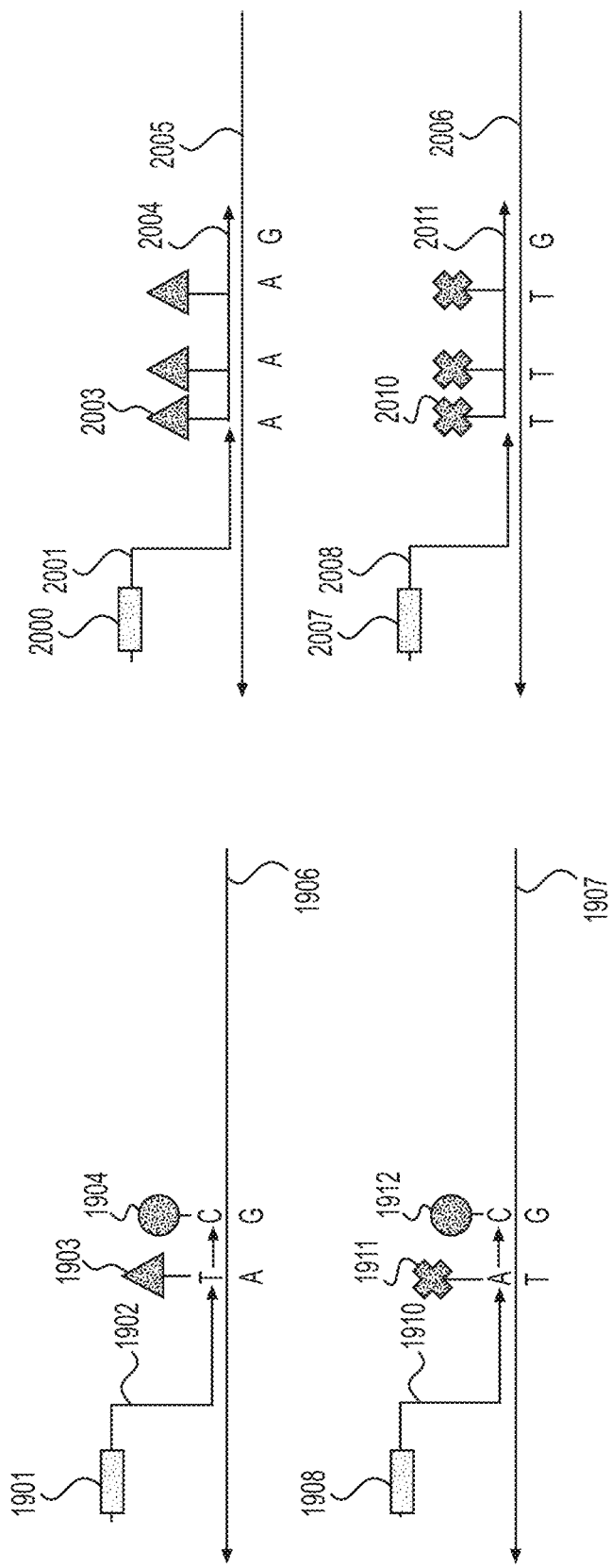

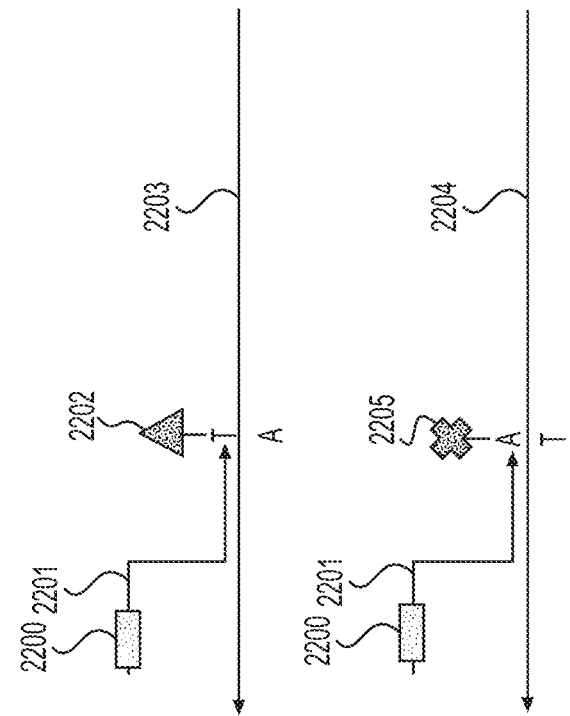
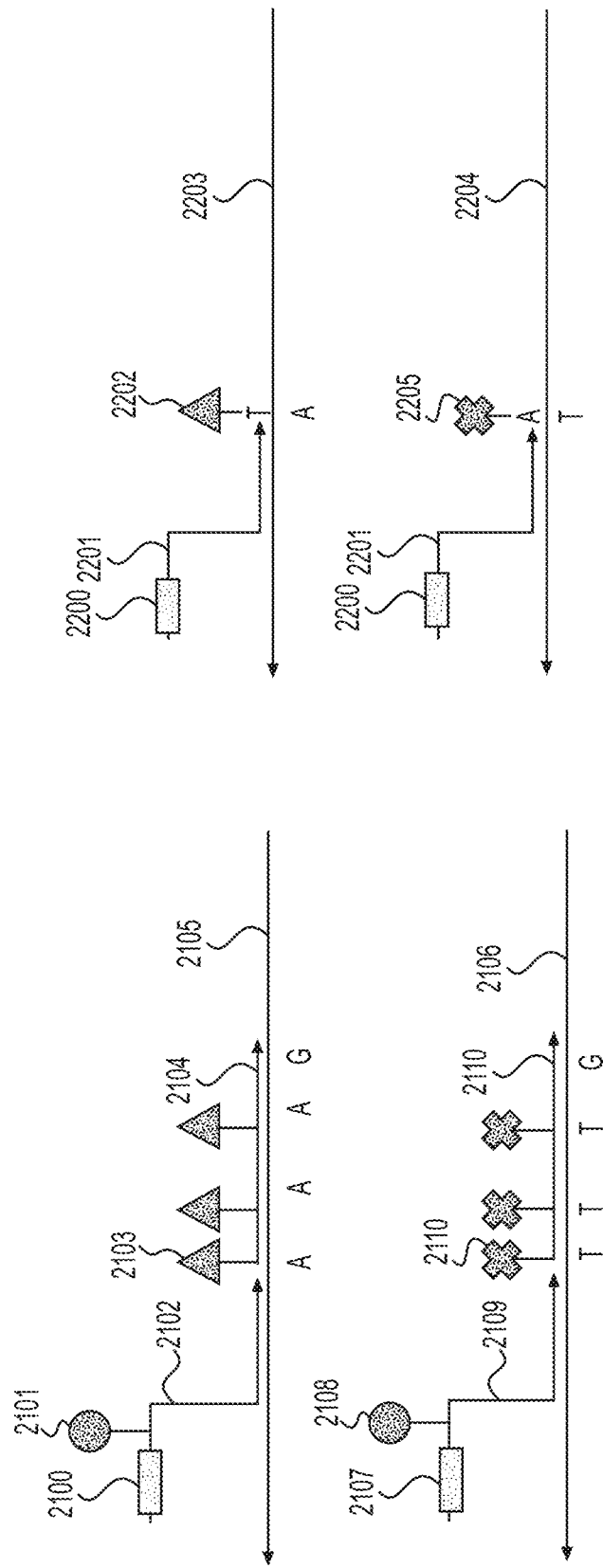
FIG. 42
FIG. 41

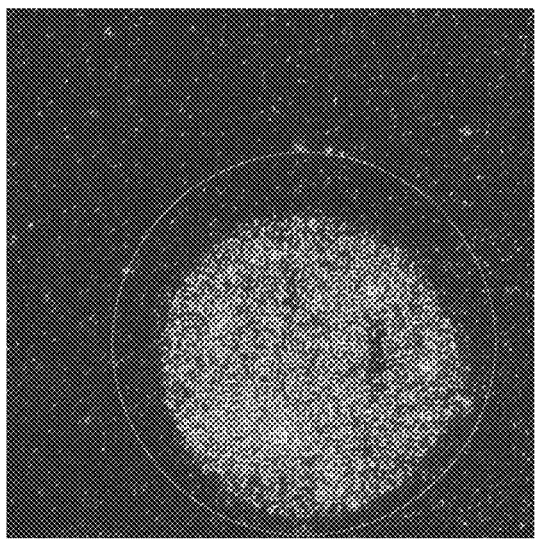 (i) BALANCED SPOT, GREEN CHANNEL
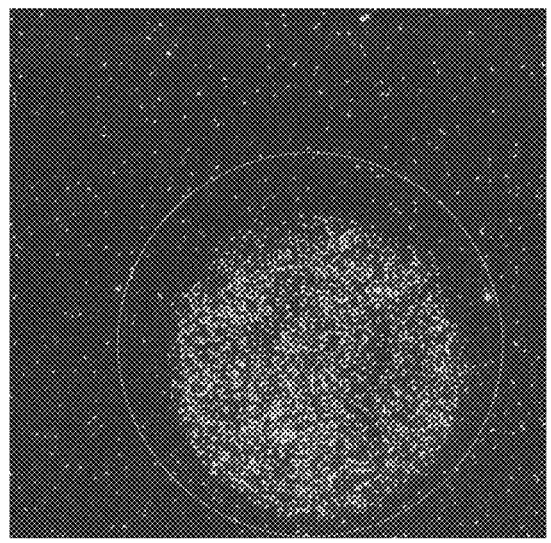 (ii) BALANCED SPOT, RED CHANNEL
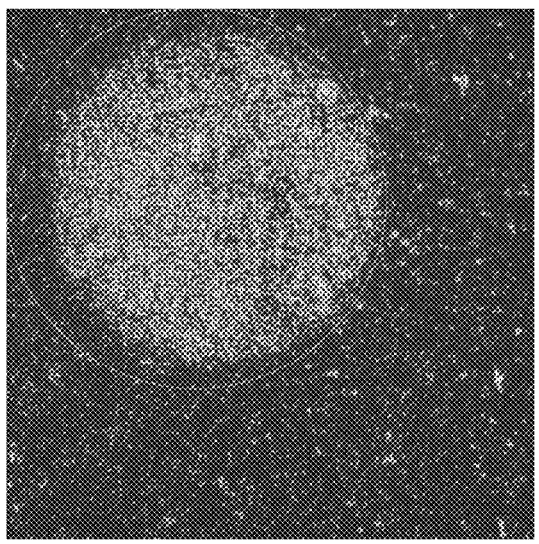 (iii) INCREASED SPOT, GREEN CHANNEL
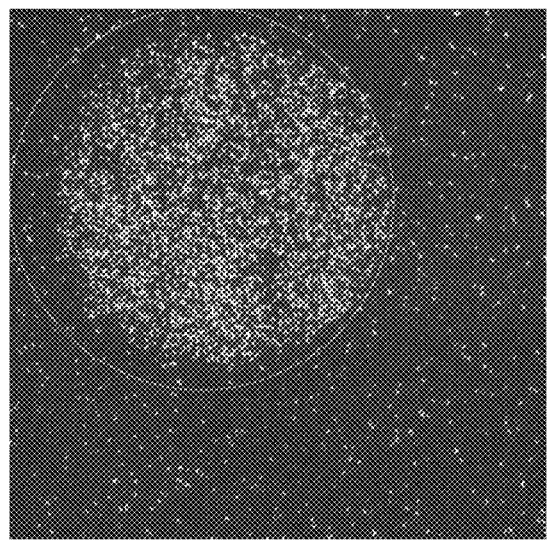 (iv) INCREASED SPOT, RED CHANNEL
FIG. 61A

*Encoded probing of single molecules*

*Complementary strand synthesis by ligation*

*Gap Fill Ligation*

Each element of the biosensor array contains distinct sngle molecule probe sequences (Asterisks), eg to detect different pathogens

ARRAYS FOR SINGLE MOLECULE DETECTION AND USE THEREOF

SEQUENCE LISTING SUBMISSION VIA EFS-WEB

A computer readable text file, entitled "SequenceListing.txt," created on or about Aug. 15, 2017 with a file size of about 72 kb contains the sequence listing for this application and is hereby incorporated by reference in its entirety.

BACKGROUND OF THE INVENTION

The invention relates to methods of detecting a genetic variation in a genetic sample from a subject. Detecting a genetic variation is important in many aspects of human biology. The invention also relates to manufacturing and using spatially addressable low density or high density molecular arrays and analytical approaches based on single molecule detection techniques.

Progress in the human genome project has seeded the need to (i) analyze the expression characteristics of genes and gene products and (ii) analyze the variations in genes and genomes. This has precipitated great interest in methods for large-scale, parallel studies. Interest in developing new methods for detecting variation has further been fueled by the success of using DNA markers in finding genes for monogenic inherited disorders and recent proposals on large-scale association studies for dissecting complex traits. There is also a need for large-scale studies and high-throughput screening in the search for drugs in the pharmaceutical industry.

This interest in large scale studies may also in the future extend to other areas such as the semiconductor industry where the emergence of devices based on organic molecules such as poly(p-phenylene vinylidene), PPV, and the nascent fields of molecular electronics and nanotechnology seed the demand for new molecules with novel or desirable features and this in turn may seed the need to turn to large scale searching.

In the biotechnology and pharmaceutical sector, large scale studies are preferably done either in homogeneous assays on a microtitre plate (96 well and 384 well plates are common and higher capacity plates are available) or in an array format. Spatially addressable arrays (where the sequence identity of a molecule is specified by the location of the member in which the molecule is contained, within the array of members) of chemical or biochemical species have found wide use in genetics, biology, chemistry and materials science. Arrays can be formed in (i) a disperse solid phase such as beads and bundled hollow fibres/optical fibres, (ii) individual wells of microtitre plates/nanovials, (iii) on a homogeneous medium/surface on which individual members can be spatially addressed or (iv) a surface with nanowells or other physical structures. The types of arrays (iii) or (iv) can be made on semi-permeable materials such as gels, gel pads, porous silicon, microchannel arrays (so called 3-D biochips) (Benoit et al; Anal. Chem 2001 73:2412-2420) and impermeable supports such as silicon wafers, glass, gold coated surfaces, ceramics and plastics. They can also be made within the walls of microfluidic channels (Gao et al; Nucleic Acids Res. 2001 29: 4744-4750). Furthermore the surface or sub-surface may comprise a functional layer such as an electrode.

All members in arrays of type (i) and (iii) are contained within a single reaction volume, whilst each member of (ii) is contained in a separate reaction volume.

All members in arrays of the present invention may be contained within a single reaction volume or they may be in a separate reaction volume.

To date, methods have involved analyzing the reactions of molecules in bulk. Although bulk or ensemble approaches have in the past proved useful, there are barriers to progress in a number of directions. The results generated are usually an average of millions of reactions where multiple events, multi-step events and variations from the average cannot be resolved and detection methods that are adapted for high frequency events are insensitive to rare events. The practical limitations associated with bulk analysis include the following:

1. The techniques used for the detection of events in bulk phase analysis are not sensitive enough to detect rare events which may be due to low sample amount or weak interaction with probes. a. Detecting the presence of rare transcripts in mRNA profiling. This problem is related to the limited dynamic range of bulk analysis which is in the order of $10^4$ whereas the different abundance levels of mRNAs in a cell are in the $10^5$ range. Hence to cater for the more common events, detection methods are not sensitive enough to detect rare events. b. In the amounts of samples that are usually available to perform genetic analysis there are not enough copies of each sequence in genomic DNA to be detected. Therefore the Polymerase Chain Reaction (PCR) is used to increase the amount of material from genomic DNA so that sufficient signal for detection can be obtained from the desired loci. c. Due to secondary structure around certain target loci very few hybridization events go to completion. The few that do, need to be detected. These events may be too few to be detected by conventional bulk measurements. d. The number of analyte molecules in the sample is vanishingly small. For example, in pre-implantation analysis a single molecule must be analysed. In analysis of ancient DNA the amount of sample material available is often also very small.

2. A rare event in a background of common events at a particular locus is impossible to detect in the bulk phase due to it being masked by the more common events. There are a number of instances where this is important: a. Detecting loss of heterozygosity (LOH) in tumours comprising mixed cell populations and early events in tumourigenesis. b. Determining minimal residual disease in patients with cancer and early detection of relapse by detecting mutation within a wild type background. c. Prenatal diagnosis of genetic disorders directly from the small number of foetal cells in the maternal circulation (hence detection from mother's blood rather than from amniocentesis). d. Detection of specific alleles in pooled population samples.

3. It is difficult to resolve heterogeneous events. For example it is difficult to separate out the contribution (or the lack of) to signal from errors such as foldback, mis-priming or self-priming from genuine signals based on the interactions being measured.

4. Complex samples such as genomic DNA and mRNA populations pose difficulties. a. One problem is cross reactions of analyte species within the sample. b. On arrays, Another is the high degree of erroneous interactions which in many cases are likely to be due to mismatch interactions driven by high effective concentrations of certain species. This is one reason for low signal to noise. A ratio as low as 1:1.2 has been used in published array studies for base calling (Cronin et al, Human Mutation 7:244-55, 1996). c. In some cases erroneous interactions can even be responsible for the majority of signal (Mir, K; D. Phil thesis, Oxford University, 1995). d. Detecting a true representative signal of a rare mRNA transcript within a mRNA population is difficult. e. PCR is used in genetic analysis to reduce the complexity of sample from genomic DNA, so that the desired loci become enriched.

5. The bulk nature of conventional methods does not allow access to specific characteristics (particularly, more than one feature) of individual molecules. One example in genetic analysis is the need to obtain genetic phase or haplotype information—the specific alleles associated with each chromosome. Bulk analysis cannot resolve haplotype from a heterozygotic sample. Current molecular biology techniques that are available, such as allele-specific or single molecule PCR are difficult to optimise and apply on a large scale.

6. Transient processes are difficult to resolve. This is needed when deciphering the molecular mechanisms of processes. Also transient molecular binding events (such as nucleation of a hybridization event which is blocked from propagation due to secondary structure in the target) have fractional occupancy times which cannot be detected by conventional solid-phase binding assays.

When two samples are compared, small differences in concentration (less than twofold difference) are difficult to unequivocally discern.

Microarray gene expression analysis using unamplified cDNA target typically requires $10^6$ cells or 100 micrograms of tissue. Neither expression analysis nor analysis of genetic variation can be performed directly on material obtained from a single cell which would be advantageous in a number of cases (e.g. analysis of mRNA from cells in early development or genomic DNA from sperm).

Further, it would be highly desirable if the amplification processes that are required before most biological or genetic analysis could be avoided.

PCR is used for the analysis of Variable Number of Tandem Repeats is central to Forensics and Paternity testing. Linkage studies have traditionally used Short Tandem repeats as markers analysis which is performed by PCR.

The need to avoid PCR is particularly acute in the large scale analysis of SNPs. The need to design primers and perform PCR on a large number of SNP sites presents a major drawback. The largest scales of analysis that are currently being implemented (e.g. using Orchid Bioscience and Sequenom systems) remain too expensive to allow meaningful association studies to be performed by all but a few large organizations such as the Pharmaceutical companies. Although, the number of SNPs needed for association studies has been actively debated, the highest estimates are being revised down due to recent reports that there are large blocks of linkage disequilibrium within the genome. Hence, the number of SNPS needed to represent the diversity in the genome could be 10 fold fewer than was expected. However, this needs to be taken with the caveat that there are some regions of the genome where the extent of linkage disequilibrium is far lower and a greater number of SNPs would be needed to represent the diversity in these areas. Even so, if each site had to be amplified individually the task would be enormous. In practice, PCR can be multiplexed. However, the extent to which this can be done is limited and increased errors, such as primer-dimer formation and mismatches as well as the increased viscosity of reaction, present barriers to success and limits multiplexing to around ten sites in most laboratories.

It is clear that the cost of performing SNP detection reactions on the scale required for high-throughput analysis of polymorphisms in a population is prohibitive if each reaction needs to be conducted separately, or if only a limited multiplexing possibility exists. A highly multiplexed, simple and cost-effective route to SNP analysis will be required if the potential of pharmacogenomics, pharmacogenetics as well as large-scale genetics is to be realised. DNA pooling is a solution for some aspects of genetic analysis but accurate allele frequencies must be obtained which is difficult especially for rare alleles.

Since it involves determining the association of a series of alleles along a single chromosome, the haploype is thought to be far more informative than the analysis of individual SNP. An international effort is underway for making a comprehensive haplotype map of the human genome. Generally, haplotypes are determined is by long-range allele specific PCR. However, the construction of somatic cell hybrids prior to haplotype determination is an alternative method.

A method for haplotyping on single molecules in solution has been proposed in patent (WO 01/90418), however, in this method the molecules are not surface captured, positional information of the SNP is not obtained and each SNP must be coded with a different colour.

For several years, plans for large scale SNP analysis have been laid around the common disease-common variant (CD/CV) (i.e. common SNP) hypothesis of complex diseases (Reich D E and Lander E S Trends Genet 17: 502-50 2001)). The SNP consortium has amassed more than a million putatively common SNPs. However practical use of this set is confounded by the fact that different SNPs may be common in different ethnic populations and many of the putative SNPs may not be truly polymorphic. Furthermore, the CD/CV hypothesis has recently come under challenge from assertions that rare alleles may contribute to the common diseases (Weiss K M, Clark A G, Trends Genet 2002 January; 18(1):19-24). If this were the case, although "new" rare alleles would be sufficiently in linkage disequilibrium with a common SNP for the association with the region that contains both to be successfully made, if the allele was "ancient" and rare then the common SNPs and haplotype maps would not represent the diversity. In this scenario alternative strategies are needed to find causative regions. Instead of genome-wide scan of common SNPs it may be that there will be a need for whole genome sequencing or re-sequencing of thousands of case and control samples to access all variants. The commercial sequencing of the human genome, which built on information from the public genome project, cost approximately 300 million dollars over a period of about one year. This cost and timescale is prohibitive as an alternative to SNP analysis for finding associations between DNA sequence and disease. Clearly, if sequencing is to replace current approaches to large scale genetic studies, radically different methods are needed.

It would be advantageous if sequencing runs could be on the scale of genomes or at least small genomes or whole genes. Even increasing read-lengths beyond 300-500 nt would be useful. Today, sequencing is almost exclusively done by the Sanger dideoxy method. A number of alternative sequencing methods have been suggested but none are in use today. These methods include: 1 Sequencing by synthesis; 2 Direct analysis of the sequence of a single molecule; and 3 Sequencing by Hybridization.

Re-sequencing by chip methods is an alternative to denovo sequencing. The 21.7 million bases of non-repetitive sequence of chromosome 21 has recently been re-sequenced by chip methods by Patil et al (Science 294: 1719-1722, 2001). The haplotype structure was conserved in this study by making somatic cell hybrids prior to chip analysis.

However, the cost of large scale re-sequencing by this method is still high and only 65% of the bases that were probed gave results of enough confidence for the base to be called.

SUMMARY

The invention relates to methods of performing an assay, including detecting a genetic variation in a genetic sample from a subject. The invention further relates to methods of detecting a genetic variation in a genetic sample from a subject using labeled probes and counting the number of labels in the probes. The invention also relates to methods of manufacturing and using spatially addressable molecular arrays and analytical approaches based on single molecule detection techniques. The invention further relates to use of the arrays as indicated for performing an assay, including a genetic variation in a genetic sample from a subject.

The invention relates to methods of performing an assay on a molecular array comprising: (a) producing a molecular array comprising producing labeled, immobilized oligonucleotides on a solid phase at least by (i) optionally preselecting oligonucleotides to be immobilized, (ii) immobilizing to the solid phase at least a portion of the oligonucleotides, and (iii) labeling at least a portion of the oligonucleotides with at least two different labels before or after the immobilizing step, wherein at least a portion of the labeled, immobilized oligonucleotides on the solid phase are individually optically resolvable from other labeled immobilized oligonucleotides on the solid phase; and (b) performing the assay comprising counting the number of at least a portion of the individually optically resolvable, labeled, immobilized oligonucleotides that are individually optically resolvable on the solid phase to perform the assay. The invention also relates to methods of performing an assay on a molecular array comprising: (a) producing a molecular array comprising producing labeled, immobilized oligonucleotides on a solid phase at least by (i) preselecting a plurality of oligonucleotides to be immobilized, (ii) immobilizing to the solid phase at least a portion of the plurality of oligonucleotides, and (iii) labeling at least a portion of the plurality of oligonucleotides with at least two different labels before or after the immobilizing step, at least a portion of the labeled, immobilized oligonucleotides on the solid phase are arranged in two or more spatially addressable, separate and discrete elements and are individually optically resolvable from other labeled immobilized oligonucleotides on the solid phase; and (b) performing the assay comprising counting the number of at least a portion of the labeled, immobilized oligonucleotides that are individually optically resolvable on the solid phase. In one aspect, the immobilizing step comprises immobilizing to the solid phase said at least a portion of the oligonucleotides to form two or more separate and discrete elements, at least two of said two or more elements being spatially addressable, each of said at least two elements comprising one or more immobilized oligonucleotides, wherein sequence identity of at least a portion of the immobilized oligonucleotides in the at least two separate and discrete elements is specified by a location of at least one element of the at least two separate and discrete elements comprising the at least a portion of the immobilized oligonucleotides. In another aspect, the labeled, immobilized oligonucleotides comprise one or more first labeled immobilized oligonucleotide and one or more second labeled immobilized oligonucleotide which have different labels, and each of said at least two elements comprises the one or more first labeled immobilized oligonucleotide and the one or more second labeled immobilized oligonucleotide. In another aspect, the methods may further comprise comparing a counted number of the one or more first labeled immobilized oligonucleotide to a counted number of the one or more second labeled immobilized oligonucleotide in at least one of the at least two elements. In another aspect, the producing step may comprise ligating at least a portion of the oligonucleotides to target nucleic acids to form probe-target molecule complexes. In some embodiments, the probe-target molecule complexes comprise circularized DNA. In another aspect, the producing step may further comprise amplifying at least a portion of the probe-target molecule complexes by rolling circle amplification. In another aspect, the producing step may further comprise primer extension of at least a portion of the probe-target molecule complexes with labeled primers. In another aspect, the at least a portion of the oligonucleotides are immobilized to the solid support by a means selected from the group consisting of Biotin-oligonucleotide complexed with Avidin, Strepatavidin or Neutravidin; SH-oligonucleotide covalently linked via a disulphide bond to a SH-surface; Amine-oligonucleotide covalently linked to an activated carboxylate or an aldehyde group; Phenylboronic acid (PBA)-oligonucleotide complexed with salicylhydroxamic acid (SHA); and Acrydite-oligonucleotide reacted with thiol or silane surface or co-polyemerized with acrylamide monomer to form polyacrylamide. In another aspect, the two or more discrete elements are separated by a raised region or an etched trench.

The invention also relates to methods of producing a molecular array comprising: providing a solid support comprising a plurality of physically discrete elements, wherein said physically discrete elements are separated from one another by one or more raised regions or trenches; and immobilizing a plurality of target oligonucleotide molecules onto said plurality of physically discrete elements, wherein after said immobilizing, at least two of said plurality of physically discrete elements comprise only a single immobilized target oligonucleotide molecule per element. In another aspect, the invention relates to methods of producing a molecular array comprising: providing a solid support comprising a plurality of physically discrete wells; and immobilizing a plurality of target oligonucleotide molecules into said wells, wherein after said immobilizing, at least two of said plurality of wells comprise only a single immobilized target oligonucleotide molecule per well. In another aspect, the invention relates to methods of producing a molecular array comprising: providing a solid support comprising a plurality of physically discrete, spatially addressable wells, wherein at least a portion of the plurality of wells each comprises a plurality of immobilized oligonucleotides; immobilizing a plurality of target oligonucleotide molecules into said plurality of physically discrete, spatially addressable wells, wherein after said immobilizing, at least two of said plurality of physically discrete, spatially addressable wells comprise only a single immobilized target oligonucleotide molecule per well; amplifying said single immobilized target oligonucleotide molecule in said at least two physically discrete, spatially addressable wells to create a plurality of immobilized target oligonucleotide molecules per each of said at least two physically discrete, spatially addressable wells, said plurality of immobilized target oligonucleotide molecules consisting of a single molecule species per well; and labeling, for each of said at least two physically discrete, spatially addressable wells, at least a portion of the plurality of immobilized target oligonucleotide molecules with one or more labels, thereby producing at least one labeled target oligonucleotide molecule per each of said at least two wells. In another aspect, the invention also relates to methods of producing a molecular array comprising: providing a solid support comprising a plurality of physically discrete elements, wherein at least a portion of the plurality of physically discrete elements each comprises a plurality of immobilized oligonucleotides, and said physically discrete elements are separated from one another by one or more raised regions or trenches; and hybridizing a plurality of target oligonucleotide molecules to said immobilized oligonucleotides, wherein after said hybridizing, at least two of said plurality of physically discrete elements comprise only a single immobilized target oligonucleotide molecule per element.

The invention relates to methods of producing a molecular array comprising: (i) optionally preselecting a plurality of oligonucleotides to be immobilized; (ii) labeling at least a portion of the plurality of oligonucleotides with one or more labels, thereby producing labeled oligonucleotides; (iii) immobilizing at least a portion of the labeled oligonucleotides on a solid support at a density to allow each of said at least a portion of the labeled oligonucleotides on the solid support to be individually resolved, thereby forming two or more separate and discrete elements, at least two elements of said two or more elements being spatially addressable, each of said at least two elements comprising a plurality of labeled immobilized oligonucleotides from said at least a portion of the labeled oligonucleotides, wherein sequence identities of said at least a portion of the plurality of labeled immobilized oligonucleotides in each of said at least two elements is specified by a location of each of said at least two elements in which the oligonucleotides are contained; and (iv) analyzing whether at least a portion of the labeled immobilized oligonucleotides of said at least two elements is individually optically resolvable from another portion of the labeled immobilized oligonucleotides, whereby said at least a portion of the labeled immobilized oligonucleotides on each of said at least two elements is individually optically resolvable from the another portion of the labeled immobilized oligonucleotides.

The invention relates to methods of producing a biosensor comprising: depositing oligonucleotides on a solid support; and labeling at least a portion of the oligonucleotides with at least two different labels before or after the depositing, whereby at least a portion of the oligonucleotides that are deposited and labeled are separated from other deposited labeled oligonucleotides on the solid support to produce a plurality of separated labeled oligonucleotides. The invention also relates to methods of producing a molecular array comprising immobilizing directly or indirectly a plurality of oligonucleotides to a solid phase to form at two or more separate and discrete elements, at least two of said two or more separate and discrete elements being spatially addressable and comprising a plurality of immobilized oligonucleotides; and labeling, with two or more labels, at least a portion of the plurality of immobilized oligonucleotides, wherein said at least two elements comprise a plurality of labeled immobilized oligonucleotides, wherein at least a portion of the plurality of labeled immobilised oligonucleotides are individually resolvable. The invention also relates to methods of producing a molecular array comprising: labeling, with two or more labels, a plurality of oligonucleotides to form a plurality of labeled oligonucleotides; and immobilizing directly or indirectly to a solid phase at least a portion of the plurality of labeled oligonucleotides to form two or more separate and discrete elements, at least two of said two or more separate and discrete elements being spatially addressable, said at least two elements comprising a plurality of labeled immobilized oligonucleotides, wherein at least a portion of the plurality of labeled immobilised oligonucleotides are individually resolvable. The invention also relates to methods of performing a genetic analysis comprising: depositing a plurality of labeled oligonucleotides to one or more wells in a microtitre plate to form a plurality of labeled deposited oligonucleotides, and performing the genetic analysis comprising counting a number of at least a portion of the plurality of labeled deposited oligonucleotides, wherein the plurality of labeled deposited oligonucleotides are deposited at a density which allows the at least a portion of the plurality of labeled deposited oligonucleotides to be individually resolved, and the at least a portion of the plurality of labeled deposited oligonucleotides are labeled with at least two different labels. The invention also relates to methods of prenatal diagnosis, comprising providing a plurality of probes complementary to at least a portion of nucleic acids present in a sample from a maternal blood; hybridizing said at least a portion of nucleic acids to the plurality of probes to produce hybridized molecules; and counting at least a portion of said hybridized molecules to determine frequency of the nucleic acids. The invention also relates to methods of performing a single molecule counting, comprising contacting a plurality of probes with target molecules to form probe-target molecule complexes in a solution, wherein the probe-target molecule complexes are labeled directly or indirectly with at least two different labels, applying the solution comprising the probe-target molecule complexes to a solid phase before or after the contacting, and determining relative numbers of the target molecules by comparing numbers of signals from the at least two different labels.

The invention relates to methods of detecting trisomy in a fetus of a pregnant human subject, comprising contacting first and second probe sets to a cell-free DNA sample from the pregnant human subject, wherein the first probe set comprises a first labeling probe and a first tagging probe, the second probe set comprises a second labeling probe and a second tagging probe, the first and second tagging probes comprise a common tagging nucleotide sequence; hybridizing at least parts of the first and second probe sets to nucleotide molecules located in first and second chromosomes present in the cell-free DNA sample, respectively; ligating at least parts of the first probe set by ligating the first labeling probe and the first tagging probe to form a first ligated probe set; ligating at least parts of the second probe set by ligating the second labeling probe and the second tagging probe to form a second ligated probe set; amplifying (i) the first ligated probe set with first forward and reverse primers, wherein at least one of the first forward and reverse primers comprises a first label and hybridizes to the first labeling probe of the first ligated probe set, and (ii) the second ligated probe set with second forward and reverse primers, wherein at least one of the second forward and reverse primers comprises a second label and hybridizes to the second labeling probe of the second ligated probe set, to form amplified first and second ligated probe sets comprising (i) the first and second labels, respectively, and (ii) an amplified common tagging nucleotide sequence amplified from said common tagging nucleotide sequence, wherein the first and second labels are different; immobilizing by hybridizing at least a part of the amplified common tagging nucleotide sequence to affinity nucleotide tags immobilized on a substrate, at a density in which the first and second labels of the amplified first and second ligated probe sets are optically resolvable after immobilization, wherein the affinity nucleotide tags comprise a complementary sequence of the at least a part of the amplified common tagging nucleotide sequence; optionally reading the first and second labels on the substrate in first and second imaging channels that correspond to the first and second labels, respectively; optionally producing one or more images of the substrate, wherein the first and second labels are optically resolvable in the one or more images; optionally distinguishing a first optical signal from a single first label from the rest of the optical signals from background and/or multiple first labels by calculating a relative signal and/or signal-to-noise intensity of the first optical signal compared to an intensity of an optical signal from a single first label, and determining whether the optical signal is from a single label; optionally distinguishing a second optical signal from a single second label from the rest of the optical signals from background and/or multiple second labels by calculating a relative signal and/or signal-to-noise intensity of the second optical signal compared to an intensity of an optical signal from a single second label, and determining whether the optical signal is from a single label; counting (i) a first number of the first label from said first optical signal from the single first label, wherein the first number corresponds to a number of the amplified first ligated probe set immobilized to the substrate, and (ii) a second number of the second label from said second optical signal from the single second label, wherein the second number corresponds to a number of the amplified second ligated probe set immobilized to the substrate; and comparing the first and second numbers to determine whether a copy number of the first chromosome is greater than a copy number of the second chromosome, wherein the copy number of the first chromosome greater than the copy number of the second chromosome indicates the presence of trisomy of the first chromosome in the fetus. The invention also relates to methods of detecting trisomy in a fetus of a pregnant human subject, comprising contacting first and second probe sets to a genetic sample isolated from a blood sample of the pregnant human subject, wherein the first probe set comprises a first labeling probe and a first tagging probe, and the second probe set comprises a second labeling probe and a second tagging probe; hybridizing at least parts of the first and second probe sets to nucleotide molecules present in the genetic sample; ligating at least parts of the first probe set at least by ligating the first labeling probe and the first tagging probe to form a first ligated probe set; ligating at least parts of the second probe set at least by ligating the second labeling probe and the second tagging probe to form a second ligated probe set; amplifying (i) the first ligated probe set with first forward and reverse primers, wherein at least one of the first forward and reverse primers comprises a first label, and (ii) the second ligated probe set with second forward and reverse primers, wherein at least one of the second forward and reverse primers comprises a second label, to form amplified first and second ligated probe sets comprising the first and second labels, respectively, wherein the first and second labels are different; immobilizing at least parts of the amplified first and second ligated probe sets on a substrate, wherein the first and second labels of the amplified first and second ligated probe sets are optically resolvable after immobilization; counting (i) a first number of the first label in the amplified first probe set immobilized to the substrate, and (ii) a second number of the second label in the amplified second probe set immobilized to the substrate; and comparing the first and second numbers to determine the presence of trisomy in the fetus.

The invention relates to methods of detecting a nucleic acid copy number variation in a genetic sample from a subject, comprising contacting first and second probe sets to the genetic sample, wherein the first probe set comprises a first labeling probe and a first tagging probe, and the second probe set comprises a second labeling probe and a second tagging probe; hybridizing at least parts of the first and second probe sets to first and second nucleic acid regions of interest in nucleotide molecules present in the genetic sample, respectively; optionally amplifying the first and second probe sets to form first and second amplified probe sets, respectively; labeling at least parts of the first and second labeling probes and/or first and second amplified probe sets with first and second labels, respectively; immobilizing at least parts of the first and second probe sets and/or first and second amplified probe sets to a substrate at a density in which the first and second labels of the first and second probe sets and/or first and second amplified probe sets are optically resolvable after immobilization; counting (i) a first number of the first label immobilized to the substrate, wherein the first number corresponds to a number of the first probe set and/or the first amplified probe set immobilized to the substrate, and (ii) a second number of the second label immobilized to the substrate, wherein the second number corresponds to a number of the second probe set and/or the second amplified probe set immobilized to the substrate; and comparing the first and second numbers to determine whether a first copy number of the first nucleic acid region of interest is different from a second copy number of the second nucleic acid region of interest, wherein a difference between the first and second copy numbers indicates the presence of the nucleic acid copy number variation in the genetic sample. The invention also relates to methods of detecting a nucleic acid copy number variation in a genetic sample from a subject, comprising forming a first probe product comprising a plurality of first oligonucleotides by hybridizing one or more first oligonucleotide probe to a first nucleic acid region of interest in nucleotide molecules present in the genetic sample; forming a second probe product comprising a plurality of second oligonucleotides by hybridizing one or more second oligonucleotide probe to a second nucleic acid region of interest in nucleotide molecules present in the genetic sample; ligating at least two oligonucleotides of the plurality of first oligonucleotides to form a first ligated probe product; ligating at least two oligonucleotides of the plurality of second oligonucleotides to form a second ligated probe product; optionally amplifying at least portions of the first and second ligated probe products to form first and second amplified probe products, respectively; labeling at least parts of the first and second ligated probe products and/or first and second amplified probe products with first and second labels, respectively; immobilizing at least parts of the first and second ligated probe products and/or first and second amplified probe products to a substrate at a density in which the first and second labels of the first and second ligated probe products and/or first and second amplified probe products are optically resolvable after immobilization; counting (i) a first number of the first label immobilized to the substrate, wherein the first number corresponds to a number of the first ligated probe products and/or the first amplified probe product immobilized to the substrate, and (ii) a second number of the second label immobilized to the substrate, wherein the second number corresponds to a number of the second ligated probe products and/or the second amplified probe product immobilized to the substrate; and comparing the first and second numbers to determine whether a first copy number of the first nucleic acid region of interest is different from a second copy number of the second nucleic acid region of interest, wherein a difference between the first and second copy numbers indicates the presence of the nucleic acid copy number variation in the genetic sample.

BRIEF DESCRIPTION OF THE DRAWINGS

FIGS. 21-46 depict exemplary probe sets described herein.

FIGS. 61A, 61B, and 61C provide evidence that mixtures of probe products may be used to generate quantitative microarray data.

DETAILED DESCRIPTION OF THE INVENTION

Figure 1:
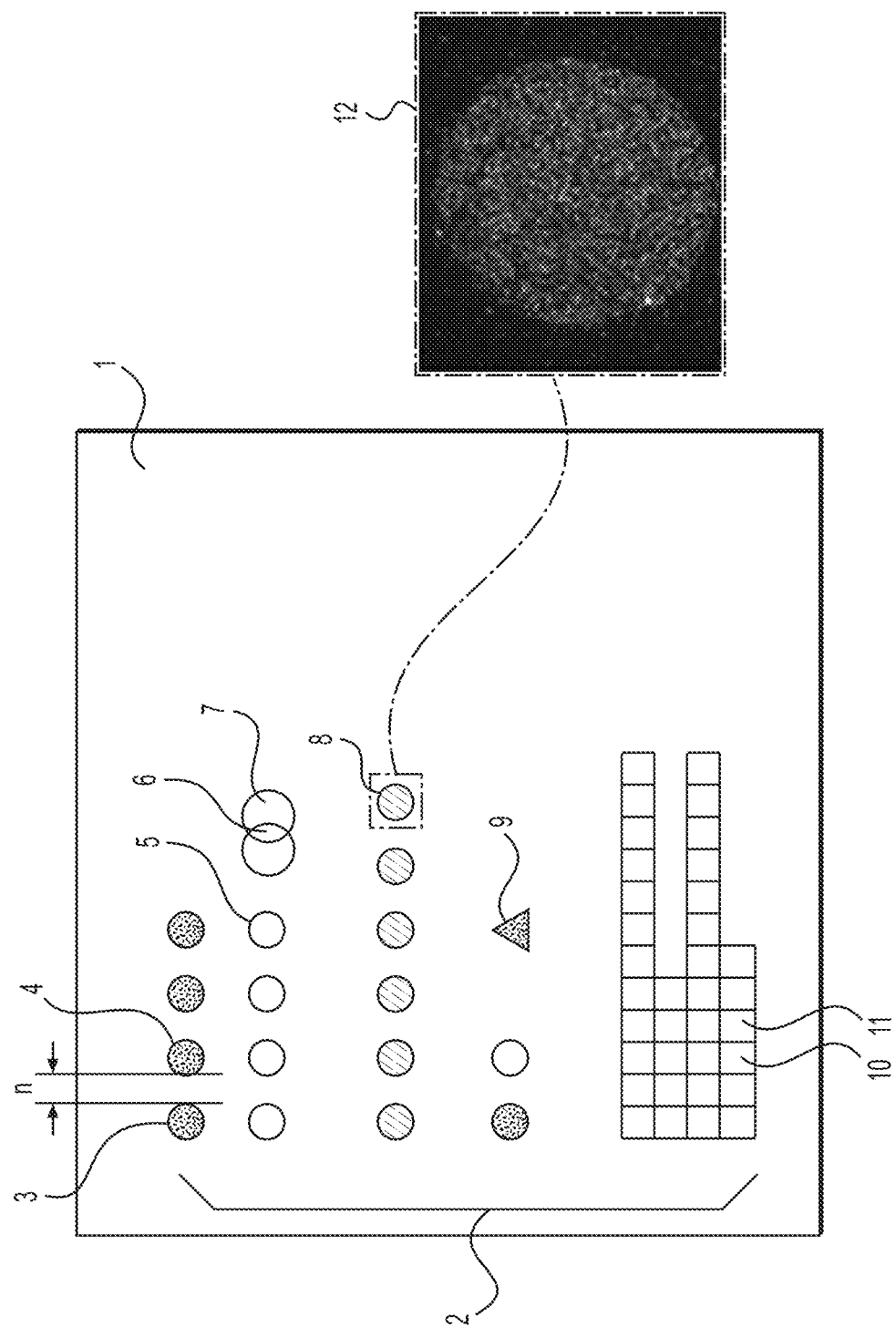
FIG. 1 depicts exemplary array members comprising binding partners, tags, affinity tags, tagging probes, probe sets, and/or litigated probe sets described herein on a substrate.

The methods described herein may employ, unless otherwise indicated, conventional techniques and descriptions of molecular biology (including recombinant techniques), cell biology, biochemistry, and microarray and sequencing technology, which are within the skill of those who practice in the art. Such conventional techniques include polymer array synthesis, hybridization and ligation of oligonucleotides, sequencing of oligonucleotides, and detection of hybridization using a label. Specific illustrations of suitable techniques can be had by reference to the examples herein. However, equivalent conventional procedures can, of course, also be used. Such conventional techniques and descriptions can be found, for example, in Kimmel and Oliver, DNA Microarrays (2006) Elsevier; Campbell, DNA Microarray, Synthesis and Synthetic DNA (2012) Nova Science; Bowtell and Sambrook, DNA Microarrays: Molecular Cloning Manual (2003) Cold Spring Harbor Laboratory Press. Before the present compositions, research tools and methods are described, it is to be understood that this invention is not limited to the specific methods, compositions, targets and uses described, as such may, of course, vary. It is also to be understood that the terminology used herein is for the purpose of describing particular aspects only and is not intended to limit the scope of the present invention, which will be limited only by appended claims.

The invention relates to methods of detecting a genetic variation in a genetic sample from a subject. The genetic variation herein may include, but is not limited to, one or more substitution, inversion, insertion, deletion, or mutation in nucleotide sequences (e.g., DNA and RNA) and proteins (e.g., peptide and protein), one or more microdeletion, one or more rare allele, polymorphism, single nucleotide polymorphism (SNP), large-scale genetic polymorphism, such as inversions and translocations, differences in the abundance and/or copy number (e.g., copy number variants, CNVs) of one or more nucleotide molecules (e.g., DNA), trisomy, monosomy, and genomic rearrangements. In some embodiments, the genetic variation may be related to metastasis, presence, absence, and/or risk of a disease, such as cancer, pharmacokinetic variability, drug toxicity, adverse events, recurrence, and/or presence, absence, or risk of organ transplant rejection in the subject. For example, copy number changes in the HER2 gene affect whether a breast cancer patient will respond to Herceptin treatment or not. Similarly, detecting an increase in copy number of chromosome 21 (or 18, or 13, or sex chromosomes) in blood from a pregnant woman may be used to as a non-invasive diagnostic for Down's Syndrome (or Patau's Syndrome or Edwards' Syndrome) in an unborn child. An additional example is the detection of alleles from a transplanted organ that are not present in the recipient genome—monitoring the frequency, or copy number, of these alleles may identify signs of potential organ rejection. Various methods may be used to detect such changes (e.g., rtPCR, sequencing and microarrays). One of the methods is to count individual, labeled molecules to either detect the presence of a mutation (e.g., EGFR mutation in cancer) or an excess of a specific genomic sequence or region (e.g., Chromosome 21 in Down's Syndrome). Counting single molecules may be done in a number of ways, with a common readout being to deposit the molecules on a surface and image.

Moreover, the genetic variation may be de novo genetic mutations, such as single- or multi-base mutations, translocations, subchromosomal amplifications and deletions, and aneuploidy. In some embodiments, the genetic variation may mean an alternative nucleotide sequence at a genetic locus that may be present in a population of individuals and that includes nucleotide substitutions, insertions, and deletions with respect to other members of the population. In additional embodiments, the genetic variation may be aneuploidy. In yet additional embodiments, the genetic variation may be trisomy 13, trisomy 18, trisomy 21, aneuploidy of X (e.g., trisomy XXX and trisomy XXY), or aneuploidy of Y (e.g., trisomy XYY). In further embodiments, the genetic variation may be in region 22q11.2, 1821.1, 9834, 1p36, 4p, 5p, 7811.23, 11q24.1, 17p, 11p15, 18q, or 22813. In further embodiments, the genetic variation may be a microdeletion or microamplification.

In some embodiments, detecting, discovering, determining, measuring, evaluating, counting, and assessing the genetic variation are used interchangeably and include quantitative and/or qualitative determinations, including, for example, identifying the genetic variation, determining presence and/or absence of the genetic variation, and quantifying the genetic variation. In further embodiments, the methods of the present disclosure may detect multiple genetic variations. The term "and/or" used herein is defined to indicate any combination of the components. Moreover, the singular forms "a," "an," and "the" may further include plural referents unless the context clearly dictates otherwise. Thus, for example, reference to "a nucleotide region" refers to one, more than one, or mixtures of such regions, and reference to "an assay" may include reference to equivalent steps and methods known to those skilled in the art, and so forth.

"Sample" means a quantity of material from a biological, environmental, medical, or patient source in which detection, measurement, or labeling of target nucleic acids, peptides, and/or proteins is sought. On the one hand it is meant to include a specimen or culture (e.g., microbiological cultures). On the other hand, it is meant to include both biological and environmental samples. A sample may include a specimen of synthetic origin. Environmental samples include environmental material, such as surface matter, soil, water and industrial samples, as well as samples obtained from food and dairy processing instruments, apparatus, equipment, utensils, disposable and non-disposable items. "Genetic sample" may be any liquid or solid sample with heritable and/or non-heritable biological information coded in the nucleotide sequences of nucleic acids. The sample may be obtained from a source, including, but not limited to, whole blood, serum, plasma, urine, saliva, sweat, fecal matter, tears, intestinal fluid, mucous membrane samples, lung tissue, tumors, transplanted organs, fetus, and/or other sources. Genetic samples may be from an animal, including human, fluid, solid (e.g., stool) or tissue. Genetic samples may include materials taken from a patient including, but not limited to cultures, blood, saliva, cerebral spinal fluid, pleural fluid, milk, lymph, sputum, semen, needle aspirates, and the like. Moreover, the genetic sample may be a fetal genetic material from a maternal blood sample. The fetal genetic material may be isolated and separated from the maternal blood sample. The genetic sample may be a mixture of fetal and maternal genetic material. In addition, the genetic sample may include aberrant genetic sequences arising from tumor formation or metastasis, and/or donor DNA signatures present in a transplant recipient. In additional embodiments, when the genetic sample is plasma, the method may comprise isolating the plasma from a blood sample of the subject. In further embodiments, when genetic sample is serum, the method may comprise isolating the serum from a blood sample of the subject. In yet additional embodiments, when the genetic sample is a cell free DNA (cfDNA) sample, the method further comprises isolating the cell free DNA sample from a sample obtained from the source described herein. The cell free DNA sample herein means a population of DNA molecules circulating freely in the bloodstream, outside of any cell or organelle. In the case of a pregnancy, cell free DNA from the mother carries a mixture of both maternal DNA as well as fetal DNA. These examples are not to be construed as limiting the sample types applicable to the present invention. In yet another embodiment, the samples is formalin-fixed, paraffin-embedded. For example, a heterogeneous tumor sample including multiple tumors and diluted tumor cells in normal cells may be used. The present invention allows the detection of rare cell-types, tumor heterogeneity, or nucleic acids from tumors in a dilute mixture of tumor and normal nucleic acids.

In one aspect, the sample may include cell-free DNA (cfDNA), cell-free RNA (cfRNA), extracellular DNA, and/or exosomes. In additional embodiments, the sample may be enriched for DNA fragments in a specific size range. For example, cfDNA is typically from 100 to 300 bp in length, and enriching for fragments that are likely to be cfDNA rather than cellular DNA in a sample may increase the sensitivity of a test for that sample or reduce the amount of the material needed to perform a test. In the context of prenatal testing, enriching for cfDNA may enrich the fetal fraction compared to the unenriched sample. Furthermore, cfDNA fragments derived from the fetus are shorter than those derived from the mother as a portion fetal DNA fragments are shorter than 300 bp, whereas a portion of maternal DNA fragments are >300 bp. Thus, an additional benefit to sensitivity may result from enriching the cfDNA for the population of fragments that are fetal in origin. Size selection of the cfDNA population may also provide a benefit in other clinical contexts, such as monitoring cancer diagnostics where a size difference between tumor-derived and noncancer cell-derived DNA has been demonstrated, or in transplantation where a size difference between donor-derived and recipient-derived DNA has been reported.

Transplanted organs include, but are not limited to, heart, liver, kidney, lung, blood or other tissues.

In additional embodiments, methods of enriching include bead-based methods, molecular nets, nanoparticles (for example, Nano Vison; nvigen.com/dna_sizerange.php), gel based selection (e.g. gel electrophoresis), Solid Phase Reversible Immobilization (SPRI) technologies, purification columns, selection by mass among other methods. In further embodiments, beads may be coated with capture probes (optionally with other linkers) either in a monolayer in three dimensional structures (e.g. a three-dimensional matrix containing capture probes and linkers and/or spacers). In some embodiments, such a three dimensional structure may be immobilized on a substrate such as a bead. Immobilization may be covalent or non-covalent. A sample may be contacted to the three-dimensional structure in order to size select, purify and/or enrich the sample. The density, spacing and structural elements of these molecules (e.g. capture probes or moieties, spacers, bridge molecules) may allow fragments of a certain size to be capture, excluding some or all of the other fragments in the sample. The beads may then be removed and the sample eluted. Capture may be based on the inclusion or exclusion of nucleic acids below a given size, inclusion or exclusion of nucleic acids above a given size or by selecting fragments within a certain size range. Alternatively, beads may be coated with carboxyl groups that will selectively bind DNA molecules of different sizes based on their total charge. The molecule size that binds may be controlled by modifying the components of the solution that the beads and DNA are in. Bead based methods are particularly suited to automation in microtiter plates using standard fluidics handling.

Other methods to use beads or gels with different pore sizes may be used to generate a packing material that enables differential exclusion of molecules from the pores based on size or molecular weight. Size enrichment may also be accomplished using either agarose or acrylamide gel electrophoresis in which molecules are separated based on their charge or by preparative capillary electrophoresis with fractionation. Another option is to use a microfabricated sieve through which molecules of different sizes move based on their heir diffusion coefficients.

Cell-free RNA or any other nucleic acid may be enriched in a similar manner described above.

In another aspect, the distribution of fragment sizes may be used to assess the fetal fraction and the presence of trisomy. This information may be used in combination with an array of the current invention to provide more information on the presence of fetal material in the sample and the disease status of the fetus (for example, where it carries a trisomy).

These enrichment methods for cfDNA can be used with many different technologies including, but not limited to, DNA sequencing, genotyping, qPCR, single-molecule counting.

Samples may be fragmented, amplified, denatured or otherwise modified before an assay is performed or before they are immobilized on the array.

In some embodiments, the method of the present disclosure may comprise enriching the fetal or tumor genetic material by enriching fetal or tumor cells, exosomes or vesicles. For example, protein markers may be used to selectively capture tumor cells, though the resulting material will usually not contain 100% tumor cells as normal (non-tumor) cells will also be included. However, this enrichment increases the proportion of tumor DNA in the sample. The cells can be used in conjunction with cfDNA or independently. Enrichment may also be by selecting material based on size (for example, fetal cfDNA molecules may be smaller on average than maternal cfDNA molecules).

Non-invasive prenatal testing (NIPT) has become common for high risk pregnancies. These may include women 35 years or older, women positive for serum or other screening tests or women with a family history of childhood disorders (e.g. a previous abnormal pregnancy). Current NIPT tests are sequence based which, because of its cost, has meant it is typically only used for high risk pregnancies. The current invention involves the manufacturing of a low cost single molecule array that can be used for screening all pregnancies. It can also be used for prognostic, monitoring and diagnostic prenatal tests.

In some embodiments, the method of the present disclosure may comprise selecting and/or isolating genetic locus or loci of interest, and quantifying the amount of each locus present (for example for determining copy number) and/or the relative amounts of different locus variants (for example two alleles of a given DNA sequence). Region, region of interest, locus, or locus of interest in reference to a genome or target polynucleotide used herein means a contiguous sub-region or segment of the genome or target polynucleotide. As used herein, region, regions or interest, locus, locus, or locus of interest in a nucleotide molecule may refer to the position of a nucleotide, a gene or a portion of a gene in a genome, including mitochondrial DNA or other non-chromosomal DNA, or it may refer to any contiguous portion of genomic sequence whether or not it is within, or associated with, a gene. A region, region of interest, locus, locus, or locus of interest in a nucleotide molecule may be from a single nucleotide to a segment of a few hundred or a few thousand nucleotides in length or more. In some embodiments, a region or locus of interest may have a reference sequence associated with it. "Reference sequence" used herein denotes a sequence to which a locus of interest in a nucleic acid is being compared. In certain embodiments, a reference sequence is considered a "wild type" sequence for a locus of interest. A nucleic acid that contains a locus of interest having a sequence that varies from a reference sequence for the locus of interest is sometimes referred to as "polymorphic" or "mutant" or "genetic variation." A nucleic acid that contains a locus of interest having a sequence that does not vary from a reference sequence for the locus of interest is sometimes referred to as "non-polymorphic" or "wild type" or "non-genetic variation." In certain embodiments, a locus of interest may have more than one distinct reference sequence associated with it (e.g., where a locus of interest is known to have a polymorphism that is to be considered a normal or wild type). In some embodiments, the method of the present disclosure may also comprise electing and/or isolating peptide or peptides of interest, and qualifying the amount of each peptide present and/or relative amounts of different peptides.

In additional embodiments, the region of interest described herein may include "consensus genetic variant sequence" which refers to the nucleic acid or protein sequence, the nucleic or amino acids of which are known to occur with high frequency in a population of individuals who carry the gene which codes for a protein not functioning normally, or in which the nucleic acid itself does not function normally. Moreover, the region of interest described herein may include "consensus normal gene sequence" which refers to a nucleic acid sequence, the nucleic acid of which are known to occur at their respective positions with high frequency in a population of individuals who carry the gene which codes for a protein not functioning normally, or which itself does not function normally. In further embodiments, the control region that is not the region of interest or the reference sequence described herein may include "consensus normal sequence" which refers to the nucleic acid or protein sequence, the nucleic or amino acids of which are known to occur with high frequency in a population of individuals who carry the gene which codes for a normally functioning protein, or in which the nucleic acid itself has normal function.

The methods described herein may produce highly accurate measurements of genetic variation. One type of variation described herein includes the relative abundance of two or more distinct genomic loci. In this case, the loci may be small (e.g., as small as about 300, 250, 200, 150, 100, or 50 nucleotides or less), moderate in size (e.g., from 1,000, 10,000, 100,000 or one million nucleotides), and as large as a portion of a chromosome arm or the entire chromosome or sets of chromosomes. The results of this method may determine the abundance of one locus to another. The precision and accuracy of the methods of the present disclosure may enable the detection of very small changes in copy number (as low as about 25, 10, 5, 4, 3, 2, 1, 0.5, 0.1, 0.05, 0.02 or 0.01% or less), which enables identification of a very dilute signature of genetic variation. For Example, a signature of fetal aneuploidy may be found in a maternal blood sample where the fetal genetic aberration is diluted by the maternal blood, and an observable copy number of change of about 2% is indicative of fetal trisomy.

As used herein, the term "about" means modifying, for example, lengths of nucleotide sequences, degrees of errors, dimensions, the quantity of an ingredient in a composition, concentrations, volumes, process temperature, process time, yields, flow rates, pressures, and like values, and ranges thereof, refers to variation in the numerical quantity that may occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of, for example, a composition, formulation, or cell culture with a particular initial concentration or mixture, and amounts that differ due to mixing or processing a composition or formulation with a particular initial concentration or mixture. Whether modified by the term "about" the claims appended hereto include equivalents to these quantities. The term "about" further may refer to a range of values that are similar to the stated reference value. In certain embodiments, the term "about" refers to a range of values that fall within 50, 25, 10, 9, 8, 7, 6, 5, 4, 3, 2, 1 percent or less of the stated reference value.

In some embodiments, the subject may be a pregnant subject, human, a subject with a high risk of a genetic disease (e.g., cancer), all of the various families of domestic animals, as well as feral or wild animals. In some embodiments, the genetic variation may be a genetic variation in the fetus of the pregnant subject (e.g., copy number variants and aneuploidy in the fetus). In some embodiments, the subject is a pregnant subject, and the genetic variation is a variation in the fetus of the pregnant subject in a region selected from the group consisting of 22q11.2, 1q21.1, 9q34, 1p36, 4p, 5p, 7q11.23, 11q24.1, 17p, 11p15, 18q, and 22q13, (e.g., a mutation and/or copy number change in any of regions 22q11.2, 1q21.1, 9q34, 1p36, 4p, 5p, 7q11.23, 11q24.1, 17p, 11p15, 18q, and 22q13). Fetus described herein means an unborn offspring of a human or other animal. In some embodiments, the fetus may be the offspring more than 1, 2, 3, 4, 5, 6, 7, 8, 9, 10, 11, 12, 13, 14, 15, 16, 17, 18, 19, 20 weeks after conception. In additional embodiments, the fetus may be an offspring conceived by implants, in vitro fertilization, multiple pregnancies, or twinning. In additional embodiments, the fetus may be part of a pair of twins (identical or non-identical), or a trio of triplets (identical or non-identical)

The inventions according to some embodiments encompass at least two major components: an assay for the selective identification of genomic loci, and a technology for quantifying these loci with high accuracy. The assay may include methods of selectively labeling and/or isolating one or more nucleic acid sequences, in such a manner that the labeling step itself is sufficient to yield molecules (defined as "probe products," "ligated probe set," "conjugated probe set," "ligated probes," "conjugated probes," or "labeled molecules" in this invention) containing all necessary information for identification of a particular sequence in the context of a particular assay. For example, the assay may comprise contacting, binding, and/or hybridizing probes to a sample, ligating and/or conjugating the probes, optionally amplifying the ligated/conjugated probes, and immobilizing the probes to a substrate. In some embodiments, the assays and methods described herein may be performed on a single input sample in parallel as a multiplex assay as described herein The probe product, ligated probe set, conjugated probe set, ligated probes, conjugated probes, and labeled molecules may be single, contiguous molecule resulting from the performance of enzymatic action on a probe set, such as an assay. In a probe product or a labeled molecule, one or more individual probes from a probe set may be covalently modified such that they form a singular distinct molecular species as compared to either probes or probe sets. As a result, probe products or a labeled molecule may be chemically distinct and may therefore be identified, counted, isolated, or further manipulated apart from probes or probe sets. In one embodiment, at least 10, at least 1,000, at least 10,000 probe sets are used to interrogate the same locus.

For example, probe products may contain one or more identification labels, and one or more affinity tags for isolation and/or immobilization. In some embodiments, no additional modifications of probe products (e.g., DNA sequence determination) need to be performed. In some embodiments, no additional interrogations of the DNA sequence are required. The probe products containing the labels may be directly counted, typically after an immobilization step onto a solid substrate. For example, organic fluorophore labels are used to label probe products, and the probe products are directly counted by immobilizing the probe products to a glass substrate and subsequent imaging via a fluorescent microscope and a digital camera. In other embodiments, the label may be selectively quenched or removed depending on whether the labeled molecule has interacted with its complementary genomic locus. In additional embodiments, two labels on opposite portions of the probe product may work in concert to deliver a fluorescence resonance energy transfer (FRET) signal depending on whether the labeled molecule has interacted with its complementary genomic locus. For a given genomic locus, labeling probes containing the labels be designed for any sequence region within that locus. A set of multiple labeling probes with same or different labels may also be designed for a single genomic locus. In this case, a probe may selectively isolate and label a different region within a particular locus, or overlapping regions or the same region within a locus. In some embodiments, the probe products containing affinity tags are immobilized onto the substrate via the affinity tags. For example, affinity tags are used to immobilize probe products onto the substrate, and the probe products containing the affinity tags are directly counted. For a given genomic locus, tagging probes containing the affinity tags be designed for any sequence region within that locus. A set of multiple tagging probes with same or different affinity tags may also be designed for a single genomic locus. In this case, a probe may selectively isolate and tag a different region within a particular locus, or overlapping regions within a locus.

In one aspect, the methods of the present disclosure may comprise contacting probe sets described herein with the genetic sample described herein. In some embodiments, the methods of the present disclosure may comprise contacting multiple probe sets, such as first and second probe sets, to the genetic sample. In additional embodiments, each of the probe sets comprises a labeling probe and a tagging probe. For example, the first probe set comprises a first labeling probe and a first tagging probe, and the second probe set comprises a second labeling probe and a second tagging probe.

Contacting the probe sets to the genetic sample may be performed simultaneously or after hybridizing, ligating, amplifying and/or immobilizing the probes. Moreover, contacting the probe sets to the genetic sample may be performed simultaneously or before hybridizing, ligating, amplifying, and/or immobilizing the probes.

For a given genomic locus or region of a nucleotide molecule in the genetic sample, a single nucleic acid sequence within that locus, or multiple nucleic acid sequences within that locus may be interrogated and/or quantified via the creation of probe products. The interrogated sequences within a genomic locus may be distinct and/or overlapping, and may or may not contain genetic polymorphisms. A probe product is formed by the design of one or more oligonucleotides called a "probe set." For example, the probe product may be formed by ligating the probe set by ligating the probes in the probe set. A probe set comprises at least one probe that hybridize, conjugate, bind, or immobilize to a target molecule, including nucleic acids (e.g., DNA and RNA), peptides, and proteins. In some embodiments, a probe may comprise an isolated, purified, naturally-occurring, non-naturally occurring, and/or artificial material, for example, including oligonucleotides of any length (e.g., 5, 10, 20, 30, 40, 50, 100, or 150 nucleotides or less), in which at least a portion(s) (e.g., 50, 60, 70, 80, 85, 90, 91, 92, 93, 94, 95, 96, 97, 98, 99, or 100%) of the oligonucleotide sequences is complementary to a sequence motif and/or hybridization domain present in one or more target molecules, such that the probe is configured to hybridize (or interact in a similar manner) in part or in total to one or more target molecules or nucleic acid region of interest. The part of the target molecule or the nucleic acid region of interest to which a probe hybridizes is called the probe's "hybridization domain," which may be in part or in total of the target molecule or the nucleic acid region of interest as described herein.

A probe may be single-stranded or double-stranded. In some embodiments, the probe may be prepared from in a purified restriction digest or produced synthetically, recombinantly or by PCR amplification. In additional embodiments, the probe may comprise a material that binds to a particular peptide sequence. A probe set described herein may comprise a set of one or more probes designed to correspond to a single genomic location or a peptide in a protein sequence.

"Nucleotide" used herein means either a deoxyribonucleotide or a ribonucleotide or any nucleotide analogue (e.g., DNA and RNA). Nucleotide analogues include nucleotides having modifications in the chemical structure of the base, sugar and/or phosphate, including, but not limited to 5'-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, $NH_2$, NHR, $NR_2$, or CN, shRNAs also may comprise non-natural elements such as non-natural nucleotides, ionosin and xanthine, non-natural sugars, 2'-methoxy ribose, or non-natural phosphodiester linkages, e.g., methylphosphonates, phosphorothioates and peptides. In one embodiment, the shRNA further comprises an element or a modification that renders the shRNA resistant to nuclease digestion. "Polynucleotide" or "oligonucleotide" is used interchangeably and each means a linear polymer of nucleotide monomers. Monomers making up polynucleotides and oligonucleotides are capable of specifically binding to a natural and/or artificial polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogues thereof, e.g., naturally occurring or non-naturally occurring analogues. Non-naturally occurring analogues may include PNAs, LNAs, phosphorothioate internucleosidic linkages, nucleotides containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogues of internucleosidic linkages, sugar moieties, or nucleotides at any or some positions. Polynucleotides typically range in size from a few monomeric units when they are referred to as "oligonucleotides" to several thousand monomeric units. Whenever a polynucleotide or oligonucleotide is represented by a sequence of letters (upper or lower case), such as "ATGCCTG," it will be understood that the nucleotides are in 5'→3' order from left to right. Usually polynucleotides comprise the four natural nucleosides (e.g., deoxyadenosine, deoxycytidine, deoxyguanosine, deoxythymidine for DNA or their ribose counterparts for RNA) linked by phosphodiester linkages; however, they may also comprise non-natural nucleotide analogues, e.g., including modified nucleotides, sugars, or internucleosidic linkages. It is clear to those skilled in the art that where an enzyme has specific oligonucleotide or polynucleotide substrate requirements for activity, e.g., single stranded DNA, RNA, RNA/DNA duplex, or the like, then selection of appropriate composition for the oligonucleotide or polynucleotide substrates is well within the knowledge of one of ordinary skill.

In another aspect, the methods of the present disclosure may comprise hybridizing at least parts of the first and second probe sets to first and second nucleic acid regions of interest in nucleotide molecules of the genetic sample, respectively. The hybridization of the probes to the nucleic acid of interest may be performed simultaneously or after contacting the probes to the genetic sample, ligating, amplifying and/or immobilizing the probes. Moreover, the hybridization of the probes to the nucleic acid of interest may be performed simultaneously or before ligating, amplifying, and/or immobilizing the probes. A part or full part of the probe may hybridize to a part or full part of the region of interest in single or double stranded nucleotide molecules, protein, or antibody in a sample. The region of interest hybridized to the probe may be from 1 to 50 nucleotides, 50 to 1000 nucleotides, 100 to 500 nucleotides, 5, 10, 50, 100, 200 nucleotides or less, or 2, 5, 10, 50, 100, 200, 500, 1000 nucleotides or more. Probes may be designed or configured to hybridize perfectly with a target region or molecule, or they may be designed such that a single-base mismatch (e.g., at a single nucleotide polymorphism, or SNP site), or a small number of such mismatches, fails to yield a hybrid of probe and target molecule.

Labels of certain structures may be susceptible to ozone degradation. This may be particularly true when they transition from a wet to dry state. For example, Alexa647 is significantly degraded by ozone at normal levels. In the context of single molecule arrays, such degradation will cause a bias in counting that must be corrected or else it may lead to false results. This is in contrast to traditional arrays where ozone degradation will lead to lower signal intensity. In some cases, some or all of the assay and array hybridization steps can be performed in an ozone-free or reduced-ozone environment. While ozone degradation is a known phenomenon, it is particularly deleterious for single molecule counting as each lost flour directly affects the accuracy of the counting. Methods of measuring ozone depletion of specific dyes can be used as a QC method or in error correction.

In additional embodiments, the first labeling probe and/or the first tagging probe are hybridized to the first nucleic acid region of interest, and the second labeling probe and/or the second tagging probes are hybridized to the second nucleic acid region of interest. In additional embodiments, multiple or all probes and/or other components (e.g., labelling probes, tagging probes, and gap probes) of a probe set that are hybridized to a nucleic acid region of interest are adjacent to each other. When two of the probes and/or components hybridized to the nucleic acid region of interest are "adjacent" or "immediately adjacent," there is no nucleotide between the hybridization domains of the two probes in the nucleic acid region of interest. In this embodiment, the different probes within a probe set may be covalently ligated together to form a larger oligonucleotide molecule. In another embodiment, a probe set may be designed to hybridize to a non-contiguous, but proximal, portion of the nucleic acid region of interest, such that there is a "gap" of one or more nucleotides on the nucleic acid region of interest, in between hybridized probes from a probe set, that is not occupied by a probe. In this embodiment, a DNA polymerase or another enzyme may be used to synthesize a new polynucleotide sequence, in some cases covalently joining two probes from a single probe set. Within a probe set, any probe may bear one or more labels, or affinity tags used for either locus identification or isolation. In one aspect, the first and second labeling probes are hybridized to the first and second nucleic acid regions of interest in nucleotide molecules of the genetic sample, respectively; the first and second tagging probes are hybridized to the first and second nucleic acid regions of interest in nucleotide molecules of the genetic sample, respectively; the first labeling probe is hybridized to a region adjacent to where the first tagging probe is hybridized; and the second labeling probe is hybridized to a region adjacent to where the second tagging probe is hybridized.

The hybridization occurs in such a manner that the probes within a probe set may be modified to form a new, larger molecular entity (e.g., a probe product). The probes herein may hybridize to the nucleic acid regions of interest under stringent conditions. As used herein the term "stringency" is used in reference to the conditions of temperature, ionic strength, and the presence of other compounds such as organic solvents, under which nucleic acid hybridizations are conducted. "Stringency" typically occurs in a range from about $T_m°$ C. to about 20° C. to 25° C. below $T_m$. A stringent hybridization may be used to isolate and detect identical polynucleotide sequences or to isolate and detect similar or related polynucleotide sequences. Under "stringent conditions" the nucleotide sequence, in its entirety or portions thereof, will hybridize to its exact complement and closely related sequences. Low stringency conditions comprise conditions equivalent to binding or hybridization at 68° C. in a solution consisting of 5×SSPE (43.8 g/l NaCl, 6.9 g/l $NaH_2PO_4·H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400), 5 g BSA) and 100 µg/ml denatured salmon sperm DNA followed by washing in a solution comprising 2.0+SSPE, 0.1% SDS at room temperature when a probe of about 100 to about 1000 nucleotides in length is employed. It is well known in the art that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) are well known in the art. High stringency conditions, when used in reference to nucleic acid hybridization, comprise conditions equivalent to binding or hybridization at 68° C. in a solution consisting of 5+SSPE, 1% SDS, 5×Denhardt's reagent and 100 µg/ml denatured salmon sperm DNA followed by washing in a solution comprising 0.1+SSPE and 0.1% SDS at 68° C. when a probe of about 100 to about 1000 nucleotides in length is employed.

In some embodiments, the probe product may be formed only if the probes within a probe set are correctly hybridized. Therefore, the probe products may be formed with high stringency and high accuracy. Again, the probe products may contain sufficient information for identifying the genomic sequence for which the probe product was designed to interrogate. Therefore, generation and direct quantification of a particular probe product (in this case, by molecular counting) may reflect the abundance of a particular genetic sequence in the originating sample.

In additional embodiments, the nucleic acid regions of interest, to which the probes are configured to hybridize to, are located in different chromosomes. For example, the first nucleic acid region of interest is located in chromosome 21, and the second nucleic acid region of interest is not located in chromosome 21 (e.g., located in chromosome 18).

In another aspect, the methods of the present disclosure may comprise ligating the first labeling probe and the first tagging probe, and ligating the second labeling probe and the second tagging probe. The ligation of the probes may be performed simultaneously or after contacting the probes to the genetic sample, amplifying and/or immobilizing the probes. Moreover, the ligation of the probes may be performed simultaneously or before contacting the probes to the genetic sample, amplifying, and/or immobilizing the probes. The ligation herein means the process of joining two probes (e.g., joining two nucleotide molecules) together. For example, ligation herein may involve the formation of a 3',5'-phosphodiester bond that links two nucleotides, and a joining agent that is an agent capable of causing ligation may be an enzyme or a chemical.

In another aspect, the methods of the present disclosure may comprise amplifying the ligated probes and/or ligated probe sets. The amplification of the ligated probes may be performed simultaneously or after contacting the probes to the genetic sample, ligating, hybridizing and/or immobilizing the probes. Moreover, the amplification of the ligated probes may be performed simultaneously or before immobilizing the probes. Amplification herein is defined as the production of additional copies of the probe and/or probe product and may be carried out using polymerase chain reaction technologies well known in the art. As used herein, the term "polymerase chain reaction" ("PCR") refers to a method for increasing the concentration of a segment of a target sequence (e.g., in a mixture of genomic DNA) without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified." With PCR, it is possible to amplify a single copy of a specific target sequence in genomic DNA to a level detectable by several different methodologies (e.g., hybridization with a labeled probe). In addition to genomic DNA, any oligonucleotide sequence may be amplified with the appropriate set of primer molecules. In particular, the amplified segments created by the PCR process itself are, themselves, efficient templates for subsequent PCR amplifications. An amplification may be a "real-time" amplification if a detection chemistry is available that permits a reaction product to be measured as the amplification reaction progresses, e.g., "real-time PCR," or "real-time NASBA" as described in Leone et al, Nucleic Acids Research, 26: 2150-2155 (1998).

Primers are usually single-stranded for maximum efficiency in amplification, but may alternatively be double-stranded. If double-stranded, the primer is usually first treated to separate its strands before being used to prepare extension products. This denaturation step is typically influenced by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded nucleotides linked at its 3' end complementary to the template in the process of DNA synthesis.

A "primer pair" as used herein refers to a forward primer and a corresponding reverse primer, having nucleic acid sequences suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer may be designed as a "forward primer" (which initiates nucleic acid synthesis from a 3'-end of the target nucleic acid) or as a "reverse primer" (which initiates nucleic acid synthesis from a 3'-end of the extension product produced from synthesis initiated from the forward primer). Likewise, the second primer may be designed as a forward primer or a reverse primer.

In some embodiments, the nucleic acid region of interest in the nucleotide molecule herein may be amplified by the amplification methods described herein. The nucleic acids in a sample may or may not be amplified prior to analysis, using a universal amplification method (e.g., whole genome amplification and whole genome PCR). The amplification of the nucleic acid region of interest may be performed simultaneously or after contacting the probes to the genetic sample, ligating, amplifying and/or immobilizing the probes. Moreover, the amplification of the ligated probes may be performed simultaneously or before contacting the probes to the genetic sample, ligating the probes, immobilizing the probes, and/or counting the labels.

In additional embodiments, the method excludes amplification of the nucleotide molecules of the genetic sample after the hybridization or the ligation. In further embodiments, the method excludes amplification of the nucleotide molecules of the genetic sample after the hybridization and the ligation.

In another aspect, the methods of the present disclosure may comprise immobilizing the tagging probes to a predetermined location on a substrate. The immobilization of the probe to a substrate may be performed simultaneously or after contacting the probes to the genetic sample, hybridizing the probes to the nucleic acid region of interest, ligating and/or amplifying the probes. Moreover, the immobilization of the probe to a substrate may be performed simultaneously or before contacting the probes to the genetic sample, hybridizing the probes to the nucleic acid region of interest, ligating, amplifying and/or counting the probes Immobilization herein means directly or indirectly binding the tagging probes to the pre-determined location on the substrate by a physical or chemical bond. In some embodiments, the substrate herein may comprise a binding partner that is configured to contact and bind to a part or full tag in the tagging probe described herein and immobilize the tag and thus the tagging probe comprising the tag. The tag of the tagging probe may comprise a corresponding binding partner of the binding partner on the substrate as described herein.

In some embodiments, the substrate may comprise one or more fiducials to locate a position on the substrate. In other embodiments, the substrate may comprise one or more blank spots that can be used to determine the background levels. These include the particulate background caused by labeled molecules adhering to the surface in a non-specific manner and other particulate material that might be mistaken for a labeled molecule.

Immobilization may be performed by hybridizing a part or full tagging probe to a part or full binding partner on the substrate. For example, the immobilizing step comprises hybridizing at least a part of the tag or tagging nucleotide sequence to a corresponding nucleotide molecule immobilized on the substrate. Here, the corresponding nucleotide molecule is a binding partner of the tag or tagging nucleotide sequence that is configured to hybridize partially or fully to the tag or tagging nucleotide sequence. In some embodiments, the oligonucleotide or polynucleotide binding partners may be single stranded and may be covalently attached to the substrate, for example, by 5'-end or a 3'-end. Immobilization may also be performed by the following exemplary binding partners and binding means: Biotin-oligonucleotide complexed with Avidin, Strepatavidin or Neutravidin; SH-oligonucleotide covalently linked via a disulphide bond to a SH-surface; Amine-oligonucleotide covalently linked to an activated carboxylate or an aldehyde group; Phenylboronic acid (PBA)-oligonucleotide complexed with salicylhydroxamic acid (SHA); Acrydite-oligonucleotide reacted with thiol or silane surface or co-polyemerized with acrylamide monomer to form polyacrylamide, or by other methods known in the art. For some applications where it is preferable to have a charged surface, surface layers may be composed of a polyelectrolyte multilayer (PEM) structure as shown in U.S. Patent Application Publication No. 2002/025529. In some embodiments, the immobilization may be performed by well-known procedures, for example, comprising contacting the probes with the support having binding partners attached for a certain period of time, and after the probes are depleted for the extension, the support with the immobilized extension products is optionally rinsed using a suitable liquid. In additional embodiments, immobilizing probe products onto a substrate may allow for rigorous washing for removing components from the biological sample and the assay, thus reducing background noise and improving accuracy.

"Solid support," "support," "substrate," and "solid phase support" are used interchangeably and refer to a material or group of materials having a rigid or semi-rigid surface or surfaces. In some embodiments, at least one surface of the substrate will be substantially flat, although in some embodiments it may be desirable to physically separate synthesis regions for different compounds with, for example, wells, nanowells, raised regions, pins, etched trenches, or the like. In additional embodiments, the substrate may comprise at least one planar solid phase support (e.g., a glass microscope slide, microscope coverslip). According to other embodiments, the substrate(s) will take the form of beads, resins, gels, microspheres, droplets, or other geometric configurations. In one aspect, the substrate according to some embodiments of the present disclosure excludes beads, resins, gels, droplets and/or microspheres. In some embodiments it may be desirable to physically separate regions, for example, wells, nanowells, microwells on a semiconductor chip, nanovials, photodiodes, electrodes, nanopores, raised regions, pins, etched trenches, or other physical structures. In another embodiment, the solid support will be divided by chemical means, such as having hydrophobic or hydrophilic regions that repel or attract material deposited on the substrate.

The substrate may be mounted in a holder, support, cartridge, stage insert or other format that provides, stability, protection from environment, easier or more precise handling, easier or more precise imaging, the ability to automate or other desirable properties.

In some embodiments, as shown in FIG. 1, the binding partners, the tags, the affinity tags, labels, the probes (e.g., tagging probes and labeling probes), and/or the probe sets described herein may be immobilized on a substrate (1) as an array (2). The array herein has multiple members (3-10) that may or may not have an overlap (6) between the members. Each member may have at least an area with no overlap with another member (3-5 and 7-10). In additional embodiments, each member may have different shapes (e.g., circular spots (3-8), triangles (9), and squares (10)) and dimensions. A member of an array may have an area about from 1 to $10^7$ micron$^2$, from 100 to $10^7$ micron$^2$, from $10^3$ to $10^8$ micron$^2$, from $10^4$ to $10^7$ micron$^2$; from $10^5$ to $10^7$ micron$^2$; about 0.0001, 0.001, 0.01, 0.1, 1, 10, 100, $10^3$, $10^4$, $10^5$, $10^6$, $10^7$, $10^8$ or more micron$^2$; and/or about 0.001, 0.01, 0.1, 1, 10, 100, $10^3$, $10^4$, $10^5$, $10^6$, $10^7$, $10^8$ or less micron$^2$.

In additional embodiments, the members described herein may have at least two different tags or affinity tags in one or more members. Various combinations of tags may be present in a single member, or in multiple members.

An array may encompass a set of the same or different arrays. Members of the set may be substrates, microtiter plates, arrays, microarrays, flow cells or a mixture of these. In some embodiments, the same sample is tested on one or more of the set of arrays, either with the same or different probes. Each array in the set may test for the same or different genetic variations. A given array in the set may test multiple different samples with the same or different probes. For example, an array of this type might include a set of microtiter plates. In each well of the plate, a different sample may be tested. In the first microtiter plate of the set, all samples may be tested for a particular genetic variation. In the second microtiter plate, a different genetic variation may be tested for the same samples.

An image of an exemplary member (8) according to some embodiments of the present invention is shown as item 12. Moreover, two or more members comprising the binding partners, the tags, the affinity tags, labels, the probes (e.g., tagging probes and labeling probes), and/or the probe sets of the same type may have the same shape and dimension. Specifically, the members of an array comprising the binding partners, tags, affinity tags, labels, tagging probes and/or probe sets configured or used to detect the same genetic variation or a control according to the methods described herein may have the same shapes and dimensions. Further, each and every member of the arrays on the substrate may have the same shapes and dimensions. In other embodiments, the members of an array comprising the binding partners, tags, affinity tags, labels, probes and/or probe sets configured or used to detect different genetic variations and/or controls according to the methods described herein may have the same shapes and dimensions. In addition, each member of the array may comprise different binding partners, the tags, the affinity tags, labels, the probes, and/or the probe sets.

In some embodiments, two members of the array may be separated by (i) a distance, in which there may be no or only very few binding partners, the tags, the affinity tags, labels, the probes (e.g., tagging probes and labeling probes), and/or the probe sets immobilized, and/or (ii) any separator distinguishing one member from the other (e.g., heightened substrate, any material preventing binding of the binding partners, the tags, the affinity tags, the probes (e.g., tagging probes), and/or the probe sets to the substrate, and any non-probe material between the members). In additional embodiments, the members of the array may be distinguished from each other at least by their locations alone. The members of the array may be separated by a distance about from 0 to $10^4$ microns, from 0 to $10^3$ microns, from $10^2$ to $10^4$ microns, or from $10^2$ to $10^3$ microns; about 0, 0.001, 0.1, 1, 2, 3, 4, 5, 10, 50, 100, $10^3$, $10^4$, $10^5$, $10^6$, $10^7$, or $10^8$ microns or more; and/or about 0, 0.001, 0.1, 1, 2, 3, 4, 5, 10, 50, 100, $10^3$, $10^4$, $10^5$, $10^6$, $10^7$, or $10^8$ microns or less. Here, the distance by which two members of the array are separated may be determined by the shortest distance between the edges of the members. For example, in FIG. 1, the distance by which two members, items 3 and 4, of an array (2) are separated is the distance indicated by item n. Moreover, for example, the shortest distance by which the members of the array (2) on a substrate (1) are separated is 0, as the distance by which two members, items 10 and 11, of the array are separated. In other embodiments, two members of the array may not be separated and may be overlapped (6).

In such embodiments, each member may have at least an area with no overlap with another member (7).

In some embodiments, the size of an array member and the density of labeled probes described herein may be controlled by the volume of material deposited on the substrate. For example, concentrations of on average 0.1 nM, 1 nM, 5 nM, 10 nM, 50 nM, 100 nM, 200 nM, 500 nM, 1000 nM, or 2000 nM may be used to create members of an average desired size or containing an average desired number of molecules. In additional examples, concentrations of on average less than 0.1 nM, 1 nM, 5 nM, 10 nM, 50 nM, 100 nM, 200 nM, 500 nM, 1000 nM, or 2000 nM may be used to create members of an average desired size or containing an average desired number of molecules. In further examples, concentrations of on average more than 0.1 nM, 1 nM, 5 nM, 10 nM, 50 nM, 100 nM, 200 nM, 500 nM, 1000 nM, or 2000 nM may be used to create members of an average desired size or containing an average desired number of molecules.

In additional embodiments, the method described herein may comprise utilizing spacers (e.g. Oligo DT), sarcosine, detergents or other additives to create more uniform distributions of labeled probes immobilized on the substrate. These spacers may have no function and do not interact in any specific way with the labeled oligonucleotides. For example, there is no sequence specific interaction between the spacer oligonucleotide and the labeled oligonucleotide or immobilized oligonucleotide.

In further embodiments, an array and the members of the array comprising the binding partners, the tags, the affinity tags, labels, the probes, and/or the probe sets described herein may be located on predetermined locations on the substrate, and the shapes and dimensions of each member of the array and the distance between the members may be predetermined prior to the immobilization. The predetermined location herein means a location that is determined or identified prior to the immobilization. For example, the shape and dimension of each member of an array is determined or identified prior to the immobilization.

In additional embodiments, the substrate may comprise an array of binding partners, each member of the array comprising the binding partners, such as oligonucleotides or polynucleotides, that are immobilized (e.g., by a chemical bond that would be not broken during the hybridization of probes to the binding partners of the substrate described herein) to a spatially defined region or location; that is, the regions or locations are spatially discrete or separated by a defined region or location on the substrate. In further embodiments, the substrate may comprise an array, each member of which comprises binding partners binding to a spatially defined region or location. Each of the spatially defined locations configured to comprise the binding partners may additionally be "addressable" in that its location and the identity of its immobilized binding partners are known or predetermined, for example, prior to its use, analysis, or attaching to their binding partners in tagging probes and/or probe sets. The term "addressable" with respect to the probe sets immobilized to the substrate means that the nucleotide sequence or other physical and/or chemical characteristics of an end-attached part (e.g., a binding partner of the binding partner of the substrate, tag, affinity tag, and tagging probe) of a probe set described herein may be determined from its address, i.e., a one-to-one correspondence between the sequence or other property of the end-attached part of the probe set and a spatial location on, or characteristic of, the substrate to which the probe set is immobilized. For example, an address of an end-attached part of a probe set is a spatial location, e.g., the planar coordinates of a particular region immobilizing copies of the end-attached part of the probe set. However, end-attached parts of probe sets may be addressed in other ways too, e.g., by color, frequency of micro-transponder, or the like, e.g., Chandler et al, PCT publication WO 97/14028, which is herein incorporated by reference in their entirety for all purposes. In further embodiments, the methods described herein exclude "random microarray," which refers to a microarray whose spatially discrete regions of binding partners (e.g., oligonucleotides or polynucleotides) of the substrate and/or the end-attached parts of probe sets are not spatially addressed. That is, the identity of the attached binding partners, tag. affinity tag, tagging probe, and/or probe sets is not discernable, at least initially, from its location. In one aspect, the methods described herein exclude random microarrays that are planar arrays of microbeads.

An array of nucleic acid according to some embodiments of the present disclosure may be produced by any method well known in the art, including but not limited to those described in U.S. Patent Application Publication No. 2013/0172216, which is incorporated by reference in its entirety for all purpose; Schena, Microarrays: A Practical Approach (IRL Press, Oxford, 2000). For example, a DNA capture array may be used. The DNA capture array is a solid substrate (e.g., a glass slide) with localized oligonucleotides covalently attached to the surface. These oligonucleotides may have one or more types on the surface, and may further be segregated geographically across the substrate. Under hybridization conditions, DNA capture arrays will preferentially bind complementary targets compared to other non-specific moieties, thereby acting to both localize targets to the surface and separate them from un-desired species.

In some embodiments, the first and second labeling probes and/or the amplified labeling probes thereof ligated to the immobilized tagging probes comprise first and second labels, respectively.

The labeling probe herein means a probe that comprises or is configured to bind to a label. The labeling probe itself may comprise a label or may be modified to comprise or bind to a label. The amplified probe herein is defined to be the additional copies of an initial probe produced after amplification of the initial probe as described herein. Accordingly, the amplified probes may have a sequence that is the nucleotide sequences of the initial probes and/or complementary sequence of the nucleotide sequences of the initial probes. The amplified probes may contain a sequence that is partial or complete match to the nucleotide sequences of the initial probes. The terms "complementary" or "complementarity" are used in reference to a sequence of nucleotides related by the base-pairing rules. For example, the sequence "5'-CAGT-3'," is complementary to the sequence "5'-ACTG-3'." Complementarity may be "partial" or "total." "Partial" complementarity is where one or more nucleic acid nucleotides in a probe is not matched according to the base pairing rules while others are matched. "Total" or "complete" complementarity between nucleic acids is where each and every nucleic acid base in the probe is matched with another base under the base pairing rules.

Immobilized probe herein is defined to be a probe that is directly or indirectly binding to the substrate by a physical or chemical bond. In some embodiments, a labeling probe may be immobilized to a substrate indirectly via ligation to a tagging probe immobilized to the substrate described herein.

A label herein means an organic, naturally occurring, synthetic, artificial, or non-naturally occurring molecule, dye, or moiety having a property or characteristic that is capable of detection and, optionally, of quantitation. A label may be directly detectable (e.g., radioisotopes, fluorophores, chemiluminophores, enzymes, colloidal particles, fluorescent substances, Quantum dots or other nanoparticles, nanostructures, metal compounds, organometallic labels, and peptide aptamers); or a label may be indirectly detectable using specific binding partners. Examples of the fluorescent substances include fluorescent dyes such as fluorescein, phosphor, rhodamine, polymethine dye derivatives, and the like. Examples of a commercially available fluorescent substance include fluorescent dyes, such as BODYPY FL (trademark, produced by Molecular Probes, Inc.), FluorePrime (product name, produced by Amersham Pharmacia Biotech, Inc.), Fluoredite (product name, produced by Millipore Corporation), FAM (produced by ABI Inc.), Cy 3 and Cy 5 (produced by Amersham pharmacia), TAMRA (produced by Molecular Probes, Inc.), Pacific Blue, TAMRA, Alexa 488, Alexa 594, Alexa 647, Atto 488, Atto 590, Atto 647N and the like. "Quantum dot" (QD) means a nano-scale semiconductor crystalline structure, usually made from cadmium selenide, and absorbs light and then re-emits it a couple of nanoseconds later in a specific color. QDs with a variety of conjugated or reactive surfaces, e.g., amino, carboxyl, streptavidin, protein A, biotin, and immunoglobulins, are also encompassed in the present disclosure.

In some embodiments, the label described herein may comprise an infra-red dyes. A longer wavelength dye (for example, red-shifted dyes at more than 580 nM) shows less single-molecule contamination than blue-shifted dyes. As such, combinations of dyes and filters in this range may be used for single molecule counting described herein. An example of a pair that can be used together are Atto590 and Atto647N. With the appropriate filters, bleed-through can be minimized so that flours can be distinguished by the detecting methods described below. Whereas single molecule contamination has little effect on traditional arrays, it contributes false or erroneous counts to digital, single molecule arrays.

Labeling may include methods of signal amplification including, but not limited to, duplication, multiplication or increasing of the signal. This signal amplification may be associated with amplification of the nucleic acid that the label is labeling (e.g. labeled PCR) or independent of the nucleic acid being labeled (e.g. branch-DNA).

Labels may also be transient properties, such as the temporary quenching of a dye molecule.

Detection of a label may be direct observation or measurement or by detecting a resultant property or secondary effect, such as the result of the interaction between and probe and target. For example, the incorporation of a deoxyribonucleotide triphosphate (dNTP) into a DNA strand causes the release of a hydrogen ion that can be detected by an ion sensor (for example, an array of ion-sensitive field-effect transistors).

Unlike many biological applications, the signal from single molecule arrays cannot be seen by the human eye. In this way, whether the dye emits in the visible wavelength is less important than for many biological applications. Infrared (IR) or near infra-red dyes are therefore particularly well suited to this application as they have low contamination.

In additional embodiments, the first and second labels are different so that the labels may be distinguished from each other. In further embodiments, the first and second labels are different in their physical, optical, and/or chemical properties.

In some embodiments, the immobilized labels are optically resolvable. The term "optically resolvable label" or "optically individually resolvable label" or "optically separated labels" herein means a group of labels that may be distinguished from each other by their photonic emission, or other optical properties, for example, after immobilization as described herein. In additional embodiments, even though the labels may have the same optical and/or spectral emission properties, the immobilized labels may be distinguished from each other spatially. In some embodiments, the labels of the same type, which is defined to be labels having the same optical properties, are immobilized on the substrate, for example as a member of an array described herein, at a density and/or spacing such that the individual probe products are resolvable as shown in item 12 of FIG. 1. In this disclosure, the "same labels" are defined to be labels having identical chemical and physical compositions. The "different labels" herein mean labels having different chemical and/or physical compositions, including "labels of different types" having different optical properties. The "different labels of the same type" herein means labels having different chemical and/or physical compositions, but the same optical properties.

Item 12 of FIG. 1 depicts an image of an exemplary member of an array comprising immobilized labels. In these embodiments, the labels are spatially addressable as the location of a molecule specifies its identity (and in spatial combinatorial synthesis, the identity is a consequence of location). In additional embodiments, one member of the array on the substrate may have one or multiple labeled probes immobilized to the member. When multiple labeled probes are immobilized to one member of the array, the labels of the same type in the labeled probes immobilized to the one member of an array on the substrate may be distinguished from each other spatially as shown in item 12 of FIG. 1. In some embodiments, the immobilized labels of the same type are separated by a distance about from 1 to 1000 nm, from 5 to 100 nm, or from 10 to 100 nm; about 100, 150, 200, 250, 300, 350, or 400 nm or more; and/or about 50, 100, 150, 200, 250, 300, 350, or 400 nm or less in all dimensions. The density of the probe products and their labels on the substrates may be up to many millions (and up to one billion or more) probe products to be counted per substrate. The ability to count large numbers of probe products containing the labels allows for accurate quantification of nucleic acid sequences. In some embodiments, the immobilized first and second tagging probes and/or the amplified tagging probes thereof comprise first and second tags, respectively. The tagging probe herein means a probe that is configured to directly or indirectly bind to the substrate. The tagging probe itself may bind to the substrate or may be modified to bind to the substrate. A tag or affinity tag herein means a motif for specific isolation, enrichment or immobilization of probe products. Examples of the tag or affinity tag include a binding partner described herein, unique DNA sequences allowing for sequence-specific capture including natural genomic and/or artificial non-genomic sequence, biotin-streptavidin, His-tags, FLAG octapeptide, click chemistry (e.g., pairs of functional groups that rapidly and selectively react with each other under mild, aqueous conditions), and antibodies (e.g., azide-cycline). For example, the immobilizing step comprises hybridizing at least a part of the tag, affinity tag, or tagging nucleotide sequence to a corresponding nucleotide molecule immobilized on the substrate. The tag or affinity tag is configured to bind to entities including, but not limited to a bead, a magnetic bead, a microscope slide, a coverslip, a microarray or a molecule. In some embodiments, the immobilizing step is performed by immobilizing the tags to the predetermined location of the substrate.

In another aspect, the numbers of different labels immobilized on the substrate and thus the numbers of different immobilized probe products comprising the labels are counted. For example, the probe products from each genetic locus are grouped together, and the labels in the immobilized probe products are counted. In some embodiments, multiple sequences within a genomic locus may be interrogated via the creation of multiple probe product types. For this example, different probe products for the same genomic locus may be combined (possibly via immobilization to a common location of a substrate, e.g., as a member of an array described herein), and the labels in these probe products may be directly counted. Different probe products for the same genomic locus may be also separated (possibly via immobilization to different locations of a substrate, e.g., as different members of an array described herein), and the labels in these probe products may be directly counted. In additional embodiments, the substrate may have one or more specific affinity tag in each location on a substrate, e.g., as a member of an array on the substrate. Therefore, another method for quantifying nucleic acid sequences occurs via immobilization of probe products for a single genomic locus (this may be one probe product type, or may be a set of more than one probe product for a particular genomic locus) to the same location of a substrate (e.g., as the same member of an array described herein) as probe products corresponding to a second genomic locus, which may or may not serve as a reference or control locus. In this case, the probe products from the first genomic locus will be distinguishable from the probe products from the second genomic locus, based on the presence of different labels used in generating the probe products.

In one example, for detecting trisomy 21 (aneuploidy) of a fetus through examination of a maternal blood sample, a set of probe products corresponding to chromosome 21 would be generated, for example with a red fluorophore label, and counted. A second set of probe products would also be generated from a reference, or control locus, for example chromosome 18, and counted. This second set of probe products may be generated, for example, with a green fluorophore label.

In some embodiments, these probe products may be prepared such that they are grouped together by locus (in this case chromosome 21 or chromosome 18) and counted separately on a substrate. That is, the probe products corresponding to chromosome 21 may be isolated and counted separately, and the probe products corresponding to chromosome 18 may be isolated and counted separately. In additional embodiments, these probe products may be also prepared in such a way that they are grouped together in the same location of a substrate (e.g., as the same member of an array described herein). In this case, on the same region of a substrate, the probe products bearing a red fluorophore will correspond to chromosome 21, and the probe products with a green fluorophore will correspond to chromosome 18. For example, since all of these probe products are individually resolvable and may therefore be counted very accurately, an increased frequency of chromosome 21 probe products relative to chromosome 18 probe products (even as small as 0.01, 0.1, one or more percent or less) will signify the presence of trisomy 21 in a fetus. In this case, the probe products for chromosome 18 may serve as a control.

In another aspect, the methods of the present disclosure may comprise counting the labels of the probe sets immobilized to the substrate. In another aspect, the methods may comprise enumerating, quantitating, detecting, discovering, determining, measuring, evaluating, calculating, counting, and assessing the labels, probes, probe sets described herein, for example, including quantitative and/or qualitative determinations, including, for example, identifying the labels, probes, probe sets, determining presence and/or absence, proportion, relative signals, or relative counts of the labels, probes, probe sets, and quantifying the labels, probes, probe sets. In some embodiments, the methods may comprise enumerating, quantitating, detecting, discovering, determining, measuring, evaluating, calculating, counting, and/or assessing (i) a first number of the first label immobilized to the substrate, and (ii) a second number of the second label immobilized to the substrate. The detecting, discovering, determining, measuring, evaluating, calculating, counting, and/or assessing step may be performed after immobilizing the ligated probe set to a substrate, and the substrate with immobilized ligated probe sets may be stored in a condition to prevent degradation of the ligated probe sets (e.g., at room temperature or a temperature below the room temperature) before this step is performed.

In some embodiments, the counting step comprises determining the numbers of labels, probes or probe sets based on an intensity, energy, relative signal, signal-to-noise, focus, sharpness, size, or shape of one or more putative labels. The putative labels include, for example, labels, particulate, punctate, discrete or granular background, and/or other background signals or false signals that mimic or are similar to labels. The methods described herein may include the step of enumerating, quantitating, detecting, discovering, determining, measuring, evaluating, calculating, counting, and/or assessing the labels, probes, and probe sets. This step is not limited to integer counting of the labels, probes, and probe sets. For example, counts may be weighted by the intensity of the signal from the label. In some embodiments, higher intensity signals are given greater weight and result in a higher counted number compared to lower intensity signals. In the instance where two molecules are very close together (for example, when imaging is diffraction limited), the two labels will not be easily resolved from one another. In this case they may appear to be a single label, but with greater intensity than a typical single label (i.e. the cumulative signal of both the labels). As such, counting can be more accurate when the intensity or other metrics of the label, such as size and shape described below is considered or weighted compared to counting the number of labels in the image without considering these metrics. In some embodiments, the shapes of the labels are considered, and the counting may include or exclude one or more of the labels depending on the shapes of the labels. In additional embodiments, the size of one or more labels or items, objects, or spots on an image may be considered, and the counting may include, exclude, or adjusted depending on the size. In further embodiments, counting may be done on any scale, including but not limited to integers, rational or irrational numbers. Any properties of the label or multiple labels may be used to define the count given to the observation.

In additional embodiments, the counting step may include determining the numbers of labels, probes or probe sets by summation over a vector or matrix containing the information (e.g. intensity, energy, relative signal, signal-to-noise, focus, sharpness, size or shape) about the putative label. For example, for each discrete observation of a label, information on its size, shape, energy, relative signal, signal-to-noise, focus, sharpness, intensity and other factors may be used to weight the count. Certain examples of the value of this approach would be when two fluors are coincident and appear as a single point. In this case, two fluors would have higher intensity than one fluor, and thus this information may be used to correct the count (i.e. counting 2 instead of 1). In some embodiments, the count can be corrected or adjusted by performing the calibrating described below. The vector or matrix may contain integer, rational, irrational or other numeric types. In some embodiments, weighting may also include determining, evaluating, calculating, or assessing likelihoods or probabilities, for example, the probability that an observation is a label, not a background particle. These probabilities may be based on prior observations, theoretical predictions or other factors. In additional embodiments, the initial count is the number of putative labels observed. This number may then be improved, corrected or calibrated by weighting each of the putative labels in the appropriate manner.

In one aspect, the counts described herein may be normalized, for example, by the density of the labels on the surface, the observed density of background particles (that mimic labels) or other factors. In another aspect, counts may be transformed using standard mathematical functions and transformations (e.g. logarithm). In another aspect, counts can be used to produce ratios. For example if the count of Label 1 and Label 2 are X and Y, the ratio X/Y may be used to combine the two numbers. These ratios can be compared within and between samples. In some instances, if Label 1 represents Chromosome 21 and Label 2 Chromosome 1, the ratio X/Y would be expected to be higher in cfDNA from a pregnant woman whose fetus has Down's Syndrome than it would be in cfDNA from a pregnant woman whose fetus did not have Down's Syndrome.

In order to accurately quantify the relative abundance of different genomic sequences, for example, for quantification of DNA copy number or for quantification of allele frequency, a large number of probe products may be counted. For example, a label may be detected and counted based on measuring, for example, physicochemical, electromagnetic, electrical, optoelectronic or electrochemical properties, or characteristics of the immobilized label.

In some embodiments, the label may be detected by scanning probe microscopy (SPM), scanning tunneling microscopy (STM) and atomic force microscopy (AFM), electron microscopy, optical interrogation/detection techniques including, but not limited to, near-field scanning optical microscopy (NSOM), confocal microscopy and evanescent wave excitation. More specific versions of these techniques include far-field confocal microscopy, two-photon microscopy, wide-field epi-illumination, and total internal reflection (TIR) microscopy. Many of the above techniques may also be used in a spectroscopic mode. The actual detection is by charge coupled device (CCD) cameras and intensified CCDs, photodiodes and/or photomultiplier tubes. In some embodiments, the counting step comprises an optical analysis, detecting an optical property of a label. In additional embodiments, the optical analysis comprises an image analysis as described herein.

In another aspect, for the methods described herein, a rapid turnaround time is desirable. Scan time measures the time from the start of imaging to the completion of collection of sufficient data for the given application of the methods. Some embodiments of the present invention provide an array that can be scanned in less than 60 minutes.

That is, enough data can be collected in less than 60 minutes to calculate a clear result of the specific test. More ideally, it can be scanned in less than 30 minutes or less than 15 minutes. Larger arrays can be scanned in less than 120 minutes, less than 180 minutes or less than 240 minutes. In some embodiments, the scan time may be more than 1, 3, 5, 10, 15, 20, or 30 minutes. The scan time may be proportional to the number of molecules counted with longer scan times giving higher sensitivity and/or lower false positive and/or lower false negative rates. Novel steps to decrease the scan time include automated focus finding, the use of fiducials to locate position on the array, specific combination of labels and filters, hardware optimization of hardware (e.g. light sources), optimal substrate and differential exposure times tailored to the properties of the labels. Further, for example, 63×oil immersion and 40×dry objective may be used to optimize the size of the label in the context of the pixel size of the sensor used for detection. A 40×objective (40× magnification) with 6.5 microns squared pixel size (e g Hamamatsu Orca Flash 4.0) with a label (e.g. Alexa488) being encapsulated by 9 pixels (a 3 by 3 square) with signal-to-noise of 3:1 in the majority of cases. This may allow the immobilized labeled oligonucleotides to be efficiently packed to decrease the scan time and so increase the throughput.

In prenatal testing, scan time is important because of the large numbers of samples that need to be scanned (there are 4,000,000 pregnancies in the U.S. per year on average and in a screening paradigm, all 4,000,000 would be tested). This would require almost 50 samples to be scanned per hour, every hour for every day of the year. As such, inventions that reduce scan time are particularly important.

Ideally, samples are scanned individual. That is, they are not pooled or mixed together. For sequencing based approaches to prenatal testing, samples are barcoded and then pooled and sequenced as a batch. All current prenatal testing methods use sample multiplexing. This multiplexing leads to potential error or mis-reporting of results. It further requires the scanning to be tailored to the sample with the lowest fetal fraction. If the samples are analyzed one by one, then each can be scanned to count the appropriate number of probes to have the required statistical power. This may be a very different number of counts for samples with low fetal fraction (very high numbers of counts required) compared to samples with high fetal fraction (relatively lower numbers of counts required). Sample multiplexing also requires that a batch of samples is available in order to efficiently run the instrument. As such, it may be that samples are delayed as a lab waits for the optimal number of samples to be reached. In the current invention, the samples can be run as they arrive, with no need to wait for multiple samples to be available. Each sample can have a unique substrate or samples can be located at different regions of the same substrate. In a preferred embodiment, each sample is scanned on a unique substrate.

In another aspect, the counting step comprises reading the substrate in first and second imaging channels that correspond to the first and second labels, respectively, and producing one or more images of the substrate, wherein the first and second labeling probes are resolvable in the one or more images. In some embodiments, the counting step comprises spatial filtering for image segmentation. In additional embodiments, the counting step comprises watershedding analysis, or a hybrid method for image segmentation. Individual methods may be applied more than once, with the same or different parameters or conditions. For, example, watershedding may divide the image into a set of regions, and then a re-application of watershedding within each region may be used to detect one or more labels within the regions defined by the initial watershedding analysis.

In another aspect, the sharpness or distinct shape of the point-spread function can be used to differentiate labels from other noise or types of signals.

The methods described herein may also look at the frequency of different alleles at the same genetic locus (e.g., two alleles of a given single nucleotide polymorphisms). The accuracy of these methods may detect very small changes in frequency (e.g., as low as about 10, 5, 4, 3, 2, 1, 0.5, 0.1 or 0.01% or less). As an example, in the case of organ transplantation, a blood sample will contain a very dilute genetic signature from the donated organ. This signature may be the presence of an allele that is not in the recipient of the donated organ's genome. The methods described herein may detect very small deviations in allele frequency (e.g., as low as about 10, 5, 4, 3, 2, 1, 0.5, 0.1 or 0.01% or less) and may identify the presence of donor DNA in a host sample (e.g., blood sample). An unhealthy transplanted organ may result in elevated levels of donor DNA in the host blood—a rise of only a few percent (e.g., as low as about 10, 5, 4, 3, 2, 1, 0.5, 0.1 or 0.01% or less). The methods described herein may be sensitive enough to identify changes in allele frequency with the necessary sensitivity, and therefore may accurately determine the presence and changing amounts of donor DNA in host blood.

In another aspect, the methods of the present disclosure may comprise comparing the first and second numbers to determine the genetic variation in the genetic sample. In some embodiments, the comparing step comprises obtaining an estimate of a relative number of the nucleotide molecules having the first and second nucleic acid regions of interest.

In another aspect, the methods of the present disclosure may comprise labeling the first and second labeling probes with the first and second labels, respectively, prior to the contacting step (e.g., during manufacturing the probes). Labeling the probe may be performed simultaneously or after contacting the probes to the genetic sample, hybridizing, ligating, amplifying and/or immobilizing the probes. Moreover, labeling the probe may be performed simultaneously or before contacting the probes to the genetic sample, hybridizing, ligating, amplifying, and/or immobilizing the probes. Labeling a probe may comprise adding, immobilizing, or binding a label to the probe by a physical or chemical bond. Labels may be placed anywhere within the sequence of a probe, including at the 5' or 3'-end.

In another aspect, the methods of the present disclosure may comprise tagging the first and second tagging probes with first and second tags, respectively, prior to the contacting step. (e.g., during the manufacturing the probes). Tagging the probe may be performed simultaneously or after contacting the probes to the genetic sample, hybridizing, ligating, amplifying and/or labeling the probes. Moreover, tagging the probe may be performed simultaneously or before contacting the probes to the genetic sample, hybridizing, ligating, amplifying, immobilizing and/or labeling the probes. Tagging a probe may comprise adding, immobilizing, or binding a tag to the probe by a physical or chemical bond. Tags may be placed anywhere within the sequence of a probe, including at the 5' or 3'-end.

In another aspect, the probe sets herein may be designed to have tags according to the predetermined locations to which the tags are to be immobilized. In some embodiments, the tags in all probe sets configured to detect a genetic variation are the same and are configured to be immobilized to same locations on the substrate directly or indirectly. In additional embodiments, the first and second tags are the same, and each of the rest of the tags is different from the first or second tag. In further embodiments, each or a group of members of the array of multiple predetermined locations on a substrate may have a unique tag to be immobilized.

In another aspect, the probe sets according to some embodiments may be amplified, and labeled probe sets may be produced during the process of amplification. In another aspect, each of the labeling probes may comprise a forward or reverse priming sequence, and each of the tagging probes may comprise a corresponding reverse or forward priming sequence and a tagging nucleotide sequence as a tag. The forward and reverse priming sequences are the sequences that are configured to hybridize to the corresponding forward and reverse primers, respectively. In some embodiments, the amplifying step comprises amplifying (i) the ligated first labeling and tagging probes with first forward and reverse primers hybridizing to the forward and reverse priming sequences, respectively, wherein the first forward or reverse primer hybridizing to the first labeling probe comprises the first label, and (ii) the ligated second labeling and tagging probes with second forward and reverse primers hybridizing to the forward and reverse priming sequences, respectively, wherein the second forward or reverse primer hybridizing to the second labeling probe comprises the second label. In additional embodiments, the amplified tagging nucleotide sequences of the tagging probes are immobilized to a pre-determined location on a substrate, wherein the amplified tagging nucleotide sequences of the first and second tagging probes are the first and second tags. In some embodiments, the first and second tags are the same and/or are configured to bind to the same location on the substrate. In another embodiment, the first and second tags are different and/or are configured to bind to different locations on the substrate. In further embodiments, when the probes are amplified, the method comprises counting numbers of the labels in the amplified probes and/or probe sets immobilized on the substrate. For example, the first number is the number of the first label in the amplified first probe set immobilized to the substrate, and the second number is the number of the second label in the amplified second probe set immobilized to the substrate.

In another aspect, the probe sets according to some embodiments may be amplified, and labeled probe sets may be produced using labeled reverse primers without using a forward primer. In another aspect, each of the labeling probes may comprise a reverse priming sequence, and each of the tagging probes may comprise a tagging nucleotide sequence as a tag. In some embodiments, the amplifying step may comprise amplifying (i) the ligated first labeling and tagging probes with a first reverse primer hybridizing to a first reverse priming sequence of the first labeling probe, wherein the first reverse primer comprises the first label, and (ii) the ligated second labeling and tagging probes with a second reverse primer hybridizing to a second reverse priming sequence of the second labeling probe, wherein the second reverse primer comprises the second label. In additional embodiments, the amplified tagging nucleotide sequences of the tagging probes are immobilized to a pre-determined location on a substrate, wherein the amplified tagging nucleotide sequences of the first and second tagging probes are the first and second tags. In further embodiments, the first number is the number of the first label in the amplified first probe set immobilized to the substrate, and the second number is the number of the second label in the amplified second probe set immobilized to the substrate.

In another aspect, the ligated probe sets according to some embodiments may be produced using a ligase chain reaction. In another aspect, the method described herein comprises contacting third and fourth probe sets to the genetic sample, wherein the third probe set comprises a third labeling probe and a third tagging probe, and the fourth probe set comprises a fourth labeling probe and a fourth tagging probe. The method may further comprise hybridizing the first and second probe sets to first and second sense nucleic acid strands of interest in single stranded nucleotide molecules from the double stranded nucleotide molecules of the genetic sample, respectively; and hybridizing the third and fourth probe sets to anti-sense nucleic acid strands of the first and second sense nucleic acid strands of interest, respectively. The method may further comprise producing ligated first, second, third, and fourth probe sets at least by ligating (i) the first labeling probe and the first tagging probe, (ii) the second labeling probe and the second tagging probe, (iii) the third labeling probe and the third tagging probe, and (iv) the fourth labeling probe and the fourth tagging probe. The method may further comprise performing a ligase chain reaction known in the art to amplify the ligated probe and/or ligated probe sets. In some embodiments, the ligase chain reaction may comprise hybridizing non-ligated first, second, third and fourth probe sets to the ligated third, fourth, first, and second probe sets, respectively, and ligating at least (i) the first labeling probe and the first tagging probe, (ii) the second labeling probe and the second tagging probe, (iii) the third labeling probe and the third tagging probe, and (iv) the fourth labeling probe and the fourth tagging probe of the non-ligated probe sets. The method may further comprise immobilizing the tagging probes to the pre-determined location on a substrate, wherein the first, second, third and fourth labeling probes ligated to the immobilized first, second, third and fourth tagging probes, respectively, comprise first, second, third and fourth labels, respectively; the immobilized labels are optically resolvable; the immobilized first, second, third and fourth tagging probes comprise first, second, third and fourth tags, respectively, and the immobilizing step is performed by immobilizing the tags to the predetermined location. The method may further comprise counting (i) the first sum of the first and third labels immobilized to the substrate, and (ii) the second sum of the second and fourth labels immobilized to the substrate, and comparing the first and second sums to determine the genetic variation in the genetic sample. In yet additional embodiments, the method further comprises labeling the first, second, third and fourth labeling probes with the first, second, third and fourth labels, respectively, prior to the contacting step. In yet further embodiments, the first and third labels are the same, and the second and fourth labels are the same.

In another aspect, the method described herein comprises contacting third and fourth probe sets to the genetic sample, wherein the third probe set comprises a third labeling probe and a third tagging probe, and the fourth probe set comprises a fourth labeling probe and a fourth tagging probe, the first and third labeling probes comprises a first reverse priming sequence, the second and fourth labeling probes comprises a second reverse priming sequence, and each of the tagging probes comprises a tagging nucleotide sequence as a tag. The method may further comprise hybridizing the first and second probe sets to first and second sense nucleic acid strands of interest, respectively, in single stranded nucleotide molecules from double stranded nucleotide molecules of the genetic sample; and hybridizing at least parts of the third and fourth probe sets to anti-sense nucleic acid strands of the first and second sense nucleic acid strands of interest, respectively; producing ligated first, second, third, and fourth probe sets by ligating (i) the first labeling probe and the first tagging probe, (ii) the second labeling probe and the second tagging probe, (iii) the third labeling probe and the third tagging probe, and (iv) the fourth labeling probe and the fourth tagging probe. The method may further comprise performing a ligase chain reaction. In some embodiments, the ligase chain reaction comprises hybridizing at least parts of the non-ligated first, second, third and fourth probe sets to the ligated third, fourth, first, and second probe sets, respectively, and ligating (i) the first labeling probe and the first tagging probe, (ii) the second labeling probe and the second tagging probe, (iii) the third labeling probe and the third tagging probe, and (iv) the fourth labeling probe and the fourth tagging probe of the non-ligated probe set. The method may further comprise amplifying (i) the ligated first and third probe sets with a first reverse primer hybridizing to the first reverse priming sequence, wherein the first reverse primer comprises the first label, and (ii) the ligated second and fourth probe sets with a second reverse primer hybridizing to the second reverse priming sequence, wherein the second reverse primer comprises the second label, the amplified tagging nucleotide sequences of the tagging probes are immobilized to a pre-determined location on a substrate, wherein the amplified tagging nucleotide sequences of the first, second, third and fourth tagging probes are first, second, third and fourth tags, the first number is the number of the first label in the amplified first and third probe sets immobilized to the substrate, and the second number is the number of the second label in the amplified second and fourth probe sets immobilized to the substrate.

In another aspect, the ligated first and second labeling probes are at the 3'-end of the first and second ligated probe set and comprise first and second reverse priming sequences hybridizing to the first and second reverse primers, respectively. In some embodiments, the first and second reverse primers comprise the first and second labels. In additional embodiments, the ligated first and second tagging probes are at the 5'-end of the first and second ligated probe set. In further embodiments, the ligated first and second tagging probes are at the 5'-end of the first and second ligated probe set and comprise first and second corresponding forward priming sequences hybridizing to the first and second forward primers, respectively.

In another aspect, the method herein comprises digesting double stranded molecules in the sample to produce single stranded molecules. In some embodiments, the amplifying step comprises contacting an exonuclease to the amplified probe and/or probe set, and digesting the amplified probe and/or probe set from the 5'-end of one strand of the double stranded amplified probe and/or probe set. For example, the amplifying step comprises contacting an exonuclease to the amplified probe in a probe set, and digesting the amplified probe set from the 5'-end of one strand of the double stranded amplified probe set. In additional embodiments, the one strand of the amplified probe and probe set contacting the exonuclease does not have any label at the 5'-end. The contacting of the exonuclease to the unlabeled double stranded probes may digest the unlabeled strand from the 5'-end producing single stranded probes. In another aspect, the 5'-end of the amplified probe set comprising the label at the 5'-end may be protected from exonuclease digestion.

In another aspect, the method may detect from 1 to 100, from 1 to 50, from 2 to 40, or from 5 to 10 genetic variations; 2, 3, 4, 5, 6, 7, 8, 9, 10 or more genetic variations; and 100, 50, 30, 20, 10 or less genetic variations. In some embodiments, the method described herein may detect x number of genetic variations using at least (x+1) number of different probe sets. In these embodiments, a number of labels from one type of probe sets may be compared with one or more numbers of labels from the rest of the different types of probe sets. In some embodiments, the method described herein may detect genetic variation in a continuous manner across the entire genome at various resolutions, for example, at 300,000 base resolution such that 100 distributed variations across all chromosomes are separately interrogated and quantified. In additional embodiments, the base resolution is in the range of one or ten to 100 thousand nucleotides up to one million, ten million, or 100 million or more nucleotides.

In another aspect, the method according to some embodiments may detect at least two genetic variations. In some embodiments, the method described herein may further comprise contacting a fifth probe set to the genetic sample, wherein the fifth probe set comprises a fifth labeling probe and a fifth tagging probe. The method may further comprise hybridizing at least a part of the fifth probe set to the third nucleic acid region of interest in nucleotide molecules of the genetic sample, wherein the third nucleic acid region of interest is different from the first and second nucleic acid regions of interest. The method may further comprise ligating the fifth probe set at least by ligating the fifth labeling probe and the fifth tagging probe. The method may further comprise amplifying the ligated probe sets. The method may further comprise immobilizing each of the tagging probe to a pre-determined location on a substrate, wherein the fifth labeling probe and/or the amplified labeling probe thereof ligated to the immobilized tagging probe comprise a fifth label, the fifth label is different from the first and second labels, the immobilized labels are optically resolvable, the immobilized fifth tagging probe and/or the amplified tagging probe thereof comprise a fifth tag, and the immobilizing step is performed by immobilizing the tags to the predetermined location. The method may comprise counting a third number of the fifth label immobilized to the substrate, and comparing the third number to the first and/or second number(s) to determine the second genetic variation in the genetic sample. In some embodiments, the subject may be a pregnant subject, the first genetic variation is trisomy 21 in the fetus of the pregnant subject, and the second genetic variation is selected from the group consisting of trisomy 13, trisomy 18, aneuploidy of X, and aneuploidy of Y in the fetus of the pregnant subject.

In another aspect, the method according to some embodiments may detect at least three genetic variations. In some embodiments, the method described herein further comprises contacting a sixth probe set to the genetic sample, wherein the sixth probe set comprises a sixth labeling probe and a sixth tagging probe. The method may further comprise hybridizing at least a part of the sixth probe set to the fourth nucleic acid region of interest in nucleotide molecules of the genetic sample, wherein the fourth nucleic acid region of interest is different from the first, second, and third nucleic acid regions of interest. The method may further comprise ligating the sixth probe set at least by ligating the sixth labeling probe and the sixth tagging probe. The method may further comprise amplifying the ligated probe sets. The method may further comprise immobilizing each of the tagging probes to a pre-determined location on a substrate, wherein the sixth labeling probe and/or the amplified labeling probe thereof ligated to the immobilized tagging probe comprise a sixth label, the sixth label is different from the first and second labels, the immobilized labels are optically resolvable, the immobilized sixth tagging probe and/or the amplified tagging probe thereof comprise a sixth tag, and the immobilizing step is performed by immobilizing the tags to the predetermined location. The method may further comprise counting a fourth number of the sixth label immobilized to the substrate, and comparing the fourth number to the first, second and/or third number to determine the third genetic variation in the genetic sample.

In another aspect, the method may according to some embodiments detect at least four genetic variations. In some embodiments, the method described herein further comprises contacting a seventh probe set to the genetic sample, wherein the seventh probe set comprises a seventh labeling probe and a seventh tagging probe. The method may further comprise hybridizing at least a part of the seventh probe set to the fifth nucleic acid region of interest in nucleotide molecules of the genetic sample, wherein the fifth nucleic acid region of interest is different from the first, second, third and fourth nucleic acid regions of interest. The method may further comprise ligating the seventh probe set at least by ligating the seventh labeling probe and the seventh tagging probe. The method may further comprise optionally amplifying the ligated probe sets. The method may further comprise immobilizing each of the tagging probes to a pre-determined location on a substrate, wherein the seventh labeling probe and/or the amplified labeling probe thereof ligated to the immobilized tagging probe comprise a seventh label, the seventh label is different from the first and second labels, the immobilized labels are optically resolvable, the immobilized seventh tagging probe and/or the amplified tagging probe thereof comprise a seventh tag, and the immobilizing step is performed by immobilizing the tags to the predetermined location. The method may further comprise counting a fifth number of the seventh label immobilized to the substrate, and comparing the fifth number to the first, second, third and/or fourth number(s) to determine the fourth genetic variation in the genetic sample.

In another aspect, the method according to some embodiments may detect at least five genetic variations. In some embodiments, the method described herein further comprises contacting an eighth probe set to the genetic sample, wherein the eighth probe set comprises a eighth labeling probe and a eighth tagging probe. The method may further comprise hybridizing at least a part of the eighth probe set to the sixth nucleic acid region of interest in nucleotide molecules of the genetic sample, wherein the sixth nucleic acid region of interest is different from the first, second, third, fourth, and fifth nucleic acid regions of interest. The method may further comprise ligating the eighth probe set at least by ligating the eighth labeling probe and the eighth tagging probe. The method may further comprise amplifying the ligated probe sets. The method may further comprise immobilizing each of the tagging probes to a pre-determined location on a substrate, wherein the eighth labeling probe and/or the amplified labeling probe thereof ligated to the immobilized tagging probe comprise a eighth label, the eighth label is different from the first and second labels, the immobilized labels are optically resolvable, the immobilized eighth tagging probe and/or the amplified tagging probe thereof comprise a eighth tag, and the immobilizing step is performed by immobilizing the tags to the predetermined location. The method may further comprise counting a sixth number of the eighth label immobilized to the substrate, and comparing the sixth number to the first, second, third, fourth and/or fifth number(s) to determine the fifth genetic variation in the genetic sample. In some embodiments, the subject is a pregnant subject, and the first, second, third, fourth, and fifth genetic variations are trisomy 13, trisomy 18, trisomy 21, aneuploidy X, and aneuploidy Y in the fetus of the pregnant subject.

In another aspect, the subject is a pregnant subject, the genetic variation is trisomy 21 in the fetus of the pregnant subject, the first nucleic acid region of interest is located in chromosome 21, and the second nucleic acid region of interest is not located in the chromosome 21.

In another aspect, the subject is a pregnant subject, the genetic variation is trisomy 21 in the fetus of the pregnant subject, the first nucleic acid region of interest is located in chromosome 21, and the second nucleic acid region of interest is located in chromosome 18.

In one aspect, the probe set herein may comprise two, three, four, five or more labeling probes, and/or two, three, four, five or more labels. In some embodiments, the method described herein may further comprise the first and second probe sets further comprise third and fourth labeling probes, respectively; the immobilized first probe set and/or amplified first probe set further comprise a ninth label in the third labeling probe and/or amplified product thereof; and the immobilized second probe set and/or amplified second probe set further comprise a tenth label in the fourth labeling probe and/or amplified product thereof. In these embodiments, if the ninth and tenth labels are different from the first and second labels, this method may be used to confirm the number counted for the first and second labels. If the ninth and tenth labels are the same from the first and second labels, respectively, this method may be used to improve the accuracy of detection labels immobilized to each of the nucleic acid regions of interest. For example, using multiple labels would be brighter than using one label, and therefore multiple labels may be more easily detected than one label. Further the number of labels may be used to quantify the molecule or molecules. With more labels giving a brighter signal. An advantage of multiple labels is that the cumulative signal from multiple labels will usually be easier to detect than a single label. This allows higher throughput scanning, a thicker substrate, lower magnification imaging, shorter exposure time and other properties.

In additional embodiments, (i) the immobilized first probe set and/or amplified first probe set further comprise an eleventh label in the labeling probe, and (ii) the immobilized second probe set and/or amplified second probe set further comprises a twelfth label that is different from the eleventh label in the labeling probe. In further embodiments, wherein the first, second, eleventh and twelfth labels are different from one another, and the counting step further comprises counting numbers of the eleventh and twelfth labels immobilized on the substrate.

In another aspect, the method described herein may be performed with a control sample. In some embodiments, the method may further comprise repeating the steps with a control sample different from the genetic sample from the subject. The method may further comprise counting control numbers of the labels immobilized to the substrate, and comparing the control numbers to the first, second, third, fourth, fifth and/or sixth number to confirm the genetic variation in the genetic sample.

In another aspect, the subject may be a pregnant subject, and the genetic variation is a genetic variation in the fetus of the pregnant subject. In such embodiments, the method may use a Single Nucleotide Polymorphism (SNP) site to determine whether the proportion (e.g., concentration, and number percentage based on the number of nucleotide molecules in the sample) of fetal material (e.g., the fetal fraction) is sufficient so that the genetic variation of the fetus may be detected from a sample from the pregnant subject with a reasonable statistical significance. In additional embodiments, the method may further comprise contacting maternal and paternal probe sets to the genetic sample, wherein the maternal probe set comprises a maternal labeling probe and a maternal tagging probe, and the paternal probe set comprises a paternal labeling probe and a paternal tagging probe. The method may further comprise hybridizing at least a part of each of the maternal and paternal probe sets to a nucleic acid region of interest in nucleotide molecules of the genetic sample, the nucleic acid region of interest comprising a predetermined SNP site, wherein the at least a part of the maternal probe set hybridizes to a first allele at the SNP site, the at least a part of the paternal probe set hybridizes to a second allele at the SNP site, and the first and second alleles are different from each other. The method may further comprise ligating the material and paternal probe sets at least by ligating (i) the maternal labeling and tagging probes, and (ii) the paternal labeling and tagging probes. The method may further comprise amplifying the ligated probes. The method may further comprise immobilizing the tagging probes to a pre-determined location on a substrate, wherein the maternal and paternal labeling probes and/or the amplified labeling probes thereof ligated to the immobilized tagging probes comprise maternal and paternal labels, respectively; the maternal and paternal labels are different, and the immobilized labels are optically resolvable. The method may further comprise counting the numbers of the maternal and paternal labels, and determining whether a proportion of a fetal material in the genetic sample is sufficient to detect the genetic variation in the fetus based on the numbers of the maternal and paternal labels. The method may further comprise determining the proportion of the fetal material in the genetic sample.

In another aspect, tumor fraction is analogous to the fetal material or fetal fraction described herein. The tumor fraction may be a measure of the proportion of the material that comes from the tumor in a way that is analogous to the fetal fraction measuring the proportion of the material that comes from the fetus and/or placenta. In general, the tumor fraction is <1% when the cancer is at an early stage (e.g. Stage II or earlier).

In some embodiments, when the subject is a pregnant subject, and the genetic variation is a genetic variation in the fetus of the pregnant subject, the method may further comprise contacting allele A and allele B probe sets that are allele-specific to the genetic sample, wherein the allele A probe set comprises an allele A labeling probe and an allele A tagging probe, and the allele B probe set comprises an allele B labeling probe and an allele B tagging probe. The method may further comprise hybridizing at least a part of each of the allele A and allele B probe sets to a nucleic acid region of interest in nucleotide molecules of the genetic sample, the nucleic acid region of interest comprising a predetermined single nucleotide polymorphism (SNP) site for which a maternal allelic profile (i.e., genotype) differs from a fetal allelic profile at the SNP site (For example, maternal allelic composition may be AA and fetal allelic composition may be AB, or BB. In another example, maternal allelic composition may be AB and fetal allelic composition may be AA, or BB), wherein the at least a part of the allele A probe set hybridizes to a first allele at the SNP site, the at least a part of the allele B probe set hybridizes to a second allele at the SNP site, and the first and second alleles are different from each other. The method may further comprise ligating the allele A and allele B probe sets at least by ligating (i) the allele A labeling and tagging probes, and (ii) the allele B labeling and tagging probes. The method may further comprise amplifying the ligated probe sets. The method may further comprise immobilizing the tagging probes to a pre-determined location on a substrate, wherein the allele A and allele B labeling probes and/or the amplified labeling probes thereof ligated to the immobilized tagging probes comprise allele A and allele B labels, respectively, the allele A and allele B labels are different, and the immobilized labels are optically resolvable. The method may further comprise counting the numbers of the allele A and allele B labels, and determining whether a proportion of a fetal material in the genetic sample is sufficient to detect the genetic variation in the fetus based on the numbers of the allele A and allele B labels. The method may further comprise determining the proportion of the fetal material in the genetic sample.

In some embodiments, when the subject is a pregnant subject, the genetic variation is a genetic variation in the fetus of the pregnant subject, and the genetic sample comprises a Y chromosome, the method may further comprise contacting maternal and paternal probe sets to the genetic sample, wherein the maternal probe set comprises a maternal labeling probe and a maternal tagging probe, and the paternal probe set comprises a paternal labeling probe and a paternal tagging probe. The method may further comprise hybridizing at least parts of the maternal and paternal probe sets to maternal and paternal nucleic acid regions of interest in nucleotide molecules of the genetic sample, respectively, wherein the paternal nucleic acid region of interest is located in the Y chromosome, and the maternal nucleic acid region of interest is not located in the Y chromosome. The method may further comprise ligating the maternal and paternal probe sets at least by ligating (i) the maternal labeling and tagging probes, and (ii) the paternal labeling and tagging probes. The method may further comprise amplifying the ligated probes. The method may further comprise nucleic acid region of interest comprising a predetermined single nucleotide polymorphism (SNP) site containing more than one SNP, for example two or three SNPs. Further, the SNP site may contain SNPs with high linkage disequilibrium such that labeling and tagging probes are configured to take advantage of the improved energetics of multiple SNP matches or mismatches versus only one. The method may further comprise immobilizing the tagging probes to a pre-determined location on a substrate, wherein the maternal and paternal labeling probes and/or the amplified labeling probes thereof ligated to the immobilized tagging probes comprise maternal and paternal labels, respectively, the maternal and paternal labels are different, and the immobilized labels are optically resolvable. The method may further comprise counting the numbers of the maternal and paternal labels, and determining whether a proportion of a fetal material in the genetic sample is sufficient to detect the genetic variation in the fetus based on the numbers of the maternal and paternal labels. The method may further comprise determining the proportion of the fetal material in the genetic sample.

In additional embodiments, other genetic variations (e.g., single base deletion, microsatellite, and small insertions) may be used in place of the genetic variation at the SNP site described herein.

In one aspect, the probe set described herein may comprise three or more probes, including at least one probe between the labeling and tagging probes. In some embodiments, the first and second probe sets further comprises first and second gap probes, respectively; the first gap probe hybridizes to a region between the regions where the first labeling probe and the first tagging probe hybridize; the second gap probe hybridizes to a region between the regions where the second labeling probe and the second tagging probe hybridize. The method may further comprise the ligating step comprises ligating at least (i) the first labeling probe, the first tagging probe, and the first gap probe, and (ii) the second labeling probe, the second tagging probe, and the second gap probe. In additional embodiments, the gap probe may comprise a label. For example, the first and second gap probes and/or amplified products thereof are labeled with labels (e.g., thirteenth and fourteenth labels, respectively), and each of the labels may be different from the rest of the labels (e.g., the first and second labels). The labels in the gap probes (e.g., thirteenth and fourteenth labels) may be the same or different from each other. In another aspect, the first and second labeling probes are hybridized to the first and second nucleic acid regions of interest in nucleotide molecules of the genetic sample, respectively; the first and second tagging probes are hybridized to the first and second nucleic acid regions of interest in nucleotide molecules of the genetic sample, respectively; the first and second gap probes are hybridized to the first and second nucleic acid regions of interest in nucleotide molecules of the genetic sample, respectively. In some embodiments, there are from 0 to 100 nucleotides, 1 to 100 nucleotides, 2 to 50 nucleotides; 3 to 30 nucleotides, 0, 1, 2, 3, 4, 5, 6, 7, 8, 9, 10, 20, 30, 40, 50, 100, 150, or 200 or more; or 1, 2, 3, 4, 5, 6, 7, 8, 9, 10, 15, 25, 35, 45, 55, 110, 160, or 300 or less between the regions where the first labeling probe and tagging probes are hybridized; and there are from 0 to 100 nucleotides, 1 to 100 nucleotides, 2 to 50 nucleotides; 3 to 30 nucleotides, 0, 1, 2, 3, 4, 5, 6, 7, 8, 9, 10, 20, 30, 40, 50, 100, 150, or 200 nucleotides or more; or 1, 2, 3, 4, 5, 6, 7, 8, 9, 10, 15, 25, 35, 45, 55, 110, 160, or 300 nucleotides or less between the regions where the second labeling probe and tagging probes are hybridized. In additional embodiments, the gap probe between a labeling probe and a tagging probe may have a length from 0 to 100 nucleotides, 1 to 100 nucleotides, 2 to 50 nucleotides; 3 to 30 nucleotides, 0, 1, 2, 3, 4, 5, 6, 7, 8, 9, 10, 20, 30, 40, 50, 100, 150, or 200 or more; or 1, 2, 3, 4, 5, 6, 7, 8, 9, 10, 15, 25, 35, 45, 55, 110, 160, or 300 or less.

In another aspect, the probe set described herein may comprise a spacer ligated and/or conjugated to the labeling probe and the tagging probe. The spacer may or may not comprise oligonucleotides. The spacer may comprise an isolated, purified, naturally-occurring, or non-naturally occurring material, including oligonucleotide of any length (e.g., 5, 10, 20, 30, 40, 50, 100, or 150 nucleotides or less). In some embodiments, the probe may be in a purified restriction digest or produced synthetically, recombinantly or by PCR amplification. For example, the first labeling and tagging probes are conjugated by a first spacer, the second labeling and tagging probes are conjugated by a second spacer, and the first and second spacers are not hybridized to the nucleotide molecules of the genetic sample. In some embodiments, the method further comprises digesting the hybridized genetic sample with an enzyme, and breaking a bond in the first and second spacers after the digestion.

In another aspect, the method described herein excludes identifying a sequence in the nucleotide molecules of the genetic sample, and/or sequencing of the nucleic acid region(s) of interest and/or the probes. In some embodiments, the method excluding sequencing of the probes includes excluding sequencing a barcode and/or affinity tag in a tagging probe. In additional embodiments, the immobilized probe sets to detect different genetic variations, nucleotide regions of interest, and/or peptides of interest need not be detected or scanned separately because sequencing is not required in the methods described herein. In additional embodiments, the numbers of different labels immobilized to the substrate were counted simultaneously (e.g., by a single scanning and/or imaging), and thus the numbers of different labels were not separately counted. In another aspect, the method described herein excludes bulk array readout or analog quantification. The bulk array readout herein means a single measurement that measures the cumulative, combined signal from multiple labels of a single type, optionally combined with a second measurement of the cumulative, combined signal from numerous labels of a second type, without resolving a signal from each label. A result is drawn from the combination of the one or more such measurements in which the individual labels are not resolved. In another aspect, the method described herein may include a single measurement that measures the same labels, different labels of the same type, and/or labels of the same type in which the individual labels are resolved. The method described herein may exclude analog quantification and may employ digital quantification, in which only the number of labels is determined (ascertained through measurements of individual label intensity and shape), and not the cumulative or combined optical intensity of the labels.

In another aspect, the probe set described herein may comprise a binder. A binder is the same material as the tag or affinity tag describe herein. In some embodiments, the method further comprises immobilizing the binder to a solid phase after the ligating steps. The method may further comprise isolating the ligated probe sets from non-ligated probes. In additional embodiments, the binder comprises biotin, and the solid phase comprises a magnetic bead.

In another aspect, the counting step described herein may further comprise calibrating, verifying, and/or confirming the counted numbers. Calibrating herein means checking and/or adjusting the accuracy of the counted number. Verifying and confirming herein mean determining whether the counted number is accurate or not, and/or how much the error is, if exists.

Figure 2:
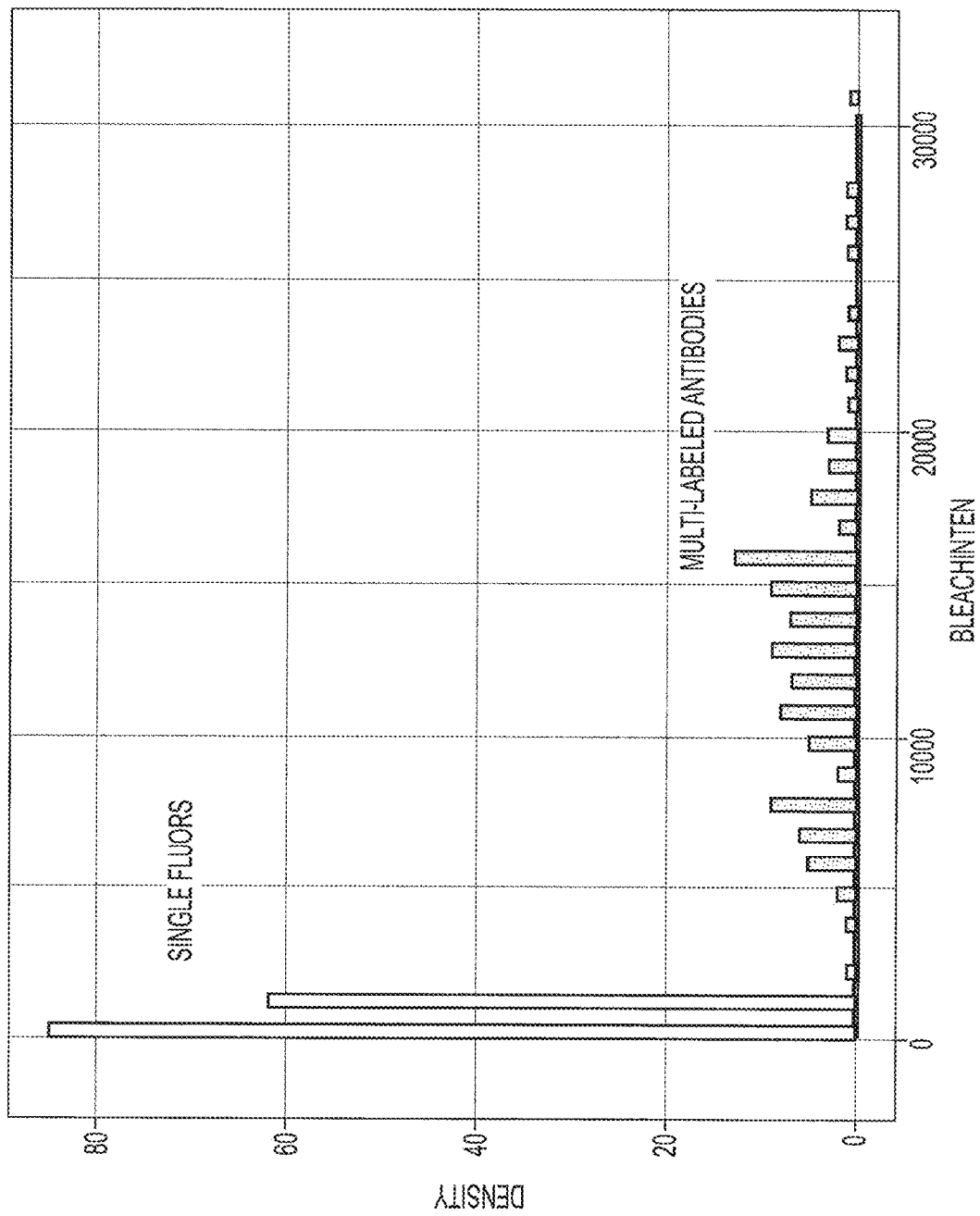
FIG. 2 depicts a normalized histogram of signal intensity measured from both single label samples and multi-label antibodies.

In another aspect, intensity and/or single-to-noise is used as a method of identifying single labels. When dye molecules or other optical labels are in close proximity, they are often impossible to discriminate with fluorescence-based imaging due to the intrinsic limit of the diffraction of light. That is, two labels that are close together will be indistinguishable with no visible gap between them. One exemplary method for determining the number of labels at a given location is to examine the relative signal and/or signal-to-noise compared to locations known to have a single fluor. Two or more labels will usually emit a brighter signal (and one that can more clearly be differentiated from the background) than will a single fluor. FIG. 2 shows the normalized histogram of signal intensity measured from both single label samples and multi-label antibodies (both Alexa 546; verified through bleach profiles). The two populations were clearly separable, and multiple labels may be clearly distinguished from single labels.

Figure 81:
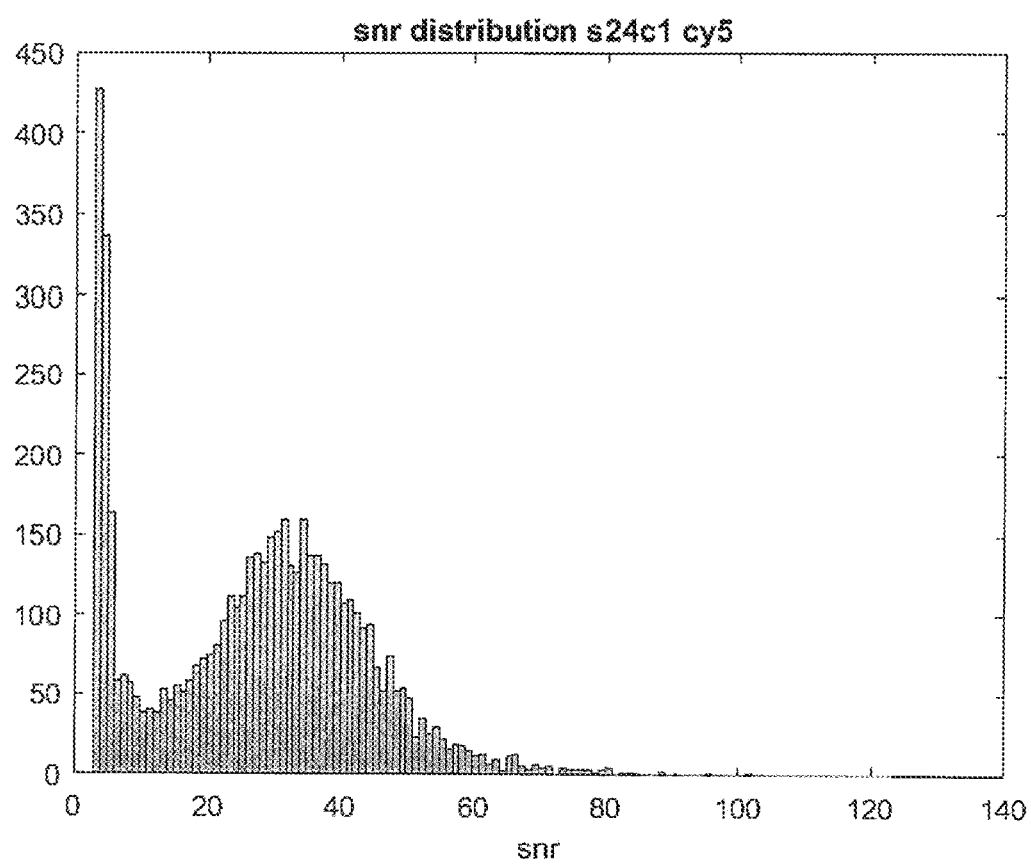
FIG. 81 shows an exemplary signal-to-noise distribution for observed putative labels from a single image. The distribution is bimodal, with this first peak being background and the second being true labels (for example, oligos labeled with Cy5).

In another aspect, energy, relative signal, signal-to-noise, focus, sharpness, size, shape and/or other properties is used as a method of distinguishing single labels from particulate, punctate, discrete or granular background or other background signals or false signals that mimic or are similar to labels. These false signals may be caused by particulate matter, for example, unlabeled molecules, differently labeled molecules, bleed through from other dyes, inorganic or organic particulate material, and/or stochastic effects such as noise, shot noise or other factors. Some exemplary methods for differentiating the label from particulate, punctate, discrete or granular background at a given location is to examine the energy, relative signal, signal-to-noise, focus, sharpness, size, or shape of putative labels on a substrate. Labels will usually emit a brighter (or dimmer) signal than will particulate, punctate, discrete or granular background. For example, FIG. 81 shows an exemplary signal-to-noise (SNR) distribution for counted putative labels from an image. Labels in this example are a fluorescent dye (Cy5). The first peak (left) is background particles and the second peak (right) are actual labels. SNR can be used to differentiate, determine or weight the observations and to categorize them into background and labels.

In some embodiments, the counting step may comprise measuring optical signals from the immobilized labels, and calibrating the counted numbers by distinguishing an optical signal from a single label from the rest of the optical signals from background and/or multiple labels. In some embodiments, the distinguishing comprises calculating a relative signal and/or single-to-noise intensity of the optical signal compared to an intensity of an optical signal from a single label. The distinguishing may further comprise determining whether the optical signal is from a single label. In additional embodiments, the optical signal is from a single label if the relative signal and/or single-to-noise intensity of an optical signal differs from an intensity of an optical signal from a single label by a predetermined amount or less. In further embodiments, the predetermined amount is from 0% to 100%, from 0% to 150%, 10% to 200%, 0, 1, 2, 3, 4, 5, 10, 20, 30, or 40% or more, and/or 300, 200, 100, 50, 30, 10, or 5% or less of the intensity of the optical signal from a single label.

In another aspect, different labels may have different blinking and bleaching properties. They may also have different excitation properties. In order to compare the number of dye molecules for two different labels, it is necessary to ensure that the two dyes are behaving in a similar manner and have similar emission characteristics. For example, if one dye is much dimmer than another, the number of molecules may be under-counted in this channel Several factors may be titrated to give the optimal equivalence between the dyes. For example, the counting step and/or calibrating step may comprise optimizing (i) powers of light sources to excite the labels, (ii) types of the light sources, (iii) exposure times for the labels, and/or (iv) filter sets for the labels to match the optical signals from the labels, and measuring optical signals from the labels. These factors may be varied singly or in combination. Further, the metric being optimized may vary. For example, it may be overall intensity, signal-to-noise, least background, lowest variance in intensity or any other characteristic.

Figure 3:
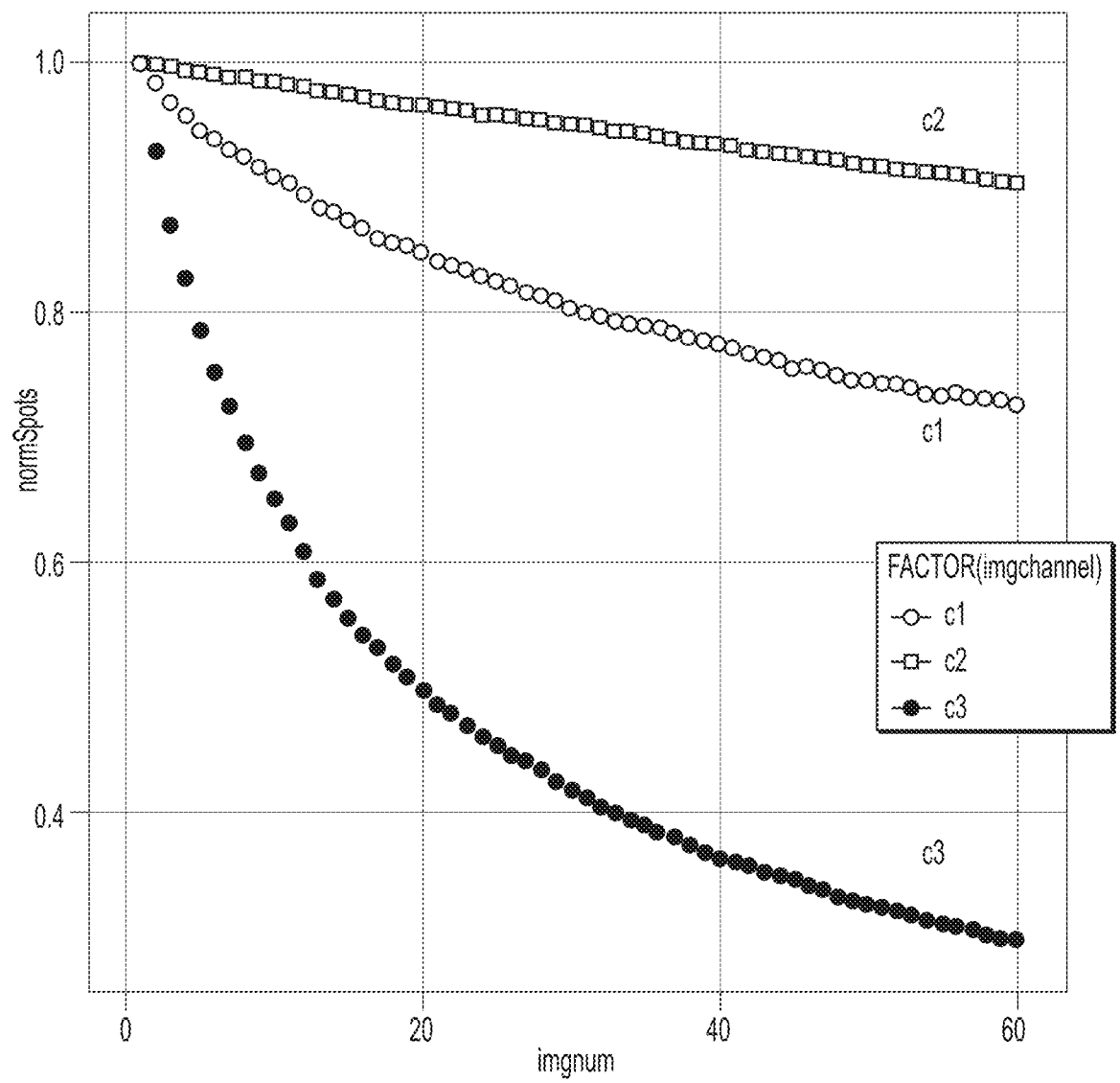
FIG. 3 depicts average bleaching profiles from various labels.
Figure 4:
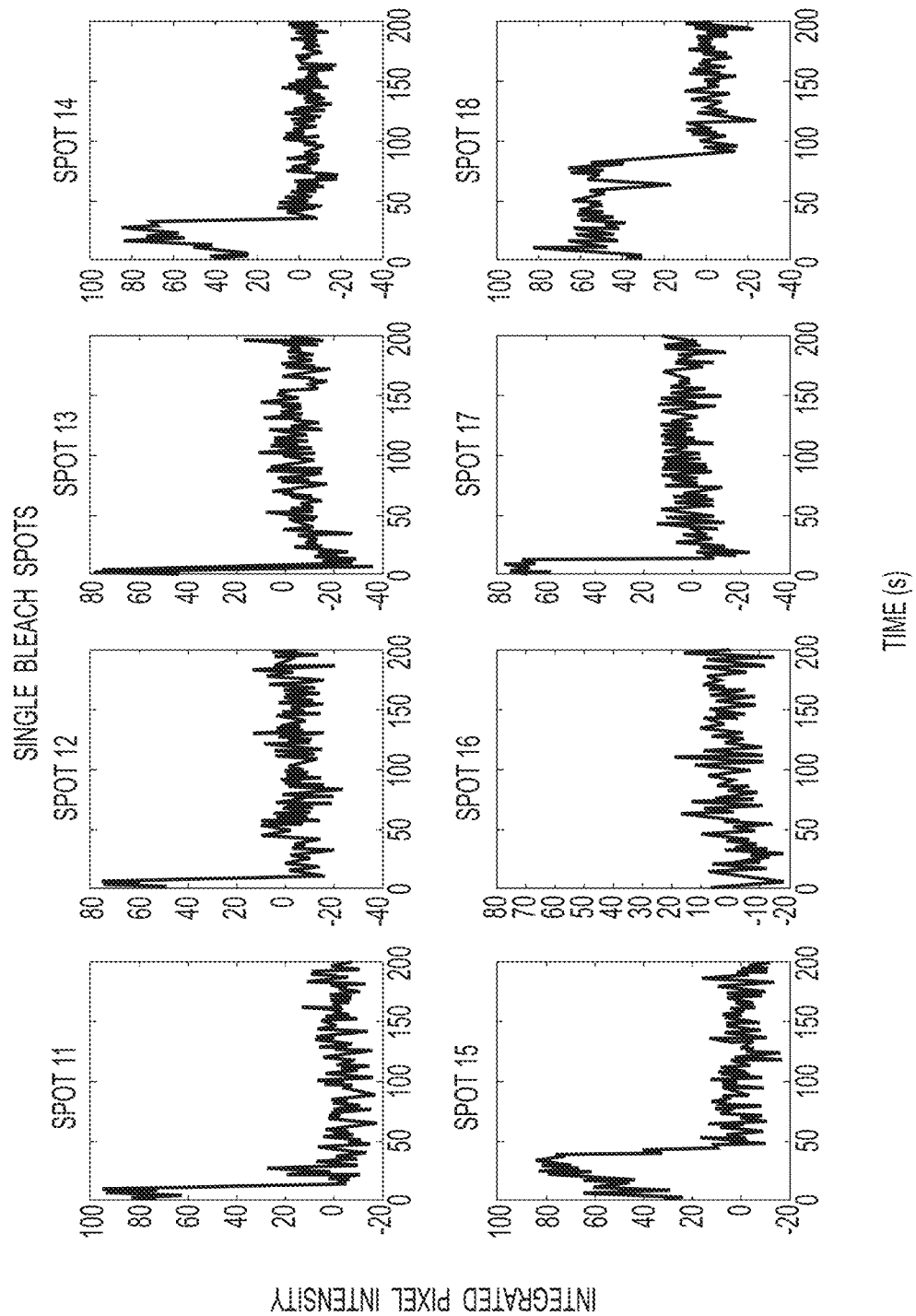
FIGS. 4-13 show the integrated label intensity graphs over time for various Alexa 488 labels.
Figure 5:
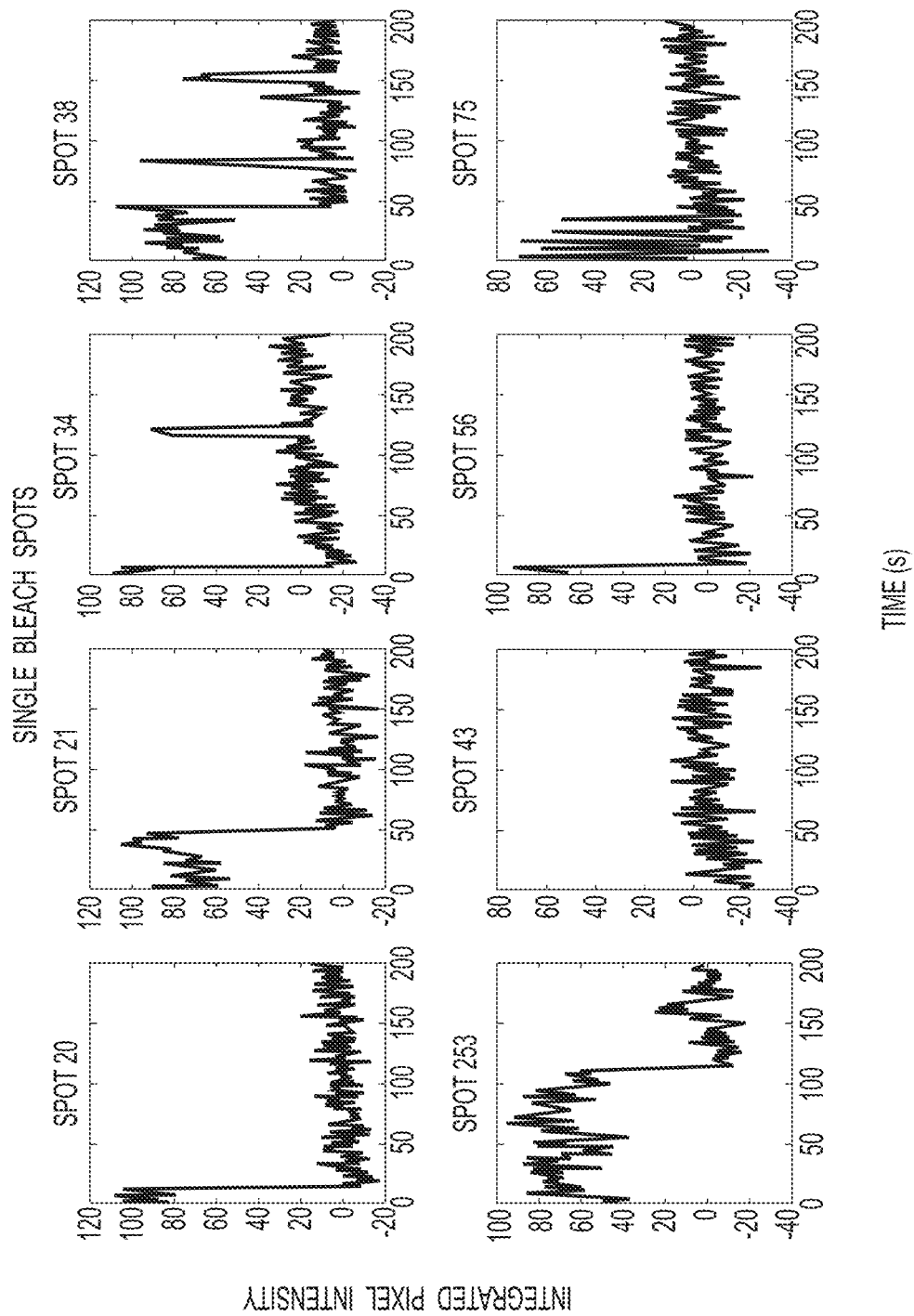

Bleaching profiles are label specific and may be used to add information for distinguishing label types. FIG. 3 shows average bleaching profiles from various labels. The plot shows the normalized counts per label type as a function of successive images that were collected over a 60 second interval. Item c1 is Cy3 fluor, item c2 is Atto647 fluor, and item c3 is Alexa488 fluor.

In another aspect, blinking behavior may be used as a method of identifying single labels. Many dye molecules are known to temporarily go into a dark state (e.g., Burnette et al., Proc. Natl. Acad. Sci. USA (2011) 108: 21081-21086). This produces a blinking effect, where a label will go through one or more steps of bright-dark-bright. The length and number of these dark periods may vary. The current invention uses this blinking behavior to discriminate one label from two or more labels that may appear similar in diffraction limited imaging. If there are multiple labels present, it is unlikely the signal will completely disappear during the blinking More likely is that the intensity will fall as one of the labels goes dark, but the others do not. The probability of all the labels blinking simultaneously (and so looking like a single fluor) may be calculated based on the specific blinking characteristics of a dye.

In some embodiments, the optical signals from the labels are measured for at least two time points, and an optical signal is from a single label if the intensity of the optical signal is reduced by a single step function. In some embodiments, the two time points may be separated by from 0.1 to 30 minutes, from 1 second to 20 minutes, from 10 seconds to 10 minutes; 0.01, 0.1, 1, 2, 3, 4, 5, 10, 20, 30, 40, 50, 60 seconds or more; and/or 1, 2, 3, 4, 5, 10, 20, 30, 40, 50, 60 seconds or less. In additional embodiments, an intensity of the optical signal from a single label has a single step decrease over time, and an intensity of the optical signal from two or more labels has multiple step decreases over time. In further embodiments, the optical signals from the labels are measured for at least two time points and are normalized to bleaching profiles of the labels. In another aspect, the method described herein and/or the counting step may further comprises measuring an optical signal from a control label for at least two time points, and comparing the optical signal from the control label with the optical signals from the labels to determine an increase or decrease of the optical signal from the labels.

In another aspect, the counting step further comprises confirming the counting by using a control molecule. A control molecule may be used to determine the change in frequency of a molecule type. Often, the experimental goal is to determine the abundance of two or more types of molecules either in the absolute or in relation to one another. Consider the example of two molecules labeled with two different dyes. If the null hypothesis is that they are at equal frequency, they may be enumerated on a single-molecule array and the ratio of the counts compared to the null hypothesis. The "single-molecule array" herein is defined as an array configured to detect a single molecule, including, for example, the arrays described in U.S. Patent Application Publication No. 2013/0172216. If the ratio varies from 1:1, this implies they two molecules are at different frequencies. However, it may not be clear a priori whether one has increased abundance or the other has decreased abundance. If a third dye is used as a control molecule that should also be at equal frequency, this should have a 1:1 ratio with both the other dyes. Consider the example of two molecules labeled with dyes A and B, the goal being to see if the molecule labeled with dye B is at increased or decreased frequency compared to the molecule labeled with dye A. A third molecule labeled with dye C is included in the experiment in a way that it should be at the same abundance as the other two molecules. If the ratio of molecules labeled A and B respectively is 1:2, then either the first molecule has decreased frequency or the second has increased frequency. If the ratio of the molecules labeled A and C is 1:1 and the ratio of molecules labeled B and C is 1:2, then it is likely that the molecule labeled with dye B has increased with frequency with respect to the molecule labeled with dye A. An example of this would be in determining DNA copy number changes in a diploid genome. It is important to know if one sequence is amplified or the other deleted and using a control molecule allows for this determination. Note the control may be another region of the genome or an artificial control sequence.

In some embodiments, the results of the method described herein (e.g., counted numbers of labels) may be confirmed by using different labels but the same tags used in the initial method. Such confirming may be performed simultaneously with the initial method or after performing the initial method. In additional embodiments, the confirming described herein comprises contacting first and second control probe sets to the genetic sample, wherein the first control probe set comprises a first control labeling probe and the first tagging probe, which is the same tag of the first probe set described herein, and the second control probe set comprises a second control labeling probe and the second tagging probe, which is the same tag of the second probe set described herein. The confirmation may further comprise hybridizing at least a part of the first and second control probe sets to the first and second nucleic acid regions of interest in nucleotide molecules of the genetic sample, respectively. The confirmation may further comprise ligating the first control probe set at least by ligating the first control labeling probe and the first tagging probe. The confirmation may further comprise ligating the second control probe set at least by ligating the second control labeling probe and the second tagging probe. The confirmation may further comprise amplifying the ligated probe sets. The confirmation may further comprise immobilizing each of the tagging probes to a pre-determined location on a substrate, wherein the first and second control labeling probes and/or the amplified labeling probes thereof ligated to the immobilized tagging probes comprise first and second control labels, respectively, the first and second control labels are different, and the immobilized labels are optically resolvable. The confirmation may further comprise measuring the optical signals from the control labels immobilized to the substrate. The confirmation may further comprise comparing the optical signals from the immobilized first and second control labels to the optical signals from the immobilized first and second labels to determine whether an error based on the labels exists. The "error based on a label" used herein means any error caused by the label that may not have occurred if a different label is used in the method. In some embodiments, the first label and the second control label are the same, and the second label and the first control label are the same.

Bleaching may be used as a method of identifying single labels. A key element of the readout is that individual labels be "resolvable," i.e., distinct. This is trivial at low densities on a surface when the likelihood of labels in close proximity is very low. For higher densities, assuming the labels are at random locations (i.e., Poissonian), the chances of close neighbors increases to the point where significant numbers of labels have neighbors whose fluorescent emission partially (or fully) overlaps with their own emission. At this point, the labels are no longer "resolvable," and in a transition regime exists between single-label detection (i.e., digital detection) and classic multi-label array-type detection (e.g., analogue detection) where the average signal from many molecules is measured. Put differently, a digital counting regime of individual molecules is switched to an analog regime of average-fluorescent-intensity from many molecules.

One solution to increase the loading range while maintaining individual resolvability is to take advantage of fluorophore bleaching. Extended exposure to light may cause labels to bleach, that is, lose their property of fluorescence. That is, over time, a label may be extinguished. This usually occurs as a step function, with the label appearing to "switch off." The current invention may use this bleaching behavior to discriminate one label from two or more labels that may appear similar in diffraction limited imaging. For multiple labels, extinction would be expected to occur via a series of step-wise decreases in the signal intensity. For example, FIGS. 4-13 show the integrated label intensity vs. time (showing bleaching events as changes in intensity) graphs that were obtained for various Alexa 488 labels. Single versus multiple label species may be easily differentiated (e.g. depending on whether the intensity of the optical signal is reduced by single versus multiple step(s) as shown in the graphs).

In another aspect, the method herein may comprise calibrating and/or confirming the counted numbers by label swapping or dye swapping. In some embodiments where probe product 1 and 2 are labeled with labels 1 and 2, respectively, various modes of error may mimic the differential frequency of the probe products. For example, if a ratio of 1:2 is observed between label 1 and label 2, this may be due to genuine differences in frequency (probe product 2 is twice as common as probe product 1), differences in hybridization efficiency (the probe products are at equal abundance, but probe product 2 hybridizes more efficiently than probe product 1) or differences in the properties of the labels (for example, if the labels are fluorescent dyes, label 1 may bleach faster, blink more frequently, give lower signal or lower signal-to-noise than label 2). If the same experiment is repeated with the labels switched, the ratio should be reversed, if it is a genuine observation of different frequencies of the molecules, with label 1 now twice as common as label 2. However, if it is due to differential hybridization efficiency the ratio will be ≤2:1. If the 1:2 ratio was due to the properties of the labels, the ratio will switch to 2:1 of label 1 to label 2 if they are actually at equal frequency. This approach can be extended to any number of labeled probe sets.

In some embodiments, the first nucleic acid region of interest is located in a first chromosome, and the second nucleic acid region of interest is located in a second chromosome, different from the first chromosome. The counting step may further comprise confirming the counting, wherein the confirming step comprises contacting first and second control probe sets to the genetic sample, wherein the first control probe set comprises a first control labeling probe and a first control tagging probe, and the second control probe set comprises a second control labeling probe and the second control tagging probe. The confirming step may further comprise hybridizing at least a part of the first and second control probe sets to first and second control regions located in the first and second chromosomes, respectively, wherein the first and second control regions are different from the first and second nucleic acid regions of interest. The confirming step may further comprise ligating the first and second control probe sets at least by ligating (i) the first control labeling and tagging probes, and (ii) the second control labeling and tagging probes. The confirming step may further comprise amplifying the ligated probe sets. The confirming step may further comprise immobilizing (i) the first probe set and the second control probe set to a first pre-determined location, and (ii) the second probe set and the first control probe set to a second pre-determined location. In some embodiments, the first and second control labeling probes and/or the amplified labeling probes thereof ligated to the immobilized tagging probes comprise a first and second control labels, respectively, the first label and the second control label are different, the second label and the first control labels are different, the immobilized labels are optically resolvable, the immobilized first and second control tagging probes and/or the amplified tagging probes thereof comprise first and second control tags, respectively, and the immobilizing step is performed by immobilizing the tags to the predetermined locations. The confirming step may further comprise measuring the optical signals from the control labels immobilized to the substrate. The confirming step may further comprise comparing the optical signals from the immobilized control labels to the optical signals from the immobilized first and second labels to determine whether an error based on the nucleic acid region of interest exists. In further embodiments, the first tag and the second control tag are the same, and the second tag and the first control tag are the same.

In another aspect, the counting step of the method described herein may further comprise calibrating and/or confirming the counted numbers by (i) repeating some or all the steps of the methods (e.g., steps including the contacting, binding, hybridizing, ligating, amplifying, and/or immobilizing) described herein with a different probe set(s) configured to bind and/or hybridize to the same nucleotide and/or peptide region(s) of interest or a different region(s) in the same chromosome of interest, and (ii) averaging the counted numbers of labels in the probe sets bound and/or hybridized to the same a nucleotide and/or peptide region of interest or to the same chromosome of interest. In some embodiments, the averaging step may be performed before the comparing step so that the averaged counted numbers of labels in a group of different probe sets that bind and/or hybridize to the same nucleotide and/or peptide region of interest are compared, instead of the counted numbers of the labels in the individual probe sets. In another aspect, the method described herein may further comprise calibrating and/or confirming the detection of the genetic variation by (i) repeating some or all the steps of the methods (e.g., steps including the contacting, binding, hybridizing, ligating, amplifying, immobilizing, and/or counting) described herein with different probe sets configured to bind and/or hybridize to control regions that does not have any known genetic variation, and (ii) averaging the counted numbers of labels in the probe sets bound and/or hybridized to the control regions. In some embodiments, the averaged numbers of the labels in the probe sets that bind and/or hybridize to control regions are compared to the numbers of the labels in the probe sets that bind and/or hybridized to the regions of interest described herein to confirm the genetic variation in the genetic sample. In another aspect, the steps of the calibrating and/or confirming may be repeated simultaneously with the initial steps, or after performing the initial steps.

Figure 14:
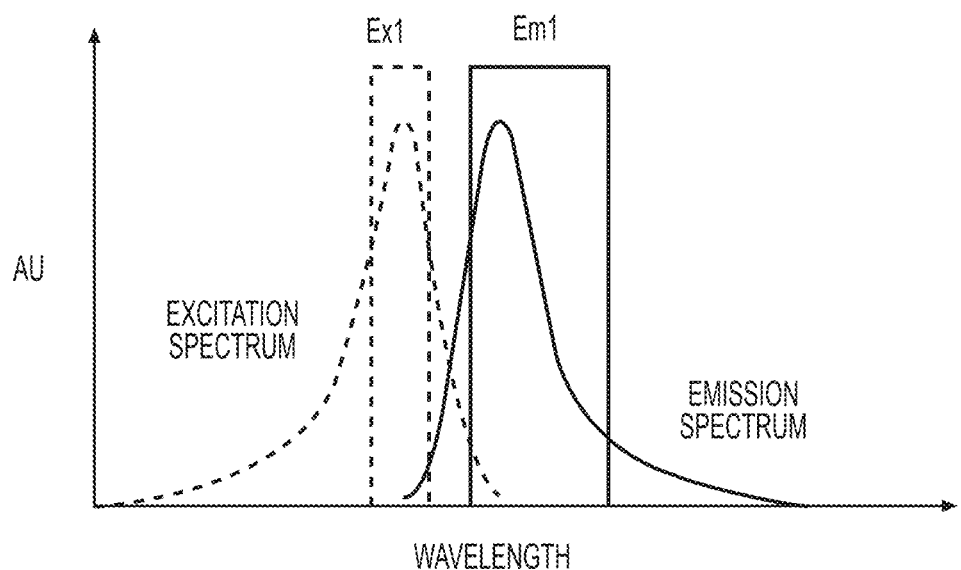
FIG. 14 depicts excitation spectrum and emission spectrum through a standard operation when excitation of a fluorophore is achieved by illuminating with a narrow spectral band aligned with the absorption maxima of that species.
Figure 15:
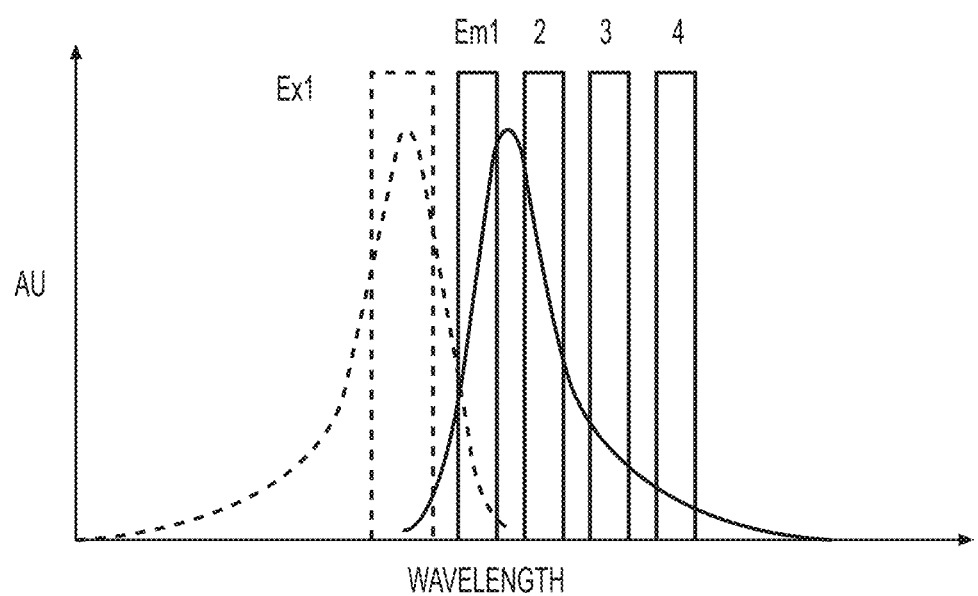
FIG. 15 depicts excitation spectrum and emission spectrum through interrogation with various excitation colors and collected emission bands different from (or in addition to) the case for the standard operation.
Figure 16:
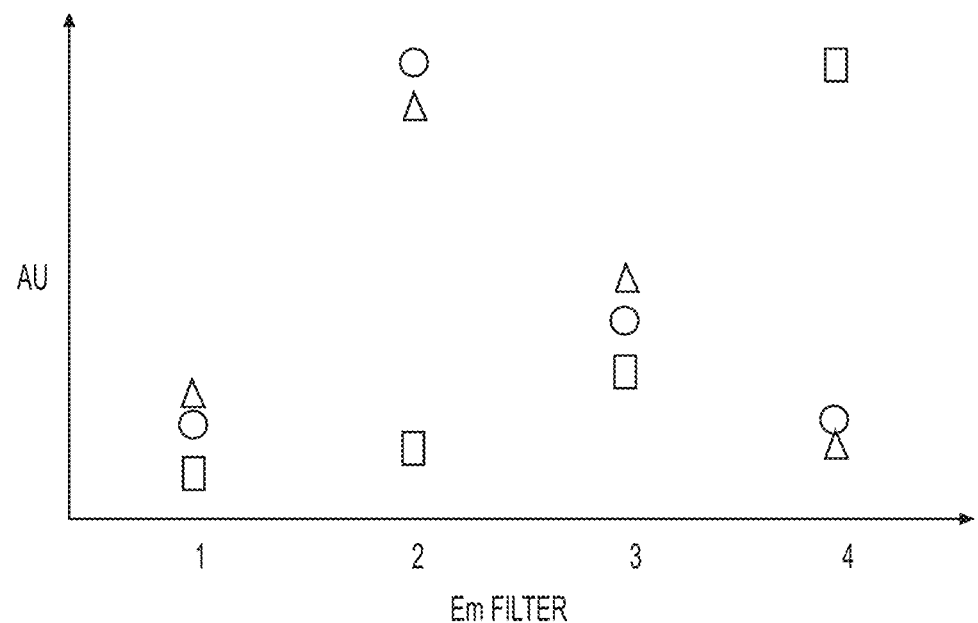
FIG. 16 shows results when the light from these various imaging configurations, e.g., various emission filters, is collected and compared to calibration values for the fluorophores of interest.
Figure 17:
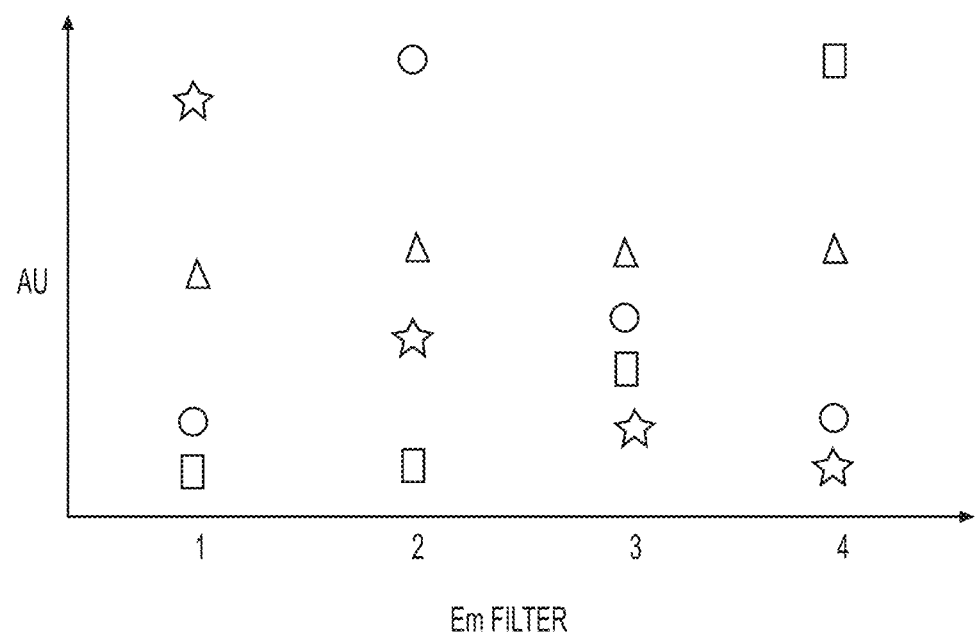
FIG. 17 shows results collected with various references, including those with a flat emission profile (Contaminant 1; triangles), or a blue-weighted profile (Contaminant 2; stars).

In another aspect, labels (e.g., fluorescent dyes) from one or more populations may be measured and/or identified based on their underlying spectral characteristics. Most fluorescent imaging systems include the option of collecting images in multiple spectral channels, controlled by the combination of light source and spectral excitation/emission/dichroic filters. This enables the same fluorescent species on a given sample to be interrogated with multiple different input light color bands as well as capturing desired output light color bands. Under normal operation, excitation of a fluorophore is achieved by illuminating with a narrow spectral band aligned with the absorption maxima of that species (e.g., with a broadband LED or arclamp and excitation filter to spectrally shape the output, or a spectrally homogenous laser), and the majority of the emission from the fluorophore is collected with a matched emission filter and a long-pass dichroic to differentiate excitation and emission (FIG. 14). In alternate operations, the unique identity of a fluorescent moiety may be confirmed through interrogation with various excitation colors and collected emission bands different from (or in addition to) the case for standard operation (FIG. 15). The light from these various imaging configurations, e.g., various emission filters, is collected and compared to calibration values for the fluorophores of interest (FIG. 16). In the example case, the experimental measurement (dots) matches the expected calibration/reference data for that fluorophore (triangles) but does not agree well with an alternate hypothesis (squares). Given test and calibration data for one or more channels, a goodness-of-fit or chi-squared may be calculated for each hypothesis calibration spectrum, and the best fit selected, in an automated and robust fashion. Various references may be of interest, including fluorophores used in the system, as well as common fluorescent contaminants, e.g., those with a flat emission profile (Contaminant 1; triangle), or a blue-weighted profile (Contaminant 2; stars) (FIG. 17).

Figure 18:
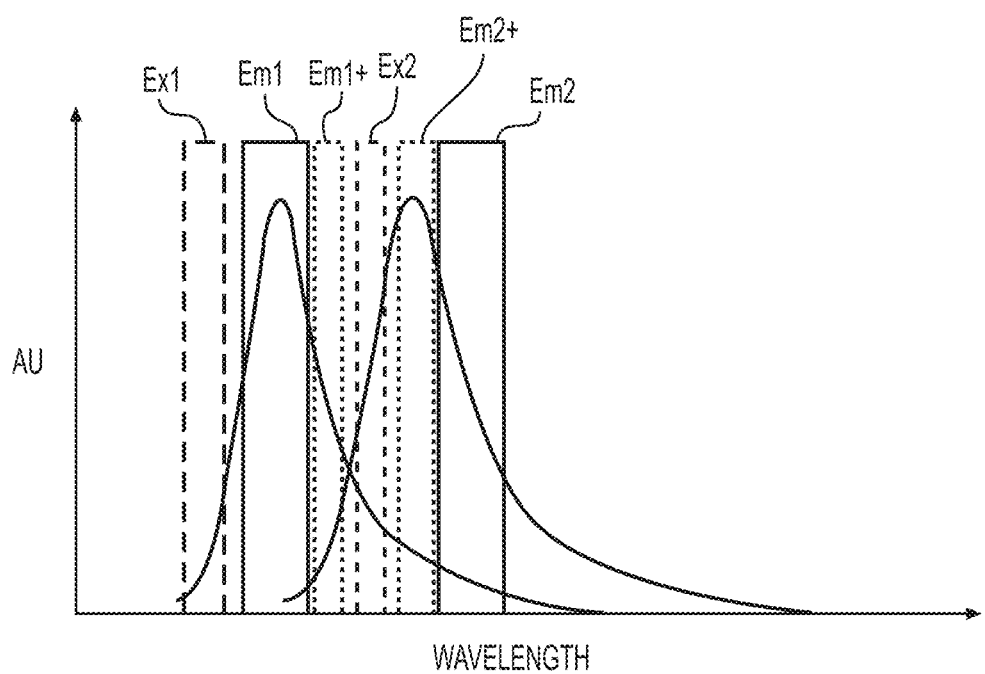
FIG. 18 depicts significantly-different excitation bands of two fluorophores.

The design constraints for filter selection may be different from standard designs for which the goal is simply to maximize collected light in a single channel while avoiding significant contributions from other channels. In our invention the goal is spectral selectivity rather than solely light collection. For example, consider two fluorophores with significantly-different excitation bands, shown in FIG. 18 (note, only the excitation regions are shown and no excitation spectra). A standard design would maximize the capture of Fluor 1 emission (with Em1 filter, solid line) and minimize catching the leading edge from Fluor 2, and Fluor 2 would be optimally captured by Em2 (which is slightly red-shifted to avoid significant collection of Fluor 1 light). In our design, verifying the presence of Fluor 2 with the Em1 filter is desired leading to widening of the band to be captured ("Em1+", fine dashed line). This creates additional information to verify the identity of Fluor 2. Similarly, Em2 may be widened or shifted towards Fluor 1 to capture more of that fluor's light (Em2+, fine dashed line). This increase in spectral information must also be balanced with the total available light from a given fluorophore to maintain detectability. Put differently, the contribution from a given fluorophore in a given channel is only significant if the corresponding signal is above the background noise, and therefore informative, unless a negative control is intended. In this way, the spectral signature of a fluorescent entity may be used for robust identification and capturing more light may be a second priority if species-unique features may be more effectively quantitated.

Given probe products may be labeled with more than one type of fluorophore such that the spectral signature is more complex. For example, probe products may always carry a universal fluor, e.g., Alexa647, and a locus-specific fluorophore, e.g., Alexa 555 for locus 1 and Alexa 594 for locus 2. Since contaminants will rarely carry yield the signature of two fluors, this may further increase the confidence of contamination rejection. Implementation would involve imaging in three or more channels in this example such that the presence or absence of each fluor may be ascertained, by the aforementioned goodness-of-fit method comparing test to reference, yielding calls of locus 1, locus 2 or not a locus product. Adding extra fluors aids fluor identification since more light is available for collection, but at the expense of yield of properly formed assay products and total imaging time (extra channels may be required). Other spectral modifiers may also be used to increase spectral information and uniqueness, including FRET pairs that shift the color when in close proximity or other moieties.

In another aspect, the array described herein may be used in conjunction with other methods of testing to improve its accuracy. For example, phenotypic data about the patient (e.g. age, weight, BMI, disease states) may be used to predict the probability of an abnormal pregnancy or of the patient's cfDNA having low amounts of fetal material (i.e. low fetal fraction). Alternatively, the array of this invention may be used directly with an assay (for example, an oligo-ligation assay, with the product being captured on the array) or with an independent assay that can be used to replicate, confirm or improve the results from the array. For example, DNA sequencing, mass spectroscopy, genotyping, standard microarrays, karyotyping, PCR-based methods or other methods could be used as an orthogonal method and the data from these methods can be integrated with data from the array of this invention to provide a more accurate or less ambiguous result. The array as described herein may be used for screening, diagnosing, replicating, confirming, validating, excluding or monitoring a disease of condition, for example, for Down's Syndrome in a fetus.

In some embodiments, the array described herein may be used with other genetic and genomic information. For example, certain genes are known or predicted to have higher methylation than their maternal equivalents (e.g. RASSF1A, APC, CASP8, RARB, SCGB3A1, DAB2IP, PTPN6, THY1, TMEFF2, and PYCARD). Using differential methylation in combination with an array described herein provides more information on the fetus, including whether it is carrying any trisomy.

In another aspect, as described herein, the method of the present disclosure may be used to detect a genetic variation in peptide or proteins. In such as case, the methods may comprise contacting first and second probe sets to the genetic sample, wherein the first probe set comprises a first labeling probe and a first tagging probe, and the second probe set comprises a second labeling probe and a second tagging probe. The methods may further comprise binding the probe sets to peptide regions of interest by a physical or chemical bond, in place of the hybridizing step described herein in the case of detecting the genetic variation in nucleic acid molecules. Specifically, the methods may further comprise binding at least parts of the first and second probe sets to first and second peptide regions of interest in a peptide of protein of the genetic sample, respectively. For example, the binding may be performed by having a binder in at least one probe in the probe set that specifically binds to the peptide region of interest.

In some embodiments, the methods to detect a genetic variation in peptide or proteins may further comprise conjugating the first probe set by a chemical bond at least by conjugating the first labeling probe and the first tagging probe, and conjugating the second probe set at least by conjugating the second labeling probe and the second tagging probe, in place of the ligating step described herein in the case of detecting the genetic variation in nucleic acid molecules. The method may further comprise immobilizing the tagging probes to a pre-determined location on a substrate as described herein. In additional embodiments, the first and second labeling probes conjugated to the immobilized tagging probes comprise first and second labels, respectively; the first and second labels are different; the immobilized labels are optically resolvable; the immobilized first and second tagging probes and/or the amplified tagging probes thereof comprise first and second tags, respectively; and the immobilizing step is performed by immobilizing the tags to the predetermined location. The methods may further comprise, as described herein, counting (i) a first number of the first label immobilized to the substrate, and (ii) a second number of the second label immobilized to the substrate; and comparing the first and second numbers to determine the genetic variation in the genetic sample.

The invention also relates to methods of manufacturing and using spatially addressable molecular arrays having members described herein. The invention further relates to analytical approaches based on single molecule detection techniques to detect a genetic variation as described above. Such approaches overcome the above-mentioned practical limitations associated with bulk analysis. This can be achieved by the precision, richness of information, speed and throughput that can be obtained by taking analysis to the level of single molecules. The present invention particularly addresses problems of large-scale and genome-wide analysis.

To date single molecule analysis has only been conducted in simple examples but as mentioned above the challenge of modern genetics and other areas is to apply tests on a large scale. An important aspect of any single molecule detection technique for rapid analysis of large numbers of molecules is a system for sorting and tracking (or following) individual reactions on single molecules in parallel. Capturing and resolving single molecules on spatially addressable arrays of single molecules of known or encoded sequence can achieve this.

In present bulk methods, analysis is done by looking at the ensemble signal from all molecules in the assay. The spatial density of probe molecules or the assay signals that are obtained are at too high a density to resolve single molecules by the methods in general use (e.g. microarray scanners, plate scanners, plate readers, microscopes).

The approach according to some embodiments of the present invention is set apart from traditional bulk array technologies inter alia by the type of information it aims to acquire. Furthermore it describes arrays in which the density of functional molecules is substantially lower than those of bulk arrays. The low density signals from these arrays may not be sufficiently readable by instrumentation typically used for analysing the results of bulk arrays particularly due to high background. The manufacture of single molecule arrays of the invention requires special measures as described herein.

Accordingly, some embodiments of the present invention provides in a first embodiment a method for producing a molecular array which method comprises immobilizing on a substrate a plurality of probes at a density which allows individual immobilized probes to be individually resolved, wherein the identity of each individual probe in the array is spatially addressable and the identity of each probe is known or determined prior to immobilization.

Additional embodiments of the present invention also provides a method for producing a molecular array which method comprises immobilizing to a substrate a plurality of defined probes at a density which allows an individual immobilized probe to be individually resolved by a method of choice, wherein each individual probe in the array is spatially addressable.

In a second embodiment, the present invention provides a method for producing a molecular array which method comprises: (i) providing a molecular array comprising a plurality of probes immobilized to a substrate at a density such that individual immobilized probes are not capable of being individually resolved; and (ii) reducing the density of functional immobilized probes in the array such that the remaining individual functional immobilized probes are capable of being individually resolved; wherein the identity of each individual probe in the resulting array is spatially addressable and the identity of each probe is known or determined prior to the density reduction step.

Further embodiments of the present invention also provides a method for producing a molecular array which method comprises: (i) providing a molecular array comprising a plurality of defined spatially addressable probes immobilized to a substrate at a density such that individual immobilized probes are not capable of being individually resolved by optical means or another method of choice; and (ii) reducing the density of functional immobilized probes in the array such that each remaining individual functional immobilized probe is capable of being individually resolved.

In another aspect, in some embodiments of the present invention, the method of producing a molecular array comprises: (i) preselecting a plurality of oligonucleotides to be immobilized; (ii) immobilizing to a solid phase at least a portion of the plurality of oligonucleotides to form two or more separate and discrete members, at least two of said two or more members being spatially addressable, said at least two members comprising a plurality of immobilized oligonucleotides; and (iii) labeling, with one or more labels, at least a portion of the plurality of immobilized oligonucleotides at each of the at least two members, wherein at least a portion of the plurality of labeled immobilised oligonucleotides at said at least two members are individually resolvable. Also, in other embodiments of the present invention, the method of producing a molecular array comprises: (i) preselecting a plurality of oligonucleotides to be labeled; (ii) labeling, with one or more labels, at least a portion of the plurality of oligonucleotides; and (iii) immobilizing to a solid phase at least a portion of the plurality of labeled oligonucleotides to form two or more separate and discrete members, at least two of said two or more members being spatially addressable, said at least two members comprising a plurality of immobilized oligonucleotides, wherein at least a portion of the plurality of labeled immobilised oligonucleotides at said at least two members are individually resolvable. Moreover, in additional embodiments of the present invention, the method of producing a microarray comprises: (i) preselecting a plurality of oligonucleotides to be immobilized; (ii) immobilizing at least a portion of the plurality of oligonucleotides on a solid support at a density to allow each of said at least a portion of the plurality of oligonucleotides on the solid support to be individually resolved upon labeling, thereby forming two or more separate and discrete members, at least two members of said two or more members being spatially addressable, each of said at least two members comprising a plurality of immobilized oligonucleotides from said at least a portion of the plurality of oligonucleotides, wherein sequence identities of said at least a portion of the plurality of immobilized oligonucleotides in each of said at least two members are specified by a location of each of said at least two members in which the oligonucleotides are contained; (iii) labeling at least a portion of the plurality of immobilized oligonucleotides at each of said at least two members with one or more labels, thereby producing labeled immobilized oligonucleotides; and (iv) analysing whether at least a portion of the labeled immobilized oligonucleotides of said at least two members are individually optically resolvable from another portion of the labeled immobilized oligonucleotides, whereby said at least a portion of the labeled immobilized oligonucleotides on each of said at least two members are individually optically resolvable from the another portion of the labeled immobilized oligonucleotides. In some embodiments, the immobilizing comprises immobilizing a first plurality of oligonucleotides of an identical sequence to a first separate and discrete member. In additional embodiments, the immobilizing further comprises immobilizing a second plurality of oligonucleotides of an identical sequence, wherein the second oligonucleotides are have a different sequence(s) from the first oligonucleotides. In further embodiments, the second plurality of oligonucleotides are immobilized to a second separate and discrete member. In yet further embodiments, the at least two of said two or more members are spatially addressable without sequencing of at least a part of one or more immobilized oligonucleotides. In additional embodiments, the oligonucleotide in the embodiments above in the method of producing a molecular array may comprise or consisting of a tag or affinity tag described herein.

Preferably, the immobilized probes are present within discrete spatially addressable members. In one such embodiment, a plurality of molecular species are present within one or more of the discrete spatially addressable members and each molecular species in an member can be distinguished from other molecular species in the member by means of a label. In another embodiment the plurality of probes are not distinguishable by a label but comprise a degenerate set of sequences, for example representing members of a gene family, according to which they can be distinguished.

In some embodiments, the array may comprise a single monolayer. In the absence of discrete or manufacture elements (made, for example, by spotting or by division using physical structures), larger monolayers can be made that cover some or all the array. In one example, there would be a single monolayer on the array. If more than one test were being performed on a sample, more than one array would be used. For example, one array per test may be produced. In other cases, multiple samples are interrogated on the same monolayer, for example, by using different fluorescent dyes to distinguish one sample from the other. In another embodiment, samples are places at different locations on the same monolayers. Instead of one sample covering the entire array, different samples are deposited at different locations. This division by deposition may produce regions that are analogous to standard array elements, but may be formed during the process of using the array, not during manufacture.

In some embodiments, the array may interrogate DNA barcodes and/or tags described herein. In additional embodiments, the array may interrogate, for example, (i) one or more chromosomes, including Chromosomes 21, 18, 13, X, Y and/or other chromosomes as described herein, (ii) microdeletions, Down's Syndrome, Patau's Syndrome, and Edwards' Syndrome as described herein, (iii) probes, not genomic DNA directly, as described herein, (iv) multiple different types of genetic variations on the same array (e.g. copy number change and mutations) as described herein, and (v) whole-genome screening for copy number change as described herein. For example, a set of probes that are spaced across the entire genome may be used. In further embodiments, the distance between adjacent probes may be approximately the same for all pairs of probes.

Low Density Probes: the present invention is in one aspect concerned with the production of molecular arrays wherein the individual probes in a member on the substrate are at a sufficiently low density such that the individual probes can be individually resolved—i.e. when visualised using the method of choice, each probe can be visualised separately from neighbouring probes, regardless of the identity of those neighbouring probes. The required density varies depending on the resolution of the visualisation method. As a guide, probes are preferably separated by a distance of approximately at least 250, 500, 600, 700 or 800 nm in both dimensions when the arrays are intended for use in relatively low resolution optical detection systems (the diffraction limit for visible light is about 300 to 500 nm). If nearest neighbour single probes are labelled with different fluors, or their functionalization (see below) can be temporally resolved, then it is possible to obtain higher resolution by deconvolution algorithms and/or image processing. Alternatively, where higher resolution detection systems are used, such as scanning near-field optical microscopy (SNOM), then separation distances down to approx. 50 nm can be used. As detection techniques improve, it may be possible to reduce further the minimum distance. The use of non-optical methods, such as AFM, allows the reduction of the feature-to-feature distance effectively to zero.

Since, for example, during many immobilization procedures or density reduction procedures, the probability of all probes being separated by at least the minimum distance required for resolution is low, it is acceptable for a proportion of probes to be closer than that minimum distance. However, it is preferred that at least 50%, more preferably at least 75, 90 or 95% of the probes are at the minimum separation distance required for individual resolution.

Furthermore, the actual density of probes in a members of the substrate can be higher than the maximum density allowed for individual resolution since only a proportion of those probes will be detectable using the resolution method of choice. Thus where resolution, for example, involves the use of labels, then provided that individually labelled probes can be resolved, the presence of higher densities of unlabeled probes is immaterial.

Hence the individual probes in the array are at densities normal to bulk analysis but the array is functionalised so that only a subset of probes, substantially all of which can be individually resolved are analysed. This functionalization can be done before an assay is performed on the array. In other instances, the functionalisation is due to the assay. For example, the assay can be configured so that the amount of sample that is added is so low that interaction only occurs with a fraction of the probes of the array. Since the label that is detected is specifically associated with the occurrence of these interactions, a low density of probes is functionalised from a higher density array. Hence a normal density array is effectively an intermediate state before the active product is achieved in which single probes can be resolved and analysed.

Probes that can be immobilized in the array include nucleic acids such as DNA and analogues and derivatives thereof, such as PNA. Nucleic acids can be obtained from any source, for example genomic DNA or cDNA or synthesised using known techniques such as step-wise synthesis. Nucleic acids can be single or double stranded. DNA nanostructures or other supramolecular structures can also be immobilized. Other probes include: compounds joined by amide linkages such as peptides, oligopeptides, polypeptides, proteins or complexes containing the same; defined chemical entities, such as organic molecules; conjugated polymers and carbohydrates or combinatorial libraries thereof.

In several embodiments, the chemical identity of the probes must be known or encoded prior to manufacture of the array by the methods of the present invention. For example, the sequence of nucleic acids (or at least all or part of the sequence of the region that is used to bind sample molecules) and the composition and structure of other compounds should be known or encoded in such a way that the sequence of molecules of interest can be determined with reference to a look-up table. The term "spatially addressable", as used herein, therefore signifies that the location of a probe specifies its identity (and in spatial combinatorial synthesis, the identity is a consequence of location).

Probes can be labelled to enable interrogation using various methods. Suitable labels include: optically active dyes, such as fluorescent dyes; nanoparticles such as fluorospheres and quantum dots, rods or nanobars; and surface plasmon resonant particles (PRPs) or resonance light scattering particles (RLSs)—particles of silver or gold that scatter light (the size and shape of PRP/RLS particles determines the wavelength of scattered light). See Schultz et al., 2000, PNAS 97: 996-1001; Yguerabide, J. and Yguerabide E., 1998, Anal Biochem 262: 137-156.

Each member is spatially addressable so the identity of the probes present in each member is known or can be determined on the basis of a prior coding. Thus if a member is interrogated to determine whether a given molecular event has taken place, the identity of the immobilized probe is already known by virtue of its position in the array. In a preferred embodiment, only one probe species is present within each member, in single or multiple copies. Where present in multiple copies, it is preferred that individual probes are individually resolvable. In one embodiment, members in the array can comprise multiple species that are individually resolvable. Typically, multiple species are differentially labelled such that they can be individually distinguished. By way of example, an member can comprise a number of different probes for detecting single nucleotide polymorphisms alleles, each probe having a different label such as a different fluorescent dye.

Molecular arrays produced by the methods of the invention preferably comprise at least 10 distinct molecular species, more preferably at least 50 or 100 different molecular species. For gene expression analysis applications, the number of array members may be ultimately determined by the number of genes. For SNP analysis the number of members may be determined by the number of SNPs required to adequately sample the diversity of the genome. For sequencing applications the number of members may be determined by the size the genome is fragmented into, for example for fragments of 50,000 kb, 20,000 members may be needed to represent all of the genome, and fewer members would be required to represent the coding regions.

Two possible approaches for manufacturing low density arrays for use in the present invention are outlined below.

i. De Novo Fabrication

In one embodiment of the present invention, low density molecular arrays are produced by immobilizing pluralities of probes of known composition to a solid phase. Typically, the probes are immobilized onto or in discrete regions of a solid substrate. The substrate can be porous to allow immobilization within the substrate (e.g. Benoit et al., 2001, Anal. Chemistry 73: 2412-242) or substantially non-porous, in which case the probes are typically immobilized on the surface of the substrate.

The solid substrate described herein can be made of any material to which the probes can be bound, either directly or indirectly. Examples of suitable solid substrates include flat glass, quartz, silicon wafers, mica, ceramics and organic polymers such as plastics, including polystyrene and polymethacrylate. The surface can be configured to act as an electrode or a thermally conductive substrate (which enhances the hybridization or discrimination process). For example, micro and sub-micro electrodes can be formed on the surface of a suitable substrate using lithographic techniques. Smaller, nanoelectrodes can be made by electron beam writing/lithography. Electrodes can also be made using conducting polymers which can be pattern asubstrate by ink-jet printing devices, by soft lithography or be applied homogenously by wet chemistry. $TnO_2$ coated glass substrates are available. Electrodes can be provided at a density such that each immobilized probe has its own electrode or at a higher density such that groups of probes or members are connected to an individual electrode. Alternatively, one electrode may be provided as a layer below the surface of the array which forms a single electrode. In another embodiment, the substrate is a semi-conductor, diode or photodiode.

The solid substrate may optionally be interfaced with a permeation layer or a buffer layer. It is also possible to use semi-permeable membranes such as nitrocellulose or nylon membranes, which are widely available. The semi-permeable membranes can be mounted on a more robust solid surface such as glass. The surface layer may comprise a sol-gel. The surfaces may optionally be coated with a layer of metal, such as gold, platinum or other transition metal. A particular example of a suitable solid substrate is the commercially available SPR BIACore™ chip (Pharmacia Biosensors). Heaton et al., 2001 (PNAS 98:3701-3704) have applied an electrostatic field to an SPR surface and used the electric field to control hybridization.

Preferably, the solid substrate is generally a material having a rigid or semi-rigid surface. In preferred embodiments, at least one surface of the substrate is substantially flat, although in some embodiments it may be desirable to physically separate discrete members with, for example, raised regions or etched trenches. For example, the solid substrate may comprise nanovials—small cavities in a flat surface e.g. 10 μm in diameter and 10 μm deep. This is particularly useful for cleaving probes from a surface and performing assays or other processes such as amplification in them. The solution phase reaction is more efficient than the solid phase reaction, whilst the results remains spatially addressable, which is advantageous.

It is also preferred that the solid substrate is suitable for the low density application of probes such as nucleic acids in discrete areas. It is also advantageous to provide channels to allow for capillary action since in certain embodiments this may be used to achieve the desired straightening of individual nucleic acid molecules. Channels can be in a 2-D arrangement (e.g. Quake S, and Scherer, 200, Science 290: 1536-1540) or in a 3-D flow through arrangement (Benoit et al., 2001, Anal. Chemistry 73: 2412-2420) Channels provide a higher surface area hence a larger number of probes can be immobilized. In the case of a 3-D flow channel array interrogation can be by confocal microscopy which images multiple slices of the channels in the direction of the z axis.

Furthermore the surface or sub-surface may comprise a functional layer such as a magnetic or a light emitting layer or light transducing layer.

In some instances array members are raised atop electrodes/electrode arrays.

In some instances, array members are diodes or photodiodes. In a further embodiment, the diodes or photodiodes are contained in wells, physical structures or nanowells.

Slides covered with transparent conducting layers such as indium tin oxide (ITO) can be used as substrate for microscopy, including Total Internal Reflection Microscopy (available from BioElectroSpec, PA, USA).

The solid substrate is conveniently divided up into sections. This can be achieved by techniques such as photo-etching, or by the application of hydrophobic inks, for example Teflon-based inks (Cel-line, USA).

Discrete positions, in which each different probes or groups of molecular species are located may have any convenient shape, e.g., circular, rectangular, elliptical, wedge-shaped, etc.

Attachment of the plurality of probes to the substrate may be by covalent or non-covalent (such as electrostatic) means. The plurality of probes can be attached to the substrate via a layer of intermediate molecules to which the plurality of probes bind. For example, the plurality of probes can be labelled with biotin and the substrate coated with avidin and/or streptavidin. A convenient feature of using biotinylated molecules is that the efficiency of coupling to the solid substrate can be determined easily. Since the plurality of probes may bind only poorly to some solid substrates, it may be necessary to provide a chemical interface between the solid substrate (such as in the case of glass) and the plurality of probes. Examples of suitable chemical interfaces include various silane linkers and polyethylene glycol spacer. Another example is the use of polylysine coated glass, the polylysine then being chemically modified if necessary using standard procedures to introduce an affinity ligand. Nucleic acids can be immobilized directly to a polylysine surface (electrostatically). The surface density of the surface charge is important to immobilize probes in a manner that allows them to be well presented for assays and detection.

Other methods for attaching probes to the surfaces of solid substrate by the use of coupling agents are known in the art, see for example WO98/49557. The probes can also be attached to the surface by a cleavable linker.

In one embodiment, probes are applied to the solid substrate by spotting (such as by the use of robotic microspotting techniques—Schena et al., 1995, Science 270: 467-470) or ink jet printing using for example robotic devices equipped with either ink jets (Canon patent) or piezo electric devices as in the known art.

For example pre-synthesized oligonucleotides dissolved 100 mM NaoH or 2-4×SSC or 50% DMSO, can be applied to glass slides coated with 3-Glycodioxypropyltrimethoxysilane or the ethoxy derivative. and then at room temperature for 12-24 hours and then placed at 4° C. Advantageously the oligonucleotides can be amino-terminated, but unmodified oligos can also be spotted (These can then be placed at 110-20 degrees for 15 minutes-20 minutes prior to room temperature incubation).

Alternatively amino-terminated oligonucleotides can be spotted onto 3-Aminopropyltrimethoxysilane in 50% DMSO and then UV cross-linked at 300 millijoules.

cDNAs or other unmodified DNA can be spotted onto the above slides or onto poly-L-lysine coated slides. 2-4×SSC or 1:1 DMSO:water can be used for spotting. Treatment with UV and succinic anhydride is optional. The slides should be washed, to wash off unbound probes before assays are performed.

Single molecule arrays can be created by spotting dilute solutions. The following are tested protocols for making single molecule arrays.

There are a number of factors that need to be taken into consideration for making single molecule arrays. The primary requirement is of course that the probes are at such a surface density that single probes can be individually resolved. General criteria for obtaining the highest quality of microarrays in general should apply here. Spots must be of the highest quality in terms of shape and internal morphology and non-specific background should be low. There must be an even distribution of the single probes within the spot area and bunching of probes or internal spot patterns such as the "doughnut" effect which is due to the spot drying process should be minimal. The shape and size of the spots should ideally be fairly similar. The arrangement of the spots should be in regular pattern and out of line spots (spots that have shifted out of register) which seem to occur when slides are kept at high humidity should be avoided.

The slide surface chemistry, spotting process and associated parameters determine the optimal concentration of oligonucleotides that must be provided in the microtitre plate well to obtain single molecule arrays. Therefore the concentration of oligonucleotides in a microtitre plate well needs to be determined empirically when each of the following is varied: the array spotting system (there are many manufacturers of equipment), types of spotting heads (i.e. ink jet, capillary, stealth pins, ring and pin), spotting parameters (e.g. the intensity with which the capillary hits the surface, how much volume is dispensed) slide chemistry, oligonucleotide chemistry and if the oligonucleotide contains any terminal modification and the type and concentration of spotting buffer and humidity during the spotting process.

There are a number of vendors who sell slides with different surface modifications and appropriate buffers, for example Corning (USA), Quantifoil (Jena, Germany), Surrmodics (USA), Zeiss (Germany) and Mosaic (Boston, USA).

Immobilization may also be by the following means: Biotin-oligonucleotide complexed with Avidin, Strepatavidin or Neutravidin; SH-oligonucleotide covalently linked via a disulphide bond to a SH-surface; Amine-oligonucleotide covalently linked to an activated carboxylate or an aldehyde group; Phenylboronic acid (PBA)-oligonucleotide complexed with salicylhydroxamic acid (SHA); Acrydite-oligonucleotide reacted with thiol or silane surface or co-polyemerized with acrylamide monomer to form polyacrylamide. Or by other methods known in the art. For some applications where it is preferable to have a charged surface, surface layers can be composed of a polyelectrolyte multi-layer (PEM) structure (US2002025529).

Arrays can also be deposited by sealing a microtitre plate against a substrate surface and centrifuging with the sample side of the microtitre plate on top of the surface. This is followed by flipping over and centrifuging with the substrate on top. Single molecule arrays can be created by as short first centrifugation and long second centrifugation. Alternatively, dilute solutions can be deposited by centrifugation.

The required low density is typically achieved by using dilute solutions. One microlitre of a $10^{-6}$ M solution spread over a 1 cm$^2$ area has been shown to give a mean intermolecular separation of 12.9 nm on the surface, a distance far too small to resolve with optical microscope. Each factor of 10 dilution increases the average intermolecular separation by a factor 3.16. Thus, a $10^{-9}$ M solution gives a mean intermolecular separation of about 400 nm and a $10^{-12}$ M gives a mean intermolecular separation of about 12.9 μm. With a mean separation of about 12.9 μm, if the probes and/or labels of the probes are focused to appear to be 0.5 μM in diameter and the average distance is 5 μM, then the chance of two probes and/or labels overlapping (i.e. centre to centre distance of 5 μM or less) is about 1% (based on M. Unger E. Kartalov, C. S Chiu, H. Lester and S. Quake, "Single Molecule Fluorescence Observed with Mercury Lamp Illumination", *Biotechniques* 27: 1008-1013 (1999)). Consequently, typical concentrations of dilute solutions used to spot or print the array, where far field optical methods are used for detection is in the order of at least $10^{-9}$ M, preferably least $10^{-10}$ M or $10^{-12}$ M. The concentration used is higher with the use of superresolution far field methods or SPM. It should also be borne in mind that only a fraction of probes that are spotted onto a surface robustly attach to the surface (0.1% to 1% for example). Thus depending on various spotting and slide parameters, between 1-500 nM of oligonucleotide may be appropriate for spotting onto epoxysilane slides and enhanced aminosilane slides and aminosliane slides. Depending on the method of immobilization, only a fraction of those probes that are robustly attached are available for hybridization or enzymatic assays. For example with the use of aminolinked oligonucleotides and spotting onto a Aminopropyltriethoxysilane (APTES) coated slide surface about 20% of the oligonucleotides are available for mini-sequencing.

Before assays are carried out it may be necessary to pre-treat the slides to block positions where non-specific binding might occur. Additionally, in for example, primer extension where labelled dNTPs or ddNTPs often stick non-specifically to the surface, it may be necessary to provide a negative charge on the surface, chemically or electronically to repel such probes.

In a second embodiment, the surface is designed in such a way that sites of attachment (i.e. chemical linkers or surface moieties) are dilute or that sites are selectively protected or blocked. In this case, the, concentration of the sample used for ink jet printing or spotting is immaterial provided the attachment is specific to these sites. In the case of in situ synthesis of probes, the lower number of available sites for initiating synthesis allows more efficient synthesis providing a higher chance of obtaining full-length products.

Polymers such as nucleic acids or polypeptides can also be synthesised in situ using photolithography and other masking techniques whereby probes are synthesised in a step-wise manner with incorporation of monomers at particular positions being controlled by means of masking techniques and photolabile reactants. For example, U.S. Pat. No. 5,837,832 describes a method for producing DNA arrays immobilized to silicon substrates based on very large scale integration technology. In particular, U.S. Pat. No. 5,837,832 describes a strategy called "tiling" to synthesise specific sets of probes at spatially-defined locations on a substrate. U.S. Pat. No. 5,837,832 also provides references for earlier techniques that can also be used. Light directed synthesis can also be carried out by using a Digital Light Micromirror chip (Texas Instruments) as described (Singh-Gasson et al., (1999) Nature Biotechnology 17:974-978). Instead of using photo-deprotecting groups which are directly processed by light, conventional deprotecting groups such as dimethoxy trityl can be employed with light directed methods where for example a photoacid is generated in a spatially addressable way which selectively deprotects the DNA monomers (Mc Gall et al PNAS 1996 93: 1355-13560; Gao et al J. Am. Chem Soc. 1998 120: 12698-12699). Electrochemical generation of acid is another means that is being developed (e.g. Combimatrix Corp.). Arrays may be produced using semiconductor methodologies and fabrication techniques.

The size of array members is typically from 0.1×0.1 microns and above as can be ink jet or spot printed onto a patterned surface or created by photolithography or physical masking. Array members created by nanolithography such as scanning probe microscopy may be smaller.

Probes can be attached to the solid phase at a single point of attachment, which can be at the end of the probe or otherwise. Alternatively, probes can be attached at two or more points of attachment. In the case of nucleic acids, it can be advantageous to use techniques that 'horizontalize' the immobilized probe relative to the solid substrate. For example, fluid fixation of drops of DNA has been shown previously to elongate and fix DNA to a derivatised surface such as silane derivatised surfaces. This can promote accessibility of the immobilized probes for target molecules. Spotting of sample by quills/pins/pens under fast evaporation conditions creates capillary forces as samples dry to elongate molecules. Means for straightening molecules by capillary action in channels have been described by Jong-in Hahm at the Cambridge Healthtech Institutes Fifth Annual meeting on Advances in Assays, Molecular Labels, Signalling and Detection, May 17-18$^{th}$ Washington D.C. Samples can be applied through an array of channels. The density of molecules stretched across a surface is typically constrained by the radius of gyration of the DNA molecule.

A method for making single molecule arrays of any substance may comprise the steps of: (i) Make a series of microarray spots with a dilution series of probes over a wide dilution range; (ii) Analyze to see which spots give single probe resolution using the desired detection method; (iii) Optionally repeat (i) and (ii) with a more focused dilution series based on information form (ii); and (iv) Make microarrays with the determined dilution.

Spatially addressable self-assembly: Immobilized probes and/or tags describe herein can also serve to bind further molecules and/or probes to complete manufacture of the array. For example, nucleic acids immobilized to the solid substrate can serve to capture further nucleic acids by hybridization, or polypeptides. Similarly, polypeptides can be incubated with other compounds, such as other polypeptides. It may be desirable to permanently "fix" these interactions using, for example UV crosslinking and appropriate cross-linking reagents. Capture of secondary molecules and/or probes can be achieved by binding to a single immobilized tag or affinity tag or to two or more tag or affinity tag. Where secondary molecules and/or probes bind to two or more tags, this can have the desirable effect of containing the secondary molecule and/or probes horizontally.

The secondary molecules and/or probes described herein can also be made horizontal and straightened out without a tag or second probe, by methods such as molecular combing and fibre FISH. One detailed method is described in Examples (see FIG. 10). This is quite distinct to the arraying of fragments of pre-sorted molecules of Junping Jing PNAS Vol. 95, Issue 14, 8046-8051, Jul. 7, 1998 (U.S. Pat. No. 6,221,592) because we have self-assembled the genomic molecules to spatially addressable sites and so it is a way of sorting the genome for highly parallel single molecule analysis. For Schwartz's arrayed spots to represent the whole genome, traditional cloning techniques would need to be used to isolate each individual genome fragment for spotting.

Where this is done, the members of the array are preferably not immediately adjacent to one another and a gap should exist between each functional array member, because stretched out DNA fibers are expected to stretch out from the edges of the member (and would protrude into immediately adjacent members). In these cases the separation of the array members is dictated by the length of probes that are immobilized. For example, for Lambda DNA the distance separating members should be 15 to 30 microns at least.

This process can self-assemble a secondary array, typically composed of target molecules, upon a spatially addressable array of tags or probes. This is a way of sorting out a complex sample such as a genome or a mRNA population and presenting it for further analysis such as haplotyping or sequencing.

ii. Density Reduction of High Density Arrays

In an alternative embodiment, the molecular array can be obtained by providing an array produced with probes at normal (high) densities using a variety of methods known in the art, followed by reduction of surface coverage.

A reduction in actual or effective surface coverage can be achieved in a number of ways. Where probes are attached to the substrate by a linker, the linker can be cleaved. Instead of taking the cleavage reaction to completion the reaction is partial, to the level required for achieving the desired density of surface coverage. In the case of probes attached to glass by an epoxide and PEG linkage, such as oligonucleotides, partial removal of probes can be achieved by heating in ammonia which is known to progressively destroy the lawn.

It is also possible to obtain a reduction in surface coverage by functional inactivation of probes in situ, for example using enzymes or chemical agents. The amount of enzyme or agent used should be sufficient to achieve the desired reduction without inactivating all of the probes. Although the end result of this process is often a substrate which has probes per se at the same density as before the density reduction step, the density of functional probes is reduced since many of the original probes have been inactivated. For example, phosphorylation of the 5' ends of 3' attached oligonucleotides by polynucleotide kinase, which renders the oligonucleotides available for ligation assays is only 10% efficient.

An alternative method for obtaining a reduction in probe density is to obtain an effective reduction in density by labelling or tagging only a proportion of the pre-existing immobilized probes so that only the labelled/tagged probes at the required density are available for interaction and/or analysis. This is particularly useful for analysing low target numbers on normal density arrays where the target introduces the label.

These density reduction steps can be applied conveniently to ready-made molecular arrays which are sold by various vendors e.g. Affymetrix, Corning, Agilent and Perkin Elmer. Alternatively, proprietary molecular arrays can be treated as required.

The present invention also provides an "array of arrays", wherein an array of molecular arrays (level 1) as described are configured into arrays (level 2) for the purpose of multiplex analysis. Multiplex analysis can be done by sealing each molecular array (level 1) in individual chambers that makes a seal with the common substrate, so that a separate sample can be applied to each. Alternatively each molecular array (level 1) can be placed at the end of a pin (as commonly used in combinatorial chemistry) or a fibre and can be dipped into a multi well plate such as a 384 well microtitre plate. The fibre can be an optical fibre which can serve to channel the signal from each array to a detector. The molecular array (level 1) can be on a bead which self-assembles onto a hollow optical fibre as described by Walt and co-workers (Illumina Inc.): Karri et al Anal. Chem 1998 70: 1242-1248. Moreover, the array may be of arrays of randomly immobilized molecules of known and defined type, for example a complete oligonucleotide set of every 17mer or genomic DNA from a particular human sample.

An array of the invention may provide probes for different applications, such as SNP typing and STR analysis as needed for some applications such as typing polymorphisms on the Y Chromosome.

Biosensors: Low density molecular arrays or low density functionalised molecular array may be used in biosensors which may be used to monitor single molecule assays on a substrate surface, such as a chip. The array may comprise, for example, between 1 and 100 different immobilized molecules (e.g. probes), an excitation source and a detector such as a CCD, all within an integrated device. Sample processing may or may not be integrated into the device.

In one aspect, the biosensor would comprise a plurality of members, each member containing distinct molecules, such as probe sequences. Each member may then be specific for the detection of, for example, different pathogenic organisms.

In a preferred embodiment the immobilized molecules would be in the form of molecular beacons and the substrate surface would be such that an evanescent wave can be created at the surface. This may be achieved by the forming a grating structure on the substrate surface or by making the array on an optical fibre (within which light is totally internally reflected) for example. The CCD detector may be placed below the array surface or above the array, separated from the surface by a short distance to allow space for the reaction volume.

Figure 6:
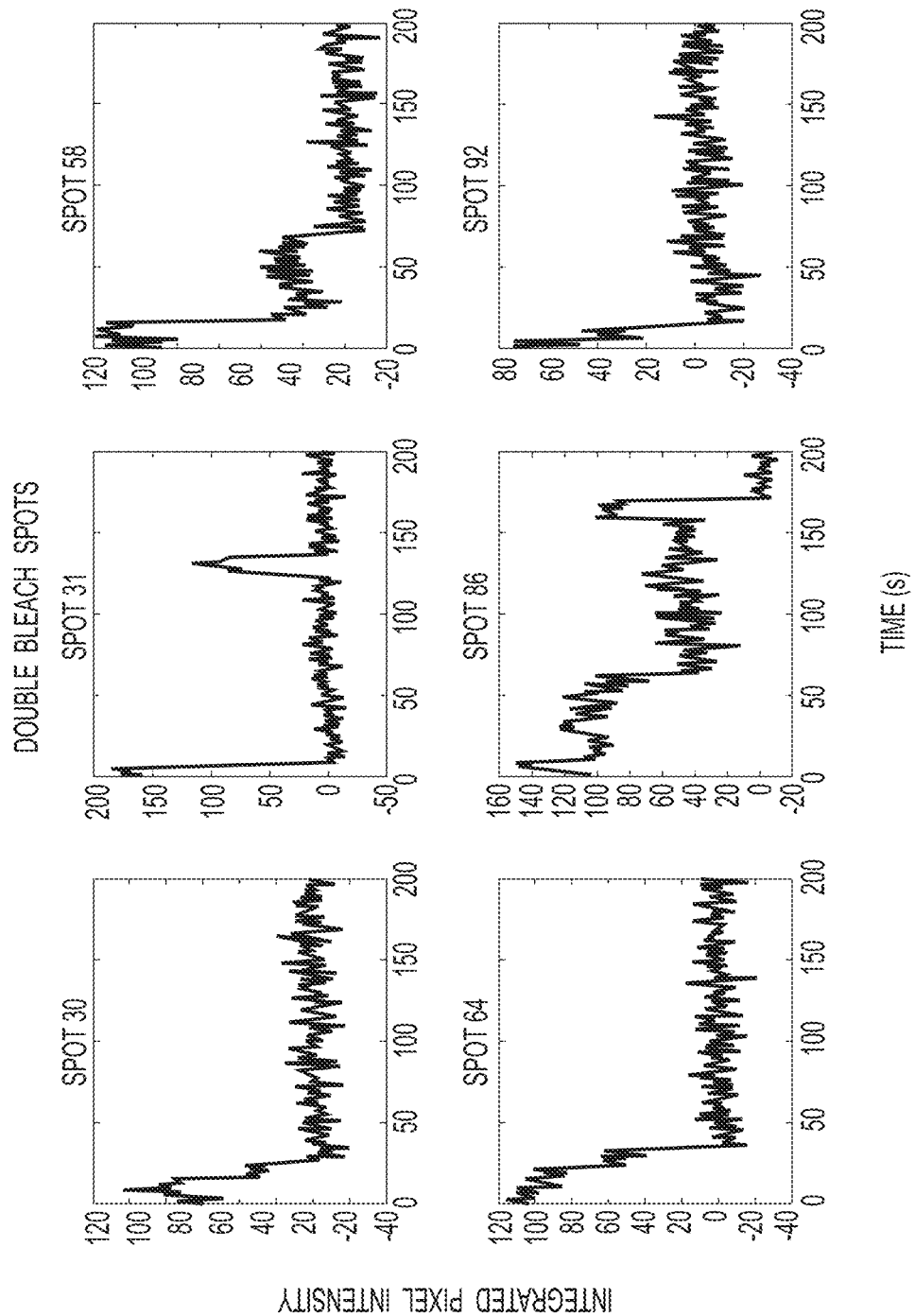
Figure 7:
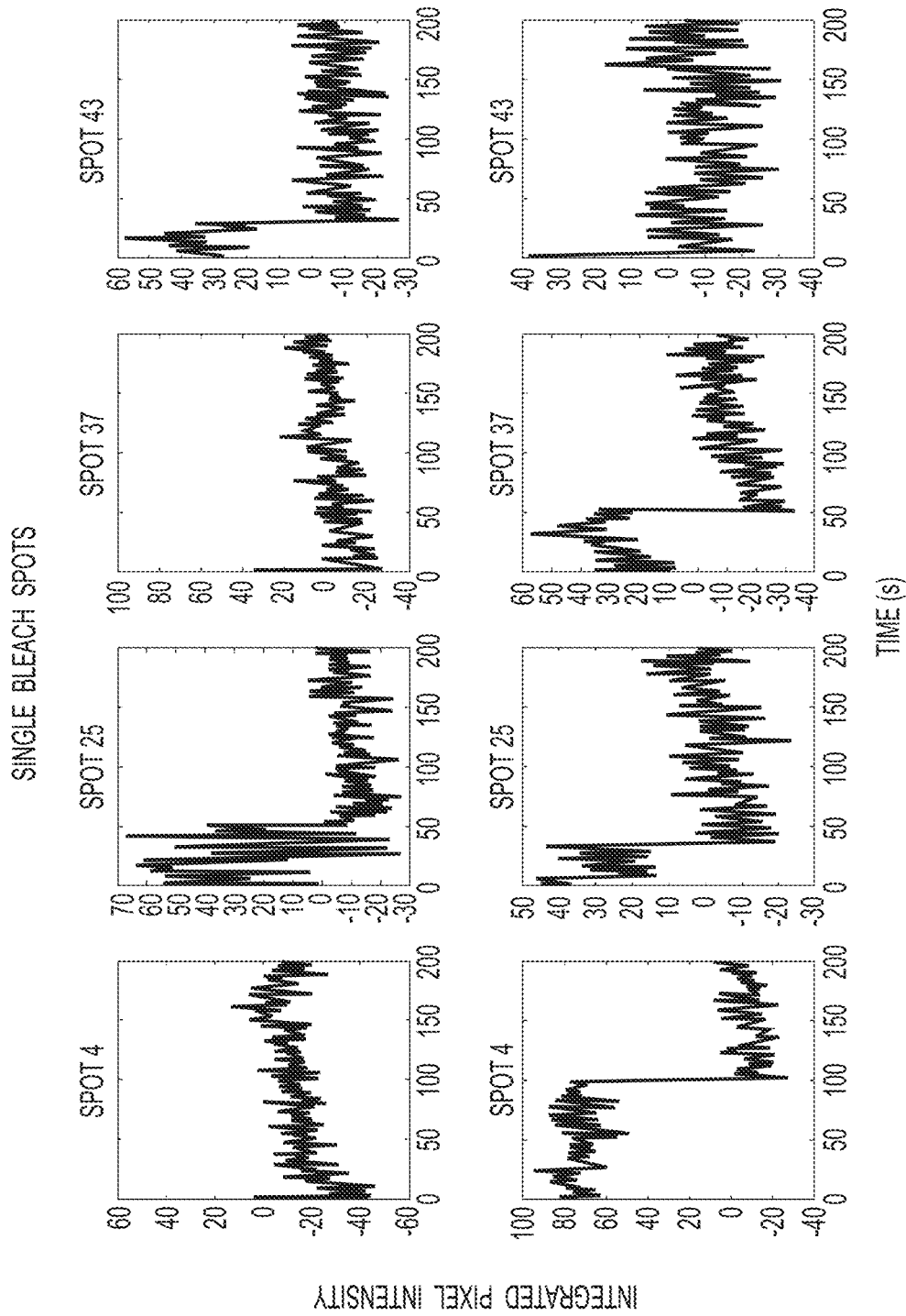
Figure 8:
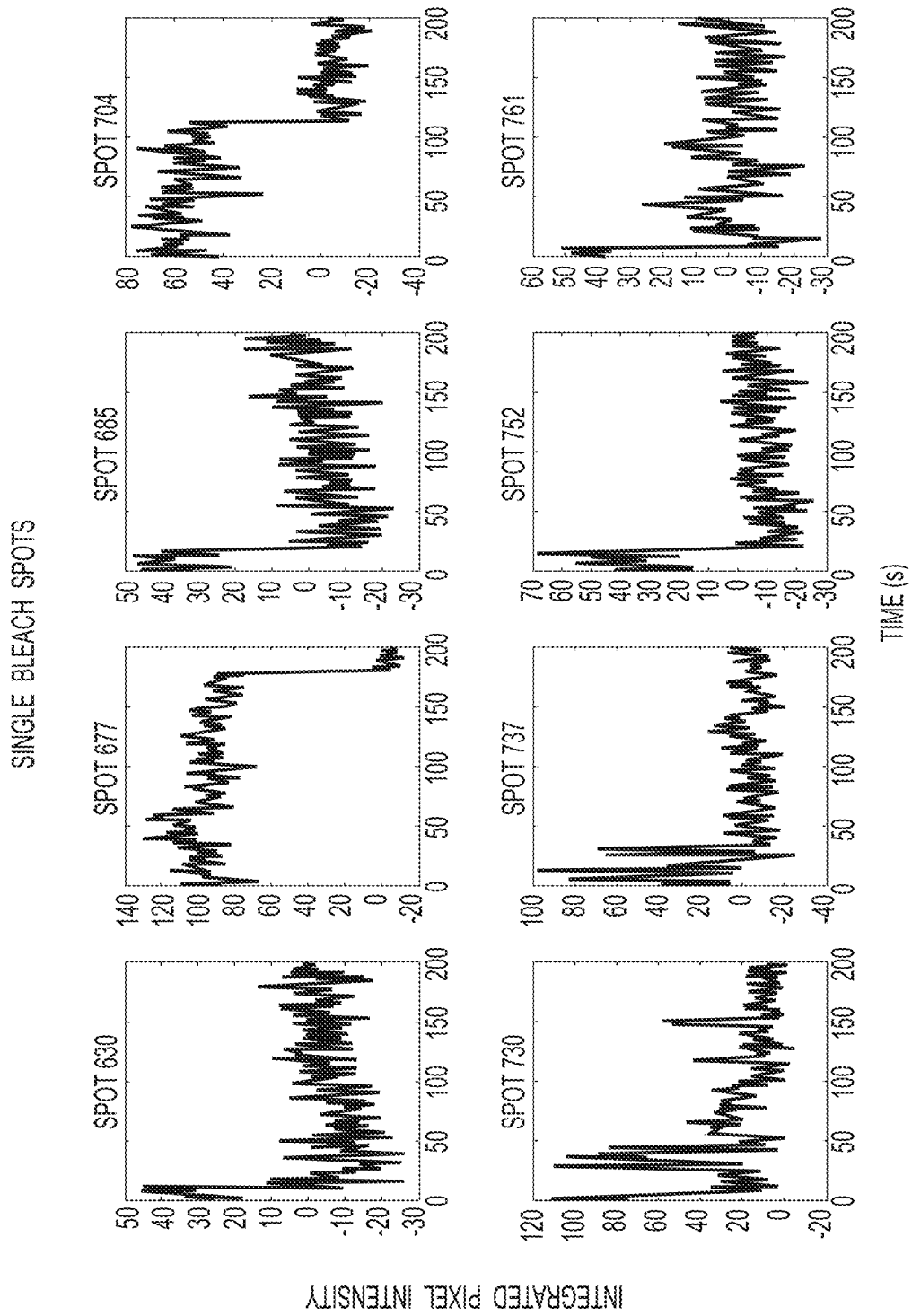
Figure 9:
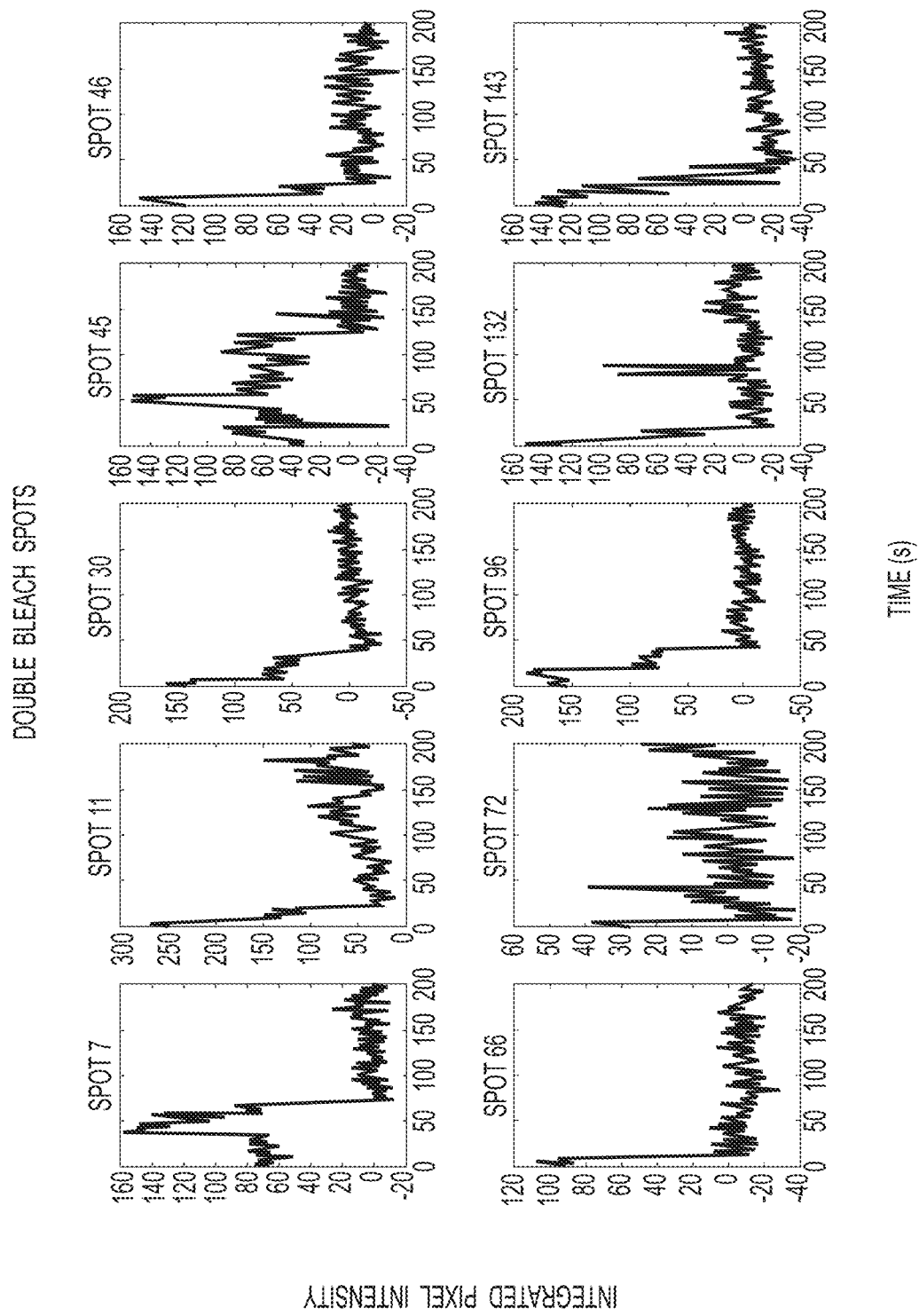
Figure 10:
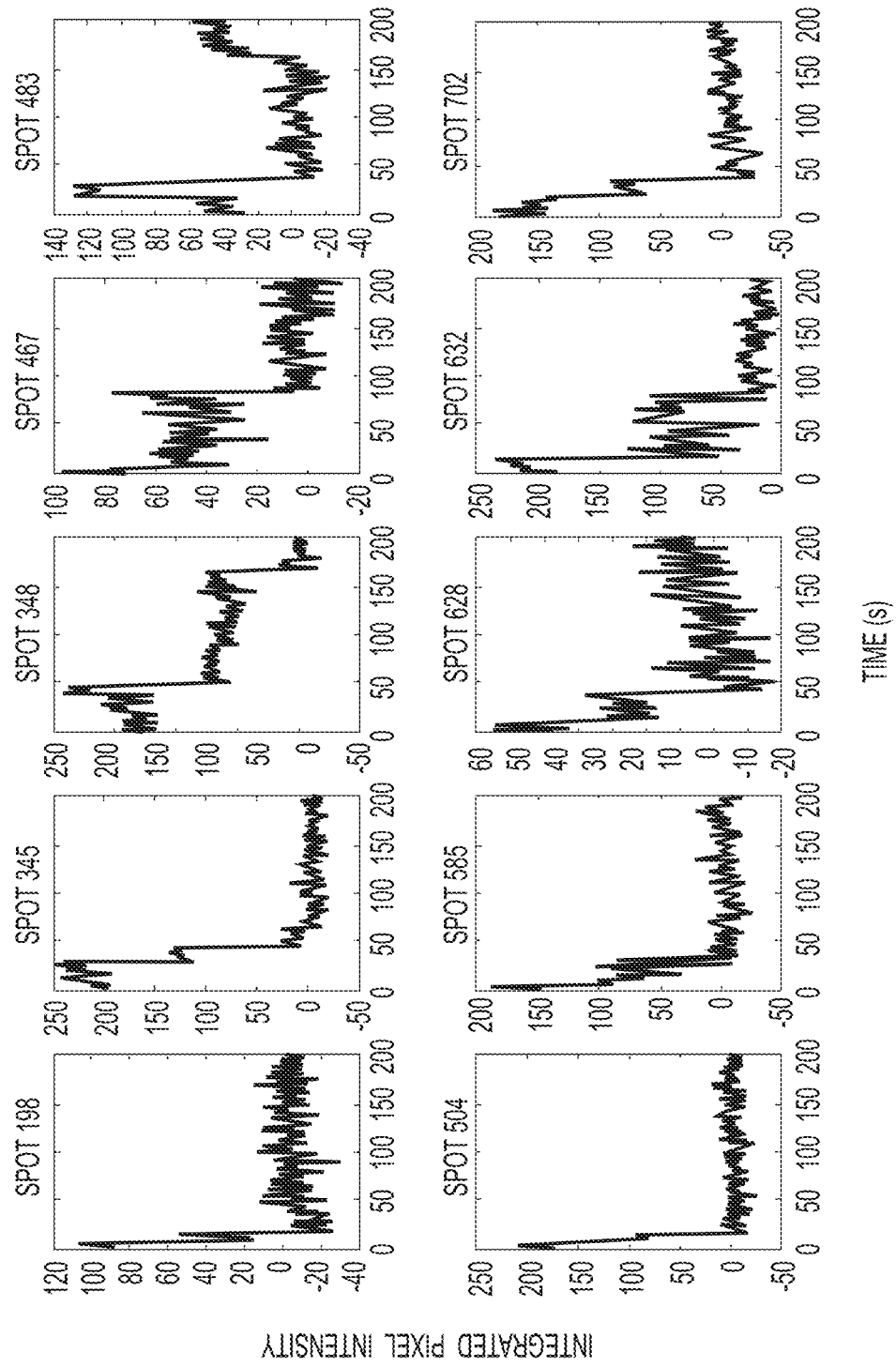
Figure 11:
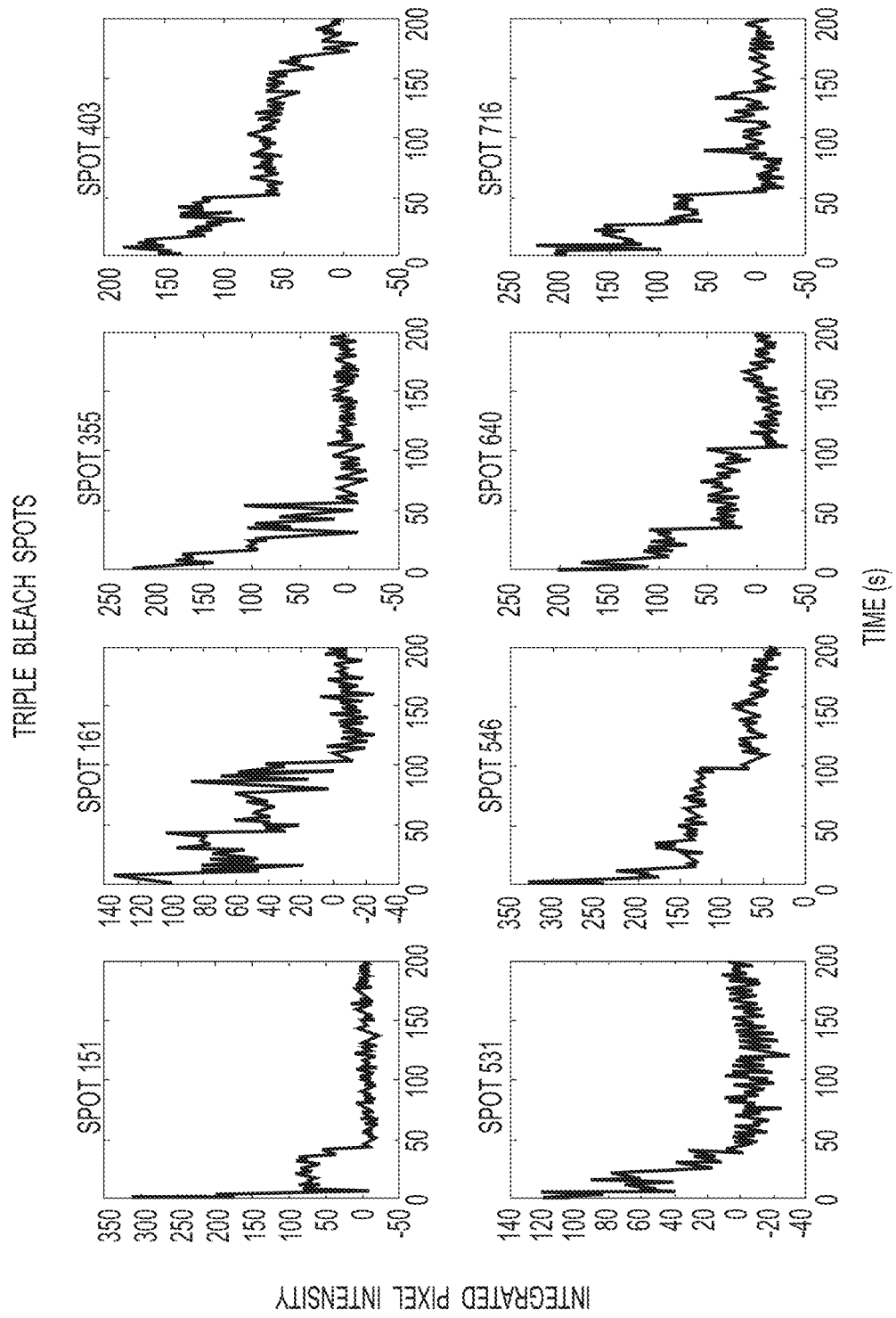
Figure 12:
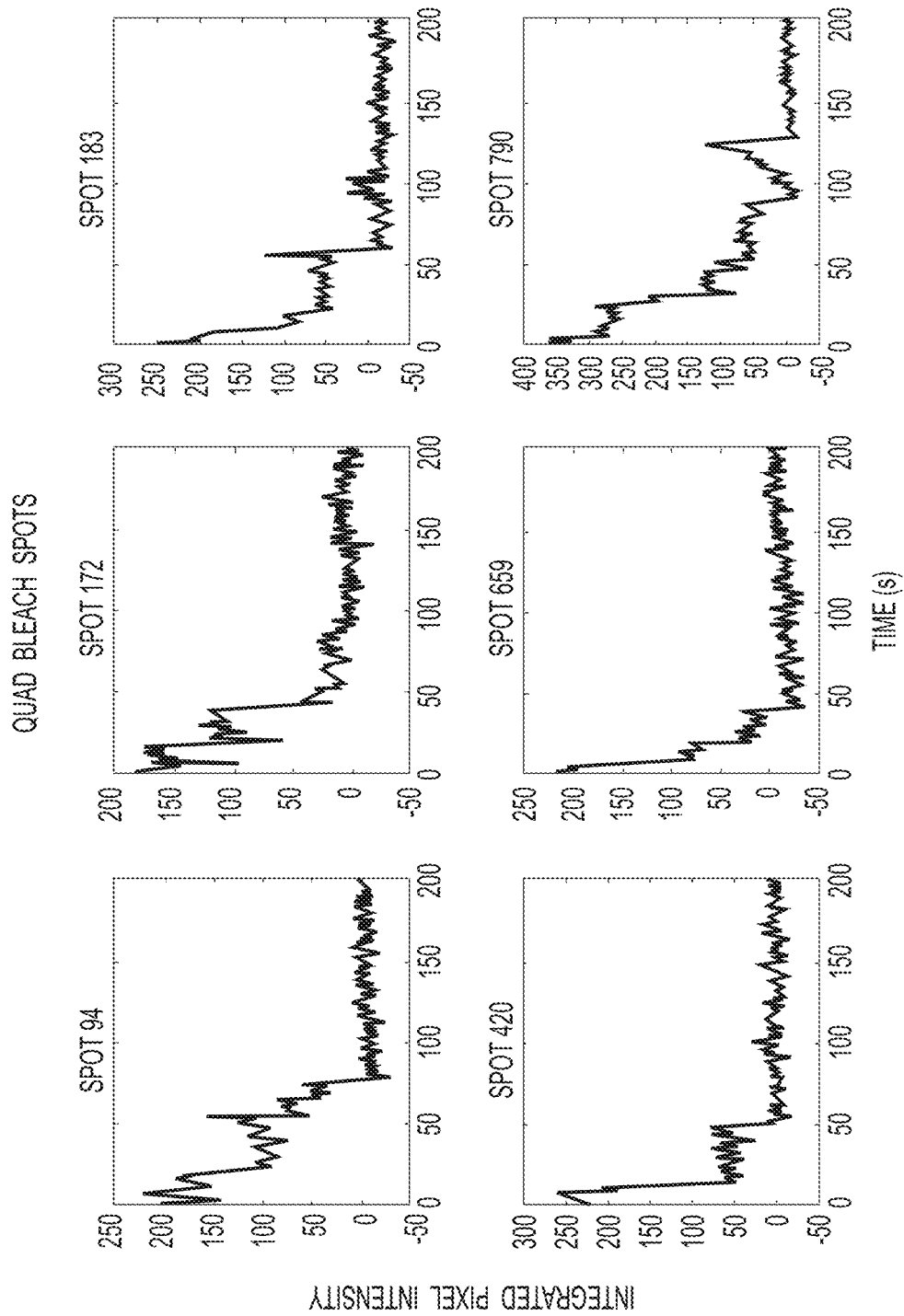
Figure 13:
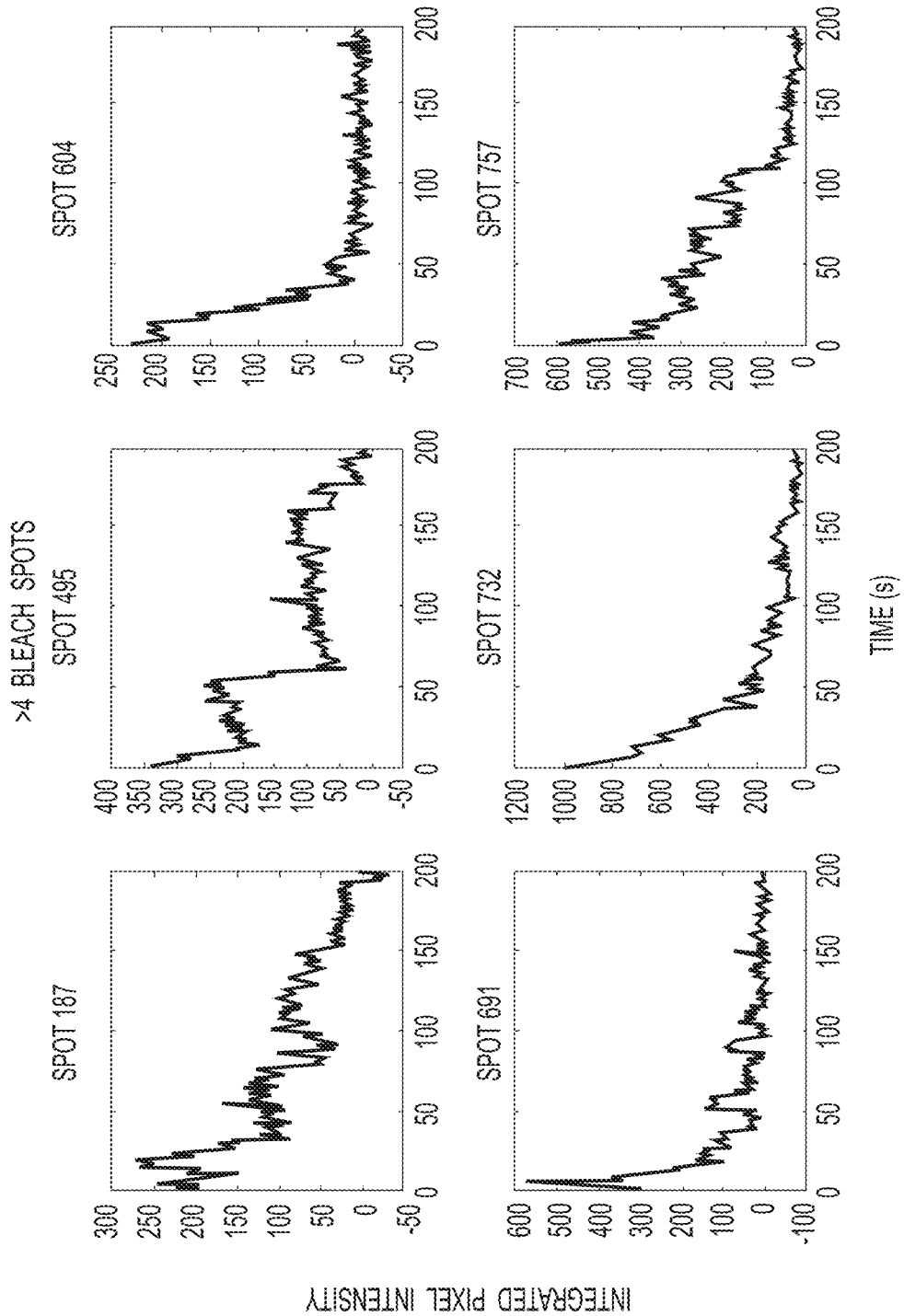

Examples of biosensor configurations are given in FIG. 6 where: (a) is an integrated detection scheme based on Fluorescence Energy Resonance Transfer (FRET). The sample is applied between two plates, one with a CCD and the other with an LED with grating structure on its surface. (b) is an integrated detection system with a molecular beacon (Tyagi et al Nat. Biotechnol. 1998, 16:49-53) on an optical fibre. Other methods such as Total Internal Reflection Fluorescence (TIRF) can be used.

Single molecules can be viewed on stripped fused silica optical fibres, essentially as described by Watterson et al. (Sensors and Actuators B 74: 27-36 (2001). Molecular Beacons can be seen in the same way (Liu et al. (2000) Analytical Biochemistry 283: 56-63). This is the basis of a biosenesor device based on single molecule analysis in an evanescent field.

The present invention also provides a molecular array obtained by the above first and second embodiments of the invention.

The present invention further provides means to analyse the single probes, wherein a physical, chemical or other property can be determined. For example, probes which fluoresce at a certain tested wavelength can be directly sampled.

The present invention further provides a number of techniques for detecting interactions between sample molecules and the probes described herein.

Accordingly, the present invention provides the use of a molecular array in a method of identifying one or more probes which interact with a target, which molecular array comprises a plurality of probes immobilized to a substrate at a density which allows each individual immobilized probe to be individually resolved, wherein the identity of each individual immobilized probe is known due to its location within a spatially addressable array and the identity of each immobilized probe is known or wherein the identity of each individual probe is encoded and can be decoded, for example with reference to a look up table.

Typically said method comprises contacting the array with the sample and interrogating one or more individual immobilized probes to determine whether a target molecule has bound.

Preferably the target molecule or the probe-target molecule complex is labelled.

Preferably interrogation is by an method for detecting electromagnetic radiation such as a method selected from far-field optical methods, near-field optical methods, epi-fluorescence spectroscopy, confocal microscopy, two-photon microscopy, and total internal reflection microscopy, where the target molecule or the probe-target molecule complex is labelled with an electromagnetic radiation emitter. Other methods of microscopy, such as atomic force microscopy (AFM) or other scanning probe microscopies (SPM) are also appropriate. Here it may not be necessary to label the target or probe-target molecule complex. Alternatively, labels that can be detected by detected by SPM can be used.

In one embodiment, the immobilized probes are of the same chemical class as the target molecules. In another embodiment, the immobilized probes are of a different chemical class to the target molecules.

Particular applications of molecular arrays according to the invention, and of single molecule detection techniques in general, are set forth herein. Particularly preferred uses include the analysis of nucleic acid, such as in SNP typing, sequencing and the like, in biosensors and in genetic approaches such as association studies and in genomics and proteomics.

In a further aspect, the invention relates to a method for typing single nucleotide polymorphisms (SNPs) and mutations in nucleic acids, comprising the steps of: a) providing a repertoire of probes complementary to one or more nucleic acids present in a sample, which nucleic acids may possess one or more polymorphisms, said repertoire being presented such that probes may be individually resolved; b) exposing the sample to the repertoire and allowing nucleic acids present in the sample to hybridize to the probes at a desired stringency, and optionally further processing; c) detecting binding events or the result of processing.

The detection of binding events can be aided by eluting the unhybridized nucleic acids from the repertoire and detecting individual hybridized nucleic acid probes.

Advantageously, the repertoire is presented as an array, which is preferably an array as described hereinbefore.

The present invention is particularly applicable to DNA pooling strategies in genetic analysis and detection of low frequency polymorphisms. DNA pooling strategies involve mixing multiple samples together and analysing them together to save costs and time.

The present invention is also applicable to detection of low frequency mutations in a wild type background.

The present invention can also be applied where the amount of sample material is low such as in biosensor or chemical sensor applications.

The invention is moreover applicable to haplotyping, in which a multiallelic probe set is used to analyse each sample molecule for two or more features simultaneously. For example, a first probe can be used to immobilize the sample nucleic acid to the substrate, and optionally simultaneously to identify one polymorphism or mutation; and a second probe can be used to hybridize with the immobilized sample nucleic acid and detect a second polymorphism or mutation. Thus, the first probe (or biallelic probe set) is arrayed on the substrate, and the second probe (or biallelic probe set) is provided in solution (or is also arrayed; see below). Further probes can be used as required. Thus, the method of the invention may comprise a further step of hybridizing the sample nucleic acids with one or more further probes in solution.

The signals generated by the first and second probes can be differentiated, for example, by the use of differentiable signal molecules such as fluorophores emitting at different wavelengths, as described in more detail below. Moreover, the signals can be differentiable based on their location along the target molecule on the substrate. To aid localisation of signal along the probe, probes can be stretched out by methods known in the art.

In a still further aspect, the invention relates to a method for determining the sequence of one or more target DNA molecules. Such a method is applicable, for example, in a method for fingerprinting a nucleic acid sample, as described below. Moreover the method can be applied to complete or partial sequence determination of a nucleic acid molecule.

Thus, the invention provides a method for determining the complete or partial sequence of a target nucleic acid, comprising the steps of a) providing a repertoire of probes complementary to one or more nucleic acids present in a sample, said first repertoire being presented such that probes may be individually resolved; b) hybridizing a sample comprising a target nucleic acid to the probes; c) hybridizing one or more further probes of defined sequence to the target nucleic acid; and d) detecting the binding of individual further probes to the target nucleic acid.

Advantageously, the further probes are labelled with labels which are differentiable, such as different fluorophores.

Advantageously, the repertoire is presented as an array, which is preferably an array as described hereinbefore.

In an advantageous embodiment, target nucleic acids are captured on the substrate surface at multiple points, which allows the probe to be arranged horizontally on the surface and optionally sites of multiple capture are in such locations that the target molecule is elongated. In a further embodiment the probe is attached by a single point and physical measures are taken to horizontalise it. Hybridization of further probes can then be determined according to position as well as according to differences in label.

In a further embodiment, the invention provides a method for determining the number of sequence repeats in a sample nucleic acid, comprising the steps of: a) providing one or more probes complementary to one or more nucleic acids present in a sample, which nucleic acids may possess one or more sequence repeats, said probes being presented such that probes may be individually resolved; b) hybridizing a sample of nucleic acid comprising the repeats c) contacting the nucleic acids with labelled probes complementary to said sequence repeats, or a polymerase and nucleotides; and d) determining the number of repeats present on each sample nucleic acid by individual assessment of the number of labels incorporated into each probe, such as by measuring the brightness of the signal produced by the labels; wherein in a preferred embodiment signal is only processed from probes to which a second solution oligonucleotide labelled with a different label is also incorporated.

The results can be analysed in terms of intensity ratios of the repeat probes labelled with first colour and the second probe labelled with a second colour.

Advantageously, the repertoire is presented as an array, which is preferably an array as described hereinbefore.

The invention moreover provides a method for analysing the expression of one or more genes in a sample, comprising the steps of a) providing a repertoire of probes complementary to one or more nucleic acids present in a sample, said repertoire being presented such that probes may be individually resolved; b) hybridizing a sample comprising said nucleic acids to the probes; c) determining the nature and quantity of individual nucleic acid species present in the sample by counting single probes which are hybridized to the probes.

In some cases the individual probe can be further probed by sequences that can differentiate alternative transcripts or different members of a gene family.

Advantageously, the repertoire is presented as an array, which is preferably an array as described hereinbefore.

Preferably, the probe repertoire comprises a plurality of probes of each given specificity, thus permitting capture of more than one of each species of nucleic acid molecule in the sample. This enables accurate quantitation of expression levels by single probe counting.

In another embodiment the target sample, containing a plurality of copies of each species is immobilized and spread out on a surface and a plurality of probes are gridded on top of this first layer. Each gridded spot contains within its area at least one copy of each target species. After a wash step, the probes that have bound are determined.

The present invention provides a method for determining the sequence of all or part of a target nucleic acid molecule which method comprises: (i) immobilizing the target molecule to a substrate at two or more points such that the molecule is substantially horizontal with respect to the surface of the substrate; (ii) straightening the target molecule during or after immobilization; (iii) contacting the target molecule with a nucleic acid probe of known sequence; and (iv) determining the position within the target molecule to which the probe hybridizes; (v) repeating steps (i) to (iv) as necessary; and (vi) reconstructing the sequence of the target molecule.

Preferably the target molecule is contacted with a plurality of probes, more preferably each probe is encoded, for example labelled with a different detectable label or tag.

The target molecule can be contacted sequentially with each of the plurality of probes. In one embodiment each probe is removed or its label is removed or photobleached from the target molecule prior to contacting the target molecule with a different probe. Typically, the probes are removed by heating, modifying the salt concentration or pH, or by applying an appropriately biased electric field. Alternatively, another oligonucleotide complementary to the probe and which forms a stronger hybrid than the target strand, can displace the target strand. In another embodiment neither the probe or its label are removed, but rather their positions of interaction along the molecule are recorded before another probe is added.

After a certain number of probe additions, bound probes must be removed before binding more probes.

Alternatively the target molecule is contacted with all of the plurality of probes substantially simultaneously.

In one embodiment the target is substantially a double stranded molecule and is hybridized to an LNA or PNA probe by strand invasion.

In another embodiment the target double strand is combed (or fibre FISH fibres are made) on a surface and denatured before or after combing.

In another embodiment the target is substantially single stranded and is made accessible for subsequent hybridization by stretching out/straightening, which can be achieved by capillary forces acting on the target in solution.

In one embodiment, where it is desired to determine the sequence of single-stranded molecules, the target nucleic acid molecule is a double-stranded molecule and is derived from such a single-stranded nucleic acid molecule of interest by synthesising a complementary strand to said single-stranded nucleic acid.

The present invention also provides a method for determining the sequence of all or part of a target single-stranded nucleic acid molecule which method comprises: (i) immobilizing the target molecule to a substrate at one, two or more points such that the molecule is substantially horizontal with respect to the surface of the substrate; (ii) straightening the target molecule during or after immobilization; (iii) contacting the target molecule with a plurality of nucleic acid probes of known sequence, each probes being labelled with a different detectable label; and (iv) ligating bound probes to form a complementary strand. Where the probes are not bound in a contiguous manner, it is preferred prior to step (iv), to fill any gaps between bound probes by polymerization primed by said bound probes.

The present invention also provides a method for determining the sequence of all or part of a target single-stranded nucleic acid molecule which method comprises: (i) contacting the target molecule with a plurality of nucleic acid probes of known sequence, each probes being labelled with a different detectable label; (ii) ligating bound probes to form a complementary strand; (iii) immobilizing the target molecule to a substrate at one or more points such that the molecule is substantially horizontal with respect to the surface of the substrate; and (iv) straightening the target molecule during or after immobilization.

Where the probes are not bound in a contiguous manner, it is preferred, prior to step (iii), to fill any gaps between bound probes by polymerization primed by said bound probes. The position where each ligation probe is attached is recorded during or after the process.

The present invention also provides an array produced or obtainable by any one of the above methods.

The invention relates to coupling the preparation of single molecule arrays and performing assays on single molecule arrays. Particularly when either or both of these are coupled to Detection/Imaging of single probes on a substrate as described herein and assays based on counting single molecules or recording and making measurements of signals on single molecules.

The present invention also provides software and algorithmic approaches for processing of data from the above methods.

Figure 19:
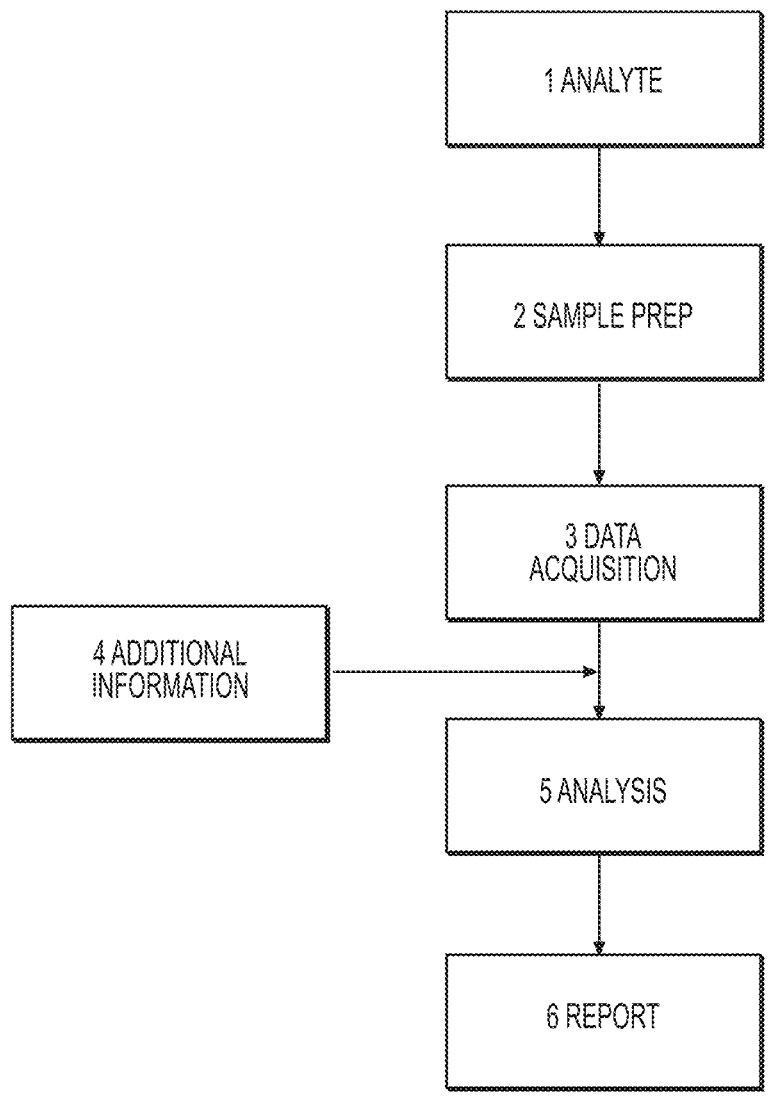
FIG. 19 depicts an exemplary system flow chart.
Figure 20:
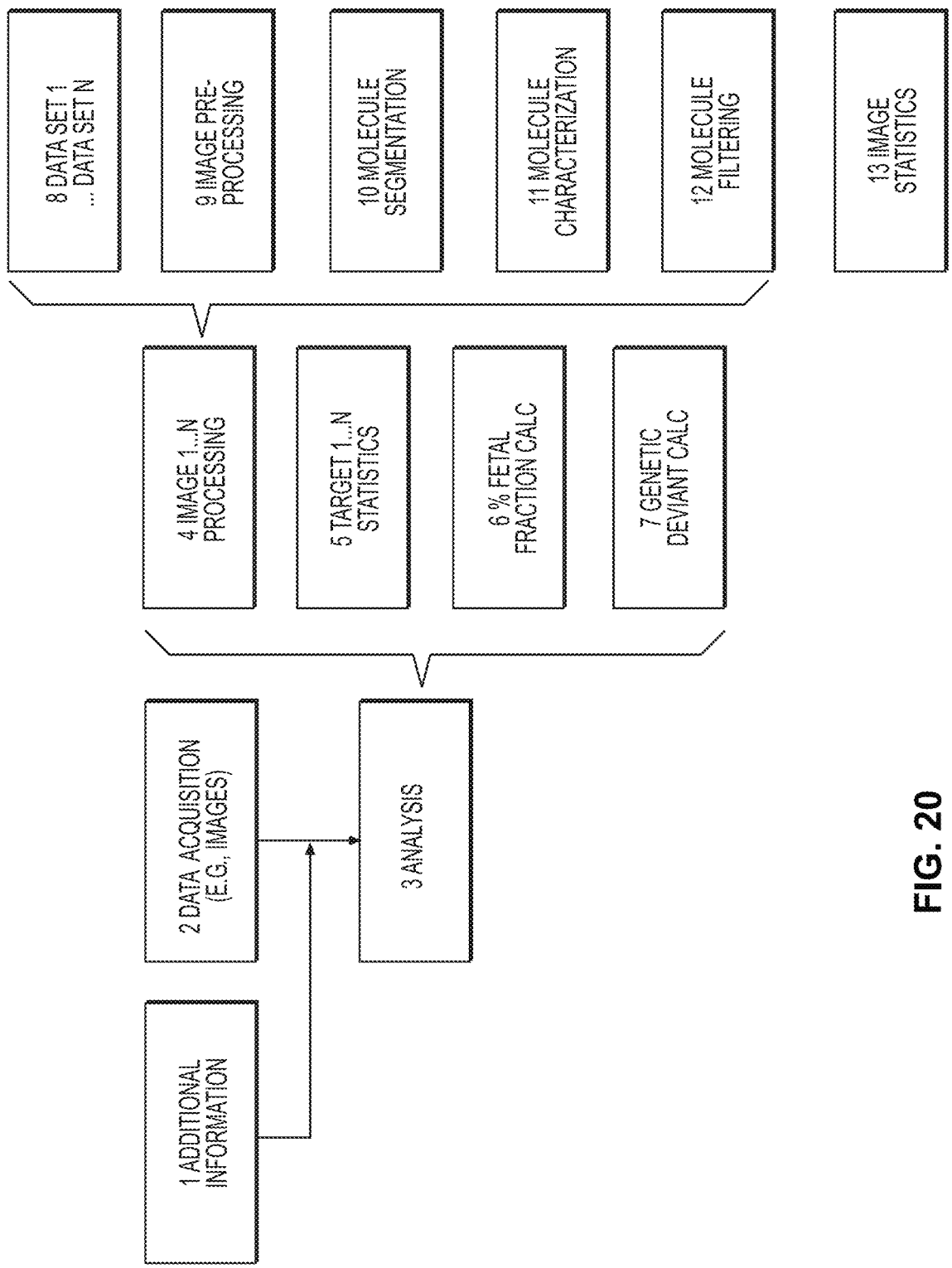
FIG. 20 depicts an exemplary system flow chart including various methods for analyzing data.

A system to detect a genetic variation according to the methods described herein includes various elements. Some elements include transforming a raw biological sample into a useful analyte. This analyte is then detected, generating data that are then processed into a report. Various modules that may be included in the system are shown in FIG. 19. More details of various methods for analyzing data, including e.g., image processing, are shown in FIG. 20. Analysis may be performed on a computer, and involve both a network connected to the device generating the data and a data server for storage of data and report. Optionally, additional information beyond the analyte data may be incorporated into the final report, e.g., maternal age or prior known risks. In some embodiments, the test system includes a series of modules, some of which are optional or may be repeated depending on the results of earlier modules. The test may comprise: (1) receiving a requisition, e.g., from an ordering clinician or physician, (2) receiving a patient sample, (3) performing an assay including quality controls on that sample resulting in a assay-product on an appropriate imaging substrate (e.g., contacting, binding, and/or hybridizing probes to a sample, ligating the probes, optionally amplifying the ligated probes, and immobilizing the probes to a substrate as described herein), (4) imaging the substrate in one or more spectral channels, (5) analyzing image data, (6) performing statistical calculations (e.g., comparing the first and second numbers to determine the genetic variation in the genetic sample), (7) creating and approving the clinical report, and (8) returning the report to the ordering clinician or physician. The test system may comprise a module configured to receive a requisition, e.g., from an ordering clinician or physician, a module configured to receive a patient sample, (3) a module configured to perform an assay including quality controls on that sample resulting in a assay-product on an appropriate imaging substrate, (4) a module configured to image the substrate in one or more spectral channels, (5) a module configured to analyze the image data, (6) a module configured to perform statistical calculations, (7) a module configured to create and confirm the clinical report, and and/or (8) a module configured to return the report to the ordering clinician or physician.

In one aspect, the assays and methods described herein may be performed on a single input sample simultaneously. For example, the method may comprise verifying the presence of fetal genomic molecules at or above a minimum threshold as described herein, followed by a step of estimating the target copy number state if and only if that minimum threshold is met. Therefore, one may separately run an allele-specific assay on the input sample for performing fetal fraction calculation, and a genomic target assay for computing the copy number state. In other embodiments, both assays and methods described herein may be carried out in parallel on the same sample at the same time in the same fluidic volume. Further quality control assays may also be carried out in parallel with the same universal assay processing steps. Since tags, affinity tags, and/or tagging probes in the probe products, ligated probe set, or labeled molecule to be immobilized to the substrate may be uniquely designed for every assay and every assay product, all of the parallel assay products may be localized, imaged and quantitated at different physical locations on the imaging substrate. In another aspect, the same assay or method (or some of their steps) described herein using the same probes and/or detecting the same genetic variation or control may be performed on multiple samples simultaneously either in the same or different modules (e.g., testing tube) described herein. In another aspect, assays and methods (or some of their steps) described herein using different probes and/or detecting different genetic variations or controls may be performed on single or multiple sample(s) simultaneously either in the same or different modules (e.g., testing tube).

In another aspect, image analysis may include image preprocessing, image segmentation to identify the labels, characterization of the label quality, filtering the population of detected labels based on quality, and performing statistical calculations depending on the nature of the image data. In some instances, such as when an allele-specific assay is performed and imaged, the fetal fraction may be computed. In others, such as the genomic target assay and imaging, the relative copy number state between two target genomic regions is computed. Analysis of the image data may occur in real-time on the same computer that is controlling the image acquisition, or on a networked computer, such that results from the analysis may be incorporated into the test workflow decision tree in near real-time.

Ideally, members of the array will be designed such that they are large enough that they encompass the field of view or size of the image being collected. That is, the entire image captured by the camera captures the area inside of a member. In some cases, >90%, >80%, >50%, 25% or >10% of the image will be of the area contained within a member.

In this case, the size of the image is a function of the size of the camera sensor, the magnification and members of the optical path (e.g. the field diaphragm). In this way, the entire sensor is filled with molecules (as opposed to the blank area outside of the members), so maximizing data collection and so sample throughput. Having members larger than the camera sensor will also reduce problems such as ringing or donating seen with spotted arrays.

This method of selecting the magnification, member size, optical path and sensor size are in contrast to traditional microarrays where a single frame includes many members. This is possible for traditional arrays because each member is giving a single measurement. Conversely in a single molecule array, each member is giving thousands, tens of thousands or hundreds of thousands of measurements (with each measurement being the presence of a labeled molecule).

If the average number of fluors per member is known, then the total number of members needed to collect a given number of counts can be calculated. In one embodiment 2, 5, 10, 50, 100, 500 or 1000 members are produced on a single array. The number of flours counted per member depends on the density of the labeled molecules. Each member may contain on average, 100, 500, 1,000, 5,000, 10,000. 20,000, 50,000, 100,000 or more labeled molecules. The combination of members and labeled molecules per member leads to the total number of labeled molecules that can be counted. The total number of molecules can be used to calculate the sensitivity, specificity, positive predictive value, negative predictive value and other parameters or factors. The total number of molecules can be used to calculate the statistical power, the expected false positive and expected false negative rates. Ideally, 10,000, 100,000, 500,000, 1,000,000, 5,000,000, 10,000,000, 100,000,000 or more labeled molecules will be counted for each samples. These will be contained in 1 or more member. The molecules may be labeled with one of more labels. In prenatal testing, the molecules will be counted for each genomic region being tested. Statistical power for the test can be calculated using standard methods and tailored for the specific application (see for example Statistical Methods in Cancer Research—Volumes I & II, edited by Breslow & Day, IARC Scientific Publications).

In prenatal testing, it is preferred to count at least 100,000 molecules and ideally at least 1,000,000 per genomic region being tested. If significant error, contamination or other form of noise are present, then the number of molecules counted will ideally be greater still. The amount of data collected from a single molecule array is very different from a sequencing based test. For example. In whole-genome sequencing, many of sequencing reads will map to chromosomes that are not being tested. Even for targeted sequencing approaches, many sequencing reads will not uniquely map to the genome, will be primer dimers or other artifacts. In a preferred embodiment, a single molecule array does not require sequencing or the mapping of sequences to the genome.

In another aspect, the number of probes that need to be counted for the methods described herein may be so high that multiple substrates are need to analyze a single sample. For example, if a coverslip (e.g. 22 mm×22 mm) is used, the number of molecules available for counting may not be enough to reach the desired sensitivity. In this case, either multiple coverslips or a larger format substrate will be needed. For prenatal testing, substrates of on average 10 mm^2, 100 mm^2, 1000 mm^2 or >1000 mm^2 may be used either individually or in combination.

In another aspect, because of the low density of flours on typical single molecule arrays, orienting the imaging process can be problematic. Accordingly, the method of the present disclosure may comprise using fiducials to determine the location on the slide either before or during the image acquisition. Fiducials may be members or other feature. If they are members they may contain high densities of labeled molecules and the label may be the same or different to the labels used at other members. Fiducials may contain more than one label or more than one type of labeled molecule. Fiducial members may be smaller, larger or the same size as other members on the array. Fiducials may also be produced by etching, lithography, or marking of the surface. Fiducials may exist in groups or be spread throughout the array or both. They may be present in a complex or asymmetric pattern to aid determination of the location of an image or snapshot. Fiducials may be used in the process of automating image acquisitions, with algorithms determining the location from one of more fiducials and then using the known location to start data collection (e.g. by moving from array member to array member).

Orientation on the surface may also be done via an asymmetric substrate or holder or cartridge holding the substrate. It may also be carried out by very precise placement of the array on the imager (e.g. a slide in the stage insert on a microscope).

In another aspect, steps (4) and (5) of the test above may be repeated multiple times for different portions of the imaging substrate such that the results dictate next steps. For example, the tests and methods described herein comprise confirming the presence and precise level of a fetal sample in a genetic sample obtained from a subject before testing for the relative copy number state of genomic targets. As described herein, an allele sensitive assay may be used to quantify the levels of fetal DNA relative to maternal DNA. The resulting probe products may be pulled down to a fetal fraction region 1 on the substrate, and imaged. In some embodiments, if and only if the calculated fetal fraction is above the minimum system requirement, the test may proceed and yield a valid result. In this way, testing of samples that fail to confirm at least the minimum input fetal fraction may be terminated before additional imaging and analysis takes place. Conversely, if the fetal fraction is above the minimum threshold, further imaging (step 4 of the test) of the genomic targets (e.g., chromosome 21, 18 or 13) may proceed followed by additional analysis (step 5 of the test). Other criteria may also be used and tested.

In another aspect, not every SNP probed in the allele-specific assay may result in useful information. For example, the maternal genomic material may have heterozygous alleles for a given SNP (e.g., allele pair AB), and the fetal material may also be heterozygous at that site (e.g., AB), hence the fetal material is indistinguishable and calculation of the fetal fraction fails. Another SNP site for the same input sample, however, may again show the maternal material to be heterozygous (e.g., AB) while the fetal material is homozygous (e.g., AA). In this example, the allele-specific assay may yield slightly more A counts than B counts due to the presence of the fetal DNA, from which the fetal fraction may be calculated. Since the SNP profile (i.e., genotype) cannot be known a priori for a given sample, multiple or numerous SNP sites should be designed such that nearly every possible sample will yield an informative SNP site. Each SNP site may be localized to a different physical location on the imaging substrate, for example by using a different tag for each SNP. However, for a given test, the fetal fraction may only be calculated successfully once. Therefore, a single or multiple locations on the substrate used to interrogate SNPs may be imaged and analyzed (e.g., in groups of one, two, three, four, five, ten, twenty, fifty or less and/or one, two, three, four, five, ten, twenty, fifty or more) until an informative SNP is detected. By alternating imaging and analysis, one may bypass imaging all possible SNP spots and significantly reduce average test duration while maintaining accuracy and robustness.

In another aspect, determining the fetal fraction of a sample may aide other aspects of the system beyond terminating tests for which the portion of fetal fraction in a sample is inadequate. For example, if the fetal fraction is high (e.g., 20%) then for a given statistical power, the number of counts required per genetic target (e.g., chr21) will be lower; if the fetal fraction is low (e.g., 1%) then for the same statistical power, a very high number of counts is required per genomic target to reach the same statistical significance. Therefore, following (4-1) imaging of the fetal fraction region 1, (5-1) analysis of those data resulting in a required counting throughput per genomic target, (4-2) imaging of genomic target region 2 commences at the required throughput, followed by (5-2) analysis of those image data and the test result for genomic variation of the input targets.

In another aspect, steps (4) and (5) of the test above may be repeated further for quality control purposes, including assessment of background levels of fluors on the imaging substrate, contaminating moieties, positive controls, or other causes of copy number variation beyond the immediate test (e.g., cancer in the mother or fetus, fetal chimeraism, twinning) Because image analysis may be real-time, and does not require completion of the entire imaging run before generating results (unlike DNA sequencing methods), intermediate results may dictate next steps from a decision tree, and tailor the test for ideal performance on an individual sample. Quality control may also encompass verification that the sample is of acceptable quality and present, the imaging substrate is properly configured, that the assay product is present and/or at the correct concentration or density, that there is acceptable levels of contamination, that the imaging instrument is functional and that analysis is yielding proper results, all feeding in to a final test report for review by the clinical team.

In another aspect, the test above comprises one or more of the following steps: (1) receiving a requisition (from, for example, an ordering clinician or physician), (2) receiving a patient sample, (3) performing an assay (including a allele-specific portion, genomic target portion and quality controls) on that sample resulting in a assay-product-containing imaging substrate, (4-1) imaging the allele-specific region of the substrate in one or more spectral channels, (5-1) analyzing allele-specific image data to compute the fetal fraction, (pending sufficient fetal fraction) (4-2) imaging the genomic target region of the substrate in one or more spectral channels, (5-2) analyzing genomic target region image data to compute the copy number state of the genomic targets, (4-3) imaging the quality control region of the substrate in one or more spectral channels, (5-3) analyzing quality control image data to compute validate and verify the test, (6) performing statistical calculations, (7) creating and approving the clinical report, and (8) sending the report back to the ordering clinician or physician.

Individual molecules in the array and their interaction with target molecules can be detected using a number of means. Detection can be based on measuring, for example physicochemical, electromagnetic, electrical, optoelectronic or electrochemical properties, or characteristics of the immobilized molecule and/or target molecule.

There are two factors that are pertinent to single molecule detection of molecules on a surface. The first is achieving sufficient spatial resolution to resolve individual molecules. The density of molecules is such that only one molecule is located in the diffraction limit spot of the microscope which is ca. 300 nm. Low signal intensities reduce the accuracy with which the spatial position of a single molecule can be determined. The second is to achieve specific detection of the desired single molecules as opposed to background signals.

Scanning probe microscopy (SPM) involves bringing a probe tip into intimate contact with molecules as the tip is scanned across a relatively flat surface to which the molecules are attached. Two well-known versions of this technique are scanning tunnelling microscopy (STM) and atomic force microscopy (AFM; see Moeller et al., 2000, NAR 28: 20, e91) in which the presence of the molecule manifests itself as a tunnel current or a deflection in the tip-height of the probe, respectively. AFM can be enhanced using carbon nanotubes attached to the probe tip (Wooley et al., 2000, Nature Biotechnology 18:760-763). An array of SPM probes which can acquire images simultaneously are being developed by many groups and can speed the image acquisition process. Gold or other material beads can be used to help scanning probe microscopy find molecules automatically.

Optical methods based on sensitive detection of absorption or emission can be used. Typically optical excitation means are used to interrogate the array, such as light of various wavelengths, often produced by a laser source. A commonly used technique is laser-induced fluorescence. Although some molecules are sufficiently inherently luminescent for detection, generally molecules in the array (and/or target molecules) need to be labelled with a chromophore such as a dye or optically active particle (see above). If necessary, the signal from a single molecule assay can, for example, be amplified by labelling with dye loaded nanoparticles, or multi-labelled dendrimers or PRPs/SPRs. Raman spectroscopy is another means for achieving high sensitivity.

Plasmon resonant particles (PRPs) are metallic nanoparticles which scatter light elastically with remarkable efficiency because of a collective resonance of the conduction electrons in the metal (i.e. the surface plasmon resonance). PRPs can be formed that have scattering peak anywhere in the visible range of the spectrum. The magnitude, peak wavelength and spectral bandwidth of the plasmon resonance associated with a nanoparticle are dependent on a particle's size, shape and material composition, as well as local environment. These particles can be used to label a molecule of interest. SERS [Surface-enhanced Raman Scattering] on nanoparticles exploit raman vibrations on metallic nanoparticles of the single molecules themselves and can be used to amplify their spectroscopic signatures.

Further, many of these techniques can be applied to fluorescence resonance energy transfer (FRET) methods of detecting interactions where, for example, the molecules in the array are labelled with a fluorescent donor and the target molecules (or reporter oligonucleotides) are labelled with a fluorescent acceptor, a fluorescent signal being generated when the molecules are in close proximity. Moreover, structures such as molecular beacons where the FRET donor and acceptor (quencher) are attached to the same molecule can be used.

The use of dye molecules encounters the problems of photobleaching and blinking Labelling with dye-loaded nanoparticles or surface plasmon resonance (SPR) particles reduces the problem. However a single dye molecule bleaches after a period of exposure to light. The photobleaching characteristics of a single dye molecule have been used to advantage in the single molecule field as a means for distinguishing signal from multiple molecules or other particles from the single molecule signal.

Spectroscopy techniques require the use of monochromatic laser light, the wavelength of which varies according to the application. However, microscopy imaging techniques can use broader spectrum electromagnetic sources.

Optical interrogation/detection techniques include near-field scanning optical microscopy (NSOM), confocal microscopy and evanescent wave excitation. More specific versions of these techniques include far-field confocal microscopy, two-photon microscopy, wide-field epi-illumination, and total internal reflection (TIR) microscopy. Many of the above techniques can also be used in a spectroscopic mode. The actual detection means include charge coupled device (CCD) cameras and intensified CCDs, photodiodes and photomultiplier tubes. These means and techniques are well-known in the art. However, a brief description of a number of these techniques is provided below.

Field Scanning Microscopy (NSOM): In NSOM, subdiffraction spatial resolutions in the order of 50-100 nm are achieved by bringing a sample to within 5-10 nm of a subwavelength-sized optical aperture. The optical signals are detected in the far field by using an objective lens either in the transmission or collection mode (see Barer, Cosslett, eds 1990, Advances in Optical and Electron Microscopy. Academic; Betzig, 1992, Science 257: 189-95). The benefits of NSOM are its improved spatial resolution and the ability to correlate spectroscopic information with topographic data. The molecules of the array need to either have an inherent optically detectable characteristic such as fluorescence, or be labelled with an optically active dye or particle, such as a fluorescent dye. It has been proposed that resolution can be taken down to just a few nanometres by scanning apertureless microscopy (Scanning Interferometric Apertureless Microscopy: Optical Imaging at 10 Angstrom Resolution" F. Zenhausern, Y. Martin, H. K. Wickramasinghe, Science 269, p. 1083; T. J. Yang, G. A. Lessard, and S. R. Quake, "An Apertureless Near-Field Microscope for Fluorescence Imaging", Applied Physics Letters 76: 378-380 (2000).

In confocal microscopy, a laser beam is brought to its diffraction-limited focus inside a sample using an oil-immersion, high-numerical-aperture objective. The fluorescent signal emerging from a 50-100 μm region of the sample is measured by a photon counting system and displayed on a video system (for further background see Pawley J. B., ed 1995, Handbook of Biological Confocal Microscopy). Improvements to the photon-counting system have allowed single molecule fluorescence to be followed in real time (see Nie et al., 1994, Science 266: 1018-21). A further development of far-field confocal microscopy is two-photon (or multi-photon) fluorescence microscopy, which can allow excitation of molecules with different excitation wavelengths with single higher wavelength source (the molecule undertakes multiple lower energy excitations see for example, Mertz et al., 1995, Opt. Lett. 20: 2532-34). The excitation is also very spatially localised.

Wide-Field Epi-Illumination: The optical excitation system used in this method generally consists of a laser source, defocusing optics, a high performance dichroic beamsplitter, and an oil-immersion, low autofluorescence objective. Highly sensitive detection is achieved by this method using a cooled, back-thinned charge-coupled device (CCD) camera or an intensified CCD (ICCD). High-powered mercury lamps can also be used to provide more uniform illumination than is possible for existing laser sources. The use of epi-fluorescence to image single myosin molecules is described in Funatsu et al., 1995, Nature 374: 555-59.

At the interface between glass and liquid/air, the optical electromagnetic field decays exponentially into the liquid phase (or air). Molecules in a thin layer of about 300 nm immediately next to this interface can be excited by the rapidly decaying optical field (known as an evanescent wave). A molecule intimate to the surface feels the field more than one that is close to 300 nm away. A description of the use of evanescent wave excitation to image single molecules is provided in Hirschfeld, 1976, Appl. Opt. 15: 2965-66 and Dickson et al., 1996, Science 274: 966-69. The imaging set-up for evanescent wave excitation typically includes a microscope configured such that total internal reflection occurs at the glass/sample interface (Axelrod D. Methods on Cell Biology 1989 30: 245-270). Alternatively a periodic optical microstructures or gratings can provide evanescent wave excitation at the optical near-field of the grating structures. This serves to increase array signals around 100 fold (surface planar waveguides have been developed by Zeptosens, Switzerland; similar technology has been developed by Wolfgag Budach et al., Novartis AG, Switzerland—poster at Cambridge Healthtech Institutes Fifth Annual meeting on "Advances in Assays, Molecular Labels, Signalling and Detection). Preferably an intensified CCD is used for detection.

Superresolution Far-Field Optical Methods: Superresolution far-field optical methods have been highlighted by Weiss, 2000 (PNAS 97: 8747-8749). One new approach is point-spread-function engineering by stimulated emission depletion (Klar et al 2000, PNAS 97: 8206-8210) which can improve far-field resolution by 10 fold. Distance measurement accuracy of better than 10 nm using far field microscopy, can be achieved by scanning a sample with nanometer size steps using a piezo-scanner (Lacoste et al PNAS 2000 97: 9461-9466). The resulting spots are localised accurately by fitting then to the known shape of the excitation point-spread function of the microscope Similar measurement capabilities by circular scanning of the excitation beam are known. Shorter distances can typically be measured by molecular labelling strategies utilising FRET (Ha et al Chem. Phys. 1999 247: 107-118) or near field methods such as SPM. These distance measurement capabilities are useful for the sequencing applications proposed in this invention.

Microarray Scanners: The burgeoning microarray field has introduced a plethora of different scanners based on many of the above described optical methods. These include scanners based on scanning confocal laser, TIRF and white light for illumination and Photomultiplier tubes, avalanche photodiodes and CCDs for detection. However, commercial array scanners in their standard form are not sensitive enough for SMD and the analysis software is inappropriate.

In this way as many or as few of the members in the array can be read and the results processed. x-y stage translation mechanisms for moving the substrate to the correct position are available for use with microscope slide mounting systems (some have a resolution of 100 nm). Movement of the stage can be controlled automatically by computer if required. Ha et al (Appl. Phys. Lett. 70: 782-784 (1997)) have described a computer controlled optical system which automatically and rapidly locates and performs spectroscopic measurements on single molecules. A galvonometer mirror or a digital micromirror device (Texas Instruments, Houston) can be used to enable scanning of the image from a stationary light source. Signals can be processed from the CCD or other imaging device and stored digitally for subsequent data processing.

Multicolour imaging: Signals of different wavelength can be obtained by multiple acquisitions or by simultaneous acquisition by splitting the signal, using RGB detectors or analysing the whole spectrum (Richard Levenson, Cambridge Healthtech Institutes, Fifth Annual meeting on Advances in Assays, Molecular Labels, Signalling and Detection, May 17-18th Washington D.C.). Several spectral lines can acquired by the use of a filter wheel or a monochromater. Electronic tunable filters such as acoustic-optic tunable filters or liquid crystal tunable filters can be used to obtain multispectral imaging (e.g. Oleg Hait, Sergey Smirnov and Chieu D. Tran, 2001, Analytical Chemistry 73: 732-739). An alternative method to obtain a spectrum is hyperspectral imaging (Schultz et al., 2001, Cytometry 43:239-247).

The Problem of Background Fluorescence: Microscopy and array scanning are not typically configured for single molecule detection. The fluorescence collection efficiency must be maximized and this can be achieved with high numerical aperture (NA) lenses and highly sensitive electro-optical detectors such as avalanche diodes that reach quantum yields of detection as high as 0.8 and CCDs that are intensified (e.g. I-PentaMAX Gen III; Roper Scientific, Trenton, N.J. USA) or cooled (e.g. Model ST-71 (Santa Barbara Instruments Group, CA, USA). However, the problem is not so much the detection of fluorescence from the desired single molecule (single fluorophores can emit ~$10^8$ photons/sec) but the rejection of background fluorescence. This can be done in part by only interrogating a minimal volume as done in confocal, two-photon and TIRF microscopy. Traditional spectral filters (e.g. 570DF30 Omega Filters) can be applied to reduce the contribution from surrounding material (largely Rayleigh and Raman scattering of the excitation laser beam by the solvent and fluorescence from contaminants).

To reduce background fluorescence to levels which allow legitimate signal from single molecules to be detected a pulsed laser illumination source synchronized with a time gated low light level CCD can be used (Enderlein et al in: Microsystem technology: A powerful tool for biomolecular studies; Eds.: M. Kohler, T. Mejevaia, H. P. Saluz (Birkhäuser, Basel, 1999) 311-29)). This is based on the phenomenon that after a sufficiently short pulse of laser excitation the decay of the analyte fluorescence is usually much longer (1-10 ns) than the decay of the light scattering (~$10^2$ ps). Pulsing of a well-chosen laser can reduce the background count rate so that individual photons from individual fluorophores can be detected. The laser power, beam size and repetition rate must be appropriately configured. A commercial array scanner and its software can be customized (Fairfield Enterprises, USA) so that robust single molecule sensitivity can be achieved. Alternatively, Time Correlated Single-Photon Counting (TCSPC) can be used to gather all the fluorescent emission after a pulsed excitation and then sort out the background emission from the target emission by their temporal profile. Suitable commercial instruments are available (e.g. LightStation, Attotec, Heidelberg, Germany).

In addition to these methods that combat fluorescence noise from within the sample volume, the instrument itself can contribute to background noise. Such thermoelectronic noise can be reduced for example by cooling of the detector. Coupling SPM measurements with optical measurements allows correlation of signals optically detected to the targeted structures rather than those due to other sources. Spatial or temporal correlation of signal from two (fluorescent) probes targeting the same molecule suggests the desired rather than extraneous signal (e.g. Castro and Williams, Anal. Chem. 1997 69: 3915-3920). A FRET based detection scheme also facilitates rejection of background.

Low fluorescence immersion oils are preferably used, as are substrates that are ultra-clean and of low intrinsic fluorescence. Glass slides/coverslips are preferably of high quality and well cleaned (e.g. with detergents such as Alconex and Chromerge (VWR Scientific, USA) and high purity water). Preferably, a substrate such as fused quartz or pure white glass is used, which has a low intrinsic fluorescence. Single fluorophores can be distinguished from contaminating particles by several features: spectral dependence, concentration dependence, quantized emission and blinking Particulate contaminants usually have broad spectrum fluorescence which is obtained in several filter sets whereas single fluorophores are only visible in specific filter sets.

The signal to noise ratio can also be improved by using labels with higher signal intensities such as fluospheres (Molecular Probes Inc.) or multilabelled dendrimers.

Scavengers can be placed into the medium to prevent photobleaching. Suitable oxygen scavanges include, for example, glycine DTT, mercaptoethanol, glycerol etc.

Label Free Detection: A number of physical phenomena can be adapted for detection, that rely on the physical properties of the immobilized molecules alone or when complexed with captured targets or that modify the activity or properties of some other elements. For example, terahertz frequency allows the difference between double stranded and single stranded DNA can be detected; Brucherseifer et al., 2000, Applied Physics Letters 77: 4049-4051. Other means include interferometry, elliposometry, refraction, the modification of the signal from a light emitting diode integrated into the surface, native electronic, optical (e.g. absorbance), optoelectronic and electrochemical properties, a quartz crystal microbalance and various modes of AFM which can detect differences on the surface in a label free manner.

Processing of Raw Data and Means for Error Limitation

Digital analysis of signals: Discrete groups of assay classification (e.g. nucleotide base calling) can be defined by various measures. A set of unique parameters are chosen to define each of several discrete groups. The result of interrogation of each individual molecule can be assigned to one of the discrete groups. One group can be assigned to represent signals that do not fall within known patterns. For example there may be groups for real base additions, a, c, g, and tin extension assays.

One of the prime reasons that single molecule resolution techniques are set apart from bulk methods is that they allow access to the behaviour of individual molecules. The most basic information that can be obtained is the frequency of occurrence of hits to a particular group. In bulk analysis the signal is represented in analogue by an (arbitrary) intensity value (from which a concentration may be inferred) and this indicates the result of the assay in terms of, say, a base call or it may indicate the level of a particular molecule in the sample, by virtue of its calibrated interaction profile (or its relative level in one sample compared with another sample). In contrast, the single molecule approach enables direct counting and classification of individual events.

A general algorithm for single molecule counting, once the single molecules have been labelled by for example thresholding, is:
Loop through all pixels, $p(x,y)$ left to right, top to bottom
a. If $p(x,y)=0$, do nothing
b. If $p(x,y)=1$, add to counter The methods of this invention require basic image processing operations and counting, measuring and assignment operations to be performed on the raw images that are obtained. The invention includes the adaptation and application of general methods including software and algorithms, known in the art for digital signal processing, counting, measuring and making assignments from the raw data. This includes Bayesian, heuristic, machine learning and knowledge based methods.

Moreover, digital data processing facilitates error correction and temporal resolution of reactions at the array surface. Thus, time-resolved microscopy techniques can be used to differentiate between bona-fide reactions between probe and sample and "noise" due to aberrant interactions which take place over extended incubation times. The use of time-gated detection or time-correlated single-photon counting is particularly preferred in such an embodiment.

The invention accordingly provides a method for sorting signals obtained from single molecule analysis according to the confidence with which the signal may be treated. A high confidence in the signal leads to the signal being added to a PASS group and counted; signals in which confidence is low are added to a FAIL group and discarded, or used in error assessment and as a resource for assay design (for example the propensity of a particular primer sequence to give rise to errors in primer extension, can be used to inform primer design in future experiments.

Signals that satisfy a number of criteria are put into a PASS table. This PASS table is the basis for base calling after counting the number of signals for each colour.

The FAIL table is made so that information about error rate can be gathered. The five different types of errors can be collected into separate compartments in the FAIL table so that the occurrence of the different types of error can be recorded. This information may aid experimental methods to reduce error, for example it can reveal which is the most common type of error. Alternatively, the failed signals can be discarded.

The five criteria that are used to assess errors are: 1. If intensity is less than p where p=a minimum threshold intensity. This is high pass filter to eliminate low fluorescence intensity artefacts; 2. If intensity is less than q, where q=a maximum intensity threshold. This is a lowpass filter to eliminate high fluorescence intensity artefacts; 3. If time is less than x where x=early time point. This is to eliminate signals due to self-priming which can occur early; 4. If time is greater than z, where z=late time point. This is to eliminate signals due to mis-priming of nucleotides which the enzyme can incorporate over an extended period. For example this can be due to priming by template on template, which is a two-step process, involving hybridization of the first template to array and then hybridization of the second template molecule to the first template molecule; and 5. Nearest neighbour pixels are compared to eliminate those in which signal is carried over multiple adjacent pixels which is indicative of signals from, for example, non-specific adsorption of clumps or aggregates of ddNTPs.

The reaction is controlled by adjusting reaction components, for example salt concentration, ddNTP concentration, temperature or pH such that the incorporations occur within the time window analysed A subroutine can be included to check that the fluorescence shows single-step photobleaching characteristic, but ignoring short-scale fluctuations which are likely to be due to blinking.

If a single dye molecule, which photobleaches after a time, is associated with each ddNTP, then an additional sub-process/routine can be added which eliminates signals that after an initial burst re-occur in the same pixel after such a number of time points that the absence cannot be attributed to blinking. This is likely to be non-specific absorption at the same foci as a legitimate extension.

A sub-routine can be included to eliminate any fluorescence that occurs in multiple filters, above the level expected for the dye being analysed Fluorescence due to a single dye molecule can be distinguished from particulate contamination by analysing the concentration dependence of the signal. This can be done if each sequence is arrayed at two or more concentrations. Signals that remain at equal concentration across the array dilution are artefacts, real signals are those whose frequency changes in line with changes in array probe concentration.

If the array is composed of members an additional process can be used to organise the data into groupings representing the array members.

Figure 80:
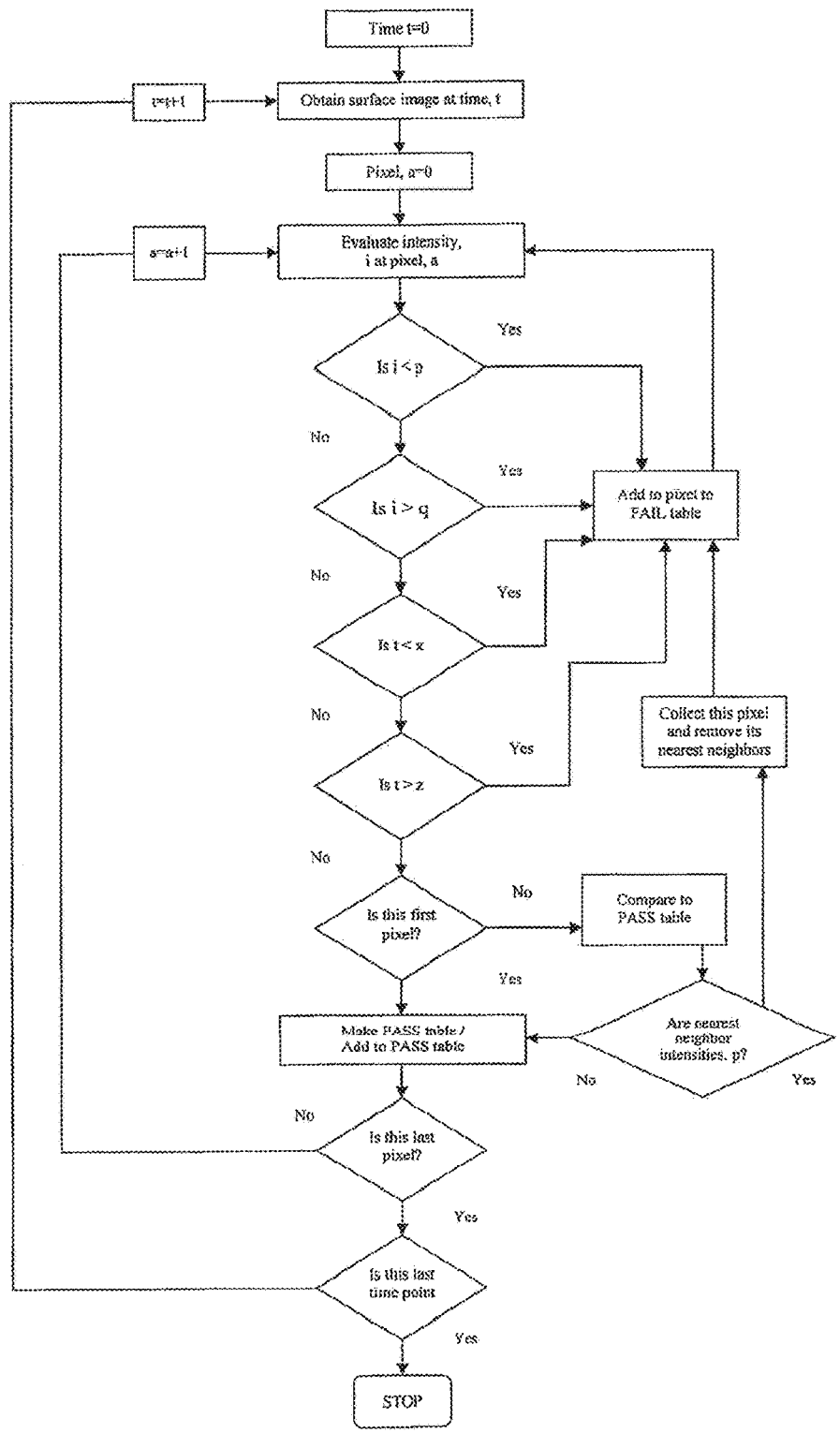
FIG. 80 shows an exemplary scheme describing a system configured such that a single pixel measures a single molecule event (statistically, in the large majority of cases). The system can be set up, for example, such that several pixels are configured to interrogate a single molecule.

In the scheme described the system is configured such that a single pixel measures a single molecule event (statistically, in the large majority of cases). The system can be set up, for example, such that several pixels are configured to interrogate a single molecule (FIG. 80).

Thus, in a preferred embodiment, the invention relates to a method for typing single nucleotide polymorphisms (SNPs) and mutations in nucleic acids, comprising the steps of: a) providing a repertoire of probes complementary to one or more nucleic acids present in a sample, which nucleic acids may possess one or more polymorphisms; b) arraying said repertoire on to a solid surface such that each probe in the repertoire is resolvable individually; c) exposing the sample to the repertoire and allowing nucleic acids present in the sample to hybridize/process with enzymes to the probes at a desired stringency such that hybridized/processed with enzymes nucleic acid/probe pairs are detectable; d) imaging the array in order to detect individual target nucleic acid/probe pairs; e) analysing the signal derived from step (d) and computing the confidence in each detection event to generate a PASS table of high-confidence results; and f) displaying results from the PASS table to type polymorphisms present in the nucleic acid sample.

Advantageously, detection events are generated by labelling the sample nucleic acids and/or the probe molecules, and imaging said labels on the array using a suitable detector. Preferred labelling and detection techniques are described herein.

Methods for reducing errors: Single molecule analysis allows access to specific properties and characteristics of individual molecules and their interactions and reactions. Specific features of the behaviour of a particular molecular event on a single molecule may belie information about its origin. For enzymatic assays, for example, there may be a slower rate of mis-incorporations than correct incorporations. Another example is that there may be a different rate of incorporations for self-priming compared to priming in which the target forms the template. The rate characteristics of self-priming are likely to be faster than from priming of sample. This is because self-priming is a unimolecular reaction whereas priming of sample DNA is bimolecular. Therefore if time-resolved microscopy is performed, the time-dependence of priming can distinguish self-priming and mis-priming from correct sample priming. Alternatively, it might be expected that DNA priming from the perfectly matched sample has the capacity to incorporate a greater number of fluorescent dye NTPs in a multi-primer primer extension approach (Dubiley et al., Nucleic Acids Research 1999 27: e19i-iv) than mis-priming and a self-priming and so gives a higher signal level or molecular brightness.

It can be difficult to differentiate between correct incorporation and mis-incorporation in the mini-sequencing (multi-base approach) because even though a wrong base may take longer to incorporate it may be associated with the primer for the same length of time as the correctly incorporated base. In order to address this problem, if the fluorescence intensity of a ddNTP is quenched to some degree when it is incorporated then the molecular brightness/fluorescence intensity can be used to distinguish between mis-incorporation, which takes longer to become fixed, and correct incorporation.

Different means for reduction of errors can be engineered into the system. For example, in genetic analysis, FRET probes can be integrated at the allelic site. The conformation of a perfect match allows the fluorescent energy to be quenched whereas the conformation of a mismatch does not. The FRET probes can be placed on a spacer, which can be configured to accentuate the distances of FRET probes between matched and mismatched base pair sets.

Mismatch errors can be eliminated in some cases by cleavage with enzymes such as Ribonuclease A. This enzyme cleaves mismatches in RNA:DNA heteroduplexes (Myers R M, Larin Z, Maniatis T. Science 1985 Dec. 13; 230(4731):1242-6)

In primer extension, the enzyme, Apyrase, a nucleotide degrading enzyme, can be employed for accurate discrimination between matched and mismatched primer-template complexes. The apyrase-mediated allele-specific extension (AMASE) protocol allows incorporation of nucleotides when the reaction kinetics are fast (matched 3'-end primer) but degrades the nucleotides before extension when the reaction kinetics are slow (mismatched 3'-end primer)(Ahmadian et al Nucleic Acids Research, 2001, Vol. 29, No. 24 e121).

In addition to false positive errors discussed above, false negatives can be a major problem in hybridization based assays. This is particularly the case when hybridization is between a short probe and a long target, where the low stringency conditions required to form stable heteroduplex concomitantly promotes the formation of secondary structure in the target which masks binding sites. The effects of this problem can be reduced by fragmenting the target, incorporating analogue bases into target (e.g. incorporating into the target analogue bases that cannot pair with each other but can pair with natural DNA bases of the probe) or probe, manipulating buffers etc. Enzymes can help reduce false negatives by trapping transient interactions and driving the hybridization reaction forward (Southern, Mir and Shchepinov, 1999, Nature Genetics 21: s5-9). This effect can also be achieved by cross-linking psoralen labelled probes to their target molecules. However, it is likely that false negatives will remain to some level. As previously mentioned, because large-scale SNP analysis without the need for PCR is enabled the fact that some SNPs do not yield data is not a major concern. For smaller scale studies, effective probes may need to be pre-selected.

In cases where the amount of sample material is low, special measures must be taken to prevent sample molecules from sticking to the walls of the reaction vessel and other vessels used for handling the material. These vessels can be silanised to reduce sticking of sample material and/or can be treated in advance with blocking material such as Denhardt's reagent or tRNA.

Managing haplotyping errors: When performing haplotyping studies (see section D2) the position along the captured target molecule of the SNP sites that will be interrogated is known (unless there are duplications or deletions in between SNPs). In some cases it may be that all the probes have bound to their SNP sites. Zhong et al (PNAS 98: 3940-3945) used Rolling circle amplification (RCA) to visualize haplotypes on FISH fibers state that many of the fibers show the binding of oligonucleotide probes to three contiguous sites along the molecule. However very often every probe will not bind to its complementary sequence and there may be gaps in the string of sites along the molecule. However, as a population of molecules will be available for analysis, the correct information about the SNP allele at each of the sites can be reconstructed algorithmically from the information obtained from all the molecules of a particular species that have been captured on the spatially addressable single molecule array.

In one embodiment the image of the fibers and the bound probes will be acquired and then the information processed. 1. Capture image in and around each array member; 2. Process information offline. There are image processing packages that are specific for this kind of application.

In another embodiment, machine vision will be used to find and track along single molecules with the option of processing information during the process ("on the fly").

The following lists show the steps that would form the basis of a computer program for removing erroneous strands from the analysis and passing on good information to the sequence reconstruction program: 1. Go to a particular microarray member; 2. Download prior data about expected positional arrangement of SNPs along strands expected to be captured in that member; 3. Recognise Fibres/strands (end markers may aid this); 4. Recognise markers (e.g. end markers); 5. Visualise position of probes along molecule; 6. Estimate distance separating probes (markers can aid this); 7. Evaluate if the distance separating consecutive probes agrees with expected; 8. If probes are at the expected separations for a given fibre go to 10; 9. If not then, a. If absence of probe binding, ignore fiber, b. If completely aberrant binding pattern, ignore fibre/add to fail table, c. If gaps in SNP sites, gather information that is present, goto 10; 10. Determine identity of label at each position where binding occurs, goto 11; and 11. Add identity of label to reconstruction algorithm. See Digital Image Processing, Rafael C. Gonzalez, Richard E. Woods, Pub: Addison-Wesley.

Reconstruction Algorithm: The reconstruction algorithm will overlap the data from the fibres and will evaluate if there are one (homozygote for the haplotype) or two (heterozygote for the haplotype) haplotypes present and what they are. In the case of pooled DNA there may be the possibility of more than two different haplotypes.

It may be that the wrong strand has been captured by the array probes. It will be simple to weed out such instances because it is unlikely that the haplotype probes will hybridize to such a molecule and if they do then it will be to aberrant positions along the molecule, which can be identified. The greater problem will be when a non-functional duplicate of the sequence (e.g. pseudogene) becomes captured. This may indicate different alleles within the haplotype than the functional copy of the sequence. Although this kind of occurrence can be detected when it is rare, it will be more difficult when it competes effectively with the functional sequence. This kind of error can be managed, however, by the prior knowledge about the organisation of the genome and the occurrence of duplications within the genome. Regions of the genome that are known to be duplicated may be avoided or their contribution will be accounted for.

Precise physical distances can be computed. The use of markers other than the labels may aid this, for example marking the ends of the molecule or other sites, including SNP sites with markers that can be distinguishable from the 2-colour SNP tags used for the majority of SNPs.

In some cases, despite stringency control, the probe may have bound but it may be a mismatch interaction. However, because of its relative rarity in the population of single molecules that are analysed it can be ignored (or added to a list of alleles that give erroneous interactions, for future reference). In Pooled DNA or when the sample is from a heterogeneous sample of cell the assay may have to allow for a small degree of error of this kind. For example, the accuracy with which the frequency of a rare allele is obtained may be 1 in a 1000+/−1.

The error management approaches outlined here may also be relevant to fingerprinting and re-sequencing (see section D3) in some instances.

Alternative methods for detection and decoding of results: The molecules can be detected, as mentioned above, using a detectable label or otherwise, and correlating the position of the label on an array with information about the nature of the arrayed probe to which the label is bound. Further detection means may be envisaged, in which the label itself provides information about the probe which is bound without requiring positional information. For example, each probe sequence can be constructed to comprise unique fluorescent or other tags (or sets thereof), which are representative of the probe sequence. Such encoding can be done by stepwise co-synthesis of probe and tag by split and pool combinatorial chemistry. Ten steps generates every 10 mer encoded oligonucleotide (around 1 million sequences). 16 steps generates every 16mer encoded oligonucleotides (around 4 billion sequences) which is expected to occur only once in the genome. Fluorescent tags that are used for encoding can be of different colours or different fluorescent lifetimes. Moreover, unique tags can be attached to individual single molecule probes and used to isolate molecules on anti-tag arrays. The anti-tag arrays may be spatially addressable or encoded.

Assay techniques and uses: A further aspect of the present invention relates to assay techniques based on single molecule detection. These assays can be conducted using molecular arrays produced by the methods of the invention or by any other suitable means.

The spatial addressable array is a way of capturing and organizing molecules. The molecules can then be assayed in a plethora of ways, including using any assay method which is suitable for single molecule detection, such as those described in WO0060114; U.S. Pat. No. 6,210,896; Watt Webb, Research Abstract: New Optical Methods for Sequencing Individual Molecules of DNA, DOE Human Genome Program Contractor-Grantee Workshop III, on Feb. 5, 2001.

In general, the assay methods of the invention comprise contacting a molecular array with a sample and interrogating all or part of the array using the interrogation/detection methods described above. Alternatively, the molecular array is itself the sample and is subsequently interrogated directly or with other molecules or probes using the interrogation/detection methods described above.

Many assay methods rely on detecting binding between immobilized molecules in the array and target molecules in the sample. However other interactions that may be identified include, for example, interactions that may be transient but which result in a modification to the properties of an immobilized molecule in the array, such as charge transfer.

Once the sample has been incubated with the array for the desired period, the array can simply be interrogated (following an optional wash step). However, in certain embodiments, notably nucleic acid-based assays, the captured target molecules can be further processed or incubated with other reactants. For example, in the case of antibody-antigen reactions, a secondary antibody which carries a label can be incubated with the array containing antigen-primary antibody complexes.

Target molecules of interest in samples applied to the arrays can include nucleic acids such as DNA and analogues and derivatives thereof, such as PNA. Nucleic acids can be obtained from any source, for example genomic DNA or cDNA or synthesised using known techniques such as step-wise synthesis. Nucleic acids may be single or double stranded. Other molecules include: compounds joined by amide linkages such as peptides, oligopeptides, polypeptides, proteins or complexes containing the same; defined chemical entities, such as organic molecules; combinatorial libraries; conjugated polymers, lipids and carbohydrates.

Due to the high sensitivity of the approach specific amplification steps can be eliminated if desired. Hence, in the case of analysis of SNPs, extracted genomic DNA can be presented directly to the array (a few rounds of whole genome amplification may be desirable for some applications). In the case of gene expression analysis normal cDNA synthesis methods can be employed but the amount of starting material can be low. Genomic DNA is typically fragmented prior to use in the methods of the present invention. For example, the genomic DNA may be fragmented such that substantially all of the DNA molecules are 1 Mb, 100 kb, 50 kb, 10 kb and/or 1 kb or less in size. Fragmentation can be achieved using standard techniques such as passing the DNA through a narrow gauge syringe, sonication, alkali treatment, free radical treatment, enzymatic treatment (e.g. DNaseI), or combinations thereof.

Target molecules may be presented as populations of molecules. More than one population can be applied to the array at the same time. In this case, the different populations are preferably differentially labelled (e.g. cDNA populations may be labelled with Cy5 or Cy3). In other cases such as analysis of pooled DNA, each population may or may not be differentially labelled.

A number of assay methods of the present invention are based on hybridization of analyte to the single molecules of the array members. The assay may stop at this point and the results of the hybridization analysed.

However, the hybridization events can also form the basis of further biochemical or chemical manipulations or hybridization events to enable further probing or to enable detection (as in a sandwich assay). These further events include primer extension from the immobilized molecule/captured molecule complex; hybridization of additional probes to the immobilized molecule/captured molecule complex and ligation of additional nucleic acid probes to the immobilized molecule/captured molecule complex.

For example, following specific capture (by hybridization or hybridization plus enzymatic or chemical attachment) of a single target strand by immobilized oligonucleotide(s), further analysis can be performed on the target molecule. This can be done on an end-immobilized target (or a copy thereof—see below). Alternatively, the immobilized oligonucleotide anchors the target strand which is then able to interact with a second (or higher number) of immobilized oligonucleotide(s), thereby causing the target strand to lay horizontally. Where the different immobilized oligonucleotides are different allelic probes for different loci, the target strand can be allelically defined at multiple loci.

The target strand can also be horizontalised and straightened, after being captured by an immobilized oligonucleotide by various physical methods known in the art. This can allow spatially addressable combing of target nucleic acids and makes them amenable to further analysis.

In one embodiment, following hybridization the array oligonucleotide can be used as a primer to produce a permanent copy of the bound target molecule which is covalently fixed in place and is addressable.

In most single molecule assays the results are based on the analysis of a population of each of the target molecular species. For example, each array spot may capture a multitude of copies of a particular species. In some cases, however the result may be based on signals from one molecule only and not on the census of a multitude of molecules.

Single molecule counting of these assays allows even a rare polymorphism/mutation in a largely homogeneous population to be detected.

Some specific assay configurations and uses are described below.

Nucleic acid arrays and accessing genetic information: To interrogate sequence, in most cases the target must be in single stranded form. The exception includes cases such as triplex formation, binding of proteins to duplex DNA (Taylor J R, Fang, M M and S. Nie, 2000, Anal. Chem. 72:1979-1986), or sequence recognition facilitated by RecA (see Seong et al., 2000, Anal. Chem. 72: 1288-1293) or by the use of PNA probes (Bukanov et al, 1998, PNAS 95: 5516-5520; Cherny et al, 1998, Biophysical Journal 1015-1023). Also, the detection of mismatches in annealed duplexes by MutS protein has been demonstrated (Sun, H B S and H Yokoto, 2000, Anal. Chem 72: 3138-3141). Long RNAs (e.g. mRNA) can form R-loops inside linear ds DNA and this can be the basis for mapping of genes on arrayed genomic DNA. Where a double stranded DNA target is arrayed, it may be necessary to provide suitable conditions to partially disrupt the native base-pairing in the duplex to enable hybridization to probe to occur. This can be achieved by heating the surface/solution of the substrate, manipulating salt concentration/pH or applying an electric field to melt the duplex.

One preferred method for probing sequences is by probing double stranded DNA using strand invasion locked nucleic acid (LNA) or peptide nucleic acid (PNA) probes. This can be done under conditions where transient breathing nodes in the duplex structure can arise, such as at 50-65° C. in 0-100 mM monovalent cation.

Software tools for the prediction of LNA melting points are available in the art, for example at www.lna-tm.com. Tools for design of PNA probes (including PNA molecular beacons) are available at www.bostonprobes.com. Also see Kuhn et al., J Am Chem Soc. 2002 Feb. 13; 124(6):1097-103) for design of PNA probes.

Molecular Combing methods: There are several methods that have been described to stretch out double stranded DNA so that it can be interrogated along its length. Methods include optical trapping, electrostatic trapping, molecular combing (Bensimon et al., Science 1994 265: 20962098), forces within an evaporating droplet/film (Yokota et al., Anal. Biochem 1998 264:158-164; Jing et al., PNAS 1998 95: 8046-8051), centrifugal force and moving the air-water interface by a jet of air (Li et al., Nucleic Acid Research (1998) 6: 4785-4786).

Molecular Combing which involves surface tension created by a moving air-water interface/mensicus and a modification to the basic technique has been used to stretch out several hundred haploid genomes on a glass surface (Michalet et al., Science. 1997 277: 1518-1523).

Relatively fewer methods have been described for single-stranded DNA. Woolley and Kelly (Nanoletters 2001 1: 345-348) achieve elongation of ssDNA by translating a droplet of DNA solution linearly across a mica surface coated with positive charge. The forces exerted on ssDNA are thought to be from a combination of fluid flow and surface tension at the travelling air-water interface. The forces within fluid flow can be sufficient to stretch out a single strand in a channel Capillary forces can be used to move solutions within channels.

These methods, in addition to stretching out DNA, overcome intermolecular secondary structures which are prevalent in ssDNA under conditions required for hybridization.

An alternative way of overcoming secondary structure formation of nucleic acids on a surface is by heating the surface of the substrate or applying an electric field to the surface.

The majority of the assays described below do not require the molecules to be linearised, as positional information along the molecules length is not required. In the cases where positional information is required, DNA needs to be linearised/horizontalised. The attachment to more than one surface immobilized probe facilitates the process. Double stranded targets can be immobilized to probes having sticky ends such as those created by restriction digestion.

In one embodiment, following capture by an immobilized oligonucleotide, a target strand is straightened. This can be done on a flat surface by molecular combing. In one embodiment the probes are placed on a narrow line on for example, the left most side of an array member and then the captured molecules are stretched out in rows form left side to the right side by a receding air-water interface.

Alternatively the captured target can be stretched out in a channel or capillary where the capture probes are attached to (one or more) walls of the vessel and the physical forces within the fluid cause the captured target to stretch out. Fluid flow facilitates mixing and makes hybridization and other processes more efficient. Reactants can be recirculated within the channels during the reactions.

Single molecules can also be captured and stretched out in a gel. For example, a gel layer can be poured onto a glass slide. Tags, probes or target molecules can be modified at the end with acrydite and co-polymerised with acrylamide monomers within a polyacrylamide gel. When an electric field is applied, as in gel electrophoresis, the molecule can be stretched out, whilst retaining attachment.

After hybridization to tag or probes, it may be advantageous to immobilise the target independently to the surface. This can occur at suitable pH, for example pH 6.5 in 10 mM MES buffer onto bare glass or in 10 mM AMPSO buffer at pH 8.5 onto aminosilane slides. Alternatively, prior to interacting with the array, the target molecule may be pre-reacted with a moiety that will allow covalent attachment to the surface after suitable activation or after given a suitable length of time to react.

In fiber FISH (Fluorescent in situ Hybridization) probes are mapped onto denatured double stranded DNA which is stretched on a surface. Probes bound to DNA give the appearance of beads on a string. It has been suggested that the bead like appearance is due to the fact the conditions used in denaturing the DNA actually cause the DNA chain to snap.

Linearised Molecules: One preferred method for probing sequences is by probing double stranded DNA using strand invasion locked nucleic acid (LNA) or peptide nucleic acid (PNA) probes under conditions where transient breathing nodes in the duplex structure can arise, such as at 50-65.degree. C. in 0-100 mM monovalent cation. Alternatively, methods from Fiber FISH could be used in which the target strand is partially denatured in situ on the slide or before making Fibers. Depending on the method of detection the, probe may be labelled with dye molecules, polylabelled Dendriers or nanoparticles or microspheres. Probes would be preferentially labelled with large nanoparticles or microspheres to be able to be easily detected by epi-fluorescence microscopy, otherwise it may be difficult to see them above background.

Reprobing linearised molecules: In some embodiments of the invention, it may be necessary to remove one or more bound probes before binding of further probes. There are a number of ways that this can be done, including heat, alkali treating, and electric field generation. For serial probing with a complete library it may be necessary to make the removal of bound probe as gentle as possible. One way would be displaced the target strand with a sequence that is complementary to the probe (For a possible mechanism see Yurke et al Nature 406: 605-608, 2000).

Alternatively, when using harsher conditions for removing probe it may be advantageous not to remove probe before each subsequent probe addition but only after several additions. For example all oligonucleotides of a particular Tm could be hybridized simultaneously and then removed. Then all oligonucleotides of another Tm would be added and removed and so on, noting positions of binding after each cycle. Where certain, first, oligonucleotides in one set does not hybridize to a single molecule due to overlap with a second oligonucleotide in the set that does hybridize, it is likely that by looking at the population of single molecules, there may be other single molecules in which the first oligonucleotide binds and the second one does not.

Another solution to the concern about the detrimental effects of the attrition caused by cycling of hybridization and denaturation on the surface.

One problem is that often molecules that are stretched out on a surface undergo light induced breakage. Snapping of the strands of combed Lambda DNA labelled with YOYO can be seen with an epi-fluorescent microscope. Where this happens the length of the DNA contracts. Although this is not desirable, the long range position of oligonucleotides that bind can still be retained. Pulsed laser excitation would be able to overcome this DNA breakage because much lower laser power can be used. Also if the probes are labelled with multilabeled dendrimers or large nanoparticles or microspheres, the fact that the signal that is detected is from many dye molecules means that the illumination intensity can be minimized.

Another way to overcome having to do hundreds or thousands of annealing-denaturation cycles on one slide, is to make a multiple of slides in which the same genome sample is captured (for this it may be necessary to do whole genome amplification first). Then probing on a first slide would be with oligonucleotide sets 1, 2, 3 on a second slide with oligonucleotide sets 4, 5, 6, a third slide with oligonucleotide sets 7, 8, 9 and so on. Information from hybridization to the same spatially addressable sites on each of these slides would be combined to provide the data that would be used to reconstruct the sequence. An array of array could be used in which each array is hybridized to different sets of probes. For example the arrays, and the captured strands may be on the surface of a flat bottomed microtre plate and each well of the plate e.g. each one from a 96 well plate might take different probe sets.

Annealing and denaturation steps could be a cycled on a thermocycler or similar device adapted to enable addition and removal of probe molecules.

Various aspects are discussed below under individual headings but are typically broadly applicable to any detection technique where simultaneous interrogation of a single molecule at multiple sites is desired.

1. Resequencing and/or Typing of Single-Nucleotide Polymorphisms (SNPs) and Mutations a. Hybridization The organisation of the array typically follow the known art as taught by Affymetrix e.g. Lipshutz et al., Nature Genetics 1999 21: s20-24; Hacia et al., Nature Genetics 21: s42-47)) for SNP resequencing or typing. In short, an SNP can be analysed with a block of array members containing defined probes, in the simplest form, with probes to each known or possible allele. This can include substitutions and simple deletions or insertions. However, whereas the Affymetrix techniques require complex tiling paths to resolve errors, advanced versions of the single molecule approach can suffice with simpler arrays, as other means for distinguishing errors can be used. Transient interactions can also be recorded.

Typically the oligonucleotides are between about 17 and 25 nucleotides in length although longer or shorter probes can be used in some instances. The longer probes are particularly useful to overcome the effects of secondary structure. However the longer the length the less easy it is to discriminate a single base difference by hybridization. The choice of conditions is important in achieving single base discrimination with longer probes. For example, Hughes et al (Nature Biotechnology 19: 342-347 2001) have shown that a one base difference in a 55mer can be discriminated. Analysis based on single molecule counting should help.

In a different implementation, a mix of probes complementary to all alleles is placed within a single array member. Each probe comprising a different allele is distinguishable from the other probes, e.g. each single molecule of a particular allele can have a specific dye associated with it. A single molecule assay system of the invention allows this space saving operation and is simple to do when pre-synthesised oligos are spotted on the array.

The probe can be appended with a sequences that promote its formation into a secondary structure that facilitate the discrimination of mismatch (e.g. a stem loop structure where the probe sequence is in the loop).

Similarly the probe sequence can be a molecular beacon making the assay free from the need for extrinsic labels.

The following are typical reaction conditions that can be used: 1M NaCl or 3-4.4 M TMACl (tetramethyl ammonium chloride) in Tris Buffer, target sample, 4 to 37° C. in a humid chamber for 30 mins to overnight.

It is recognised that hybridization of rare species is discriminated against under conventional reaction conditions, whilst species that are rich in A-T base pairs are not able to hybridize as effectively as G-T rich sequences. Certain buffers are capable of equalising hybridization of rare and A-T rich molecules, to achieve more representative outcomes in hybridization reactions. The following components may be included in hybridization buffers to improve hybridization with positive effects on specificity and/or reduce the effects of base composition and/or reduce secondary structure and/or reduce non-specific interactions and/or facilitate enzyme reactions:

1M Tripropylamine acetate; N,N-dimethylheptylamine; 1-Methyl piperdine; LiTCA; DTB; C-TAB; Betaine; Guanidinium isothyacyanate; Formamide; Tetramethy ammonium chloride (TMACl); Tetra ethyl Ammonium Chloride (TEACl); Sarkosyl; SDS (Sodium dodecyl sulphate); Dendhardt's reagent; Poly ethyene Glycol; Urea; Trehalose; Cot DNA; tRNA; Poly d(A)

N—N-dimethylisopropylamine acetate.

Buffers containing N—N-dimethylisopropylamine acetate are very good for specificity and base composition. Related compounds with similar structure and arrangement of charge and/or hydrophobic groups can also be used. Refer to WO9813527.

Probes are chosen, where possible, to have minimal potential for secondary structure (unless it is part of the design) and cross hybridization with non-targeted sequences.

Where the target molecules are genomic DNA and specific PCRs are not used to enrich the SNP regions of choice, measures need to be taken to reduce complexity. The complexity is reduced by fragmenting the target and pre-hybridizing it to $C_0t=1$ DNA. Other methods are described by Cantor and Smith (Genomics, The Science and Technology behind the Human Genome Project 1999; John Wiley and Sons]. It may also be useful to perform whole genome amplification prior to analysis.

The probes are preferentially morpholino, locked nucleic acids (LNA) or peptide nucleic acids (PNA).

Molecules and their products can be immobilized and manipulated on a charged surface such as an electrode. Applying an appropriate bias to the electrode can speed up hybridization and aid in overcoming secondary structure when the bulk solution is at high stringency. Switching polarity aids in preferentially eliminating mismatches.

b. Stacking Hybridization

Adding either sequence specific probes or a complete set of probes in solution that coaxially stack onto the immobilized probe, templated by the target, can increase the stability and specificity of the hybridization. There is a stability factor associated with stacking and this is abrogated if there is a mismatch present between the immobilized probe and the solution probe. Therefore mismatch events can be distinguished by use of appropriate temperatures and sequence.

It is advantageous to use LNA probes as these may provide better stacking features due to their pre-configured "locked" structure.

The following are typical reaction conditions that can be used: 1M NaCl in Tris Buffer; 1 to 10 nM (or higher concentration) stacking oligonucleotide; target sample; 4-37° C. 30 min to overnight.

c. Primer Extension

This is a means for improving specificity at the free end of the immobilized probe and for trapping transient interactions. There are two ways that this can be applied. The first is the multiprimer approach, whereas described for hybridization arrays, there are separate array members containing single molecules for each allele.

The second is the multi-base approach in which a single array contains a single species of primer whose last base is upstream of the polymorphic site. The different alleles are distinguished by incorporation of different bases each of which is differentially labelled. This approach is also known as mini-sequencing.

The following reaction mix and conditions can be used: 5× polymerase buffer, 200 mM Tris-HCL pH 7.5, 100 mM $MgCl_2$, 250 mM NaCl, 2.5 mM DTT; ddNTPs or dNTPs (multibase); dNTPs (multiprimer), Sequenase V.2 (0.5 μ/μl) in polymerase dilution buffer, target sample, 37° C. degrees 1 hr.

It can be advantageous to label the primer, tag or probe to lend more confidence to an extension signal, if it co-localises with labelled tag or probe.

Advantageously, a concentration of $10.^{-7}M$ dNTP, e.g. dCTP, is used. Preferably no cold dNTP corresponding to the labelled dNTP is added. Advantageously, an exopolymerase, preferably thermosequenase (Amersham) or Taquenase (promega), is used.

The target can be capture immobilized and synthesis primed using an upstream primer. Multiple primers can prime synthesis at several points along the captured target. The target may or may not be horizontalised.

d. Ligation Assay

Ligation (chemical or enzymatic) is another means for improving specificity and for trapping transient interactions. Here the target strand is captured by the immobilized oligonucleotide and then a second oligonucleotide is ligated to the first, in a target dependent manner There are two ways that this can be applied. In the first type of assay, the "second" oligonucleotides that are provided in solution are complementary in the region of the known polymorphisms under investigation. One oligo of either the array oligonucleotides or the "second" solution oligonucleotide overlaps the SNP site and the other ends one base upstream of it.

In the second type of assay, the second oligonucleotides in solution comprise the complete set, every oligonucleotide sequence of a given length. This allows analysis of every position in the target. It may be preferable to use all sequences of a given length where one or more nucleotides are LNA.

A typical ligation reaction is as follows: 5×ligation buffer, 100 mM Tris-HCL pH 8.3, 0.5% Triton X-100, 50 mM MgCl, 250 mM KCl, 5 mM NAD+, 50 mM DTT, 5 mM EDTA, solution oligonucleotide 5-10 pmol. *Thermus thermophilus* DNA ligase (Tth DNA ligase) 1 U/ul, target sample, between 37° C. and 65° C. 1 hr.

Alternatively, stacking hybridization can be performed first in high salt: 1M NaCl, 3-4.4M TMAC1, 5-10 pmol solution oligonucleotide, target sample.

After washing of excess reagents from the array under conditions that retain the solution oligonucleotide, the above reaction mix minus solution oligonucleotide and target sample is added to the reaction mix.

Combining the Power of Different Assay Methods

The power of primer extension and ligation can be combined in a technique called gap ligation (the processivity and discriminatory power of two enzymes are combined). Here a first and a second oligonucleotide are designed that hybridize in close proximity to the target but with a gap of preferably a single base. The last base of one of the oligonucleotides ends one base upstream or downstream of the polymorphic site. In cases where it ends downstream, the first level of discrimination is through hybridization. Another level of discrimination occurs through primer extension which extends the first oligonucleotide by one base. The extended first oligonucleotide now abuts the second oligonucleotide. The final level of discrimination occurs where the extended first oligonucleotide is ligated to the second oligonucleotide.

Alternatively the ligation and primer extension reactions described in c. and d. above can be performed simultaneously, with some molecules of the array giving results due to ligation and others giving results due to primer extension, within the same array member. This can increase confidence in the base call, being made independently by two assay/enzyme systems. The products of ligation may be differently labelled than the products of primer extension.

The primer or ligation oligonucleotides may be designed on purpose to have mismatch base at a site other than the base that serves to interrogate the polymorphic site. This serves to reduce error as duplex with two mismatch bases is considerably less stable than a duplex with only one mismatch.

It may be desirable to use probes that are fully or partially composed of LNA (which have improved binding characteristics and are compatible with enzymes) in the above described enzymatic assays.

The invention provides a method for SNP typing which enables the potential of genomic SNP analysis to be realised in an acceptable time-frame and at affordable cost. The ability to type SNPs through single-molecule recognition intrinsically reduces errors due to inaccuracy and PCR-induced bias which are inherent in mass-analysis techniques. Moreover, if errors occur which left a percentage of SNPs untyped, assuming errors are random with regard to position of SNP in the genome, the fact that the remaining SNPs are typed without the need to perform individual (or multi-plexed) PCR still confers an advantage. It allows large-scale association studies to be performed in a time- and cost-effective way. Thus, all available SNPs may be tested in parallel and data from those in which there is confidence selected for further analysis.

There is a concern that duplicated regions of the genome may lead to errors, where the results of an assay may be biased by DNA from a duplicated region. The direct assay of the genome by single molecule detection is no more susceptible to this problem than assays utilising PCR since in most instances PCR amplifies a small segment surrounding the SNP site (this is necessary to achieve multiplex PCR). However, with the availability of the sequence of the genome, this is less of a problem as in some cases it may be possible to select non-duplicated regions of the genome for analysis. In other cases, the sources of bias is known and so can be accounted for.

If signal is obtained from probes or labels representing only one allele then the sample is likely to be homozygous. If it is from both, in substantially a 1:1 ratio then the sample is likely to be heterozygous. As the assays are based on single molecule counting, highly accurate allele frequencies can be determined when DNA pooling strategies are used. In these case the ratio of molecules might be 1:100. Similarly, a rare mutant allele in a background of the wild-type allele might be found to have ratio of molecules as 1:1000.

Tagging Mismatches

As an alternative means for selecting SNPs or mutations is to detect the sites of mismatches when a heterozygous sample DNA (one or both of which contain 2'-amine sub-stituted nucleotides) is denatured and re-annealed to give heteroduplexes can be tagged by 2' amine acylation. Preferably, an unknown sample DNA can be hybridized to modified tester DNAs of known sequence. This is made possible by the fact that acylation occurs preferably at flexible positons in DNA and less preferably in double stranded constrained regions (John D and K Weeks, Chem. Biol. 2000, 7: 405-410). This method can be used to place bulky tags onto sites of mismatch on DNA that has been horizontalised. Detection of these sites may then be, for example, by AFM. When this is applied genome-wide the genome can be sorted by array probes or the identity of fragments obtained by use of encoded probes.

Homogeneous Assays

Low background fluorescence and the elimination of the need for post-assay processing to remove unreacted fluo-rescent labels can be achieved by two approaches. The first is the use of Molecular Beacons (Tyagi et al Nat. Biotechnol. 1998, 16:49-53) and other molecular structures comprising dye-dye interactions in which fluorescence is only emitted in the target bound state and is quenched when the structure is unbound by the target. In practice a fraction of the molecular beacons fluoresce and so an image may need to be taken before adding targets to the array to make a record of false positives.

The second is the analysis of fluorescence polarization of a dye labelled molecule (Chen et al Genome Res. 1998, 9: 492-98). For example, in a mini-sequencing assay, free and incorporated dye labels exhibit different rotary behaviour. When the dye is linked to a small molecule such as a ddNTP, it is able to rotate rapidly, but when the dye is linked to a larger molecule, as it is if added to the primer by incorporation of the ddNTP, rotation is constrained. A stationary molecule transmits back into a fixed plane, but rotation depolarises the emitted light to various degrees. An optimal set of four dye terminators are available where different emissions can be discriminated. These approaches can be configured within single molecule detection regimes. Other homogeneous assays are described by Mir and Southern (Ann Rev. Genomics and Human Genetics 2000, 1: 329-60). The principles inherent in pyrosequencing (Ronaghi M et al Science, 1998, 363-365) may also be applicable to single molecule assays.

2. Haplotyping

Capture of singly resolvable DNA molecules is the basis for haplotype determination in the target by various means. This can be done either by analysing signals from the single foci containing the single DNA molecule or by linearising the DNA and analysing the spatial arrangement of signal along the length of the DNA.

Two or more polymorphic sites on the same DNA strand can be analysed. This may involve hybridization of oligo-nucleotides to the different sites but each labelled with different fluorophores. As described, the enzymatic approaches can equally be applied to these additional sites on the captured single molecule.

In one embodiment, each probe in a biallelic probe set may be differentially labelled and these labels are distinct from the labels associated with probes for the second site. The assay readout may be by simultaneous readout, by splitting of the emission by wavelength obtained from the same foci or from a focal region defined by the 2-D radius of projection of a DNA target molecule immobilized at one end. This radius is defined by the distance between the site of immobilized probe and the second probe. If the probes from the first biallelic set are removed or their fluors photobleached then a second acquisition can be made with the second biallelic set which in this case do not need labels that are distinct from labels for the first biallelic set. In another embodiment haplotyping can be performed on single molecules captured on allele-specific microarrays. Haplotype information can be obtained for nearest neigh-bour SNPs by for example, determining the first SNP by spatially addressable allele specific probes (see FIG. 7a). The labelling is due to the allelic probes (which are provided in solution) for the second SNP. Depending on which foci colour is detected within a SNP 1 allele specific spot determines the allele for the second SNP. So spatial position of microarray spot determines the allele for the first SNP and then colour of foci within the microarray spot determines the allele for the second SNP. If the captured molecule is long enough and the array probes are far enough apart then further SNP allele specific probe, each labelled with a different colour can be resolved by co-localization of signal to the same foci.

More extensive haplotypes, for three or more SNPs can be reconstructing from analysis of overlapping nearest neighbour SNP haplotypes (see FIG. 7b) or by further probing with differently labeled probes on the same molecule.

Samples molecules may be pre-processed to bring distal sites into closer vicinity. For example this can be done by appropriate modular design of PCR or ligation probes. For example, the modular ligation probe has a 5' sequence that ligates to one site and the 3' portion has a sequence that ligates at a distal site on the target. Use of such modular probes juxtaposes two distal members of interest and cuts out the intervening region that is not of interest.

In the case where the target has been horizontalised, the labels associated with the first locus need not be distinct from labels associated with subsequent loci; the position specifies the identity.

The probes for all alleles to be analysed will be added once the target molecule has been straightened. Alternatively, the probes can be reacted with the sample DNA before array capture.

Currently efforts are underway to establish the haplotype structure of the genome. With this information available it would be possible to use much fewer SNP probes to represent the haplotype diversity. For example rather than using 30 probes to assess a haplotype on array captured/combed DNA, only 4 probes may suffice.

An alternative approach would be to use a haplotype tag (Johnson et al Nat Genet 2001 October; 29(2):233) to capture a particular haplotype. This tag would form one of the spatially addressable probe members on the array.

A limitation of DNA pooling methods for genotyping is that because individual genotypes are not analysed, the estimation of haplotypes is complicated. However, in the methods described in the present invention, DNA pooling strategies can be used to obtain Haplotype frequencies.

3. Fingerprinting

A captured target strand can be further characterised and uniquely identified by further probing by hybridization or other means. The particular oligonucleotides that associate with the target strand provide information about the sequence of the target. This can be done by multiple acquisitions with similarly labelled probes (e.g. after photobleaching or removal of the first set) or simultaneously with differentially labelled probes. A set of oligonucleotides, which are differentially labelled can be specifically used for simultaneous fingerprinting.

Again, individual molecules may be simultaneously multiply probed as described for haplotyping.

4. STR Analysis

Conventional microarray expression analysis is performed using either synthetic oligonucleotide probes (e.g. 40-75 nt) or longer cDNA or PCR product probes (typically 0.6 kb or more) immobilized to a solid substrate. These types of arrays can be made according to the present invention at low surface coverage (as described in section A). After hybridization, the level of gene expression can be determined by single molecule counting using the methods of the invention. This gives increased sensitivity and allows events due to noise to be distinguished from real events. Also, as the basic unit of counting is the single molecule, even a rare transcript can be detected. One implementation of expression analysis involves comparison of two mRNA populations by simultaneous analysis on the same chip by two-colour labelling. This can also be done at the single molecule level by counting each colour separately by for example beam splitting. Capture of a target cDNA or mRNA can allow further analysis by oligonucleotide probing. For example this can be used to distinguish alternatively spliced transcripts.

Microarray theory suggests that accurate gene expression ratios at equilibrium can be obtained when the sample material is in limiting amounts.

A permanently addressable copy of an mRNA population can be made by primer extension of molecules separated on single molecule arrays. Primers can be designed based on the available genome sequence or gene fragment sequences. Alternatively, unknown sequences can be sampled using a binary probe comprising a fixed element that can anchor all mRNA and a variable element that can address/sort the repertoire of mRNA species in a population. The fixed element may be complementary to sequence motifs that are common to all mRNA such as the Poly A sequence or the Polyadenylation signal AAUAAA or preferably to a common clamp sequence that is ligated to all mRNA or cDNA at 5' or 3' ends. The copy can be used as the basis for further analysis such as sequencing.

5. Expression Analysis

Conventional microarray expression analysis is performed using either synthetic oligonucleotide probes (e.g. 40-75 nt) or longer cDNA or PCR product probes (typically 0.6 kb or more) immobilized to a solid substrate. These types of arrays can be made according to the present invention at low surface coverage (as described in section A). After hybridization, the level of gene expression can be determined by single molecule counting using the methods of the invention. This gives increased sensitivity and allows events due to noise to be distinguished from real events. Also, as the basic unit of counting is the single molecule, even a rare transcript can be detected. One implementation of expression analysis involves comparison of two mRNA populations by simultaneous analysis on the same chip by two-colour labelling. This can also be done at the single molecule level by counting each colour separately by for example beam splitting. Capture of a target cDNA or mRNA can allow further analysis by oligonucleotide probing. For example this can be used to distinguish alternatively spliced transcripts.

Microarray theory suggests that accurate gene expression ratios at equilibrium can be obtained when the sample material is in limiting amounts.

A permanently addressable copy of an mRNA population can be made by primer extension of molecules separated on single molecule arrays. Primers can be designed based on the available genome sequence or gene fragment sequences. Alternatively, unknown sequences can be sampled using a binary probe comprising a fixed element that can anchor all mRNA and a variable element that can address/sort the repertoire of mRNA species in a population. The fixed element may be complementary to sequence motifs that are common to all mRNA such as the Poly A sequence or the Polyadenylation signal AAUAAA or preferably to a common clamp sequence that is ligated to all mRNA or cDNA at 5' or 3' ends. The copy can be used as the basis for further analysis such as sequencing.

6. Comparative Genomic Hybridization (CGH).

Gridded genomic DNA or genomic DNA immobilized by spatially addressable tags or probes (or complementary copies) is probed by genomic DNA from a different source to detect regions of differential deletions and amplifications between the two samples. The immobilized sample containing multiple copies of each species may be a reference set and genomic DNA from two different sources may be differentially labeled and compared by hybridization to the reference.

7. Detection of Target Binding to a Repertoire of Oligonucleotides

A target can be hybridized to a repertoire of ligands. Single molecule analysis is advantageous; for example it reveals binding characteristics of conformational isomers and overcome the steric hindrance associated with binding of targets to arrays in which molecules are tightly packed. Hybridization is conducted under conditions close to those that occur in the intended use of any selected ligand.

For antisense oligonucleotide binding to RNA, hybridization occurs at 0.05 to 1 M NaCl or KCl with MgCl2 concentrations between 0 and 10 mM in for example Tris Buffer. One picomole or less of target is sufficient. (Refer to EP-A-742837: Methods for discovering ligands).

8. Protein—Nucleic Acid Interactions

Interactions between biological molecules, such as proteins, and nucleic acids can be analysed in a number of ways. Double stranded DNA polynucleotides (by foldback of designed sequences) can be immobilized to a surface in which individual molecules are resolvable to form a molecular array. Immobilized DNA is then contacted with candidate proteins/polypeptides and any binding determined by the methods described above. Alternatively RNA or duplex DNA can be horizontalised and optionally straightened by any of the methods referred to herein. The sites of protein binding may then be identified within a particular RNA or DNA using the methods described herein. Candidate biological molecules typically include transcription factors, regulatory proteins and other molecules or ions such as calcium or iron. When binding to RNA is analysed meaningful secondary structure is typically retained.

The binding of labeled transcription factors or other regulatory proteins to genomic DNA immobilized and linearised by the methods referred to herein may be used to identify active coding regions or the sites of genes in the genome. This is an experimental alternative to the bioinformatic approaches that are typically used to find coding regions in the genome. Similarly, methylated regions of the genome can be identified and marked by using antibodies specific for 5-methylcytosine. Differential methylation may be an important means for epigenetic control of the genome, the study of which is becoming increasingly important. Information from tag sequence probes is can be combined with information about methylated regions and coding regions.

An alternative means for determining the methylation status of DNA are by force or chemical force analysis using AFM. For example a silicon nitride AFM tip interacts differently with methyl cytosine in DNA, which is more hydrophobic than non-methylated DNA.

9. Optical Mapping

Optical mapping, in which the restriction digestions are done directly on DNA linearised on a surface can be done in an ordered genome-wide manner by spatially addressably capturing genomic fragments by arrayed probes. The restriction digestions can then be performed. The restriction digestions would be a way of getting Restriction Fragment length Polymorphism (RFLP) information.

Other applications include RNA structure analysis and assays that involve hybridization of DNA sequence tags to anti-tag arrays.

Where immobilization is within a channel or sheath, instead of horizontalisation, the molecule may be made parallel to the channel length.

n-Mer Arrays and Assays n-mer arrays (every possible sequence of a given length) can be used for sequencing by hybridization. n-mer arrays can also be used to sort a complex sample. This is particularly advantageous where they are linked to an anchor sequence, for example polyyadenylation signal sequence or Poly A tail, or a sequence complementary to a clamp/adaptor sequence that has been ligated to target molecules. Each member of the spatially addressable array will contain a common anchor sequence and a unique member of the n-mer set. These probes can be used in hybridization, primer extension, ligation assays etc. In particular they can be used for priming sequencing by synthesis reactions, where for example the sequence has been fragmented and fragments have been ligated to a clamp. The advantage of the n-mer is that a certain amount of sequence information is already obtained from the target just by hybridization of the n-mer before a sequencing by synthesis reaction has been performed. A stem loop probe in which one strand of stem forms a sticky end onto which the target clamp hybridizes and optionally ligates may be a favourable configurations.

Other Types of Assays

The present invention is not limited to methods of analysing nucleic acids and interactions between nucleic acids. For example, in one aspect of the invention, the molecules are proteins. Antibodies may be used to bind protein. Other probes can further interrogate protein. For example, further epitopes may be accessed by antibodies or an active site by a small molecule drug.

Low density molecular arrays may also be used in methods of high-throughput screening for compounds that interact with a given molecule of interest. In this case, the plurality of molecules represent candidate compounds (of known identity). The molecule of interest is contacted with the array and the array interrogated to determine where the molecule binds. Since the array is spatially addressable, the identity of each immobilized molecule identified as binding the molecule of interest can be readily determined. The molecule of interest may, for example, be a polypeptide and the plurality of immobilized molecules may be a combinatorial library of small molecule organic compounds.

Many of the above assays involve detecting interactions between molecules in the array and target molecules in samples applied to the array. However, other assays include determining the properties/characteristics of the arrayed plurality of molecules (even though their identity is already known), for example determining the laser induced fluorescence characteristics of individual molecules. An advantage over bulk analysis is that transient processes and functional isomers are detected.

Thus in summary, the assays of the invention and the low density molecular arrays of the invention may be used in a variety of applications including genetic analysis, such as SNP detection, haplotyping, STR analysis, sequencing and gene expression studies; identifying compounds/sequences present in a sample (including environmental sampling, pathogen detection, genetically modified foodstuffs and toxicology); and high throughput screening for compounds with properties of interest. High throughput genetic analysis is useful in medical diagnosis as well as for research purposes. Advantages of the single molecule array approach can be summarised as follows: 1. Can resolve complex samples; 2. Can separate correct signals from erroneous signals; 3. Sensitivity of detection down to a single molecule in the analyte; 4. Sensitivity of detection of a single variant molecule within a pool of common (e.g. wild-type) molecules; 5. Eliminates need for sample amplification; 6. Allows individual molecules in target sample to be sorted to discrete array members and to ask specific questions of said target molecules e.g. analyse multiple polymorphic sites (i.e. haplotyping); 7. Can perform time-resolved microscopy of single molecular events within array members and hence detect transient interactions or temporal characteristics of single molecule processes; and 8. Due to single molecule counting can get very precise measurements of particular events e.g. Allele frequencies or mRNA concentration ratios.

In another aspect, the present disclosure is related to the following methods and uses.

1. A method for producing a molecular array which method comprises immobilizing to a solid phase a plurality of molecules at a density which allows individual immobilized molecules to be individually resolved, wherein each molecule in the array is spatially addressable and the identity of each molecule is known or determined prior to immobilization.

2. A method according to method 1 wherein the molecules are applied to the solid phase by a method selected from printing, electronic addressing, in situ light-directed synthesis, ink jet synthesis or physical masking.

3. A method according to method 2 wherein the molecules are applied to the solid phase by printing of dilute solutions.

4. A method for producing a molecular array which method comprises:
   (i) providing a molecular array comprising a plurality of molecules immobilized to a solid phase at a density such that individual immobilized molecules are not capable of being individually resolved; and
   (ii) reducing the density of functional immobilized molecules in the array such that remaining individual functional immobilized molecules are capable of being individually resolved;
   wherein each individual functional molecule in the resulting array is spatially addressable and the identity of each molecule is known or determined prior to the density reduction step.

5. A method according to method 4 wherein the density of functional molecules is reduced by cleaving all or part of the molecules from the solid phase.

6. A method according to method 4 wherein the density of functional molecules is reduced by functionally inactivating the molecules in situ.

7. A method according to method 4 wherein the density of functional molecules is reduced by labelling some of the plurality of molecules such that individual immobilized labelled molecules are capable of being individually resolved.

8. A method according to any one of the preceding methods wherein the immobilized molecules are present within discrete spatially addressable elements.

9. A method according to method 8 wherein the structure of molecules present in each discrete spatially addressable element is known and unintended structures are substantially absent.

10. A method according to method 8 wherein a plurality of molecular species are present within one or more elements and each molecular species in an element can be distinguished from other molecular species in the element by means of a label.

11. A method according to any one of the preceding methods wherein the plurality of molecules which are capable of being individually resolved are capable of being resolved by optical means.

12. A method according to any one of the preceding methods wherein the plurality of molecules which are capable of being individually resolved are capable of being resolved by scanning probe microscopy.

13. A method according to any one of methods 1 to 12 wherein the molecules are attached to the solid phase at a single defined point.

14. A method according to any one of methods 1 to 12 wherein the molecules are attached to the solid phase at two or more points.

15. A method according to any preceding method, wherein the molecules comprise a detectable label.

16. A method according to method 15 wherein the label can be read by optical methods.

17. A method according to method 15 or method 16 wherein the label is a single fluorescent molecule, nanoparticle or nanorod, or a plurality of fluorescent molecules, nanoparticles or nanorods.

18. A method according to method 15 where the label can be read by SPM.

19. A method according to method 18 wherein the label is a non-fluorescent molecule, nanoparticle or nanorod.

20. A method according to any one of methods 1 to 19 wherein the molecules are selected from defined chemical entities, oligonucleotides, polynucleotides, peptides, polypeptides, conjugated polymers, small organic molecules or analogues, mimetics or conjugates thereof 21. A method according to method 20 wherein the molecules are cDNAs and/or genomic DNA.

22. A method according to any one of the preceding methods wherein the immobilized molecules are present within discrete spatially addressable elements and each element comprises a distinct spatially addressable microelectrode or nanoelectrode.

23. A method according to method 22 wherein said electrodes are formed of conducting polymers.

24. A method according to method 23 wherein said electrodes are produced by a method selected from inkjet printing, soft lithography, nanoimprint lithography/lithographically induced self assembly, VLSI methods and electron beam writing.

25. A method according to any one of methods 1 to 24 wherein the immobilized molecules are immobilized onto a single electrode.

26. A method according to any one of methods 22 to 25 wherein the electrode(s) transduce a signal when a target molecule binds to an immobilized molecule present in the same element as an electrode.

27. A molecular array obtained by the method of any one of the preceding methods.

28. Use of a molecular array in a method of identifying one or more target molecules in a sample, which molecular array comprises a plurality of molecules immobilized to a solid phase at a density which allows individual immobilized molecules to be individually resolved, wherein each individual immobilized molecule in the array is spatially addressable and the identity of each immobilized molecule is known or encoded.

29. Use according to method 28 wherein said method comprises contacting the array with the sample and interrogating one or more individual immobilized molecules to determine whether a target molecule has bound.

30. Use according to method 29 wherein substantially all of the immobilized molecules are interrogated.

31. Use according to any one of methods 28 to 30 wherein interrogation is by an optical method.

32. Use according to method 31 wherein the optical method is selected from far-field optical methods, near-field optical methods, epi-fluorescence spectroscopy, scanning confocal microscopy, two-photon microscopy, total internal reflection microscopy, 33. Use according to method 32 where pulsed laser excitation illumination is coupled with Time-correlated single molecule counting (TCSPC) or synchronised time gating.

34. Use according to any one of methods 28 to 30 wherein interrogation is by scanning probe microscopy or electron microscopy.

35. Use according to any one of methods 28 to 34 wherein a physicochemical property of the immobilized molecules is determined, such as shape, size, mass, hydrophobicity or charge.

36. Use according to any one of methods 28 to 34 wherein an electromagnetic, electrical, optoelectronic and/or electrochemical property of the immobilized molecules is determined.

37. Use according to any one of methods 29 to 34 wherein a characteristic of a complex between an immobilized molecule and a target molecule is determined.

38. Use according to any one of methods 28 to 37 wherein the immobilized molecules are of the same chemical class as the target molecules.

39. Use according to any one of methods 28 to 37 wherein the immobilized molecules are of a different chemical class to the target molecules.

40. Use according to any one of methods 28 to 37 wherein the target molecules are genomic DNA or reduced complexity representations thereof 41. Use according to method 40 wherein complexity is reduced by fragmenting the target and pre-hybridizing it to $C_0t=1$ DNA 42. Use according to method 40 or method 41 wherein the genomic DNA undergoes whole genome amplification prior to analysis.

43. Use according to any one of methods 28 to 37 wherein the target molecules are mRNA or cDNA.

44. Use of a molecular array as defined in method 28 in genetic analysis, gene expression studies, identifying one or more molecules in the array which interact with a molecular target or in the detection or typing of single nucleotide polymorphisms in a sample of nucleic acids, haplotyping or sequencing.

45. Use of a molecular array as defined in method 32 wherein the immobilized molecules of the array and the target molecules are nucleic acids and the contacting step takes place under conditions which allow Hybridization of the immobilized molecules to the target molecules.

46. Use according to method 45 wherein Hybridization of a target nucleic acid to an immobilized nucleic acid is detected by means of primer extension from the resulting complex.

47. Use according to method 45 wherein observation of successive tagged monomer base additions enables sequencing by synthesis.

48. Use according to method 46 or method 47, wherein the enzyme Apyrase is used to reduce incorporation 3' end mismatch bases.

49. Use according to method 45 wherein Hybridization of a target nucleic acid to an immobilized nucleic acid is detected by means of Hybridization of nucleic acid probes to the target nucleic acid/immobilized nucleic acid complex.

50. Use according to method 49 wherein the probes are differentially labelled.

51. Use according to method 47 wherein Hybridization of a target nucleic acid to an immobilized nucleic acid is detected by means of ligation of nucleic acid probes to the target nucleic acid/immobilized nucleic acid complex.

52. Use according to method 47 wherein observation of successive ligations with tagged oligonucleotides leads enables sequencing by synthesis.

53. Use according to any one of methods 28 to 52 wherein the array is contacted with two or more populations of target molecules.

54. Use according to method 53 wherein each population of target molecules is differentially labelled.

55. A method for typing single nucleotide polymorphisms (SNPs) and mutations in nucleic acids, comprising the steps of:
   a) providing a repertoire of probes complementary to one or more nucleic acids present in a sample, which nucleic acids may possess one or more polymorphisms, said repertoire being presented such that molecules in said repertoire may be individually resolved;
   b) exposing the sample to the repertoire and allowing nucleic acids present in the sample to hybridize to the probes at a desired stringency and optionally to be processed by enzymes;
   c) detecting individual reacted nucleic acid molecules after optionally eluting the unreacted nucleic acids from the repertoire.

56. A method according to method 55, wherein the repertoire is arrayed on a solid phase.

57. A method according to method 56, wherein said array is an array according to method 27.

58. A method according to any one of methods 55 to 57, wherein the sample is exposed to a second repertoire of probes, which probes bind to one or more molecules of the sample at a different position to the probes of the first repertoire.

59. A method according to method 58, wherein said first and second repertoires are differentially labelled.

60. A method for determining the complete or partial sequence of a target nucleic acid, comprising the steps of:
   a) providing a first set of probes complementary to one or more nucleic acids present in a sample, said first set of probes being presented such that arrayed molecules may be individually resolved;
   b) hybridizing a sample comprising a target nucleic acid to the first set of probes;
   c) hybridizing one or more further probes of defined sequence to the target nucleic acid; and
   d) detecting the binding of individual further probes to the target nucleic acid.
   e) and detecting the approximate distance separating each probe or the order of each probe 61. A method according to method 60, wherein the first set of probes is a repertoire of probes.

62. A method according to method 61, wherein the repertoire is arrayed on a solid phase.

63. A method according to method 62, wherein the target nucleic acids are captured to the solid phase at one or more points.

64. A method according to any one of methods 60 to 63, wherein the repertoire is arrayed at a density which allows molecules in said repertoire to be individually resolved.

65. A method according to method 64, wherein said array is an array according to method 27.
66. A method according to any one of methods 60 to 65, wherein the probes are differentially labelled.
67. A method for determining the number of sequence repeats in a sample of nucleic acid, comprising the steps of:
   a) providing one or more probes complementary to one or more nucleic acids present in a sample, which nucleic acids may possess one or more sequence repeats, said probes being complementary to a sequence flanking one end of the repeats, said probes being presented such that molecules may be individually resolved;
   b) contacting the nucleic acids with labelled probes complementary to units of said sequence repeats and a differentially labelled probe complementary to the flanking sequence at the other end of the targeted repeats;
   c) contacting the complex formed in b) with probes in a); and
   d) determining the number of repeats present on each sample nucleic acid by individual assessment of the number of labels incorporated into each molecule and only counting those molecules to which the differentially labelled probe complementary to the flanking sequence is also associated with.
68. A method according to method 67, wherein the repertoire is arrayed on a solid phase.
69. A method according to method 67 or method 68, wherein the repertoire is arrayed at a density which allows molecules in said repertoire to be individually resolved.
70. A method according to method 69, wherein said array is an array according to method 27.
71. A method for analysing the expression of one or more genes in a sample, comprising the steps of:
   a) providing a repertoire of probes complementary to one or more nucleic acids present in a sample, said repertoire being presented such that molecules may be individually resolved;
   b) hybridizing a sample comprising said nucleic acids to the probes; and
   c) determining the nature and quantity of individual nucleic acid species present in the sample by counting single molecules which are hybridized to the probes.
72. A method according to method 71, wherein the repertoire is arrayed on a solid phase.
73. A method according to method 71 or method 72, wherein the repertoire is arrayed at a density which allows molecules in said repertoire to be individually resolved.
74. A method according to method 73, wherein said array is an array according to method 27.
75. A method according to any one of methods 71 to 74, wherein the repertoire comprises a plurality of probes of each given specificity.
76. A method for typing single nucleotide polymorphisms (SNPs) and mutations in nucleic acids, comprising the steps of:
   a) providing a repertoire of probes complementary to one or more nucleic acids present in a sample, which nucleic acids may possess one or more polymorphisms;
   b) arraying said repertoire such that each probe in the repertoire is resolvable individually;
   c) exposing the sample to the repertoire and allowing nucleic acids present in the sample to hybridize to the probes at a desired stringency and optionally be processed by enzymes such that hybridized/processed nucleic acid/probe pairs are detectable;
   d) eluting the unhybridized nucleic acids from the repertoire and detecting individual hybridized/processed nucleic acid/probe pairs;
   e) analysing the signal derived from step (d) and computing the confidence in each detection event to generate a PASS table of high-confidence results; and
   f) displaying results from the PASS table to assign base calls and type polymorphisms present in the nucleic acid sample.
77. A method according to method 76 wherein step (e) involves analysing the signal from step (d) and computing in each detection event a FAIL table of low confidence results and using this table to inform primer and assay design.
78. A method according to method 76 or method 77 where the process is iterated for sequencing by synthesis.
79. A method according to method 76, wherein confidence in each detection event is computed in accordance with FIG. 80.
80. A method according to method 76 or method 77, wherein detection events are generated by labelling the sample nucleic acids and/or the probe molecules, and imaging said labels on the array using a detector.
81. A method according to any one of methods 55 and 76-80 where the SNPs that are probed are tags for a haplotype block or a region of linkage disequilibrium.
82. A method of obtaining allele frequencies by single molecule counting of pooled DNA.
83. A method according to method 82 wherein obtained allele frequencies are used in association studies or other genetic methods.
84. A method according to any one of methods 76 to 83 where probe and/or target acts as a primer or ligation substrate.
85. A method according to any one of methods 76 to 80 wherein the probe and or target is enzymatically processed by ligases or polymerases or thermophilic varieties thereof or re-engineered/shuffled varieties thereof.
86. A method according to any one of methods 76 to 85 wherein the probe forms secondary structures which facilitate or stabilise Hybridization or improve mismatch discrimination.
87. A method for determining the sequence of all or part of a target nucleic acid molecule which method comprises:
   (i) immobilizing the target molecule to a solid phase at two or more points such that the molecule is substantially horizontal with respect to the surface of the solid phase;
   (ii) straightening the target molecule, during or after immobilization;
   (iii) contacting the target molecule with a nucleic acid probe of known sequence; and
   (iv) determining the position within the target molecule to which the probe hybridizes.
88. A method according to method 87 wherein the target molecule is contacted with a plurality of probes.
89. A method according to method 88 wherein each probe is labelled with a different detectable label.
90. A method according to method 87 or 88 wherein the target molecule is contacted sequentially with each of the plurality of probes.
91. A method according to method 90 wherein each probe is removed from the target molecule prior to contacting the target molecule with a different probe.
92. A method according to method 88 or 89 wherein the target molecule is contacted with all of the plurality of probes substantially simultaneously.

93. A method according to method 91 wherein the probes are removed by heating, modifying the salt concentration or pH, or by applying an appropriately biased electric field.
94. A method or use according to any one of method 28 to 93 wherein the target is substantially a double stranded molecule and is probed by strand invasion using PNA or LNA.
95. A method according to any one of methods 97 to 94 wherein the target nucleic acid molecule is a double-stranded molecule and is derived from a single-stranded nucleic acid molecule of interest by synthesising a complementary strand to said single-stranded nucleic acid.
96. A method or use according to any one of methods 28 to 94 wherein the target molecule is substantially single stranded and is made accessible to Hybridization by elongation or stretching out.
97. A method or use according to any one of methods 28 to 96 wherein a plurality of target molecules are analyzed simultaneously.
98. A method for determining the sequence of all or part of a target single-stranded nucleic acid molecule which method comprises:
    (i) immobilizing the target molecule to a solid phase at two or more points such that the molecule is substantially horizontal with respect to the surface of the solid phase;
    (ii) straightening the target molecule, during or after immobilization;
    (iii) contacting the target molecule with a plurality of nucleic acid probes of known sequence, each probes being labelled with a different detectable label; and
    (iv) ligating bound probes to form a complementary strand.
99. A method according to method 98 wherein prior to step (iv), any gaps between bound probes are filled by polymerization primed by said bound probes.
100. A method according to any one of methods 87 to 99 wherein the solid phase is a bead or particle.
101. A method according to any one of methods 87 to 100 wherein the solid phase is a substantially flat surface.
102. A method for arraying a plurality of nucleic acid molecules which method comprises:
    (i) contacting the plurality of nucleic acid molecules with a plurality of probes, each probe being labelled with a tag which indicates uniquely the identity of the probe, such that each molecule can be identified uniquely by detecting the probes bound to the molecule and determining the identity of the corresponding tags;
    (ii) immobilizing the plurality of nucleic acid molecules randomly to a solid substrate; and optionally
    (iii) horizontalising and straightening the molecules, during or after immobilization.
103. A method according to method 102 wherein the plurality of nucleic acid molecules are immobilized at a density such that individual immobilized molecules in the sample can be individually resolved.
104. A method according to any one of methods 102 to 103 wherein the solid phase is a substantially flat solid substrate or a bead/particle/rod/bar.
105. An array produced by the method of any one of methods 102 to 104.
106. A method for identifying and/or characterizing one or more molecules of a plurality of molecules present in a sample which method comprises:
    (i) producing a molecular array by a method comprising immobilizing to a solid phase a plurality of molecules present in a sample, wherein the plurality of molecules are immobilized at a density such that individual molecules in the sample can be individually resolved; and
    (ii) identifying and/or characterizing one or more molecule immobilized to the array by a method comprising contacting the immobilized molecules with a plurality of encoded probes; wherein each probe is encoded by virtue of being labelled with a tag which indicates uniquely the identity of the probe, such that an immobilized molecule can be identified uniquely by detecting the probes bound to the molecule and determining the identity of the corresponding tags.
107. A method according to method 106 wherein the tagged probes are produced using combinatorial chemistry.
108. A method according to method 106 wherein the tag is selected from a nanoparticle, a nanorod and a quantum dot.
109. A method according to any one of methods 106 to 108 wherein each tag comprises multiple molecular species.
110. A method according to any one of methods 106 to 109 wherein the tags are detectable by optical means.
111. A method according to method 106 wherein the tags are particulate and comprise surface groups.
112. A method according to method 106 wherein the tags are particulate and encase detectable entities.
113. A method according to any one of methods 106 to 112 wherein tags can be detected and distinguished by scanning probe microscopy.
114. A method according to any one of methods 106 to 113 wherein the solid substrate is selected from the group consisting of a bead, a particle, a rod and a bar.
115. A method according to any one of methods 106 to 114 wherein the solid phase comprises channels or capillaries within which the molecules are immobilized.
116. A method according to any one of methods 106 to 115 wherein the solid phase comprises a gel.
117. A biosensor comprising a molecular array according to any one of methods 27 or 105.
118. An integrated biosensor comprising a molecular array according to method 117, an excitation source, a detector, such as a CCD and, optionally, signal processing means.
119. A biosensor according to method 117 or 118 wherein the biosensor comprises a plurality of elements, each element containing distinct molecules, such as probe sequences.
120. A biosensor according to method 119 wherein each element is specific for the detection of a different target, such as different pathogenic organisms.
121. A biosensor according to any one of methods 117 to 120 wherein the molecular array is formed on an optical fibre or waveguide.
122. A method according to method 106 in which the plurality of probes are labeled with a tag which indicates uniquely the identity of the probe.
123. A method according to any preceding method in which the plurality of tagged probes are hybridized substantially simultaneously or in groups of probes.
124. A method according to any preceding method in which probes are grouped according to their Tm.
125. A method according to method 106, in which each of the plurality of labeled probes are successively hybridized to the immobilized nucleic acid and a record of those that hybridize to each molecule can be used to identify or re-assemble the sequence of the immobilized molecule.
126. A method for determining haplotypes by probing single molecules immobilized on a solid phase in a spatially addressable manner 127. A method according to method 126 for haplotyping in which successive SNP sites are probed with different labels.
128. A method for haplotyping in which the first SNP is defined by the address of array element that binding occurs to and subsequent SNPs are defined by different labels.
129. A method for haplotyping on arrays, where first SNP is defined by address on array and subsequent SNPs are identified by solution probes.
130. A method for haplotyping on array captured and horizontalised and/or linearises DNA, where first SNP is defined by address on array and subsequent SNPs are identified by solution probes.
131. A method according to method 130 where two different labels are used to distinguish members of the biallelic probe set and each successive SNP is identified by its position along the molecule.
132. A method according to method 131 where errors are computed according to expected position of binding of probes along molecule.
133. A method where a population of molecules is analysed and the haplotypes are computed according to the consensus of signals from single molecules.
134. A method according to any one of methods 126-132 and 44, 47, 52 and 78 in which haplotype frequencies can be determined.
135. A method according to 132 and sequencing methods where markers are added to aid position SNP sites/or position of target binding.
136. A method according to any one of the preceding methods, wherein the probe is labelled or marked and signal after target binding or assay is only deemed real when it is co-incident with the label(s) or mark(s) on the probe.
137. A method of identifying one or more target molecules in a sample comprising using a molecular array, which molecular array comprises a plurality of molecules immobilized to a solid phase at a density which allows individual immobilised molecules to be individually resolved, wherein each individual immobilised molecule in the array is spatially addressable and the identity of each immobilised molecule is known or encoded.

In the following description, various exemplary embodiments are set forth in view of the Figures.

Figures 21, 22:
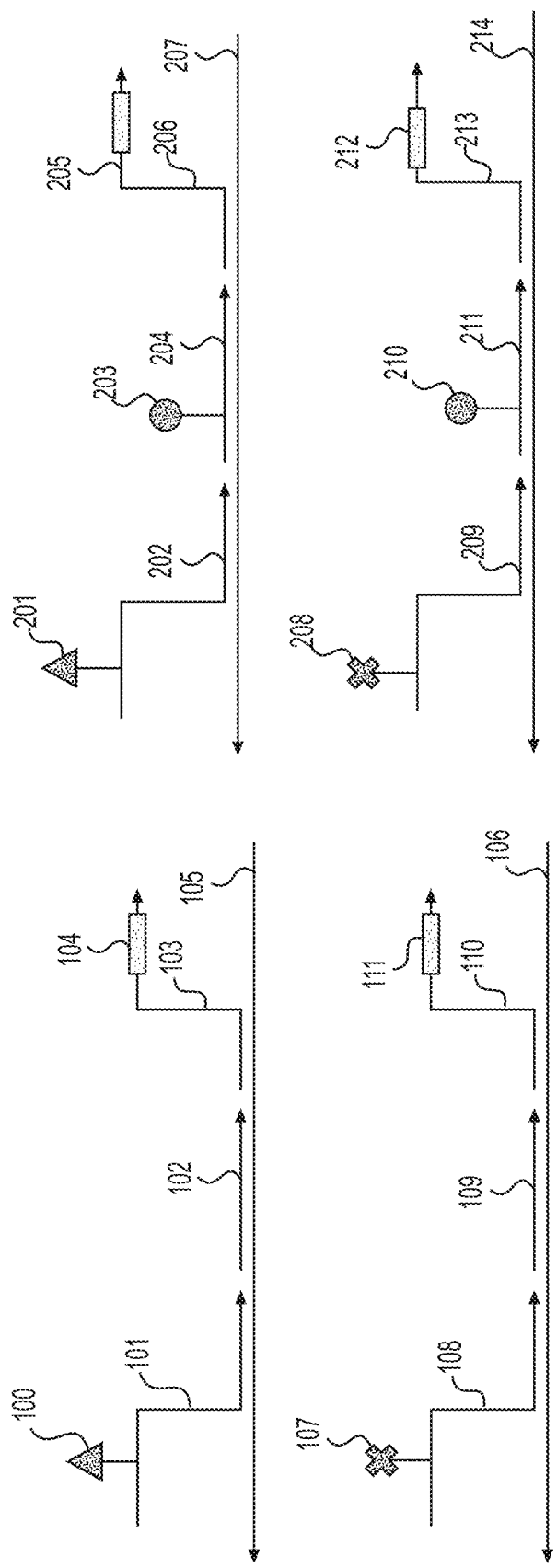

FIG. 21 is an implementation of an assay for quantifying genomic copy number at two genomic loci. In this embodiment of the assay, 105 and 106 are target molecules. 105 contains sequence corresponding to the first genomic locus "Locus 1" interrogated for copy number (example, chromosome 21), and 106 contains sequence corresponding the second genomic locus "Locus 2" interrogated for copy number (example, chromosome 18). FIG. 21 contains an example of one probe set per genomic locus, but in some embodiments of this assay, multiple probe sets will be designed to interrogate multiple regions within a genomic locus. For example, more than 10, or more than 100, or more than 500 probe sets may be designed that correspond to chromosome 21. FIG. 21 illustrates only a single probe set for each genomic locus, but importantly the scope of this invention allows for multiple probe sets for each genomic locus. FIG. 21 also illustrates a single hybridization event between a target molecule and a probe set. In practice, there will be multiple target molecules present in an assay sample. Many target molecules will contain the necessary sequences for hybridization to a probe set, and formation of a probe product. Different target molecules may hybridize to probe sets, as certain target molecules will bear genetic polymorphisms. In addition, target molecules that arise from genomic DNA may have a random assortment of molecule sizes, as well various beginning and ending sequences. In essence, there are multiple target molecules that may hybridize to a given probe set. In a single assay, multiple copies of a given probe set are added. Therefore, in a single assay up to thousands, or hundreds of thousands, or millions of specific probe products may be formed.

FIG. 21 depicts two probe sets, one probe set for Locus 1 and one probe set for Locus 2, although as aforementioned, multiple probes sets may be designed for each genomic locus. A first probe sets contains member probes 101, 102, 103. Item 101 contains label (100) type "A." Item 103 contains an affinity tag (104) which may be used for isolation and identification of the probe product. 102 may contain no modifications, such as a label or barcode. A second probe set with member probes 108, 109, 110 carries respective features as in the first probe set. However, 108 contains a label (107) of type "B," distinguishable from type "A." Item 110 contains an affinity tag (111) which may be identical to or unique from 104. Many probe sets may designed that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique, and the affinity tags for the many probe sets for Locus 2 may be identical or unique.

One or more probe sets are added to target molecules in a single vessel and exposed to sequence-specific hybridization conditions.

For each probe set, the three probes (e.g., 101, 102, 103) are hybridized (or attached via a similar probe-target interaction) to the target molecule (105) such there are no gaps in between the probes on the target molecule. That is, the probes from the probe set are adjacent to one another and ligation competent.

Ligase is added to the hybridized probes and exposed to standard ligase conditions. The ligated probes form a probe product. All (or a majority of) probe products from Locus 1 have label type "A." All probe products from Locus 2 have label type "B." Quantification of the probe products corresponding to the genomic loci 1 & 2 occurs using labels "A" and "B."

In some embodiments, the probe products are immobilized onto a substrate using their affinity tags. For example, if the affinity tag is a DNA sequence, the probe products may be hybridized to regions of a DNA capture array at appropriate density for subsequent imaging.

Figure 48:
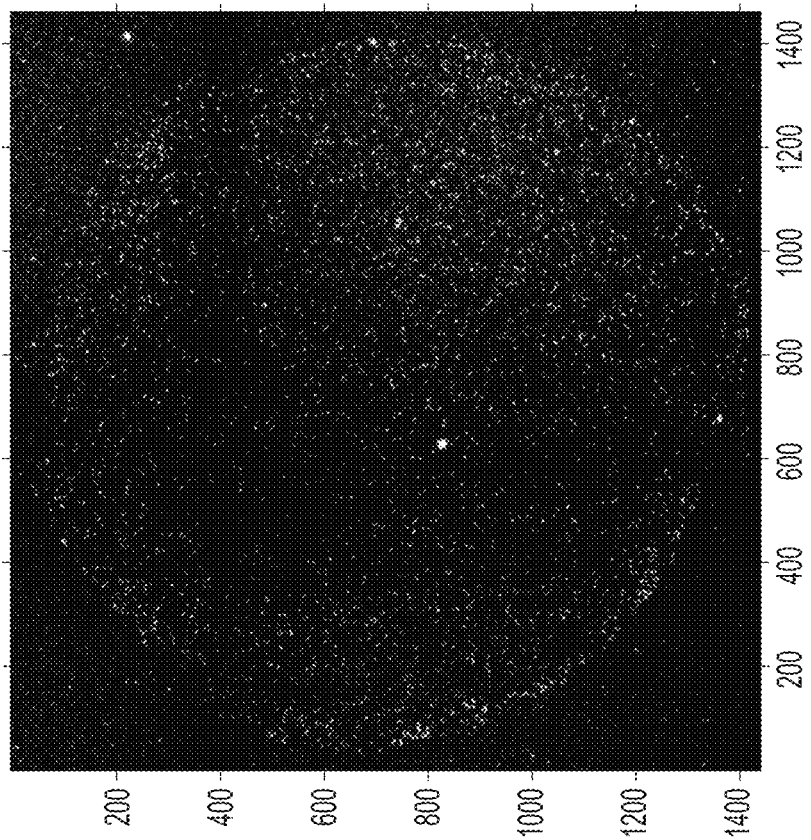
FIGS. 47 and 48 show the resulting fluorescence patterns when products contain unique affinity tag sequences and the underlying substrate contains complements to each of the unique affinity tags within the same location (e.g., as the same member) on a substrate.
Figure 47:
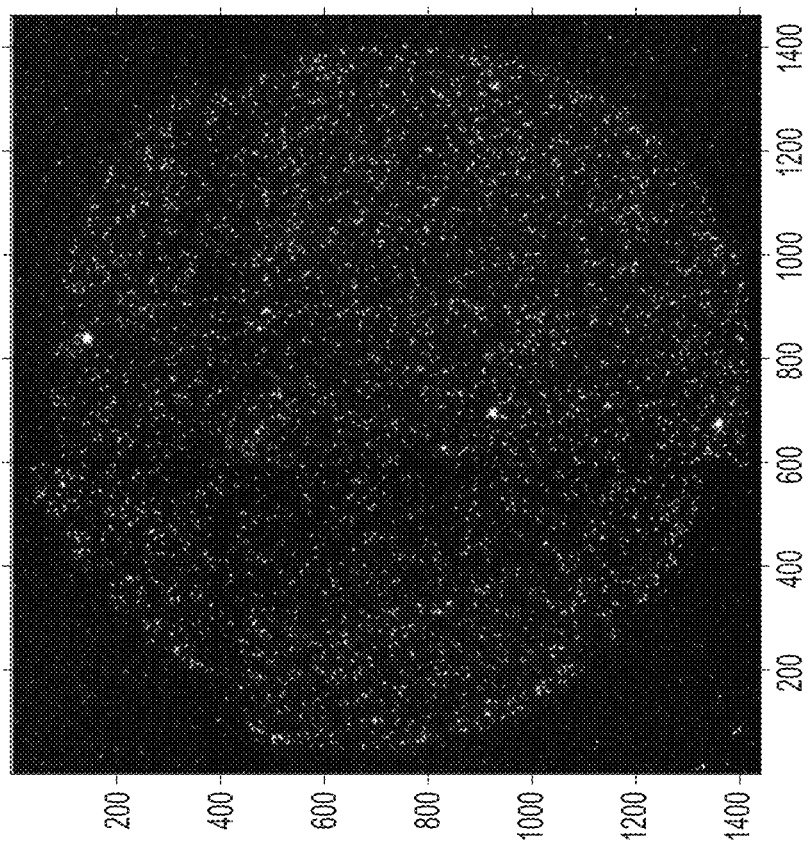

In some embodiments, affinity tags 104 and 111 contain unique and orthogonal sequences that allow surface-based positioning to one or more locations, which may be shared between hybridization products or not. FIGS. 47 and 48 show the resulting fluorescence patterns when products contain unique affinity tag sequences and the underlying substrate contains complements to each of the unique affinity tags within the same region (e.g., as the same member of an array) on a substrate. The images are of the same region of a substrate, but FIG. 47 shows Cy3 labels (covalently bound to chromosome 18 product), and FIG. 48 shows Alexa Fluor 647 labels (covalently bound to chromosome 21 product). Similar patterns may be generated for other assay embodiments that follow.

Figure 50:
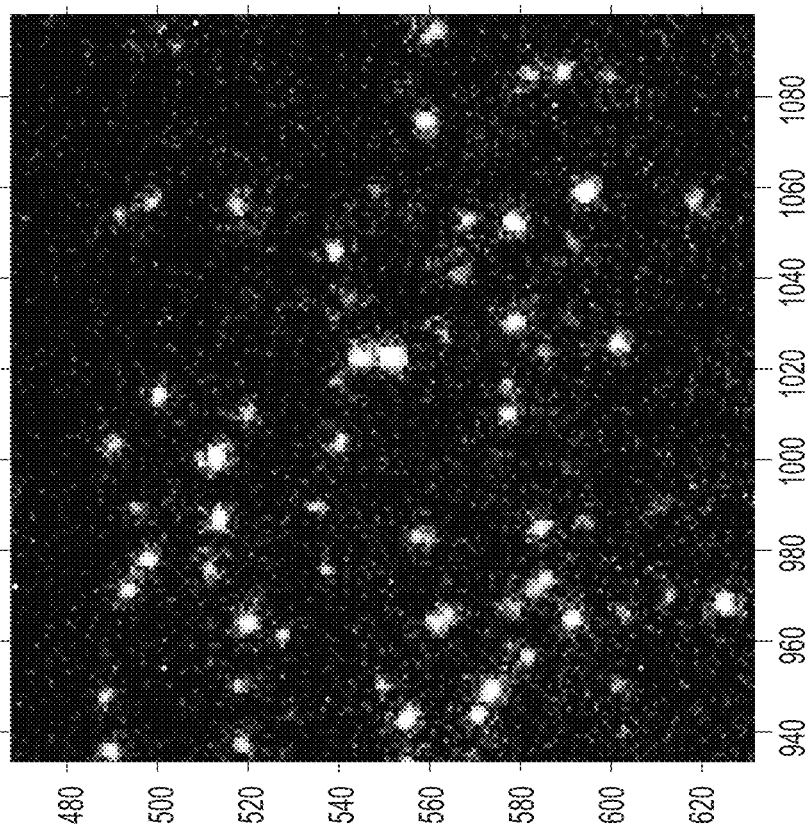
FIGS. 50 and 52 show zoomed-in locations of FIGS. 49 and 51, respectively.
Figure 49:
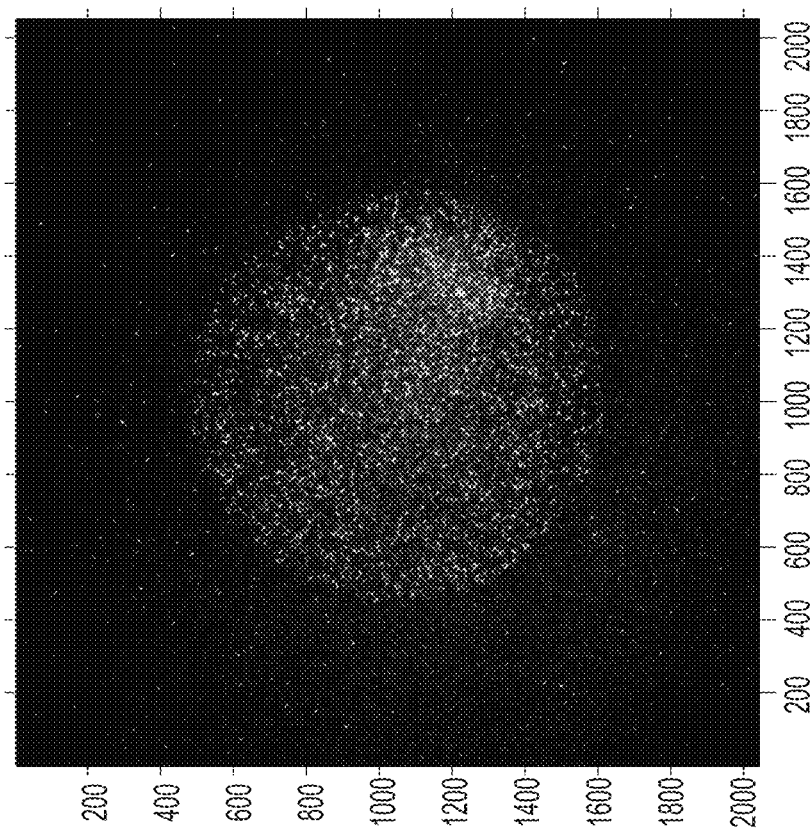
FIGS. 49 and 51 show the resulting fluorescence patterns when different products contain identical affinity tag sequences and the underlying substrate contains the complement to the affinity tag.
Figure 52:
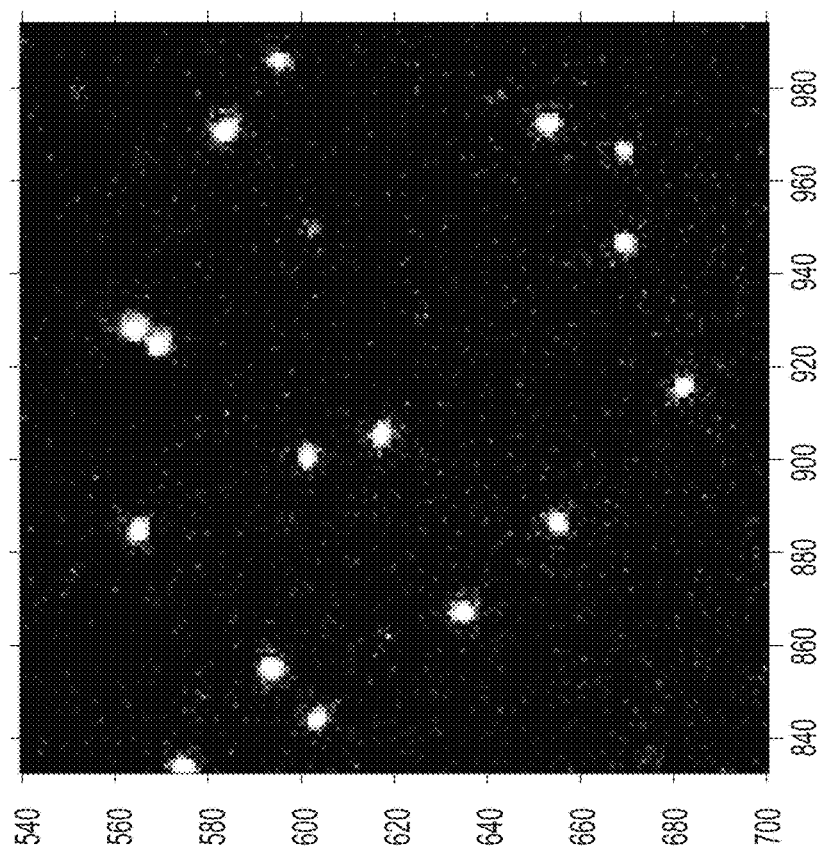
Figure 51:
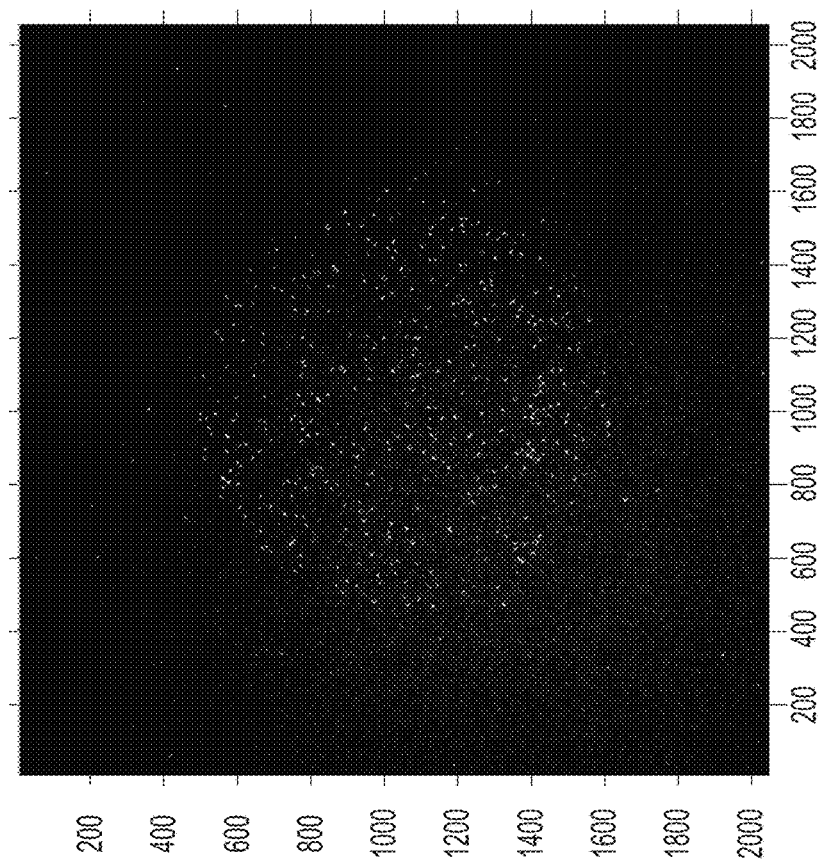

In another embodiment, affinity tags 104 and 111 contain identical sequences that allow surface-based positioning to the same region (e.g., as the same member of an array) on a substrate. That is, different products compete for the same binding sites. FIGS. 49 and 51 show the resulting fluorescence patterns when different products contain identical affinity tag sequences and the underlying substrate contains the complement to the affinity tag. The images are of the same location on a substrate, but FIG. 49 shows Cy3 labels (covalently bound to chromosome 18 product) and FIG. 51 shows Alexa Fluor 647 labels (covalently bound to chromosome 21 product). FIGS. 50 and 52 show zoomed-in regions of FIGS. 49 and 51, respectively, clearly demonstrating single-molecule resolution and individually-distinguishable labels Similar patterns may be generated for other assay embodiments that follow.

Figure 54:
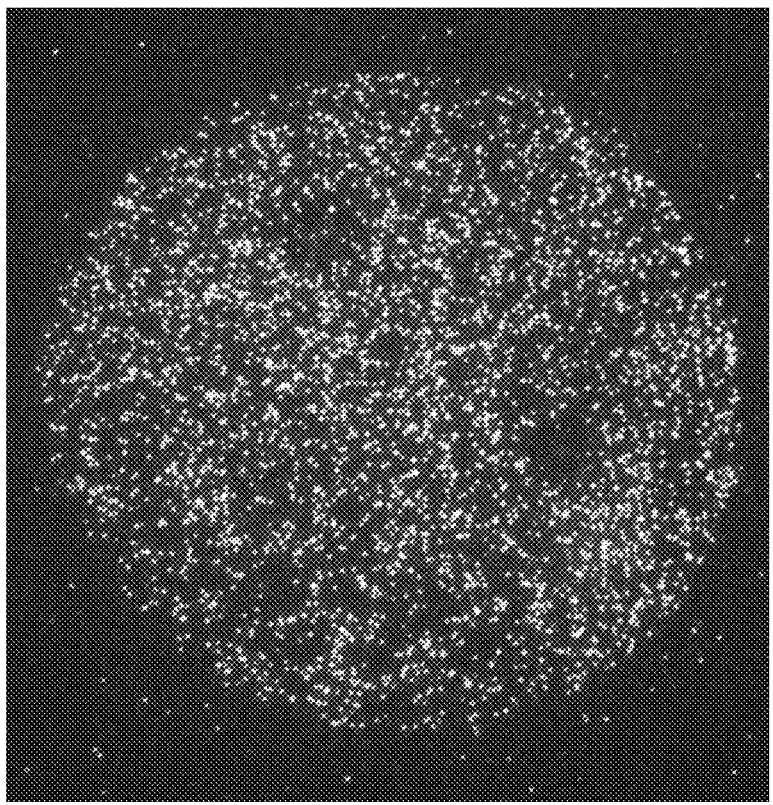
FIGS. 53 and 54 show the resulting fluorescence patterns when products contain unique affinity tag sequences and the underlying substrate has one location (e.g., as one member) containing the complement to one affinity tag complement, and another separate location (e.g., as another member) containing the complement to the other affinity tag.
Figure 53:
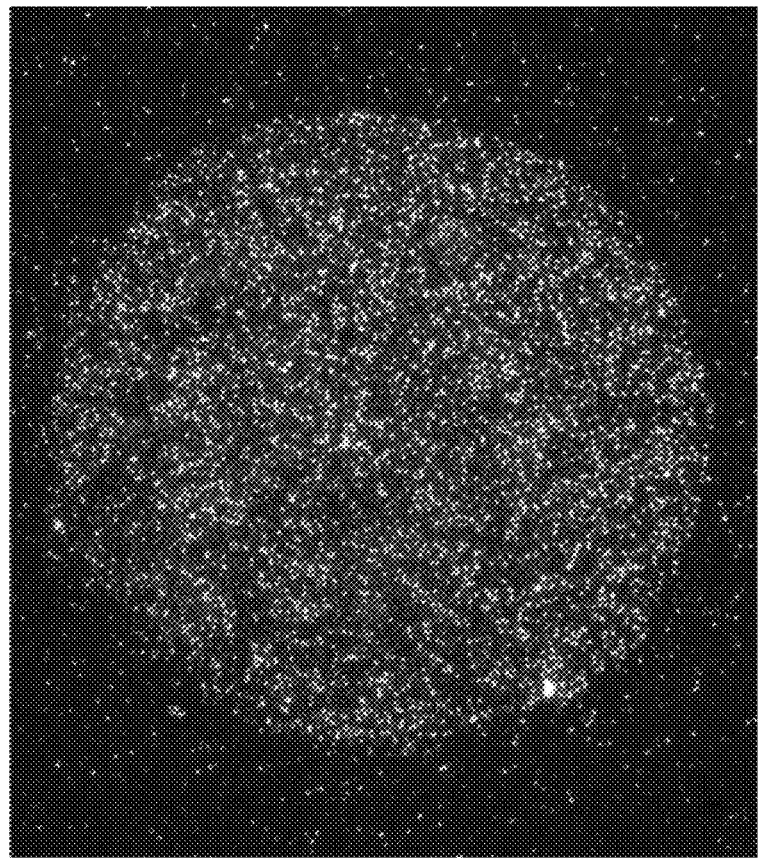

In another embodiment, affinity tags 104 and 111 contain unique and orthogonal sequences that allow surface-based positioning to more than one location on a substrate. FIGS. 53 and 54 show the resulting fluorescence patterns when products contain unique affinity tag sequences and the underlying substrate has one region containing the complement to one affinity tag complement, and another separate region containing the complement to the other affinity tag. The images are of two separate regions of a substrate, with each region containing a single affinity tag complement as previously described. FIG. 53 shows Cy3 labels (covalently bound to chromosome 21 product), and FIG. 54 shows Alexa Fluor 647 labels (covalently bound to chromosome 18 product) Similar patterns may be generated for other assay embodiments that follow.

One feature of this invention according to some embodiments is that specificity is achieved through the combination of multiple adjacent probes that must be successfully ligated together in order for the probe product to be successfully formed, captured and detected. If a probe product is not successfully formed for any reason, then it cannot be isolated, or enriched for using an affinity tag and detected. For example, if probe 101 is not successfully ligated to probe 102, then the resulting product cannot be detected. Similarly, if probe 103 is not successfully ligated to probe 102, then the resulting product cannot be isolated or enriched using an affinity tag.

Requiring all probes from the probe set to successfully hybridize to the target molecule and successfully ligate together provides high specificity and greatly reduces issues of cross-hybridization and therefore false positive signals.

In this assay, specificity is achieved through sequence-specific hybridization and ligation. In a preferred embodiment, the specificity of forming probe products occurs in the reaction vessel, prior to isolating or enriching for probe products, for example immobilization onto a surface or other solid substrate. This side-steps the challenge of standard surface based hybridization (e.g., genomic microarray) in which specificity must be entirely achieved through hybridization only with long (>40 bp) oligonucleotide sequences (e.g., Agilent and Affymetrix arrays).

The use of affinity tags allows the probe products to be immobilized on a substrate and therefore excess unbound probes to be washed away using standard methods or removed using standard methods. Therefore all or most of the labels on the surface are a part of a specifically formed probe product that is immobilized to the surface.

One feature of this invention according to some embodiments is that the surface capture does not affect the accuracy. That is, it does not introduce any bias. In one example, if the same affinity tag is used for probe sets from different genomic loci, with probe sets targeting each locus having a different label. Probe products from both genomic loci may be immobilized to the same location on the substrate using the same affinity tag. That is probe products from Locus 1 and Locus 2 will be captured with the same efficiency, so not introducing any locus specific bias.

In some embodiments, some or all of the unbound probes and/or target molecules are removed prior to surface capture using standard methods. This decreases interference between unbound probes and/or target molecules and the probe products during surface capture.

One feature of this invention according to some embodiments is that multiple affinity tag types may be placed in the same region of the substrate (for example, the same array spot or member of the array). This has many advantages, including placement of control or calibration markers. FIGS. 22-46 describe additional exemplary embodiments of this invention. These Figures do not represent all possible embodiments, and all other variations of this assay are included as a part of this invention. Additionally, all features of the embodiment described in FIG. 21 are applicable to all additional other embodiments of the assay described in this application.

FIG. 22 depicts a modification of the general procedure described in FIG. 21. FIG. 22 depicts two probe sets, one probe set for Locus 1 and one probe set for Locus 2, although as aforementioned, multiple probes sets may be designed for each genomic locus. 207 and 214 are target molecules corresponding to Locus 1 and Locus 2, respectively. A first probe sets contains member probes 202, 204, 206. 202 contains a label (201) of type "A." 206 contains an affinity tag (205) which may be used for isolation and identification of the probe product. A second probe set with member probes 209, 211, 231 carries respective features as in the first probe set. However, 209 contains a label (208) of type "B," distinguishable from type "A." 213 contains an affinity tag (212) which may be identical to or unique from 205. Many probe sets may be designed such that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique or a mixture of identical and unique, and the affinity tags for the many probe sets for Locus 2 may be identical or unique or a mixture of identical and unique. In this embodiment, the probes 204 and 211 may contain one or more labels (203, 210) of type "C." Therefore, probe products will contain a combination of labels. For Locus 1, probe products will contains labels of type "A" and type "C," whereas probe products from Locus 2 will contain labels of type "B" and type "C."

Figure 23:
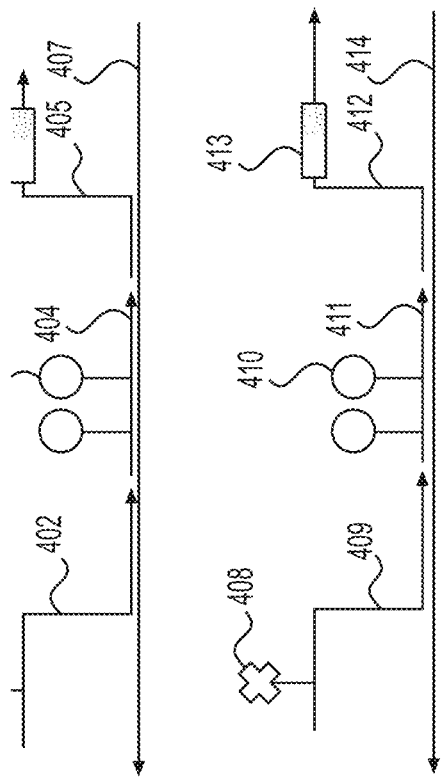

FIG. 23 depicts a modification of the general procedure described in FIG. 21. FIG. 23 depicts two probe sets, one probe set for Locus 1 and one probe set for Locus 2, although as aforementioned, multiple probes sets may be designed for each genomic locus. 307 and 314 are target molecules corresponding to Locus 1 and Locus 2, respectively. A first probe set contains member probes 302, 303, 305. 302 contains a label (301) of type "A." 305 contains an affinity tag (306) which may be used for isolation and identification of the probe product. A second probe set with member probes 309, 310, 312 carries respective features as in the first probe set. However, 309 contains a label (308) of type "B," distinguishable from type "A." 312 contains an affinity tag (313) which may be identical to or unique from 306. Many probe sets may designed that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique, and the affinity tags for the many probe sets for Locus 2 may be identical or unique. In this embodiment, the probes 305 and 312 contain one or more labels (304, 311) of type "C." Therefore, probe products will contain a combination of labels. For Locus 1, probe products will contains labels of type "A" and type "C," whereas probe products from Locus 2 will contain labels of type "B" and type "C."

Figure 24:
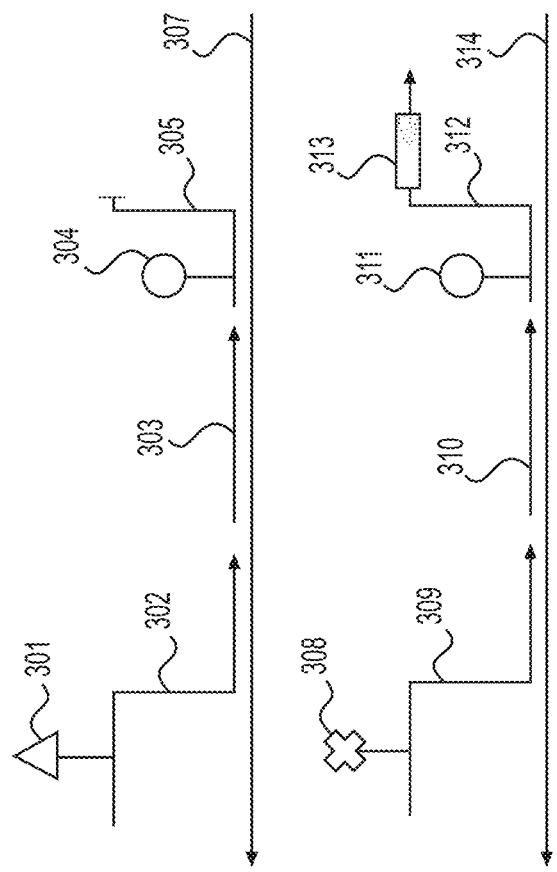

FIG. 24 depicts a modification of the general procedure described in FIG. 21. FIG. 24 depicts two probe sets, one probe set for Locus 1 and one probe set for Locus 2, although as aforementioned, multiple probes sets may be designed for each genomic locus. 407 and 414 are target molecules corresponding to Locus 1 and Locus 2, respectively.

A first probe sets contains member probes 402, 405. 402 contains a label (401) of type "A." 405 contains an affinity tag (406) which may be used for isolation and identification of the probe product.

A second probe set with member probes 409, 412 carries respective features as in the first probe set. However, 409 contains a label (408) of type "B," distinguishable from type "A." 412 contains an affinity tag (413) which may be identical to or unique from 406. Many probe sets may designed that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique, and the affinity tags for the many probe sets for Locus 2 may be identical or unique.

In this embodiment, probes 402 and 405 hybridize to sequences corresponding to Locus 1, but there is a "gap" on the target molecule consisting of one or more nucleotides between hybridized probes 402 and 405. In this embodiment, a DNA polymerase or other enzyme may be used to synthesize a new polynucleotide species (404) that covalently joins 402 and 405. That is, the probe product formed in this example is a single contiguous nucleic acid molecule with a sequence corresponding to Locus 1, and bearing the labels and/or affinity tags above. Additionally, 404 may contain one or more labels of type "C," possibly as a result of incorporation of a one of more nucleotides bearing a label of type "C." This example also conveys to the probe product formed for Locus 2, containing probes 409 and 412. Therefore, probe products will contain a combination of labels. For Locus 1, probe products will contains labels of type "A" and type "C," whereas probe products from Locus 2 will contain labels of type "B" and type "C."

Figure 25:
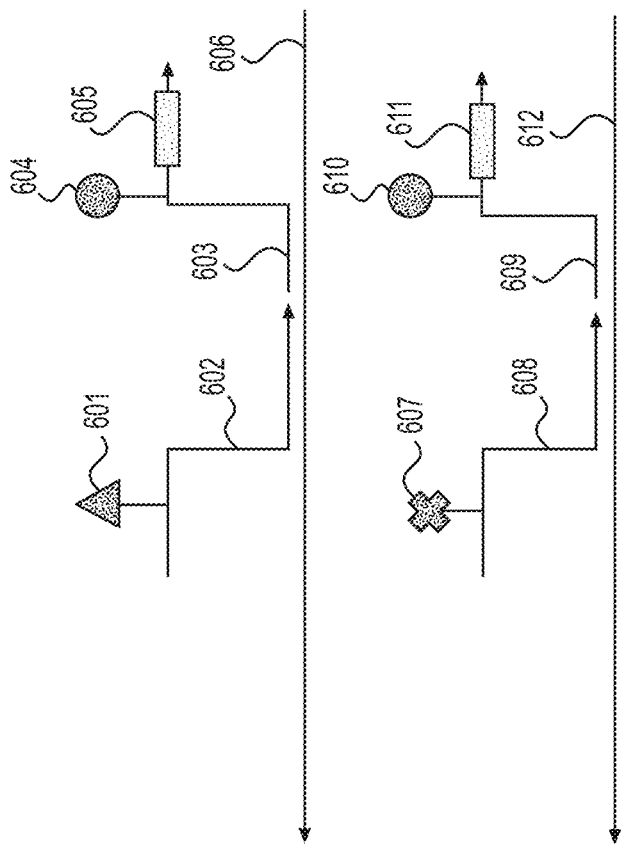

FIG. 25 depicts a modification of the general procedure described in FIG. 21. FIG. 25 depicts two probe sets, one probe set for Locus 1 and one probe set for Locus 2, although as aforementioned, multiple probes sets may be designed for each genomic locus. 505 and 510 are target molecules corresponding to Locus 1 and Locus 2, respectively. A first probe sets contains member probes 502, 503. 502 contains a label (501) of type "A." 503 contains an affinity tag (504) which may be used for isolation and identification of the probe product. A second probe set with member probes 507, 508 carries respective features as in the first probe set. However, 507 contains a label (506) of type "B," distinguishable from type "A." 508 contains an affinity tag (509) which may be identical to or unique from 504. Many probe sets may designed that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique, and the affinity tags for the many probe sets for Locus 2 may be identical or unique.

Figure 26:
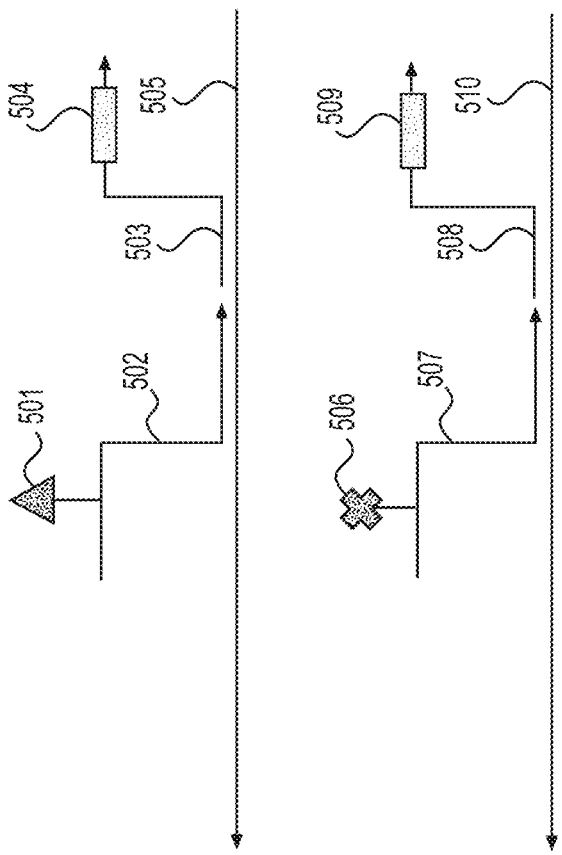

FIG. 26 depicts a modification of the general procedure described in FIG. 21. FIG. 26 depicts two probe sets, one probe set for Locus 1 and one probe set for Locus 2, although as aforementioned, multiple probes sets may be designed for each genomic locus. 606 and 612 are target molecules corresponding to Locus 1 and Locus 2, respectively. A first probe sets contains member probes 602, 603. 602 contains a label (601) of type "A." 603 contains an affinity tag (605) which may be used for isolation and identification of the probe product. A second probe set with member probes 608, 609 carries respective features as in the first probe set. However, 608 contains a label (607) of type "B," distinguishable from type "A." 609 contains an affinity tag (611) which may be identical to or unique from 605. Many probe sets may designed that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique, and the affinity tags for the many probe sets for Locus 2 may be identical or unique.

In this embodiment, the probes 603 and 609 contain one or more labels (604, 610) of type "C." Therefore, probe products will contain a combination of labels. For Locus 1, probe products will contains labels of type "A" and type "C," whereas probe products from Locus 2 will contain labels of type "B" and type "C."

Figures 27, 28:
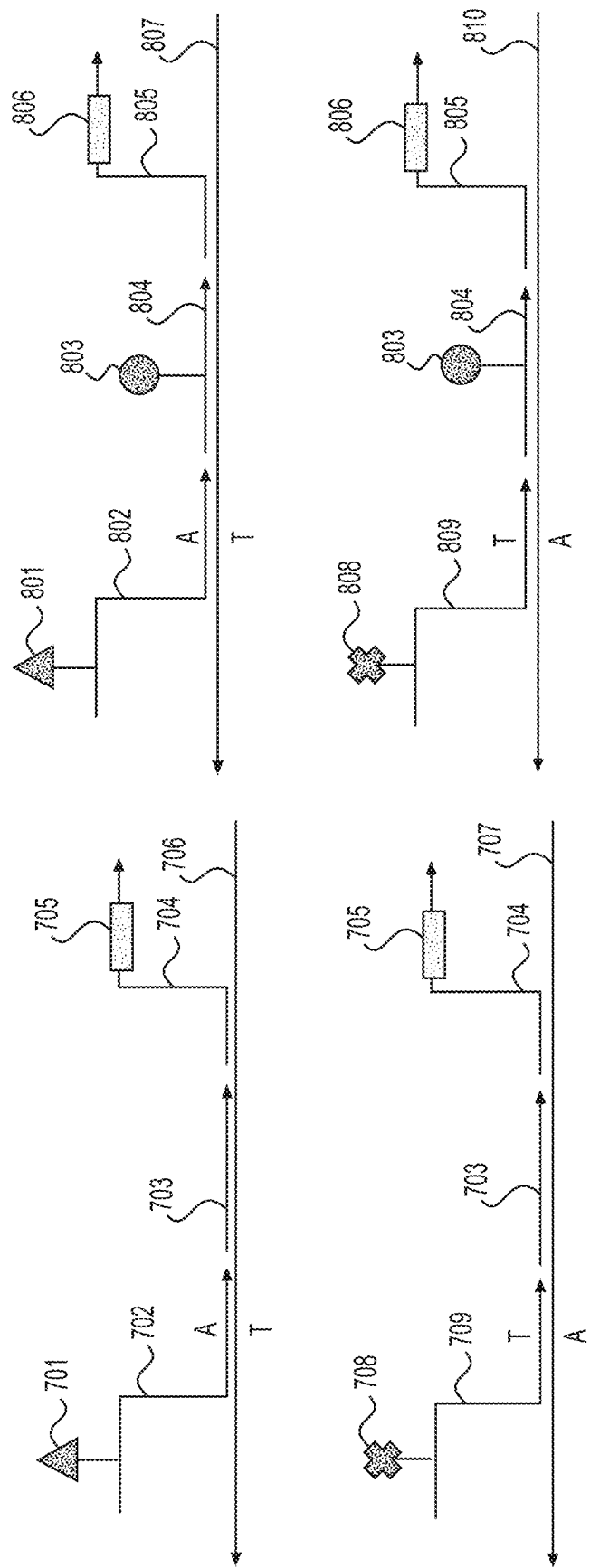

FIG. 27 depicts a modification of the general procedure described in FIG. 21. FIG. 27 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 27 depicts two probe sets—one probe set for Allele 1 and one probe set for Allele 2. 706 and 707 are target molecules corresponding to Allele 1 and Allele 2, respectively. A first probe set contains member probes 702, 703, 704. 702 contains a label (701) of type "A." 704 contains an affinity tag (705) which may be used for isolation and identification of the probe product. A second probe set with member probes 709, 703, 704 carries respective features as in the first probe set. In this embodiment, 703 and 704 are identical for both probe sets. However, 709 contains a label (708) of type "B," distinguishable from type "A." In this embodiment, 702 and 709 contain sequences that are nearly identical, and differ by only one nucleotide in the sequence. Therefore, hybridization sequences of these two probes, which are configured to hybridize to the regions for Allele 1 and Allele 2, contains complementary regions for Allele 1 (702), and Allele 2 (709). Further, the length of each hybridization domain on 702 and 709, as well as experimental hybridization conditions are designed such that probe 702 will only hybridize to Allele 1 and probe 709 will only hybridize to Allele 2. The purpose of this assay type is to accurately quantify the frequency of Allele 1 and Allele 2 in a sample.

FIG. 28 depicts a modification of the general procedure described in FIG. 21. FIG. 28 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 28 depicts two probe sets—one probe set for Allele 1 and one probe set for Allele 2. 807 and 810 are target molecules corresponding to Allele 1 and Allele 2, respectively. A first probe set contains member probes 802, 804, 805. 802 contains a label (801) of type "A." 805 contains an affinity tag (806) which may be used for isolation and identification of the probe product. A second probe set with member probes 809, 804, 805 carries respective features as in the first probe set. In this embodiment, 804 and 805 are identical for both probe sets. However, 809 contains a label (808) of type "B," distinguishable from type "A." In this embodiment, 802 and 809 contain sequences that are nearly identical, and differ by only one nucleotide in the sequence. Therefore, hybridization sequences of these two probes contain complementary regions for Allele 1 (802), and Allele 2 (809). Further, the length of each hybridization domain on 802 and 809, as well as experimental hybridization conditions are designed such that probe 802 will only hybridize to Allele 1 and probe 809 will only hybridize to Allele 2. The purpose of this assay type is to be able to accurately quantify the frequency of Allele 1 and Allele 2 in a sample. In this embodiment, the probe 804 contains one or more labels (803) of type "C." Therefore, probe products will contain a combination of labels. For Allele 1, probe products will contain labels of type "A" and type "C," whereas probe products from Allele 2 will contain labels of type "B" and type "C."

Figures 29, 30:
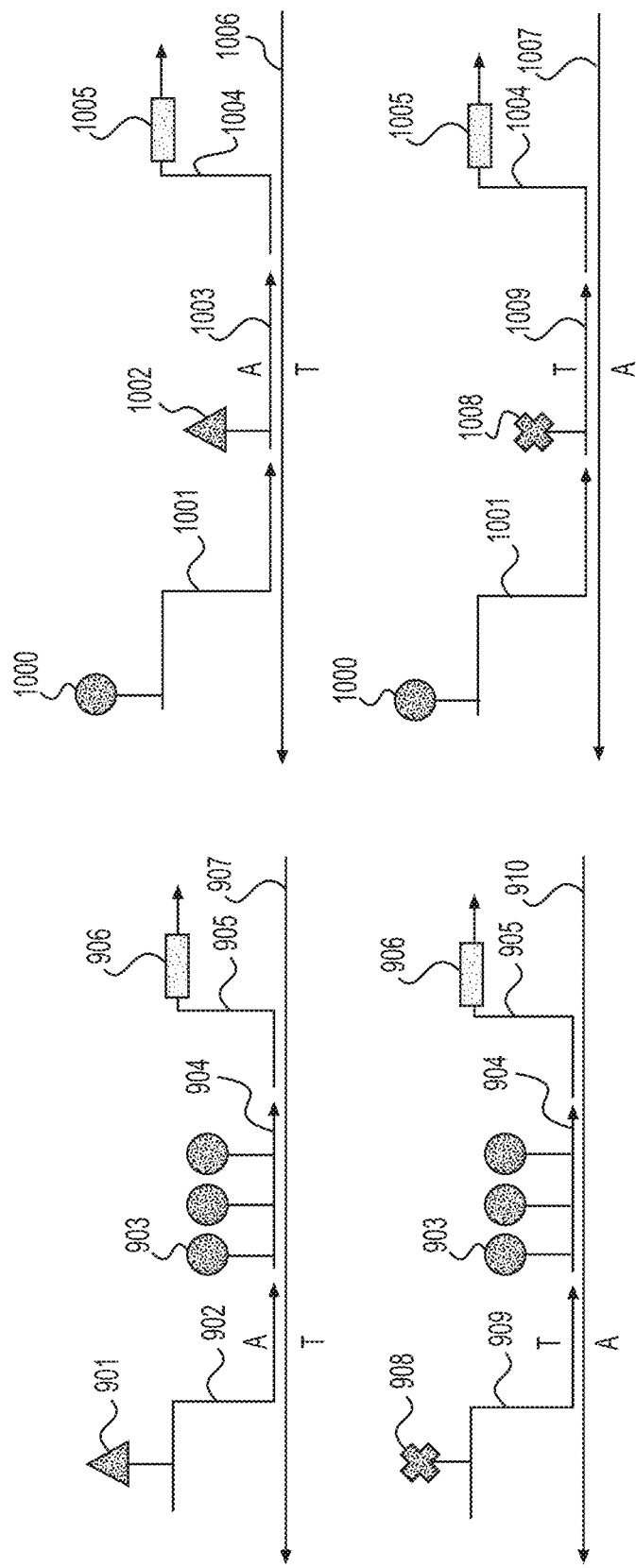

FIG. 29 depicts a modification of the general procedure described in FIG. 21. FIG. 29 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 29 depicts two probe sets, one probe set for Allele 1 and one probe set for Allele 2.

907 and 910 are target molecules corresponding to Allele 1 and Allele 2, respectively. A first probe set contains member probes 902, 905. 902 contains a label (901) of type "A." Item 905 contains an affinity tag (906) which may be used for isolation and identification of the probe product. A second probe set with member probes 909, 905 carries respective features as in the first probe set. In this embodiment, 905 is identical for both probe sets. However, 909 contains a label (908) of type "B," distinguishable from type "A." In this embodiment, 902 and 909 contain sequences that are nearly identical, and differ by only one nucleotide in the sequence. Therefore, hybridization sequences of these two probes contain complementary regions for Allele 1 (902), and Allele 2 (909). Further, the length of each hybridization domain on 902 and 909, as well as experimental hybridization conditions are designed such that probe 902 will only hybridize to Allele 1 and probe 909 will only hybridize to Allele 2. The purpose of this assay type is to be able to accurately quantify the frequency of Allele 1 and Allele 2 in a sample.

In this embodiment, probes 902 and 905 hybridize to sequences corresponding to Allele 1, such that there is a "gap" on the target molecule consisting of one or more nucleotides between hybridized probes 902 and 905. In this embodiment, a DNA polymerase or other enzyme may be used to synthesize a new polynucleotide species (904) that covalently joins 902 and 905. That is, the probe product formed in this example is a single contiguous nucleic acid molecule with a sequence corresponding to Allele 1, and bearing the labels and/or affinity tags above. Additionally, 904 may contain one or more labels of type "C," possibly as a result of incorporation of a nucleotide bearing a label of type "C." This example also conveys to the probe product formed for Allele 2, containing probes 909 and 905.

FIG. 30 depicts a modification of the general procedure described in FIG. 21. FIG. 30 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 30 depicts two probe sets, one probe set for Allele 1 and one probe set for Allele 2.

1006 and 1007 are target molecules corresponding to Allele 1 and Allele 2, respectively. A first probe set contains member probes 1001, 1003, 1004. 1003 contains a label (1002) of type "A." 1004 contains an affinity tag (1005) which may be used for isolation and identification of the probe product.

A second probe set with member probes 1001, 1009, 1004 carries respective features as in the first probe set. In this embodiment, 1001 is identical for both probe sets and 1004 is identical for both probe sets. However, 1009 contains a label (1008) of type "B," distinguishable from type "A."

In this embodiment, 1003 and 1009 contain sequences that are nearly identical, and differ by only one nucleotide in the sequence. Therefore, hybridization sequences of these two probes contains complementary regions for Allele 1 (1003), and Allele 2 (1009), respectively. Further, the length of each hybridization domain on 1003 and 1009, as well as experimental hybridization conditions are designed such that probe 1003 will only hybridize to Allele 1 and probe 1009 will only hybridize to Allele 2. The purpose of this assay type is to be able to accurately quantify the frequency of Allele 1 and Allele 2 in a sample. In this embodiment, the probe 1001 contains one or more labels (1000) of type "C." Therefore, probe products will contain a combination of labels. For Allele 1, probe products will contains labels of type "A" and type "C," whereas probe products from Allele 2 will contain labels of type "B" and type "C."

Figures 31, 32:
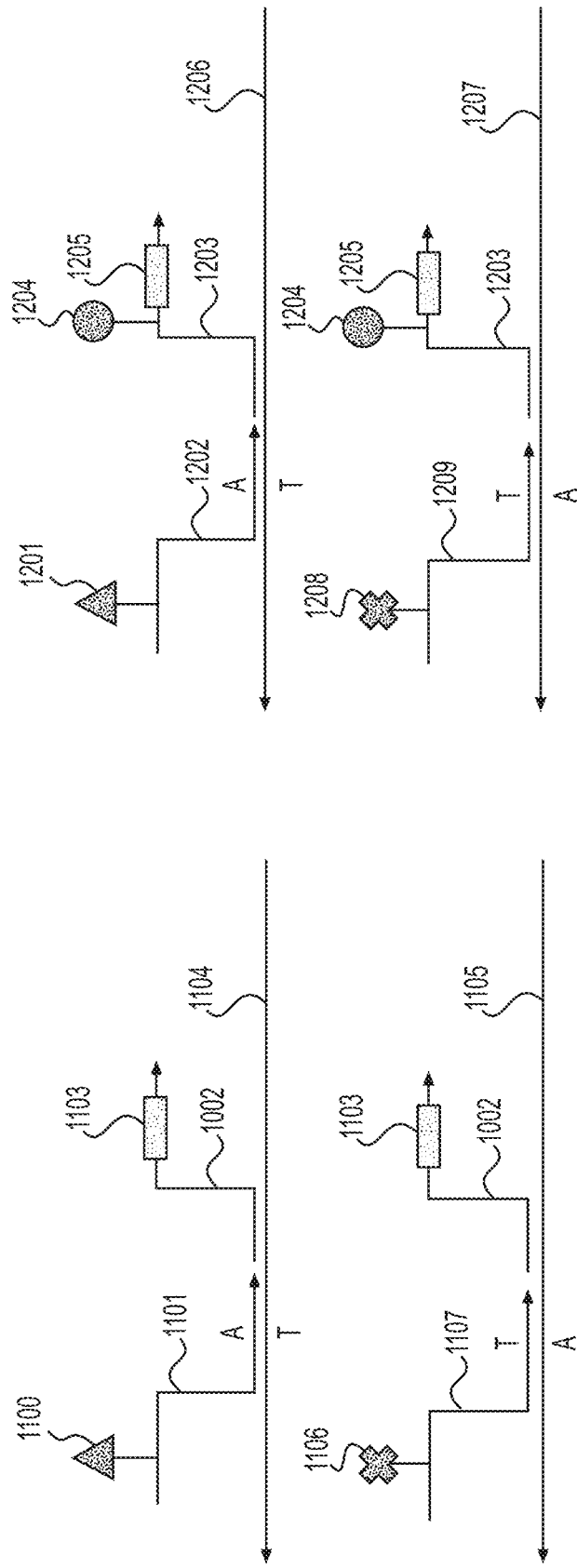

FIG. 31 depicts a modification of the general procedure described in FIG. 21. FIG. 31 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 31 depicts two probe sets—one probe set for Allele 1 and one probe set for Allele 2. 1104 and 1105 are target molecules corresponding to Allele 1 and Allele 2, respectively. A first probe set contains member probes 1101, 1102. 1101 contains a label (1100) of type "A." 1102 contains an affinity tag (1103) which may be used for isolation and identification of the probe product. A second probe set with member probes 1107, 1102 carries respective features as in the first probe set. In this embodiment, 1102 is identical for both probe sets. However, 1107 contains a label (1106) of type "B," distinguishable from type "A." In this embodiment, 1101 and 1107 contain sequences that are nearly identical, and differ by only one nucleotide in the sequence. Therefore, hybridization sequences of these two probes contains complementary regions for Allele 1 (1101), and Allele 2 (1107). Further, the length of each hybridization domain on 1101 and 1107, as well as experimental hybridization conditions are designed such that probe 1101 will only hybridize to Allele 1 and probe 1107 will only hybridize to Allele 2. The purpose of this assay type is to be able to accurately quantify the frequency of Allele 1 and Allele 2 in a sample.

FIG. 32 depicts a modification of the general procedure described in FIG. 21. FIG. 32 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 32 depicts two probe sets—one probe set for Allele 1 and one probe set for Allele 2. 1206 and 1207 are target molecules corresponding to Allele 1 and Allele 2, respectively. A first probe set contains member probes 1202, 1203. 1202 contains a label (1201) of type "A." 1203 contains an affinity tag (1205) which may be used for isolation and identification of the probe product. A second probe set with member probes 1209, 1203 carries respective features as in the first probe set. In this embodiment, 1203 is identical for both probe sets. However, 1209 contains a label (1208) of type "B," distinguishable from type "A." In this embodiment, 1202 and 1209 contain sequences that are nearly identical, and differ by only one nucleotide in the sequence. Therefore, hybridization sequences of these two probes contains complementary regions for Allele 1 (1202), and Allele 2 (1209). Further, the length of each hybridization domain on 1202 and 1209, as well as experimental hybridization conditions are designed such that probe 1202 will only hybridize to Allele 1 and probe 1209 will only hybridize to Allele 2. The purpose of this assay type is to be able to accurately quantify the frequency of Allele 1 and Allele 2 in a sample. In this embodiment, the probe 1203 contains one or more labels (1204) of type "C." Therefore, probe product will contain a combination of labels. For Allele 1, probe products will contains labels of type "A" and type "C," whereas probe products from Allele 2 will contain labels of type "B" and type "C."

FIG. 33 depicts a modification of the general procedure described in FIG. 21. FIG. 33 depicts two probe sets, one probe set for Locus 1 and one probe set for Locus 2, although as aforementioned, multiple probes sets may be designed for each genomic locus. 1304 and 1305 are target molecules corresponding to Locus 1 and Locus 2, respectively. A first probe sets contains member probes 1301, 1302. 1301 contains a label (1300) of type "A." 1301 contains an affinity tag (1303) which may be used for isolation and identification of the probe product. A second probe set with member probes 1307, 1308 carries respective features as in the first probe set. However, 1307 contains a label (1306) of type "B," distinguishable from type "A." 1307 contains an affinity tag (1309) which may be identical to or unique from 1303. Many probe sets may designed that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique, and the affinity tags for the many probe sets for Locus 2 may be identical or unique. In this embodiment, the probes 1301 and 1307 have similar structures. For example, on probe 1301 there are two distinct hybridization domains, such that probe 1302 may be ligated to each end of 1301, forming a probe product consisting of a contiguous, topologically closed molecule of DNA (e.g., a circular molecule). The non-hybridizing sequence on probe 1301 may contain additional features, possibly restriction enzyme sites, or primer binding sites for universal amplification. Other related assays can be used to form circular molecules (e.g. padlock probes, molecular inversion probes etc) that have many useful properties. For example, exonucleases can be used to digest linear nucleic acids, while not digesting circular nucleic acids, providing a way to clean up an assay, remove extraneous probes, primers or other oligonucleotides thereby purifying a sample. Circular molecules, for example circular assay products or probe products, can also be amplified using rolling-circle or other approaches. Signal amplification can be achieved in the same way, by using labelled primers or probes in the rolling circle amplification or other amplification method such as emulsion PCR, droplet-based PCR, bridge amplification, linear amplification, linear duplication and others. Amplified products can be collapsed or concentrated in a variety (for example, by hybridization) to make a more focused signal than would be achieved using a long molecule. An example of this would be DNA nanoballs.

Other assays may form specific probe-target complexes, for example where one or more probes is ligated to the target itself. This can be achieved by using a template that allows hybridization of parts of both a probe and the target and therefore allows ligation.

One feature of this embodiment is that all probe products are contiguous circular molecules. In this manner, probe products may be isolated from all other nucleic acids via enzymatic degradation of all linear nucleic acid molecules, for example, using an exonuclease.

FIG. 34 depicts a modification of the general procedure described in FIG. 21. FIG. 34 depicts two probe sets, one probe set for Locus 1 and one probe set for Locus 2, although as aforementioned, multiple probes sets may be designed for each genomic locus. 1405 and 1406 are target molecules corresponding to Locus 1 and Locus 2, respectively. A first probe sets contains member probes 1401, 1403. 1401 contains a label (1400) of type "A." 1401 contains an affinity tag (1404) which may be used for isolation and identification of the probe product. A second probe set with member probes 1408, 1410 carries respective features as in the first probe set. However, 1408 contains a label (1407) of type "B," distinguishable from type "A." 1408 contains an affinity tag (1411) which may be identical to or unique from 1404. Many probe sets may designed that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique, and the affinity tags for the many probe sets for Locus 2 may be identical or unique. In this embodiment, the probes 1401 and 1408 have similar structures. For example, on probe 1401 there are two distinct hybridization domains, such that probe 1403 may be ligated to each end of 1401, forming a probe product consisting of a contiguous, topologically closed molecule of DNA (e.g., a circular molecule). The non-hybridizing sequence on probe 1401 may contain additional features, possibly restriction enzyme sites, or primer binding sites for universal amplification.

One feature of this embodiment is that all probe products are contiguous circular molecules. In this manner, probe products may be isolated from all other nucleic acids via enzymatic degradation of all linear nucleic acid molecules, for example, using an exonuclease. In this embodiment, the probes 1403 and 1410 contain one or more labels (1402, 1409) of type "C." Therefore, probe products will contain a combination of labels. For Locus 1, probe products will contains labels of type "A" and type "C," whereas probe products from Locus 2 will contain labels of type "B" and type "C".

Figures 35, 36:
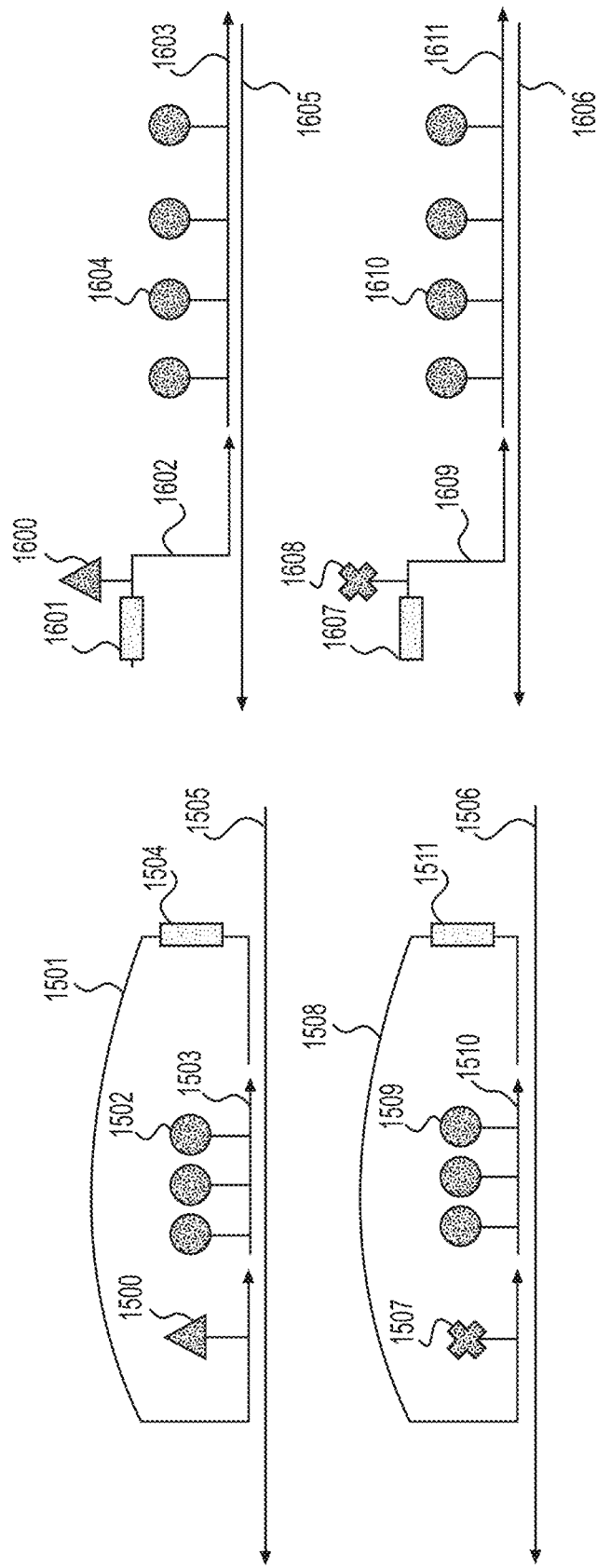

FIG. 35 depicts a modification of the general procedure described in FIG. 21. FIG. 35 depicts two probe sets, one probe set for Locus 1 and one probe set for Locus 2, although as aforementioned, multiple probes sets may be designed for each genomic locus. 1505 and 1506 are target molecules corresponding to Locus 1 and Locus 2, respectively. A first probe sets contains member probe 1501. 1501 contains a label (1500) of type "A." 1501 contains an affinity tag (1504) which may be used for isolation and identification of the probe product. A second probe set with member probe 1508 carries respective features as in the first probe set. However, 1508 contains a label (1507) of type "B," distinguishable from type "A." 1508 contains an affinity tag (1511) which may be identical to or unique from 1504. Many probe sets may designed that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique, and the affinity tags for the many probe sets for Locus 2 may be identical or unique. In this embodiment, the probes 1501 and 1508 have similar structures.

For example, on probe 1501 there are two distinct hybridization domains, such that when hybridized against a target molecule, there is a gap between the two hybridization domains. In this embodiment, a DNA polymerase or other enzyme may be used to synthesize a new polynucleotide species (1503) that covalently fills the gap between the hybridization domains of 1501. That is, the probe product formed in this example is a single, contiguous, topologically closed molecule of DNA (e.g., a circular molecule) with a sequence corresponding to Locus 1, and bearing the labels and/or affinity tags above. Additionally, 1503 may contain one or more labels of type "C," possibly as a result of incorporation of a nucleotide bearing a label of type "C." This example also conveys to the probe product formed for Locus 2, containing probe 1508. The non-hybridizing sequence on probe 1501 and probe 1508 may contain additional features, possibly restriction enzyme sites. One feature of this embodiment is that all probe products are contiguous circular molecules. In this manner, probe products may be isolated from all other nucleic acids via enzymatic degradation of all linear nucleic acid molecules, for example, using an exonuclease. Probe products will contain a combination of labels. For Locus 1, probe products will contains labels of type "A" and type "C," whereas probe products from Locus 2 will contain labels of type "B" and type "C."

FIG. 36 depicts a modification of the general procedure described in FIG. 21. FIG. 36 depicts two probe sets, one probe set for Locus 1 and one probe set for Locus 2, although as aforementioned, multiple probes sets may be designed for each genomic locus. 1605 and 1606 are target molecules corresponding to Locus 1 and Locus 2, respectively.

A first probe sets contains member probe 1602. 1602 contains a label (1600) of type "A." 1602 contains an affinity tag (1601) which may be used for isolation and identification of the probe product.

A second probe set with member probe 1609 carries respective features as in the first probe set. However, 1609 contains a label (1608) of type "B," distinguishable from type "A." 1609 contains an affinity tag (1607) which may be identical to or unique from 1601. Many probe sets may designed that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique, and the affinity tags for the many probe sets for Locus 2 may be identical or unique.

In this embodiment, probes 1602 and 1609 hybridize to sequences corresponding to Locus 1 or Locus 2 respectively, and a DNA polymerase or other enzyme may be used to synthesize a new polynucleotide sequence, for example 1603 in the case of Locus 1 or 1611 in the case of Locus 2. In this embodiment, 1603 and 1611 may contain one or more labels (1604) of type "C," possibly as a result of incorporation of one of more nucleotides bearing a label of type "C." This example also conveys to the probe product formed for Locus 2. Therefore, probe products will contain a combination of labels. For Locus 1, probe products will contains labels of type "A" and type "C," whereas probe products from Locus 2 will contain labels of type "B" and type "C." This embodiment results in probe products with high specificity for sequences in Locus 1 or Locus 2 respectively.

Figure 37:
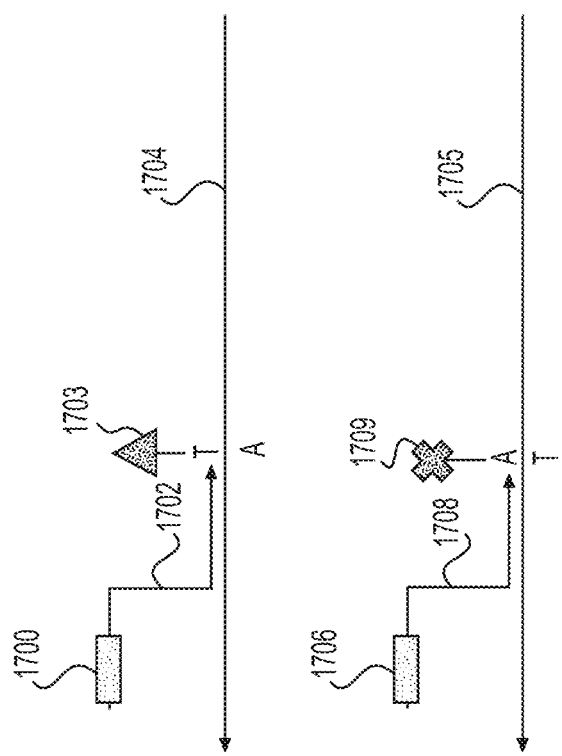

FIG. 37 depicts a modification of the general procedure described in FIG. 21. FIG. 37 depicts two probe sets, one probe set for Locus 1 and one probe set for Locus 2, although as aforementioned, multiple probes sets may be designed for each genomic locus. 1704 and 1705 are target molecules corresponding to Locus 1 and Locus 2, respectively.

A first probe sets contains member probe 1702. 1702 contains an affinity tag (1700) which may be used for isolation and identification of the probe product.

A second probe set with member probe 1708 carries respective features as in the first probe set. 1708 contains an affinity tag (1706) which may be identical to or unique from 1700. Many probe sets may designed that target "Locus 1," containing unique probe sequences. Similarly, many probe sets may be designed that target "Locus 2," containing unique probe sequences. In this embodiment, the affinity tags for the many probe sets for Locus 1 may be identical or unique, and the affinity tags for the many probe sets for Locus 2 may be identical or unique.

In this embodiment, probes 1702 and 1708 hybridize to sequences corresponding to Locus 1 and Locus 2 respectively. The designs of each probe for Locus 1 and Locus 2 are such that the first adjacent nucleotide next to the hybridization domains contains a different nucleotide for Locus 1 than for Locus 2. In this example, the first adjacent nucleotide next to the hybridization domain of 1702 is an "A," whereas the first adjacent nucleotide next to the hybridization domain of 1708 is a "T." In this embodiment, all probes for Locus 1 shall be designed such that the first nucleotide immediately adjacent to the hybridization domain shall consist of different nucleotide(s) than the first nucleotide immediately adjacent to the hybridization domain of the probes for Locus 2. That is, by design, probe sets from Locus 1 and Locus 2 may be distinguished from one another based on the identity of the first nucleotide immediately adjacent to the hybridization domain.

In this embodiment, a DNA polymerase or other enzyme will be used to add at least one additional nucleotide to each of the probe sequences. In this example, the nucleotide substrates for the DNA polymerase are competent for a single addition, for example, the nucleotides may be dideoxy chain terminators. That is, only one new nucleotide shall be added to each probe sequence. In this example, the nucleotide added to probe 1702 will contain one or more labels (1703) of type "A." The nucleotide added to probe 1708 will contain one or more labels (1709) of type "B," such that the probe products for Locus 1 may be distinguished from the probe products from Locus 2.

Figure 38:
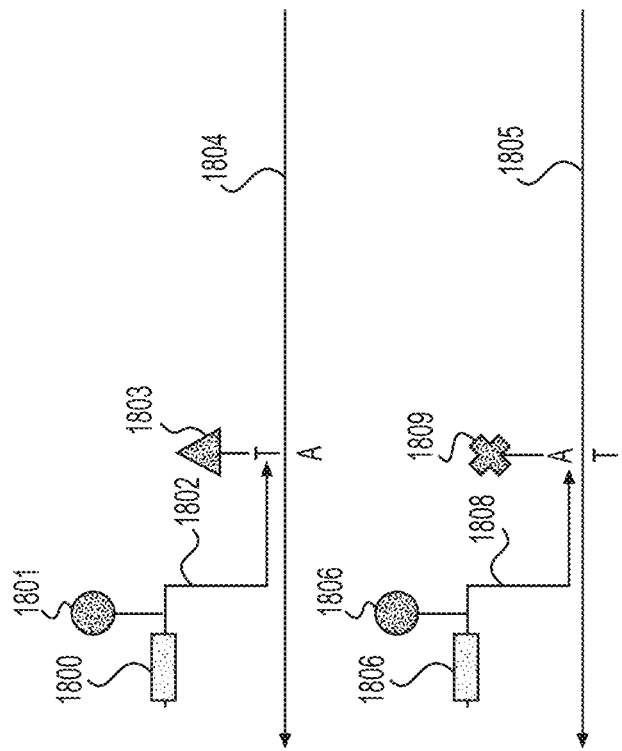

FIG. 38 depicts a modification of the general procedure described in FIG. 21. FIG. 38 depicts two probe sets, one probe set for Locus 1 and one probe set for Locus 2, although as aforementioned, multiple probes sets may be designed for each genomic locus. 1804 and 1805 are target molecules corresponding to Locus 1 and Locus 2, respectively.

A first probe sets contains member probe 1802. 1802 contains an affinity tag (1800) which may be used for isolation and identification of the probe product.

A second probe set with member probe 1808 carries respective features as in the first probe set. 1808 contains an affinity tag (1806) which may be identical to or unique from 1800. Many probe sets may be designed that target "Locus 1," containing unique probe sequences. Similarly, many probe sets may be designed that target "Locus 2," containing unique probe sequences. In this embodiment, the affinity tags for the many probe sets for Locus 1 may be identical or unique, and the affinity tags for the many probe sets for Locus 2 may be identical or unique.

In this embodiment, probes 1802 and 1808 hybridize to sequences corresponding to Locus 1 and Locus 2 respectively. The designs of each probe for Locus 1 and Locus 2 are such that the first adjacent nucleotide next to the hybridization domains contains a different nucleotide for Locus 1 than for Locus 2. In this example, the first adjacent nucleotide next to the hybridization domain of 1802 is an "A," whereas the first adjacent nucleotide next to the hybridization domain of 1808 is a "T." In this embodiment, all probes for Locus 1 shall be designed such that the first nucleotide immediately adjacent to the hybridization domain shall consist of different nucleotide(s) than the first nucleotide immediately adjacent to the hybridization domain of the probes for Locus 2. That is, by design, probe sets from Locus 1 and Locus 2 may be distinguished from one another based on the identity of the first nucleotide immediately adjacent to the hybridization domain.

In this embodiment, a DNA polymerase or other enzyme will be used to add at least one additional nucleotide to each of the probe sequences. In this example, the nucleotide substrates for the DNA polymerase are competent for a single addition, perhaps because the nucleotides added to the reaction mixture are dideoxy nucleotides. That is, only one new nucleotide shall be added to each probe sequence. In this example, the nucleotide added to probe 1802 will contain one or more labels (1803) of type "A." The nucleotide added to probe 1808 will contain one or more labels (1809) of type "B," such that the probe products for Locus 1 may be distinguished from the probe products from Locus 2.

In this embodiment, the probes 1802 and 1808 contain one or more labels (1801, 1806) of type "C." Therefore, probe products will contain a combination of labels. For Locus 1, probe products will contains labels of type "A" and type "C," whereas probe products from Locus 2 will contain labels of type "B" and type "C."

FIG. 39 depicts a modification of the general procedure described in FIG. 21. FIG. 39 depicts two probe sets, one probe set for Locus 1 and one probe set for Locus 2, although as aforementioned, multiple probes sets may be designed for each genomic locus. 1906 and 1907 are target molecules corresponding to Locus 1 and Locus 2, respectively.

A first probe set contains member probe 1902. 1902 contains an affinity tag (1901) which may be used for isolation and identification of the probe product.

A second probe set with member probe 1910 carries respective features as in the first probe set. 1910 contains an affinity tag (1908) which may be identical to or unique from 1901. Many probe sets may be designed that target "Locus 1," containing unique probe sequences. Similarly, many probe sets may be designed that target "Locus 2," containing unique probe sequences. In this embodiment, the affinity tags for the many probe sets for Locus 1 may be identical or unique, and the affinity tags for the many probe sets for Locus 2 may be identical or unique.

In this embodiment, probes 1902 and 1910 hybridize to sequences corresponding to Locus 1 and Locus 2 respectively. The designs of each probe for Locus 1 and Locus 2 are such that the first adjacent nucleotide next to the hybridization domains contains a different nucleotide for Locus 1 than Locus 2. In this example, the first adjacent nucleotide next to the hybridization domain of 1902 is an "A," whereas the first adjacent nucleotide next to the hybridization domain of 1910 is a "T." In this embodiment, all probes for Locus 1 shall be designed such that the first nucleotide immediately adjacent to the hybridization domain shall consist of different nucleotide(s) than the first nucleotide immediately adjacent to the hybridization domain of the probes for Locus 2. That is, by design, probe sets from Locus 1 and Locus 2 may be distinguished from one another nucleotide on the identity of the first nucleotide immediately adjacent to the hybridization domain. A different nucleotide, not one used to distinguish probes from Locus 1 or Locus 2 shall serve as a chain terminator. In this particular example, an "A" nucleotide on a target molecule is used do distinguish probes for Locus 1 and a "T" nucleotide is used to distinguish probes for Locus 2. In this example, a "C" nucleotide may serve as a chain terminator. In this case, a "C" nucleotide will be added to the assay not is not capable of chain elongation (for example, a dideoxy C). One additional constraint is that the probe sequences are designed such that there are no instances of an identifying nucleotide for Locus 2 present on 1906 in between the distinguishing nucleotide for Locus 1 and the chain terminating nucleotide. In this example, there will be no "T" nucleotides present on 1906 after the hybridization domain of 1902 and before the G, which will pair with the chain terminator C.

In this embodiment, DNA polymerase or a similar enzyme will be used to synthesize new nucleotide sequences, and the nucleotide added at the distinguishing nucleotide location for Locus 1 will contain one or more labels (1903) of type "A." The nucleotide added at the distinguishing nucleotide location for Locus 2 will contain 1 or more labels (1911) of type "B," such that the probe products for Locus 1 may be distinguished from the probe products from Locus 2. In this embodiment, the nucleotide added at the chain terminating position will contain one or more labels (1912) of type "C." Therefore, probe products will contain a combination of labels. For Locus 1, probe products will contains labels of type "A" and type "C," whereas probe products from Locus 2 will contain labels of type "B" and type "C."

In another embodiment, the chain terminator may contain no label. In this embodiment, a fourth nucleotide may be added to the assay that contains one or more labels of type "C." This fourth nucleotide does not pair with the identifying nucleotide for Allele 1 (in this example, A), does not pair with the identifying nucleotide for Allele 2 (in this example, T), does not pair with the chain terminating nucleotide (in this example G). In this example, the fourth nucleotide that would bear one or more labels of type "C" is G, and will pair with C locations on 1906 and 1907. Therefore, probe products will contain a combination of labels. For Locus 1, probe products will contains labels of type "A" and type "C," whereas probe products from Locus 2 will contain labels of type "B" and type "C."

FIG. 40 depicts a modification of the general procedure described in FIG. 21. FIG. 40 depicts two probe sets, one probe set for Locus 1 and one probe set for Locus 2, although as aforementioned, multiple probes sets may be designed for each genomic locus. 2005 and 2006 are target molecules corresponding to Locus 1 and Locus 2, respectively.

A first probe sets contains member probe 2001. 2001 contains an affinity tag (2000) which may be used for isolation and identification of the probe product.

A second probe set with member probe 2008 carries respective features as in the first probe set. 2008 contains an affinity tag (2007) which may be identical to or unique from 2000. Many probe sets may be designed that target "Locus 1," containing unique probe sequences. Similarly, many probe sets may be designed that target "Locus 2," containing unique probe sequences. In this embodiment, the affinity tags for the many probe sets for Locus 1 may be identical or unique, and the affinity tags for the many probe sets for Locus 2 may be identical or unique.

In this embodiment, probes 2001 and 2008 hybridize to sequences corresponding to Locus 1 and Locus 2 respectively. The designs of each probe for Locus 1 and Locus 2 are such that there are one or more instances of a distinguishing nucleotide (in this example, "A" is a distinguishing nucleotide for Locus 1 and "T" is a distinguishing nucleotide for Locus 2) followed by a chain terminating nucleotide (in this example "G") adjacent to the hybridization domain of the probes. Importantly there will be no instances of the distinguishing nucleotide for Locus 2 (in this example, "T") present in between the hybridization domain of 2001 on 2005 and the chain terminating nucleotide on 2005. Similarly, there will be no instance of the distinguishing nucleotide for Locus 1 (in this example, "A") present in between the hybridization domain of 2008 on 2006 and the chain terminating nucleotide on 2006.

In this embodiment, DNA polymerase or a similar enzyme will be used to synthesize new nucleotide sequences (2004, 2011) until the addition of a chain terminating nucleotide, one possible example would be a dideoxy C. In this embodiment, the nucleotides added at the distinguishing nucleotide locations for Locus 1 will contain one or more labels (2003) of type "A." The nucleotides added at the distinguishing nucleotide locations for Locus 2 will contain 1 or more labels (2010) of type "B," such that the probe products for Locus 1 may be clearly distinguished from the probe products from Locus 2.

FIG. 41 depicts a modification of the general procedure described in FIG. 21. FIG. 41 depicts two probe sets, one probe set for Locus 1 and one probe set for Locus 2, although as aforementioned, multiple probes sets may be designed for each genomic locus. 2105 and 2106 are target molecules corresponding to Locus 1 and Locus 2, respectively.

A first probe sets contains member probe 2102. 2102 contains an affinity tag (2100) which may be used for isolation and identification of the probe product.

A second probe set with member probe 2109 carries respective features as in the first probe set. 2109 contains an affinity tag (2107) which may be identical to or unique from 2100. Many probe sets may be designed that target "Locus 1," containing unique probe sequences. Similarly, many probe sets may be designed that target "Locus 2," containing unique probe sequences. In this embodiment, the affinity tags for the many probe sets for Locus 1 may be identical or unique, and the affinity tags for the many probe sets for Locus 2 may be identical or unique.

In this embodiment, probes 2102 and 2109 hybridize to sequences corresponding to Locus 1 and Locus 2 respectively. The designs of each probe for Locus 1 and Locus 2 are such that there are one or more instances of a distinguishing nucleotide (in this example, "A" is a distinguishing nucleotide for Locus 1 and "T" is a distinguishing nucleotide for Locus 2) followed by a chain terminating nucleotide (in this example "G") adjacent to the hybridization domain of the probes. Importantly there will be no instances of the distinguishing nucleotide for Locus 2 (in this example, "T") present in between the hybridization domain of 2102 on 2105 and the chain terminating nucleotide on 2105. Similarly, there will be no instance of the distinguishing nucleotide for Locus 1 (in this example, "A") present in between the hybridization domain of 2109 on 2106 and the chain terminating nucleotide on 2106.

In this embodiment, DNA polymerase or a similar enzyme will be used to synthesize new nucleotide sequences (2104, 2110) until the addition of a chain terminating nucleotide, one possible example would be a dideoxy C. In this embodiment, the nucleotides added at the distinguishing nucleotide locations for Locus 1 will contain one or more labels (2103) of type "A." The nucleotides added at the distinguishing nucleotide locations for Locus 2 will contain 1 or more labels (2110) of type "B," such that the probe products for Locus 1 may be clearly distinguished from the probe products from Locus 2.

In this embodiment, the probes 2102 and 2109 contain one or more labels (2101, 2108) of type "C." Therefore, probe products will contain a combination of labels. For Locus 1, probe products will contains labels of type "A" and type "C," whereas probe products from Locus 2 will contain labels of type "B" and type "C."

FIG. 42 depicts a modification of the general procedure described in FIG. 21. FIG. 42 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 42 depicts two probe sets—one probe set for Allele 1 and one probe set for Allele 2. 2203 and 2204 are target molecules corresponding to Allele 1 and Allele 2, respectively.

A first probe sets contains member probe 2201. 2201 contains an affinity tag (2200) which may be used for isolation and identification of the probe product. In this embodiment, the probe sets used for identification of the two different alleles are the same. That is, the probe set for Allele 2 consists of member probe 2201. In this embodiment, probe 2201 hybridizes to a sequence corresponding to Allele 1 and Allele 2 respectively in FIG. 42. The design of probe 2201 is such that the first adjacent nucleotide next to the hybridization domain contains a different nucleotide for Allele 1 than Allele 2. In other words, the first nucleotide adjacent to the hybridization domain may be a single nucleotide polymorphism, or SNP. In this example, the first adjacent nucleotide on 2203 next to the hybridization domain of 2201 is an "A," whereas the first adjacent nucleotide on 2204 next to the hybridization domain of 2201 is a "T." That is, probe products from Allele 1 and Allele 2 may be distinguished from one another based on the identity of the first nucleotide immediately adjacent to the hybridization domain.

In this embodiment, a DNA polymerase or other enzyme will be used to add at least one additional nucleotide to each of the probe sequences. In this example, the nucleotide substrates for the DNA polymerase are competent for a single addition, perhaps because the nucleotides added to the reaction mixture are dideoxy nucleotides. That is, only one new nucleotide shall be added to each probe sequence. In this example, the nucleotide added to probe 2201 for Allele 1 will contain one or more labels (2202) of type "A." The nucleotide added to probe 2201 for Allele 2 will contain one or more labels (2205) of type "B," such that the probe products for Allele 1 may be clearly distinguished from the probe products from Allele 2. That is, the probe product for Allele 1 consists of probe 2201 plus one additional nucleotide bearing one or more labels of type "A," and the probe products for Allele 2 consists of probe 2201 plus one additional nucleotide bearing one or more labels of type "B."

Figures 43, 44:
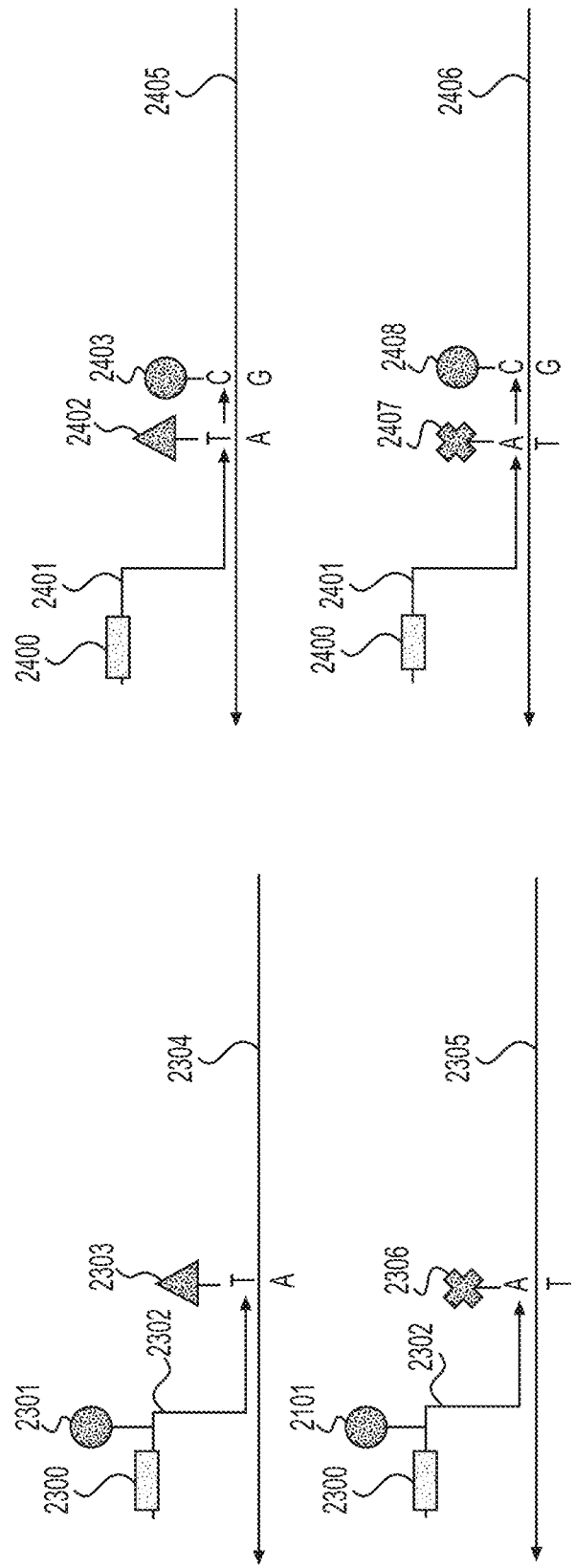

FIG. 43 depicts a modification of the general procedure described in FIG. 21. FIG. 43 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 43 depicts two probe sets—one probe set for Allele 1 and one probe set for Allele 2. 2304 and 2305 are target molecules corresponding to Allele 1 and Allele 2, respectively.

A first probe sets contains member probe 2302. 2302 contains an affinity tag (2300) which may be used for isolation and identification of the probe product. In this embodiment, the probe sets used for identification of the two different alleles are the same. That is, the probe set for Allele 2 consists of member probe 2302. In this embodiment, probe 2302 hybridizes to a sequence corresponding to Allele 1 and Allele 2 respectively in FIG. 43. The design of probe 2302 is such that the first adjacent nucleotide next to the hybridization domains contains a different nucleotide for Allele 1 than Allele 2. In other words, the first adjacent nucleotide adjacent to the hybridization domain may be a single nucleotide polymorphism, or SNP. In this example, the first adjacent nucleotide on 2304 next to the hybridization domain of 2302 is an "A," whereas the first adjacent nucleotide on 2305 next to the hybridization domain of 2302 is a "T." That is, probe products from Allele 1 and Allele 2 may be distinguished from one another based on the identity of the first nucleotide immediately adjacent to the hybridization domain.

In this embodiment, a DNA polymerase or other enzyme will be used to add at least one additional nucleotide to each of the probe sequences. In this example, the nucleotide substrates for the DNA polymerase are competent for a single addition, perhaps because the nucleotides added to the reaction mixture are dideoxy nucleotides. That is, only one new nucleotide shall be added to each probe sequence. In this example, the nucleotide added to probe 2302 for Allele 1 will contain one or more labels (2303) of type "A." The nucleotide added to probe 2302 for Allele 2 will contain one or more labels (2306) of type "B," such that the probe products for Allele 1 may be clearly distinguished from the probe products from Allele 2. That is, the probe product for Allele 1 consists of probe 2302 plus one additional nucleotide bearing one or more labels of type "A," and the probe products for Allele 2 consists of probe 2302 plus one additional nucleotide bearing one or more labels of type "B."

In this embodiment, the probes 2302 contain one or more labels (2301) of type "C." Therefore, probe products will contain a combination of labels. For Allele 1, probe products will contains labels of type "A" and type "C," whereas probe products from Allele 2 will contain labels of type "B" and type "C."

FIG. 44 depicts a modification of the general procedure described in FIG. 21. FIG. 44 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 44 depicts two probe sets—one probe set for Allele 1 and one probe set for Allele 2. 2405 and 2406 are target molecules corresponding to Allele 1 and Allele 2, respectively.

A first probe sets contains member probe 2401. 2401 contains an affinity tag (2400) which may be used for isolation and identification of the probe product. In this embodiment, the probe sets used for identification of two different alleles are the same. That is, the probe set for Allele 2 consists of member probe 2401. In this embodiment, probe 2401 hybridizes to a sequence corresponding to Allele 1 and Allele 2 respectively in FIG. 44. The design of probe for 2401 is such that the first adjacent nucleotide next to the hybridization domains contains a different nucleotide for Allele 1 than Allele 2. In other words, the first nucleotide adjacent to the hybridization domain may be a single nucleotide polymorphism, or SNP. In this example, the first adjacent nucleotide on 2405 next to the hybridization domain of 2401 is an "A," whereas the first adjacent nucleotide on 2406 next to the hybridization domain of 2401 is a "T." That is, probe products from Allele 1 and Allele 2 may be distinguished from one another based on the identity of the first nucleotide immediately adjacent to the hybridization domain.

In this embodiment, a DNA polymerase or other enzyme will be used to add at least one additional nucleotide to each of the probe sequences. In this example, the nucleotide added to probe 2401 for Allele 1 will contain one or more labels (2402) of type "A." The nucleotide added to probe 2401 for Allele 2 will contain one or more labels (2407) of type "B," such that the probe products for Locus 1 may be clearly distinguished from the probe products from Locus 2. That is, the probe product for Allele 1 contains probe 2401 plus an additional nucleotide bearing one or more labels of type "A," and the probe product for Allele 2 contains probe 2401 plus an additional nucleotide bearing one or more labels of type "B." A different nucleotide, not one used to distinguish Allele 1 from Allele 2 shall serve as a chain terminator. In this particular example, an "A" nucleotide on a target molecule is used to identify Allele 1 and a "T" nucleotide is used to identify Allele 2. In this example, a "C" nucleotide may serve as a chain terminator. In this case, a "C" nucleotide will be added to the assay that is not is not capable of chain elongation (for example, a dideoxy C). One additional constraint is that the probe sequences are designed such that there are no instances of an identifying nucleotide for Allele 2 is present on 2405 in between the distinguishing nucleotide for Allele 1 an the chain terminating nucleotide. In this example, there will be no "T" nucleotides present on 2405 after the hybridization domain of 2401 and before a G, which will pair with the chain terminator C.

In this embodiment, DNA polymerase or a similar enzyme will be used to synthesize new nucleotide sequences, and the nucleotide added at the distinguishing nucleotide location for Allele 1 will contain one or more labels (2402) of type "A." The nucleotide added at the distinguishing nucleotide location for Allele 2 will contain 1 or more labels (2407) of type "B," such that the probe products for Allele 1 may be clearly distinguished from the probe products from Allele 2. In this embodiment, the nucleotide added at the chain terminating position will contain one or more labels (2403) of type "C." Therefore, probe products will contain a combination of labels. For Allele 1, probe products will contains labels of type "A" and type "C," whereas probe products from Allele 2 will contain labels of type "B" and type "C."

Figure 45:
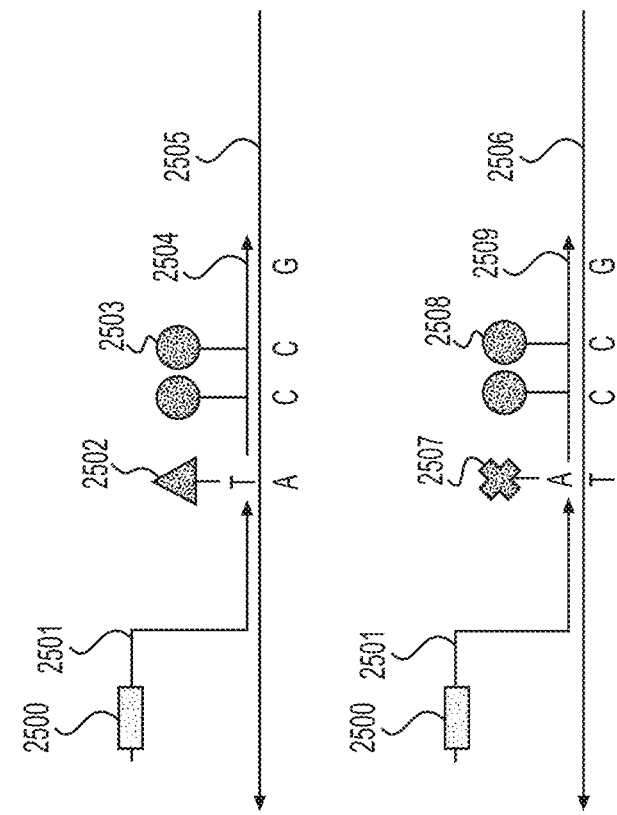

FIG. 45 depicts a modification of the general procedure described in FIG. 21. FIG. 45 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 45 depicts two probe sets—one probe set for Allele 1 and one probe set for Allele 2. 2505 and 2506 are target molecules corresponding to Allele 1 and Allele 2, respectively.

A first probe sets contains member probe 2501. 2501 contains an affinity tag (2500) which may be used for isolation and identification of the probe product. In this embodiment, the probe sets used for identification of two different alleles are the same. That is, the probe set for Allele 2 consists of member probe 2501. In this embodiment, probe 2501 hybridizes to a sequence corresponding to Allele 1 and Allele 2 respectively in FIG. 45. The design of probe for 2501 is such that the first adjacent nucleotide next to the hybridization domains contains a different nucleotide for Allele 1 than Allele 2. In other words, the first nucleotide adjacent to the hybridization domain may be a single nucleotide polymorphism, or SNP. In this example, the first adjacent nucleotide on 2505 next to the hybridization domain of 2501 is an "A," whereas the first adjacent nucleotide on 2506 next to the hybridization domain of 2501 is a "T." That is, probe products from Allele 1 and Allele 2 may be distinguished from one another based on the identity of the first base immediately adjacent to the hybridization domain.

In this embodiment, a DNA polymerase or other enzyme will be used to add at least one additional nucleotide to each of the probe sequences. In this example, the nucleotide added to probe 2501 for Allele 1 will contain one or more labels (2502) of type "A." The nucleotide added to probe 2501 for Allele 2 will contain one or more labels (2507) of type "B," such that the probe products for Locus 1 may be clearly distinguished from the probe products from Locus 2. That is, the probe product for Allele 1 contains probe 2501 plus an additional nucleotide bearing one or more labels of type "A," and the probe product for Allele 2 contains probe 2501 plus an additional nucleotide bearing one or more labels of type "B." A different nucleotide, not one used to distinguish Allele 1 from Allele 2 shall serve as a chain terminator. In this particular example, an "A" nucleotide on a target molecule is used to identify Allele 1 and a "T" nucleotide is used to identify Allele 2. In this example, a "C" nucleotide may serve as a chain terminator. In this case, a "C" nucleotide will be added to the assay that is not is not capable of chain elongation (for example, a dideoxy C). One additional constraint is that the probe sequences are designed such that no instances of an identifying nucleotide for Allele 2 are present on 2505 in between the distinguishing nucleotide for Allele 1 and the chain terminating nucleotide. In this example, there will be no "T" nucleotides present on 2505 after the hybridization domain of 2501 and before a G, which will pair with the chain terminator C.

In this embodiment, DNA polymerase or a similar enzyme will be used to synthesize new nucleotide sequences, and the nucleotide added at the distinguishing nucleotide location for Allele 1 will contain one or more labels (2502) of type "A." The nucleotide added at the distinguishing nucleotide location for Allele 2 will contain 1 or more labels (2507) of type "B," such that the probe products for Allele 1 may be clearly distinguished from the probe products from Allele 2. In this embodiment, a fourth nucleotide may be added to the assay that contains one or more labels (2508, 2503) of type "C." This fourth nucleotide does not pair with the identifying nucleotide for Allele 1 (in this example, A), does not pair with the identifying nucleotide for Allele 2 (in this example, T), does not pair with the chain terminating nucleotide (in this example G). In this example, the fourth nucleotide that would bear one or more labels of type "C" is G, and will pair with C locations on 2505 and 2506. Therefore, probe products will contain a combination of labels. For Allele 1, probe products will contains labels of type "A" and type "C," whereas probe products from Allele 2 will contain labels of type "B" and type "C."

Figure 46:
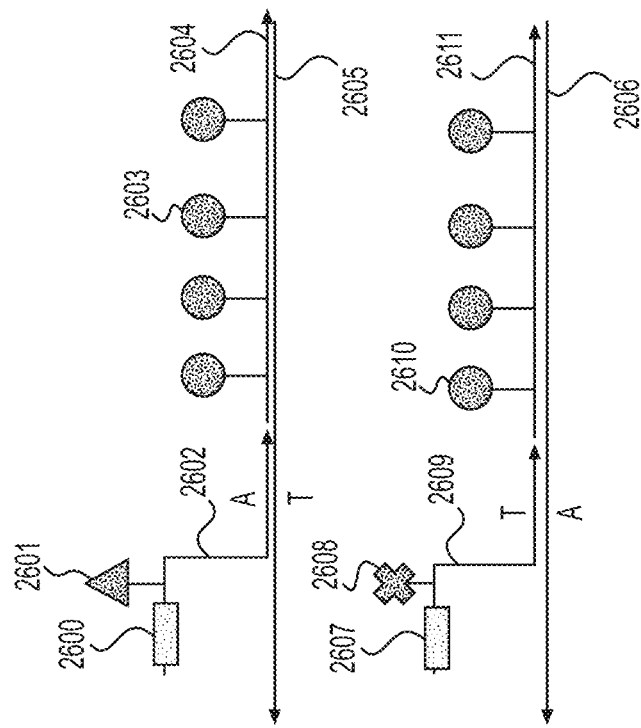

FIG. 46 depicts a modification of the general procedure described in FIG. 21. FIG. 46 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 46 depicts two probe sets—one probe set for Allele 1 and one probe set for Allele 2. 2605 and 2606 are target molecules corresponding to Allele 1 and Allele 2, respectively. A first probe set contains member probe 2602. 2602 contains a label (2601) of type "A." 2602 contains an affinity tag (2600) which may be used for isolation and identification of the probe product.

A second probe set with member probe 2609 carries respective features as in the first probe set. However, 2609 contains a label (2608) of type "B," distinguishable from type "A." 2609 contains an affinity tag (2607) which may be identical to or unique from 2600.

In this embodiment, 2602 and 2609 contain sequences that are nearly identical, and differ by only one nucleotide in the sequence. Therefore, hybridization sequences of these two probes are complementary to Allele 1 (2605), or Allele 2 (2606). Further, the length of each hybridization domain on 2602 and 2609, as well as experimental hybridization conditions are designed such that probe 2602 will only hybridize to Allele 1 and probe 2609 will only hybridize to Allele 2. The purpose of this assay type is to be able to accurately quantify the frequency of Allele 1 and Allele 2 in a sample.

In this embodiment, DNA polymerase or other enzyme may be used to synthesize a new polynucleotide sequence, for example 2604 in the case of Allele 1 or 2611 in the case of Allele 2. In this embodiment, 2604 and 2611 may contain one or more labels (2603, 2610) of type "C," possibly as a result of incorporation of a one of more nucleotides bearing a label of type "C." Therefore, probe products will contain a combination of labels. For Allele 1, probe products will contains labels of type "A" and type "C," whereas probe products from Allele 2 will contain labels of type "B" and type "C." This embodiment results in probe products with high specificity for sequences in Allele 1 or Allele 2 respectively.

Figure 55:
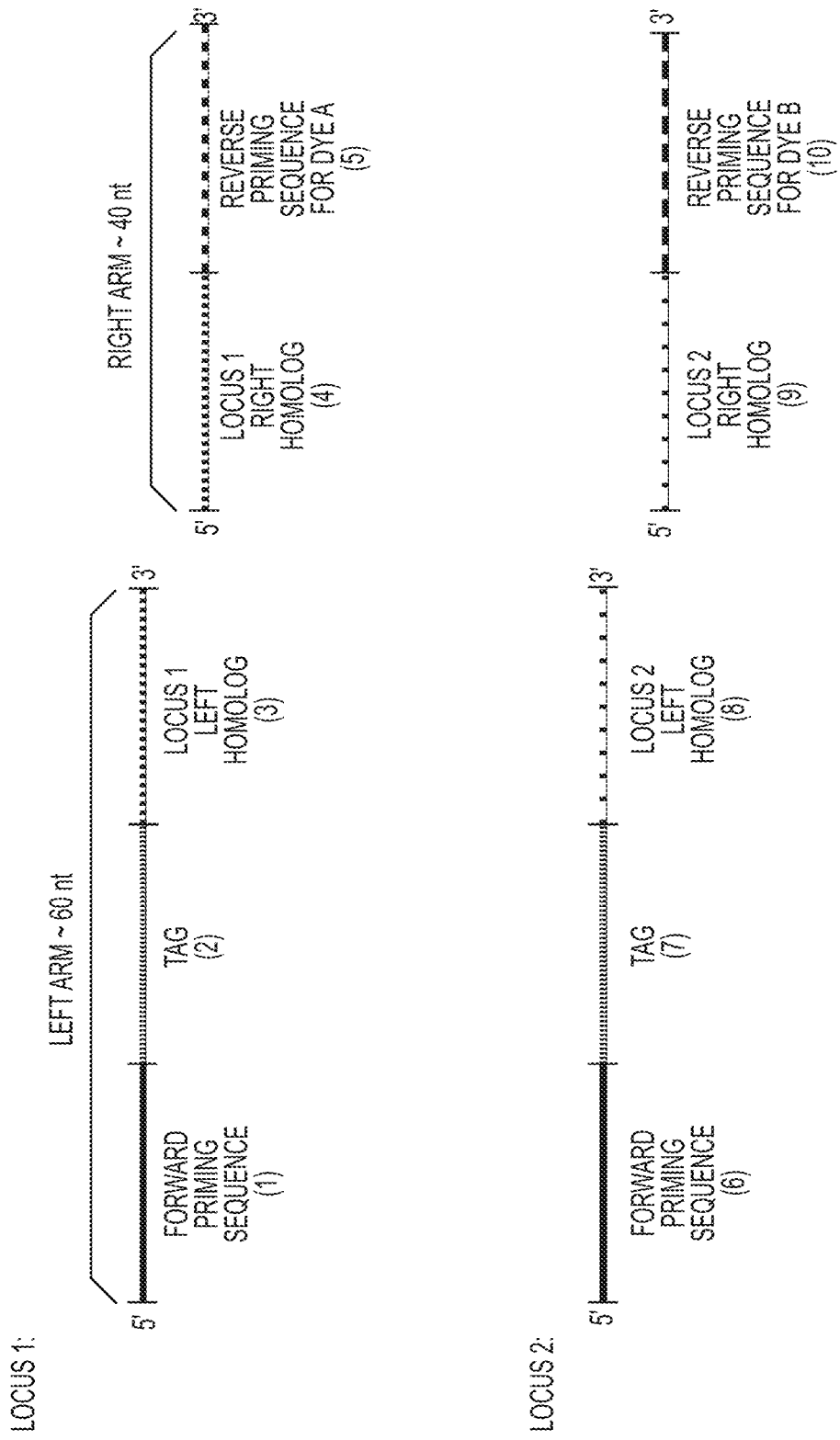
FIG. 55 depicts two probe sets; one probe set for Locus 1 and one probe set for Locus 2—although as aforementioned, multiple probes sets may be designed for each genomic locus.

FIGS. 55-58 illustrate a modification of the general procedure described with respect to FIGS. 21-46. FIG. 55 depicts two probe sets; one probe set for Locus 1 and one probe set for Locus 2—although as aforementioned, multiple probes sets may be designed for each genomic locus. The left arm of the Locus 1 probe set consists of a forward priming sequence, an affinity tag sequence and a homolog to Locus 1 sequence. The right arm of the Locus 1 probe set consists of a homolog to Locus 1 sequence and a reverse priming sequence for labeling the Locus 1 probe set with label A. The left arm of the Locus 2 probe set consists of a forward priming sequence, an affinity tag sequence and a homolog to Locus 2 sequence. The right arm of the Locus 2 probe set consists of a homolog to Locus 2 sequence and a reverse priming sequence for labeling the Locus 2 probe set with label B. The forward priming sequence and the affinity tag sequence are identical for the probe sets for both Locus 1 and Locus 2. The homologous sequences are specific to a single genomic locus. Locus homologous sequences for each probe set are immediately adjacent to one another such that when they hybridize to their target loci, they immediately abut one another and thus may be ligated to form one continuous molecule. The reverse priming sequence is specific to the label (e.g., label A or label B) to be used in labeling probe products for a particular locus for a particular affinity tag sequence.

Figure 56A:
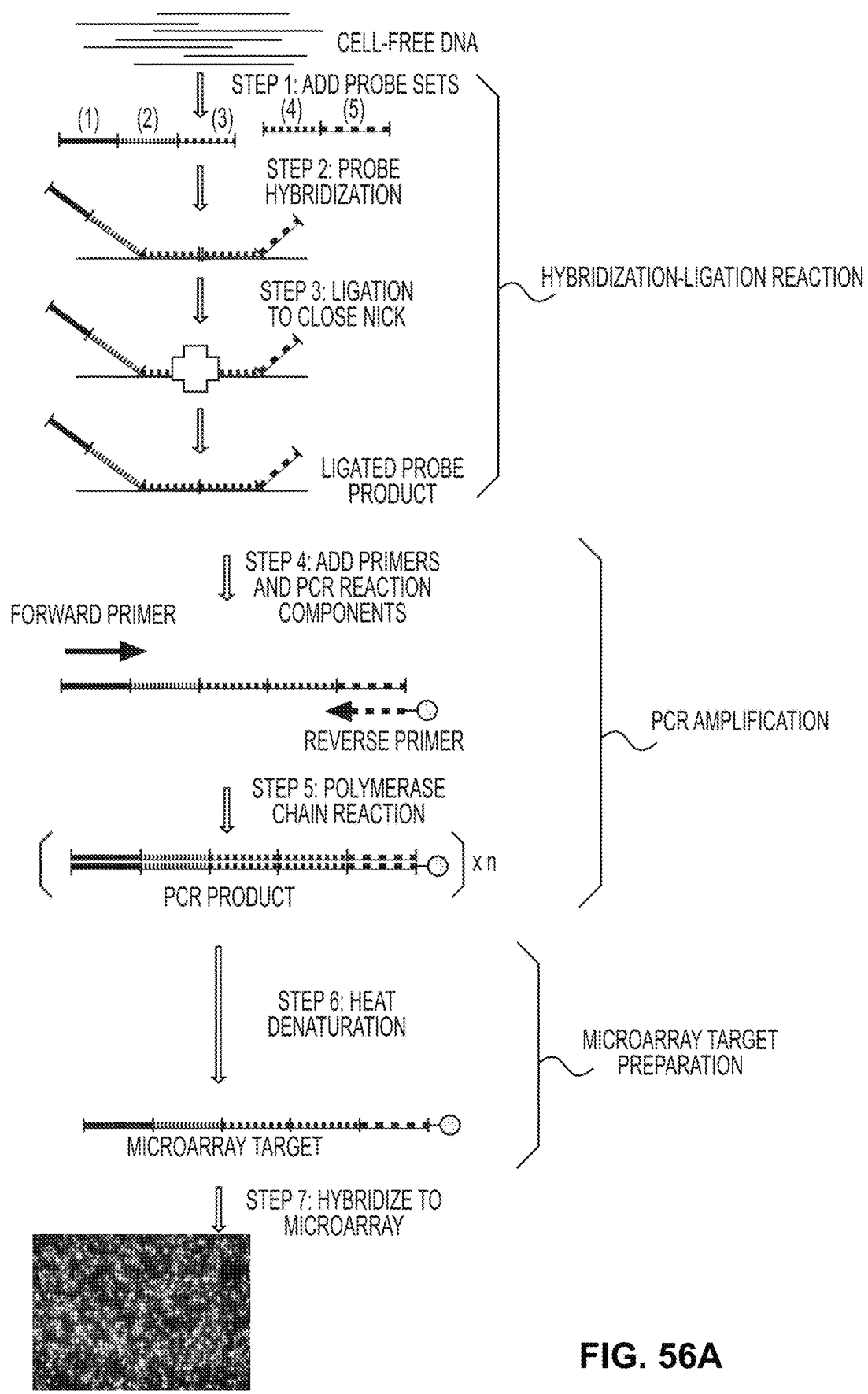
FIG. 56 depicts the procedural workflow that would be applied to the collection of probe sets.
Figure 56B:
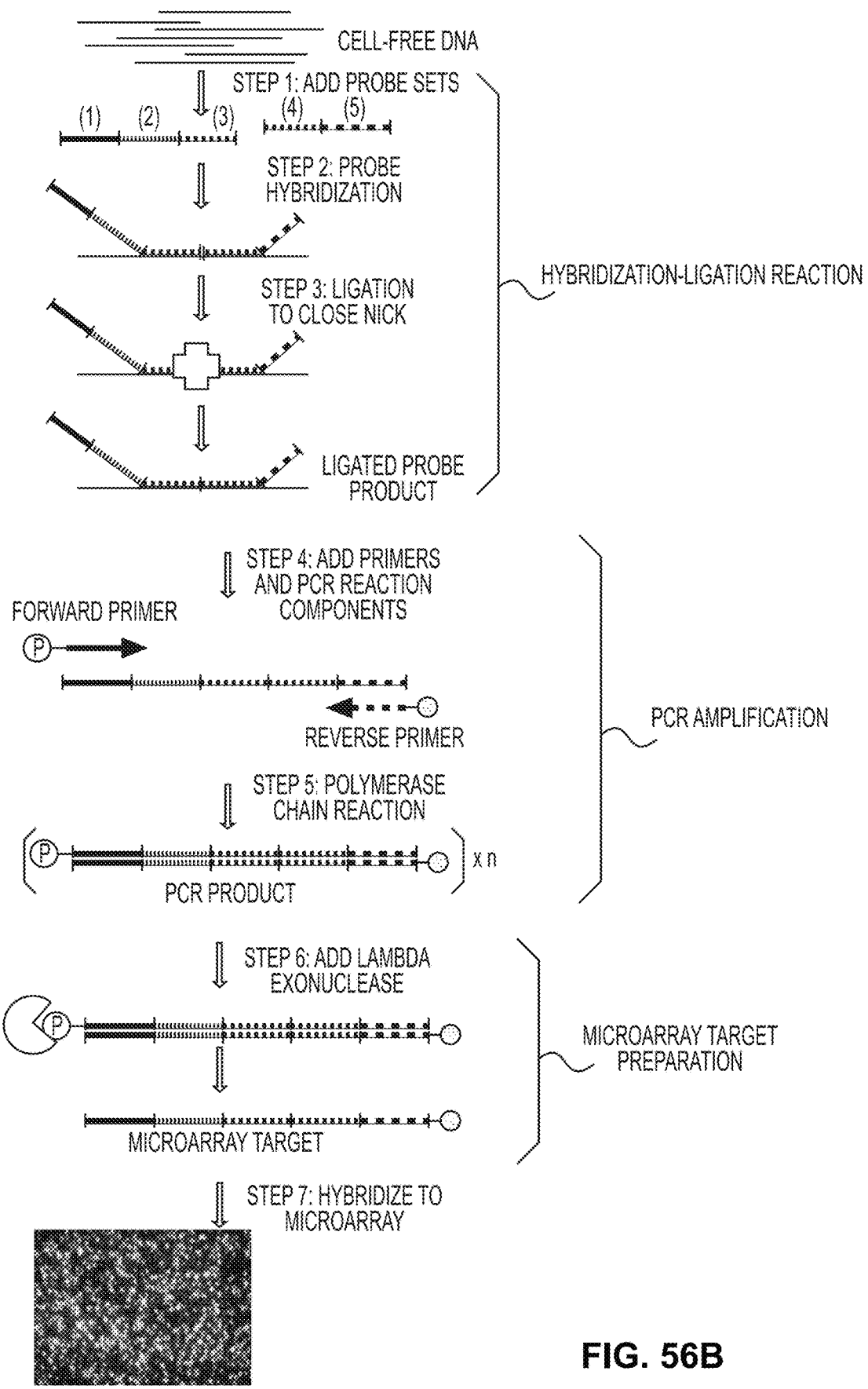

FIG. 56 depicts the procedural workflow that would be applied to the collection of probe sets, such as those probe sets illustrated in FIG. 55. This depiction is based on one probe set for one genomic locus (e.g., the probe set for Locus 1 shown in FIG. 55). In Step 1, the collection of probe sets is mixed with purified cell-free DNA. In Step 2, the locus specific sequences in each probe set hybridize to their corresponding homologous sequences in the cell-free DNA sample. In Step 3, a ligase enzyme is added to catalyze the formation of a phosphodiester bond between the 3' base on the left arm homolog and the 5' arm of the right homolog, closing the nick between the two arms and thus forming one continuous molecule which is the probe product. In Step 4, modified primers and PCR reaction components (Taq polymerase, dNTPs, and reaction buffer) are added to amplify the ligated probe product. The Forward Primer is modified in that it has a 5' phosphate group that makes it a preferred template for the Lambda exonuclease used in Step 6 and the Reverse Primer is modified in that it contains the label (blue circle) that is specific to probe products for a particular locus for a particular affinity tag. In Step 5, the probe product is PCR amplified to yield a double-stranded PCR product in which the forward strand contains a 5' phosphate group and the reverse strand contains a 5' label. In Step 6, Lambda exonuclease is added to digest the forward strand in a 5' to 3' direction—the 5' phosphate group on the forward strand makes it a preferred template for Lambda exonuclease digestion. The resulting material is single-stranded (reverse strand only) with a 5' label. This represents the labeled target material for hybridization to a microarray or monolayer.

Figure 57A:
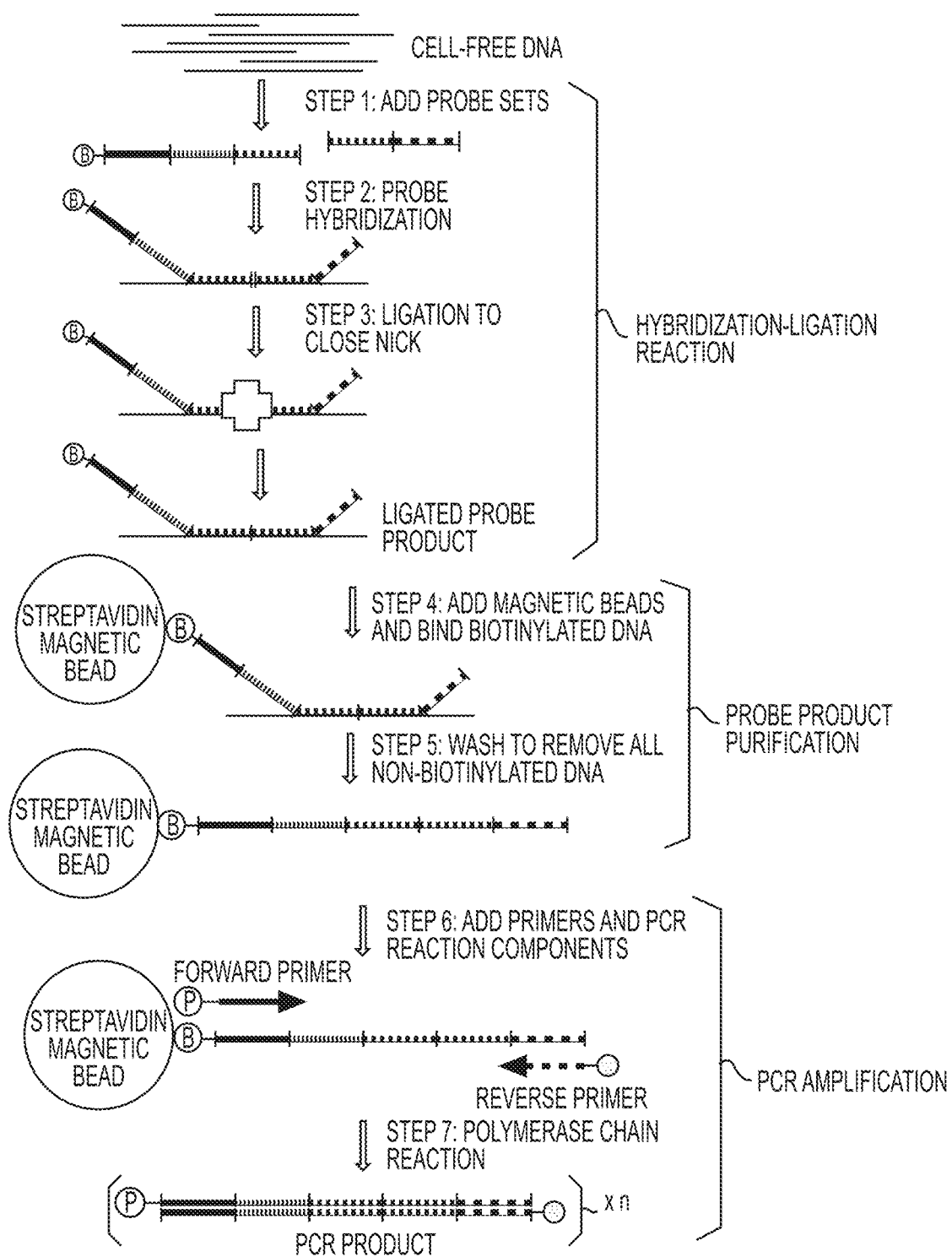
FIG. 57 depicts a modified version of the procedural workflow illustrated in FIG. 56.
Figure 57B:
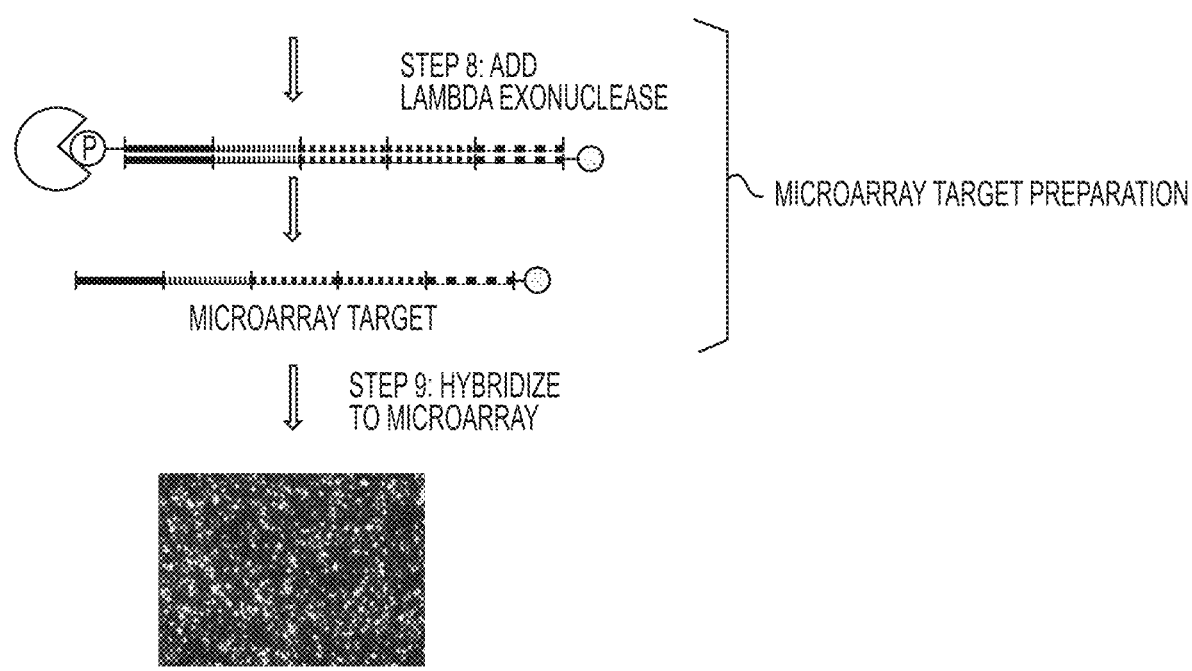

FIG. 57 depicts a modified version of the procedural workflow illustrated in FIG. 56. In this embodiment the left arm of each probe set contains a terminal biotin molecule as indicated by a "B" in Steps 1 to 6 of the Figure. This biotinylation enables the purification of the collection of probe products after completion of the hybridization-ligation reaction and prior to the PCR amplification. The workflow for this embodiment is identical to that described in FIG. 57 for Steps 1 to 3. In Step 4, streptavidin-coated magnetic beads are added to the hybridization-ligation reaction. The biotin molecule contained in the probe products will bind the products to the streptavidin. In Step 5, the magnetic beads are washed to remove the non-biotinylated DNA (cell-free genomic DNA and right arm oligonucleotides), resulting in a purified probe product. Steps 6 to 9 are performed in the same manner as described for Steps 4 to 7 in FIG. 56.

Figure 58A:
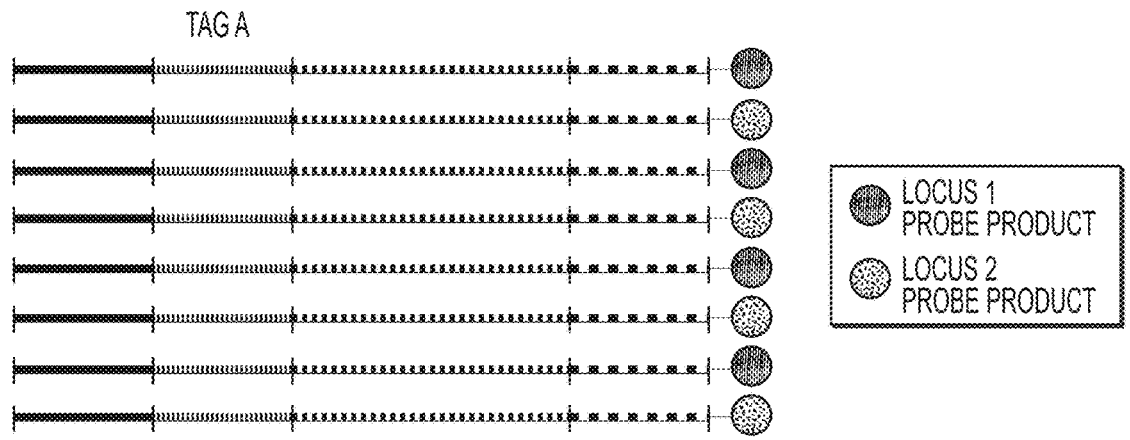
FIGS. 58A, 58B, and 58C provide an example of how probe products for Locus 1 and Locus 2 may be labeled with different label molecules.
Figure 58B:
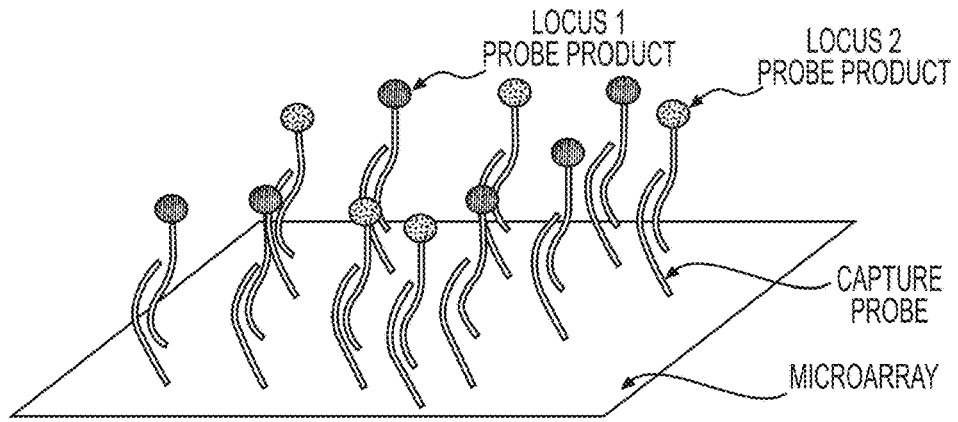
Figure 58C:
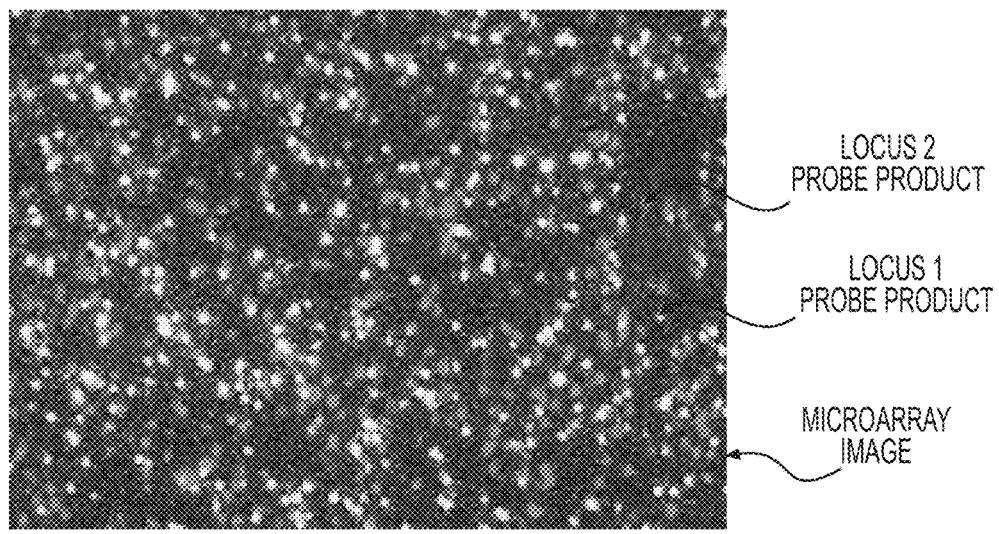

FIG. 58 provides an example of how probe products for Locus 1 and Locus 2 may be labeled with different label molecules. In FIG. 58A, Locus 1 probe products are labeled with label A (green) and Locus 2 probe products are labeled with label B (red) in one PCR amplification reaction. Probe products for both loci contain affinity tag sequence A. In FIG. 58B, the mixture of differentially labeled probe products is hybridized to a microarray location in which the capture probe sequence is complementary to the affinity tag A sequence. In FIG. 58C, the microarray location is imaged and the number of molecules of label A and label B counted to provide a relative measure of the levels of Locus 1 and Locus 2 present in the sample.

Figure 59:
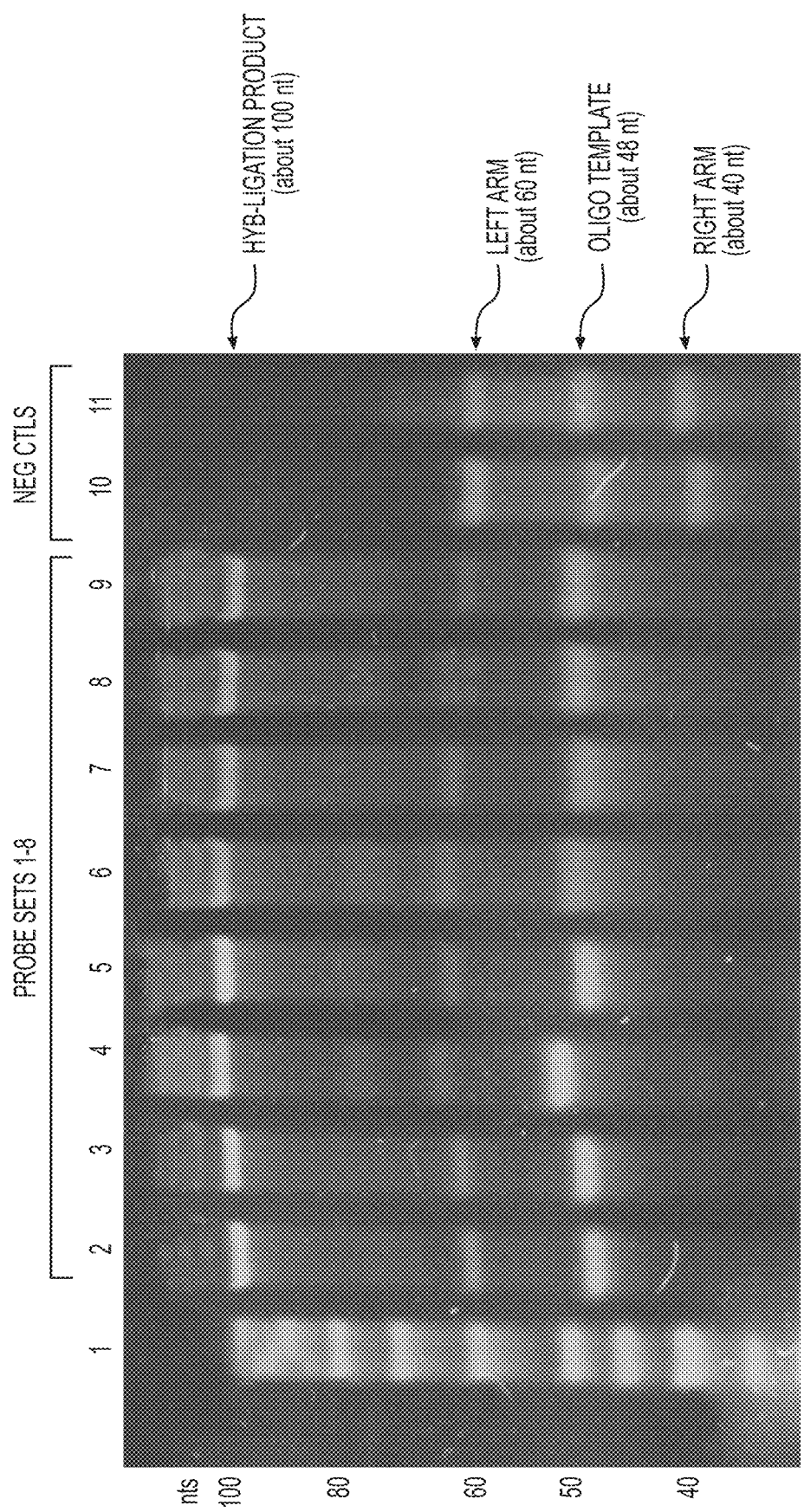
FIG. 59 provides evidence that probe products representing a multitude of genomic locations for one locus may be generated in a ligase enzyme specific manner using the hybridization-ligation process.

FIG. 59 provides evidence that probe products representing a multitude of genomic locations for one locus may be generated in a ligase enzyme specific manner using the hybridization-ligation process. Eight probe sets, each consisting of a left arm and right arm component as described in FIG. 55 and, containing homologs to eight chromosome 18 locations were hybridized to synthetic oligonucleotide templates (about 48 nucleotides) and ligated using a ligase enzyme to join the left and right arms for each. Reaction products were analyzed using denaturing polyacrylamide gel electrophoresis. Gel lane 1 contains a molecular weight ladder to indicate DNA band sizes. Lanes 2 to 9 contain hybridization-ligation reaction products for the eight chromosome 18 probe sets. A DNA band of about 100 nucleotides, representing the probe product of the about 60 nucleotide left arm and the about 40 nucleotide right arm, is present in each of lanes 2 to 9. Lanes 10 and 11 contain negative control reactions to which no ligase enzyme was added. No DNA band of about 100 nucleotides is present in lanes 10 and 11.

FIG. 60 provides data indicating that probe sets may be used to detect relative changes in copy number state. A mixture of eight probe sets containing homologs to eight distinct chromosome X locations was used to assay the cell lines containing different numbers of chromosome X indicated in Table 1.

TABLE 1

| Cell lines containing different copy numbers of chromosome X | |
|---|---|
| Coriell Cell Line ID | Number of copies of chromosome X |
| NA12138 | 1 |
| NA13783 | 2 |
| NA00254 | 3 |
| NA01416 | 4 |
| NA06061 | 5 |

Figure 60A:
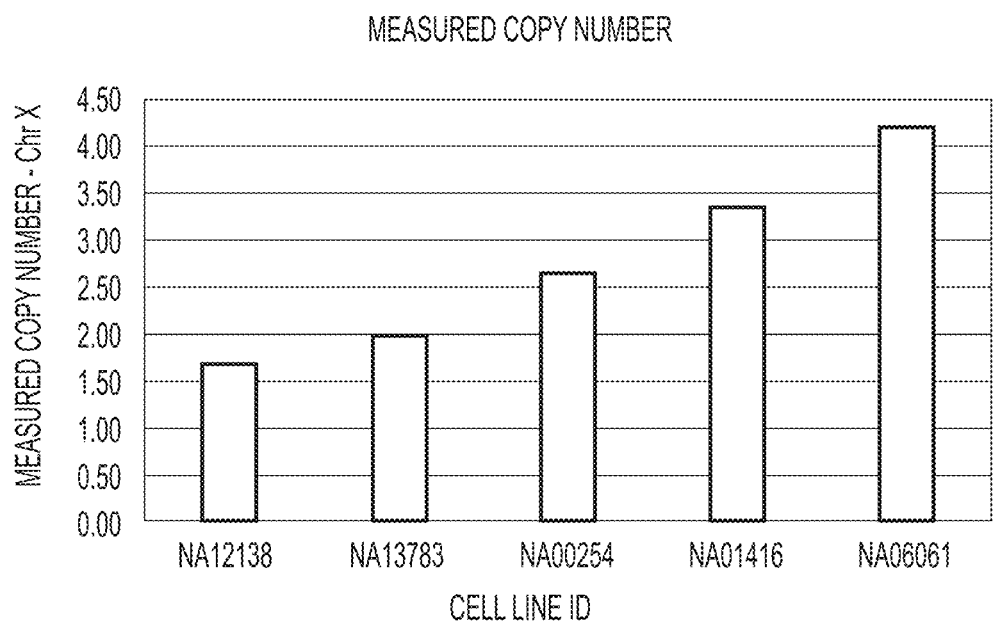
FIGS. 60A and 60B provide data indicating that probe sets may be used to detect relative changes in copy number state.
Figure 60B:
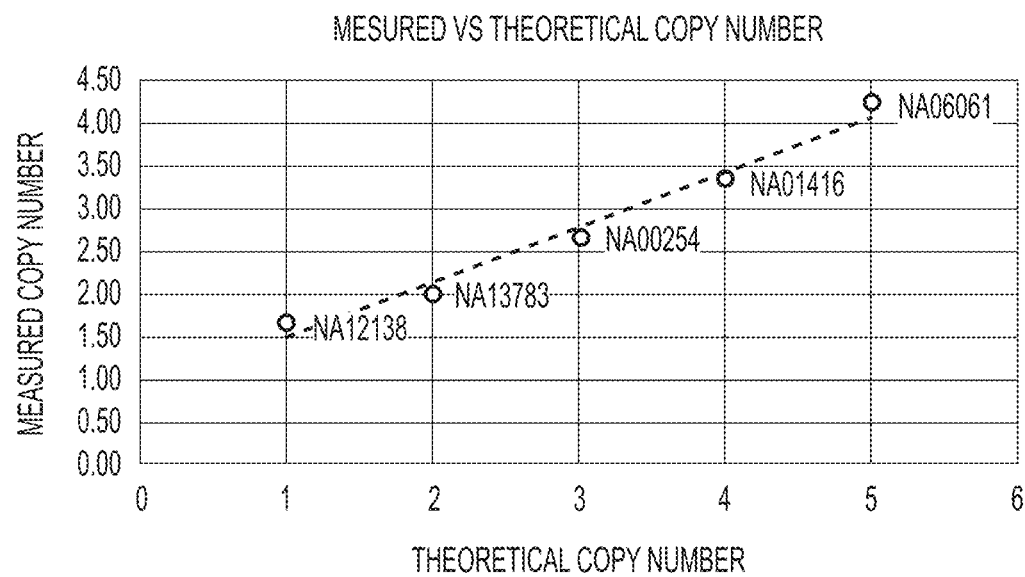

Quantitative PCR was used to determine the amount of probe product present for each cell line following the hybridization-ligation and purification processes described in FIG. 57 (Steps 1 to 5). As illustrated by FIG. 60A, the copy number state measured for the various cell lines followed the expected trend indicated in Table 1. For example, qPCR indicated a copy number state of less than two for NA12138, which has one copy of chromosome X. The measured copy number state for NA00254 (three copies of X) was greater than two, for NA01416 (four copies of X)

was greater than three, and for NA06061 (five copies of X) was greater than four. The responsiveness of the process in detecting differences in copy number state is further illustrated by FIG. 60B in which the measured copy number state is plotted against the theoretical copy number state.

FIG. 61 provides evidence that mixtures of probe products may be used to generate quantitative microarray data as described in FIGS. 56 and 57.

FIG. 61A depicts representative fluorescence images of two array spots in two orthogonal imaging channels (Alexa 488: green, Alexa 594; red). A region of interest (ROI) is automatically selected (large circle), with any undesired bright contaminants being masked from the image (smaller outlined regions within the ROI). Single fluorophores on single hybridized assay products are visualized as small punctate features within the array spot. (i) A "Balanced" spot (representing genomic targets input at a 1:1 concentration ratio to the assay) imaged in the green channel and (ii) the same spot imaged in the red channel (iii) An "Increased" spot (representing genomic targets input at a >1:1 concentration ratio to the assay) imaged in the green channel and (iv) the same spot imaged in the red channel.

Figure 61B:
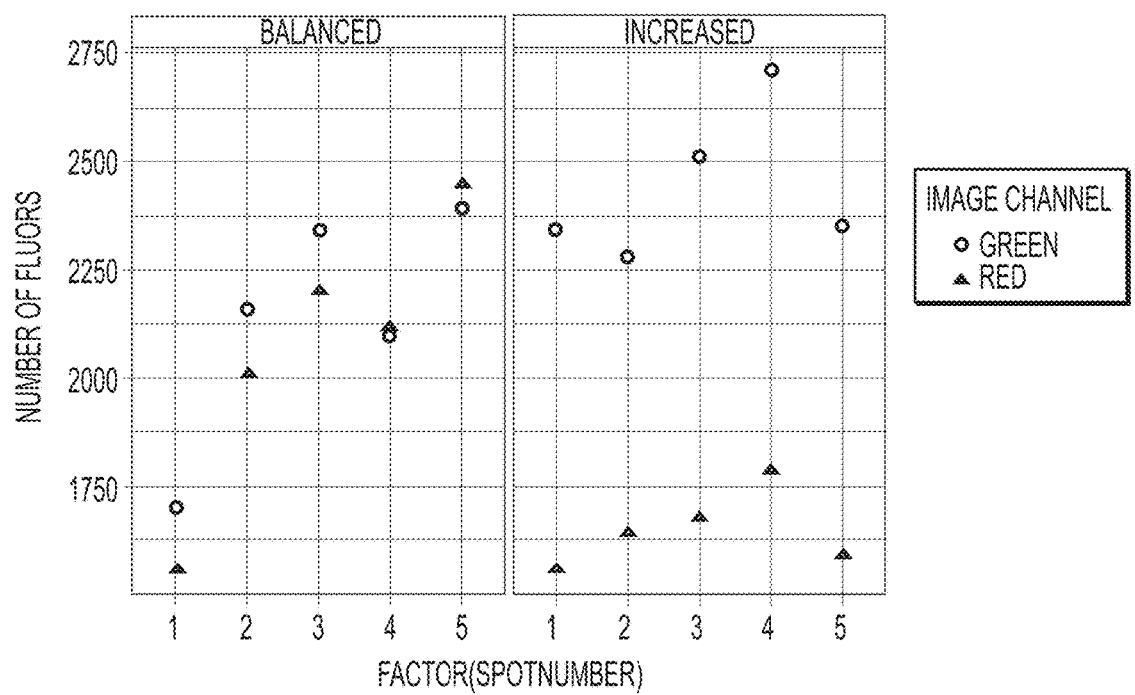

FIG. 61B presents raw counts of the detected fluorophores in two channels for five spots each of the "Balanced" and "Increased" conditions. Despite some variation in the absolute number of fluors, the numbers in the two channels track closely for the "Balanced" case, but demonstrate clear separation in the "Increased" case.

Figure 61C:
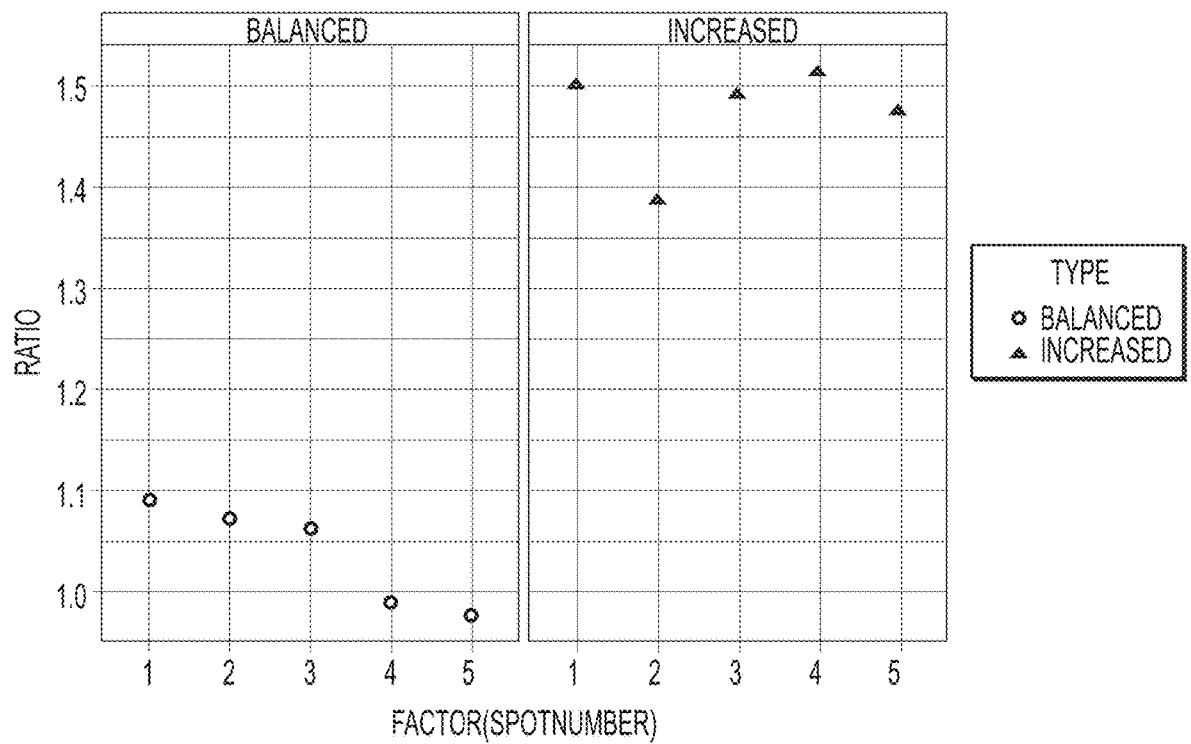

FIG. 61C presents calculated ratio values for number of fluors in the green channel divided by the number of fluors in the red channel, for the five spots from each of the "Balanced" and "Increased" conditions. The "Balanced" case centers about a ratio of 1.0 and the "Increased" case is at an elevated ratio. Considering the "Balanced" case as comparing two balanced genomic loci and the "Increased" case as one where one locus is increased relative to the other, we may calculate the confidence of separation of the two conditions using an independent, 2-group T-test, yielding a p-value of $8 \times 10^{-14}$.

Figure 62:
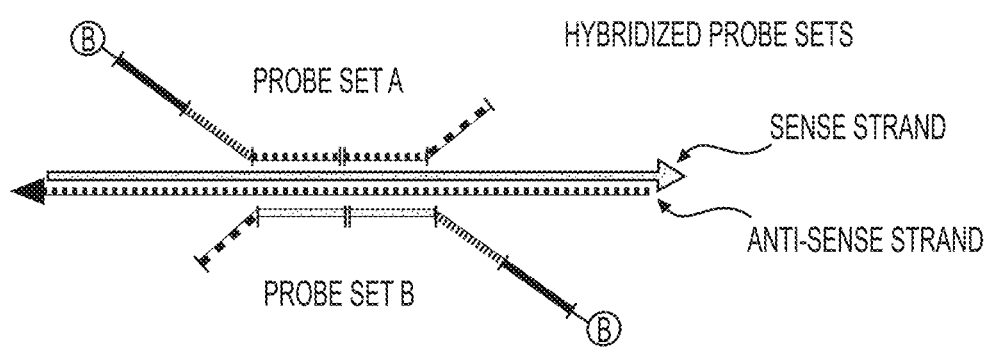
FIGS. 62-64 illustrate modifications of the general procedure described in FIGS. 55 to 58.

FIG. 62 illustrates a modification of the general procedure described in FIGS. 55 to 58. In this embodiment, a second probe set, Probe Set B is designed for each genomic location such that the genome homolog sequences in Probe Set B are a reverse complement of the genome homolog sequences in Probe Set A. Probe Set A will hybridize to the reverse strand of the genomic DNA and Probe Set B will hybridize to the forward strand of the genomic DNA. This embodiment will provide increased sensitivity relative to the embodiment described in FIGS. 55 to 58 as it will yield approximately double the number of probe products per locus.

Figure 63:
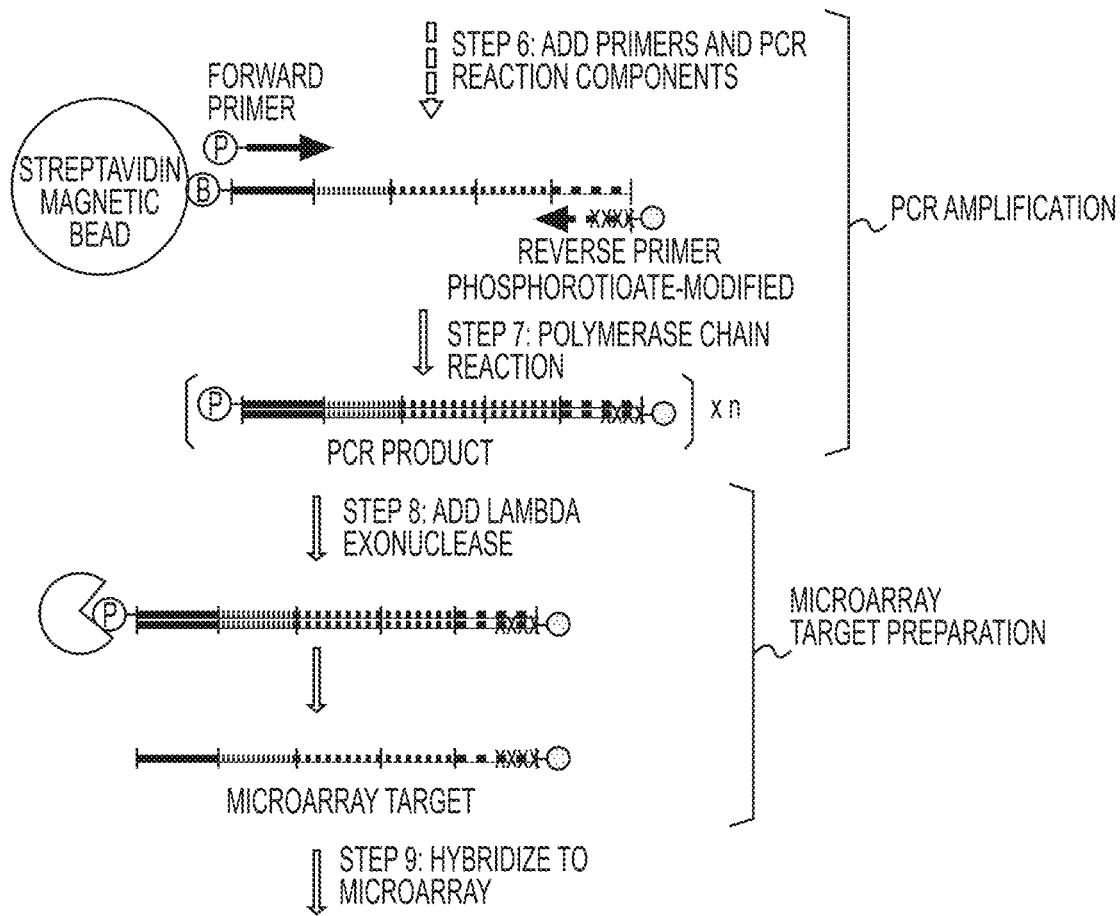

FIG. 63 illustrates a modification to the general procedure described in FIG. 57. In this embodiment, the Reverse Primer used in Step 6 is additionally modified in that the four bonds linking the first five nucleotides in the oligonucleotide sequence are phosphorothioate bonds. This modification will result in all PCR products generated during PCR amplification (Step 7) having a phosphorothioate modification on the 5' end. This modification will protect the reverse strand from any digestion that might occur during the treatment with Lambda exonuclease in Step 8.

Although the 5' phosphate group on the forward strand makes it a preferred template for Lambda exonuclease digestion, the reverse strand may still have some vulnerability to digestion. Phosphorothioate modification of the 5' end of the reverse strand will reduce its vulnerability to Lambda exonuclease digestion.

Figure 64:
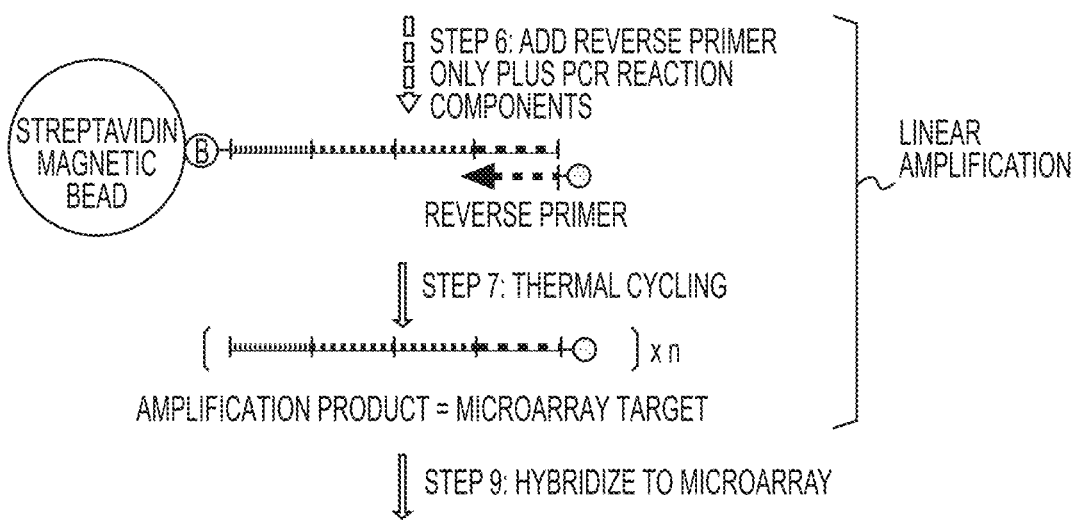

FIG. 64 illustrates a modification of the general procedure described in FIGS. 55 to 58. In this embodiment, PCR amplification of the probe product is replaced with linear amplification by adding the Reverse Primer but no Forward Primer to the amplification reaction in Step 6. If only the Reverse Primer is present the amplification product will be single stranded—the reverse strand with a label of the 5' end. As the amplification product is already single-stranded, it does not require further processing before hybridization to a microarray, i.e., Lambda exonuclease digestion may be omitted. As a forward primer is not used in this embodiment, it is unnecessary for the left arm of the probe set to contain a forward priming sequence. The left arm would consist of an affinity tag sequence and a locus homolog sequence only as illustrated in FIG. 64.

A further embodiment of the general procedure described in FIGS. 55 to 58 is one in which the single ligation reaction process in Step 3 is replaced with a cycled ligation reaction process. This is accomplished by replacing the thermolabile ligase enzyme (e.g., T4 ligase) used to catalyze the ligation reaction with a thermostable ligase (e.g., Taq ligase). When a thermostable ligase is used, the hybridization-ligation reaction may be heated to a temperature that will melt all DNA duplexes (e.g., 95° C.) after the initial cycle of hybridization and ligation has occurred. This will make the genomic template DNA fully available for another probe set hybridization and ligation. Subsequent reduction of the temperature (e.g., to 45° C.) will enable this next hybridization and ligation event to occur. Each thermocycling of the hybridization and ligation reaction between a temperature that will melt DNA duplexes and one that will allow hybridization and ligation to occur will linearly increase the amount of probe product yielded from the reaction. If the reaction is exposed to 30 such cycles, up to 30 times the amount of probe product will be yielded than from a process in which a single ligation reaction is used.

Figure 65A:
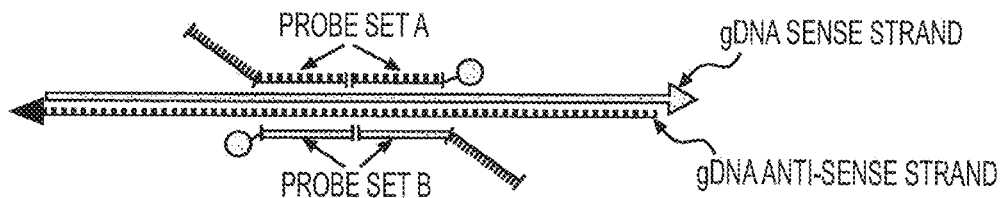
FIGS. 65A and 65B depict a further embodiment of the modified procedure described in FIG. 62.
Figure 65B:
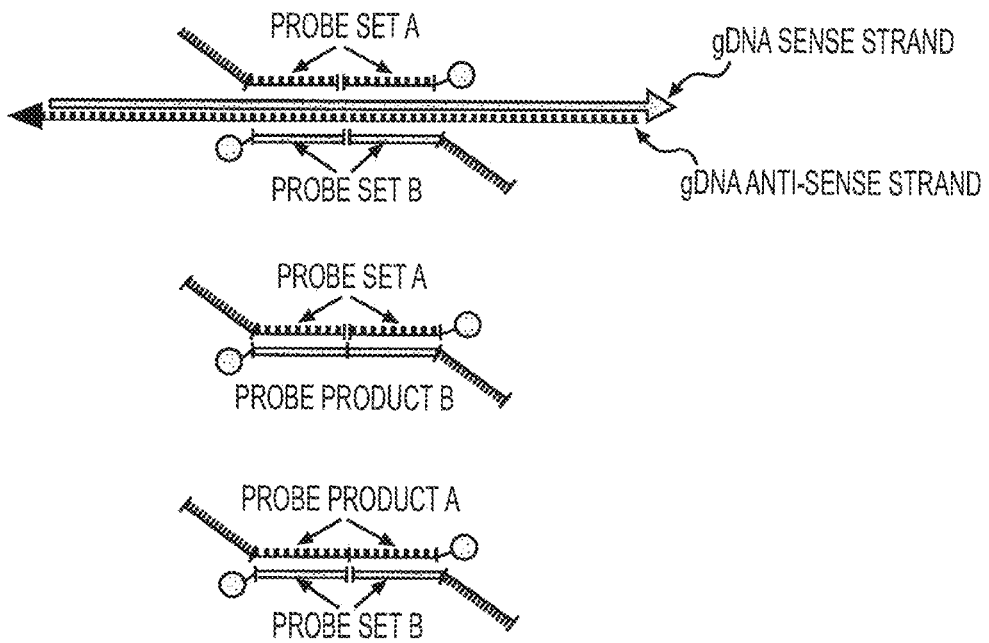

FIG. 65 depicts a further embodiment of the modified procedure described in FIG. 62. This embodiment takes advantage of the ligase chain reaction (LCR) in combining the presence of the reverse complement for each probe set with the use of a thermostable ligase to enable a cycled ligation reaction in which the product is exponentially amplified. FIG. 65 depicts two probe sets, Probe Set A and Probe Set B for one locus; where the genome homolog sequences in Probe Set B are the reverse complement of the genome homolog sequences in Probe Set A. The 5' arm of each Probe Set consists of an affinity tag sequence and a homolog while the 3' arm of each Probe Set consists of a homolog sequence with a label attached. In the first cycle of a thermocycled reaction, genomic DNA will be the only template available to enable hybridization and ligation to occur to generate a probe product as illustrated in FIG. 65A. However in the second cycle, Probe Product B generated in the first cycle will act as an additional template for Probe Set A and likewise Probe Product A generated in the first cycle will act as an additional template for Probe Set B as illustrated in FIG. 65B. In this same manner, the probe products from each successive cycle will act as template for probe set hybridization and ligation in the next cycle. This process would eliminate the need for PCR amplification of the probe product which may be directly used as microarray target.

Another embodiment of the procedure depicted in FIG. 65 is one which employs LCR but uses probe sets that have the structure described in FIG. 55, i.e., both left and right arms are flanked by priming sequences, the left arm contains a biotin molecule and the right arm does not contain a label.

After completion of LCR, the probe products are purified using magnetic beads (optional) and then PCR amplified and microarray target prepared as illustrated in FIGS. 56 and 57.

Figure 66A:
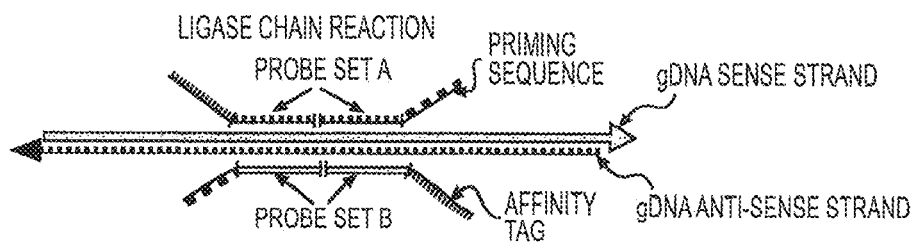
FIGS. 66A, 66B, and 66C depict yet another embodiment of the procedure depicted in FIG. 65.
Figure 66B:
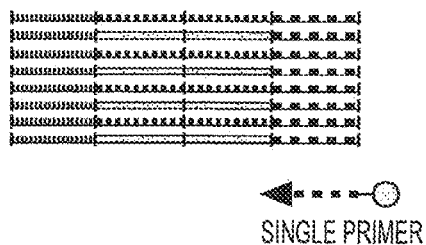
Figure 66C:
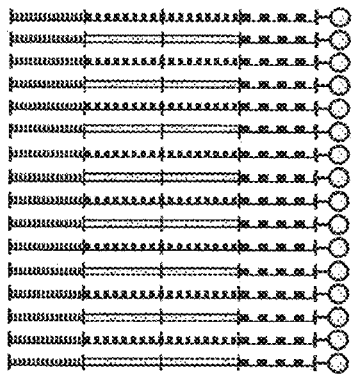

FIG. 66 depicts yet another embodiment of the procedure depicted in FIG. 65. The 5' arm of each Probe Set consists of an affinity tag sequence and a homolog while the 3' arm of each Probe Set consists of a homolog sequence and a priming sequence without a label attached as illustrated in FIG. 66A. After completion of the LCR, the probe product may be purified. The LCR product would then be amplified in a linear manner by the addition of a single primer that has a label attached, along with reaction components (Taq polymerase, dNTPs, and reaction buffer) as illustrated in FIG. 66B. The product of this amplification would be single-stranded (reverse strand only) with a 5' label as illustrated in FIG. 66C. Consequently it would not be necessary to treat it with Lambda exonuclease but rather it could instead be directly used as microarray target.

In another aspect, the genetic variation determined by the methods described herein indicates presence or absence of cancer, phamacokinetic variability, drug toxicity, transplant rejection, or aneuploidy in the subject. In another aspect, the determined genetic variation indicates presence or absence of cancer. Accordingly, the methods described herein may be performed to diagnose cancer.

A significant challenge in oncology is the early detection of cancer. This is particularly true in cancers that are hard to image or biopsy (e.g., pancreatic cancer, lung cancer). Cell free tumor DNA (tumor cfDNA) in a patient's blood offers a method to non-invasively detect a tumor. These may be solid tumors, benign tumors, micro tumors, liquid tumors, metastasis or other somatic growths. Detection may be at any stage in the tumor development, though ideally early (Stage I or Stage II). Early detection allows intervention (e.g., surgery, chemotherapy, pharmaceutical treatment) that may extend life or lead to remission. Further problems in oncology include the monitoring of the efficacy of treatment, the titration of the dose of a therapeutic agent, the recurrence of a tumor either in the same organ as the primary tumor or at distal locations and the detection of metastasis. The current invention may be used for all these applications.

In some embodiments, the probe sets of the present disclosure may be configured to target known genetic variations associated with tumors. These may include mutations, SNPs, copy number variants (e.g., amplifications, deletions), copy neutral variants (e.g., inversions, translocations), and/or complex combinations of these variants. For example, the known genetic variations associated with tumors include those listed in cancer.sanger.ac.uk/cancergenome/projects/cosmic; nature.com/ng/journal/v45/n10/full/ng.2760.html#supplementary-information; and Tables 2 and 3 below: [B]GENE=p-value from corrected to FDR within peak; [K]Known frequently amplified oncogene or deleted TSG; [P]Putative cancer gene; [E]Epigenetic regulator; [M]Mitochondria-associated gene; **Immediately adjacent to peak region; [T]Adjacent to telomere or centromere of acrocentric chromosome.

TABLE 2

Exemplary genetic variations associated with tumors (Amplification of the gene)

| Peak Name | Rank | Genomic location | Peak region | GISTIC q-value | Gene count | Target(s) | Frequently mutated genes[B] |
|---|---|---|---|---|---|---|---|
| CCND1 | 1 | 11q13.3 | chr11: 69464719-69502928 | 2.05E−278 | 2 | CCND1[K] | CCND1 = 6.6e−08 |
| EGFR | 2 | 7p11.2 | chr7: 55075808-55093954 | 2.30E−240 | 1 | EGFR[K] | EGFR = 2.2e−15 |
| MYC | 3 | 8q24.21 | chr8: 128739772-128762863 | 6.50E−180 | 1 | MYC[K] | |
| TERC | 4 | 3q26.2 | chr3: 169389459-169490555 | 5.40E−117 | 2 | TERC[P] | |
| ERBB2 | 5 | 17q12 | chr17: 37848534-37877201 | 1.59E−107 | 1 | ERBB2[K] | ERBB2 = 1.3e−06 |
| CCNE1 | 6 | 19q12 | chr19: 30306758-30316875 | 4.77E−90 | 1 | CCNE1[K] | |
| MCL1 | 7 | 1q21.3 | chr1: 150496857-150678056 | 1.25E−80 | 6 | MCL1[K] | |
| MDM2 | 8 | 12q15 | chr12: 69183279-69260755 | 2.59E−62 | 2 | MDM2[K] | |
| INTS4 | 9 | 11q14.1 | chr11: 77610143-77641464 | 1.01E−54 | 1 | INTS4 | |
| WHSC1L1 | 10 | 8p11.23 | chr8: 38191804-38260814 | 3.43E−46 | 2 | WHSC1L1[E], LETM2[M] | |
| CDK4 | 11 | 12q14.1 | chr12: 58135797-58156509 | 5.14E−41 | 5 | CDK4[K] | CDK4 = 0.0048 |
| KAT6A | 12 | 8p11.21 | chr8: 41751300-41897859 | 2.97E−39 | 2 | KAT6A[P, E], IKBKB** | |
| SOX2 | 13 | 3q26.33 | chr3: 181151312-181928394 | 1.21E−38 | 2 | SOX2[K] | |
| PDGFRA | 14 | 4q12 | chr4: 54924794-55218386 | 1.08E−37 | 3 | PDGFRA[K] | |
| BDH1 | 15 | 3q29 | chr3: 197212101-197335320 | 1.21E−31 | 1 | BDH1[M] | |
| 1q44 | 16 | 1q44[T] | chr1: 242979907-249250621 | 4.48E−31 | 83 | SMYD3[E] | |
| MDM4 | 17 | 1q32.1 | chr1: 204367383-204548517 | 1.98E−29 | 3 | MDM4[K] | |
| TERT | 18 | 5p15.33 | chr5: 1287704-1300024 | 9.34E−27 | 1 | TERT[K] | |
| KDM5A | 19 | 12p13.33[T] | chr12: 1-980639 | 1.59E−25 | 11 | KDM5A[E] | |
| MYCL1 | 20 | 1p34.2 | chr1: 40317971-40417342 | 3.99E−25 | 2 | MYCL1[K] | |
| IGF1R | 21 | 15q26.3 | chr15: 98667475-100292401 | 8.62E−25 | 9 | IGF1R[K] | |
| PARP10 | 22 | 8q24.3 | chr8: 144925436-145219779 | 5.44E−20 | 15 | PARP10[P, E], CYC1[M] | |
| G6PD | 23 | Xq28 | chrX: 153760870-153767853 | 3.66E−19 | 1 | G6PD | |
| PHF12 | 24 | 17q11.2 | chr17: 27032828-27327946 | 1.75E−16 | 21 | PHF12[E], ERAL1[M] | |
| 20q13.33 | 25 | 20q13.33 | chr20: 62187847-62214354 | 2.96E−16 | 2 | | |
| PAF1 | 26 | 19q13.2 | chr19: 39699366-39945515 | 1.66E−15 | 13 | PAF1[P, E] | IL28A = 0.021, SUPT5H = 0.084 |
| BCL2L1 | 27 | 20q11.21 | chr20: 30179028-30320705 | 2.85E−15 | 4 | BCL2L1[K] | |
| TUBD1 | 28 | 17q23.1 | chr17: 57922443-57946458 | 7.19E−15 | 1 | TUBD1 | TUBD1 = 0.009 |
| [ZNF703] | 29 | 8p11.23 | chr8: 37492669-37527108 | 2.44E−14 | 0 | | |
| 1q23.3 | 30 | 1q23.3 | chr1: 160949115-161115281 | 7.73E−13 | 9 | | |
| 8q22.2 | 31 | 8q22.2 | chr8: 101324079-101652657 | 4.22E−11 | 3 | | SNX31 = 0.015 |
| BRD4 | 32 | 19p13.12 | chr19: 15310246-15428182 | 5.04E−10 | 3 | NOTCH3[P], BRD4[P, E] | |

TABLE 2-continued

Exemplary genetic variations associated with tumors (Amplification of the gene)

| Peak Name | Rank | Genomic location | Peak region | GISTIC q-value | Gene count | Target(s) | Frequently mutated genes[B] |
|---|---|---|---|---|---|---|---|
| KRAS | 33 | 12p12.1 | chr12: 24880663-25722878 | 9.47E−10 | 7 | KRAS[K] | KRAS = 1.5e-14 |
| NKX2-1 | 34 | 14q13.2 | chr14: 35587755-37523513 | 1.33E−09 | 14 | NKX2-1[K] | NFKBIA = 0.0098, RALGAPA1 = 0.027 |
| NFE2L2 | 35 | 2q31.2 | chr2: 178072322-178171101 | 5.48E−09 | 5 | NFE2L2 | NFE2L2 = 3.9e-14 |
| ZNF217 | 36 | 20q13.2 | chr20: 52148496-52422225 | 5.83E−08 | 1 | ZNF217[K] | ZNF217 = 0.0082 |
| 13q34 | 37 | 13q34[T] | chr13: 108818892-115169878 | 6.28E−08 | 45 | ING1[E] | ING1 = 0.00026 |
| KAT6B | 38 | 10q22.2 | chr10: 76497097-77194071 | 1.41E−07 | 9 | KAT6B[E], VDAC2[M] | |
| NSD1 | 39 | 5q35.3 | chr5: 176337344-177040112 | 1.75E−06 | 22 | NSD1[E], PRELID1[M] | NSD1 = 4.9e-10 |
| FGFR3 | 40 | 4p16.3 | chr4: 1778797-1817427 | 2.14E−06 | 2 | FGFR3[P], LETM1[M] | FGFR3 = 0.00018 |
| 9p13.3 | 41 | 9p13.3 | chr9: 35652385-35739486 | 2.55E−06 | 8 | | |
| COX18 | 42 | 4q13.3 | chr4: 73530210-74658151 | 2.68E−06 | 7 | COX18[M] | |
| 7q36.3 | 43 | 7q36.3[T] | chr7: 153768037-159138663 | 3.19E−06 | 30 | PTPRN2[L], DPP6[L] | |
| 18q11.2 | 44 | 18q11.2 | chr18: 23857484-24119078 | 3.83E−06 | 2 | | |
| SOX17 | 45 | 8q11.23 | chr8: 55069781-55384342 | 2.02E−05 | 1 | SOX17 | SOX17 = 0.00092 |
| 11q22.2 | 46 | 11q22.2 | chr11: 102295593-102512085 | 0.00015337 | 3 | | |
| CBX8 | 47 | 17q25.3 | chr17: 77770110-77795534 | 0.00023029 | 1 | CBX8[E] | |
| AKT1 | 48 | 14q32.33 | chr14: 105182581-105333748 | 0.00028451 | 7 | AKT1[K] | AKT1 = 1.1e-14 |
| CDK6 | 49 | 7q21.2 | chr7: 92196092-92530348 | 0.00069831 | 3 | CDK6[K] | |
| 6p21.1 | 50 | 6p21.1 | chr6: 41519930-44297771 | 0.0010459 | 70 | | |
| EHF | 51 | 11p13 | chr11: 34574296-34857324 | 0.0011002 | 1 | EHF | |
| 6q21 | 52 | 6q21 | chr6: 107098934-107359899 | 0.0011806 | 4 | | |
| 19q13.42 | 53 | 19q13.42[T] | chr19: 55524376-59128983 | 0.0013319 | 138 | TRIM28[E], SUV420H2[E] | ZNF471 = 5.4e-05 |
| 17q21.33 | 54 | 17q21.33 | chr17: 47346425-47509605 | 0.0025775 | 2 | | |
| BPTF | 55 | 17q24.2 | chr17: 65678858-66288612 | 0.0028375 | 11 | BPTF[E] | |
| E2F3 | 56 | 6p22.3 | chr6: 19610794-22191922 | 0.0033658 | 7 | E2F3[K] | |
| 19p13.2 | 57 | 19p13.2 | chr19: 10260457-10467501 | 0.0038041 | 12 | MRPL4[M] | DNMT1 = 0.099 |
| 17q25.1 | 58 | 17q25.1 | chr17: 73568926-73594884 | 0.012337 | 2 | | |
| KDM2A | 59 | 11q13.2 | chr11: 67025375-67059633 | 0.012445 | 3 | KDM2A[E] | |
| 8q21.13 | 60 | 8q21.13 | chr8: 80432552-81861219 | 0.020548 | 6 | MRPS28[M] | |
| 2p15 | 61 | 2p15 | chr2: 59143237-63355557 | 0.021056 | 25 | | XPO1 = 1.1e-05 |
| 14q11.2 | 62 | 14q11.2[T] | chr14: 1-21645085 | 0.027803 | 57 | | |
| NEDD9 | 63 | 6p24.2 | chr6: 11180426-11620845 | 0.082606 | 2 | NEDD9[K] | |
| 5p13.1 | 64 | 5p13.1 | chr5: 35459650-50133375 | 0.094657 | 61 | | SLC1A3 = 0.0021, IL7R = 0.0021 |
| LINC00536 | 65 | 8q23.3 | chr8: 116891361-117360815 | 0.095294 | 1 | LINC00536 | |
| 10p15.1 | 66 | 10p15.1 | chr10: 4190059-6130004 | 0.10391 | 21 | | |
| 22q11.21 | 67 | 22q11.21 | chr22: 18613558-23816427 | 0.13213 | 105 | | |
| PHF3 | 68 | 6q12 | chr6: 63883156-64483307 | 0.17851 | 4 | PHF3[E], EYS[L] | PHF3 = 0.051 |
| PAX8 | 69 | 2q13 | chr2: 113990138-114122826 | 0.19717 | 2 | PAX8[K] | |
| 9p24.2 | 70 | 9p24.2[T] | chr9: 1-7379570 | 0.20405 | 45 | SMARCA2[E], KDM4C[E], UHRF2[E], KIAA2026[E] | |

TABLE 3

Exemplary genetic variations associated with tumors (Deletion of the gene)

| Peak Name | Rank | Genomic location | Peak region | GISTIC q-value | Gene count | Target(s) | Frequently mutated genes[B] |
|---|---|---|---|---|---|---|---|
| CDKN2A | 1 | 9p21.3 | chr9: 21865498-22448737 | 0 | 4 | CDKN2A[K] | CDKN2A = 4.4e-15 |
| STK11 | 2 | 19p13.3 | chr19: 1103715-1272039 | 1.46E−238 | 7 | STK11[K] | STK11 = 2.5e-13 |
| PDE4D | 3 | 5q11.2 | chr5: 58260298-59787985 | 2.02E−143 | 3 | PDE4D[L] | |
| PARK2 | 4 | 6q26 | chr6: 161693099-163153207 | 5.85E−137 | 1 | PARK2[L,K] | |
| LRP1B | 5 | 2q22.1 | chr2: 139655617-143637838 | 4.25E−107 | 1 | LRP1B[L] | |
| CSMD1 | 6 | 8p23.2 | chr8: 2079140-6262191 | 2.39E−96 | 1 | CSMD1[L] | |
| 1p36.23 | 7 | 1p36.23 | chr1: 7829287-8925111 | 1.23E−93 | 8 | | |
| ARID1A | 8 | 1p36.11 | chr1: 26900639-27155421 | 5.74E−87 | 2 | ARID1A[K] | ARID1A = 1.5e-14 |
| PTEN | 9 | 10q23.31 | chr10: 89615138-90034038 | 1.12E−79 | 2 | PTEN[K] | PTEN = 2.2e-15 |
| WWOX | 10 | 16q23.1 | chr16: 78109058-79627770 | 8.14E−76 | 1 | WWOX[L] | WWOX = 0.092 |
| RB1 | 11 | 13q14.2 | chr13: 48833767-49064807 | 3.88E−75 | 2 | RB1[K] | RB1 = 1.7e-13 |
| FAM190A | 12 | 4q22.1 | chr4: 90844993-93240505 | 9.26E−75 | 1 | FAM190A[L] | |
| 2q37.3 | 13 | 2q37.3[T] | chr2: 241544527-243199373 | 1.77E−70 | 29 | ING5[E] | |
| 22q13.32 | 14 | 22q13.32[T] | chr22: 48026910-51304566 | 8.20E−65 | 45 | BRD1[E], HDAC10[E] | |

TABLE 3-continued

Exemplary genetic variations associated with tumors (Deletion of the gene)

| Peak Name | Rank | Genomic location | Peak region | GISTIC q-value | Gene count | Target(s) | Frequently mutated genes[B] |
|---|---|---|---|---|---|---|---|
| 11p15.5 | 15 | 11p15.5[T] | chr11: 1-709860 | 1.02E−62 | 34 | SIRT3[E], PHRF1[E] | HRAS = 7.8e−13 |
| LINC00290 | 16 | 4q34.3 | chr4: 178911874-183060693 | 1.21E−55 | 1 | LINC00290 | |
| FHIT | 17 | 3p14.2 | chr3: 59034763-61547330 | 3.01E−55 | 1 | FHIT[L] | |
| RBFOX1 | 18 | 16p13.3 | chr16: 5144019-7771745 | 1.00E−45 | 1 | RBFOX1[L] | |
| PTPRD | 19 | 9p24.1 | chr9: 8310705-12693402 | 3.24E−38 | 1 | PTPRD[L] | |
| 18q23 | 20 | 18q23[T] | chr18: 74979706-78077248 | 1.69E−37 | 12 | | |
| FAT1 | 21 | 4q35.2 | chr4: 187475875-188227950 | 6.81E−36 | 1 | FAT1[K] | FAT1 = 2.4e−15 |
| MPHOSPH8 | 22 | 13q12.11[T] | chr13: 1-20535070 | 2.57E−31 | 10 | MPHOSPH8[E] | |
| 15q15.1 | 23 | 15q15.1 | chr15: 41795901-42068054 | 2.71E−29 | 4 | | MGA = 0.0083, RPAP1 = 0.035 |
| 11q25 | 24 | 11q25[T] | chr11: 133400280-135006516 | 4.93E−26 | 14 | | |
| 1p13.2 | 25 | 1p13.2 | chr1: 110048528-117687124 | 1.69E−25 | 100 | TRIM33[E] | NRAS = 1.8e−13, CD58 = 0.079 |
| NF1 | 26 | 17q11.2 | chr17: 29326736-29722618 | 6.59E−23 | 5 | NF1[K] | NF1 = 3.3e−13 |
| MACROD2 | 27 | 20p12.1 | chr20: 14302876-16036135 | 9.00E−19 | 3 | MACROD2[L] | |
| 7p22.3 | 28 | 7p22.3[T] | chr7: 1-1496620 | 1.04E−17 | 18 | | |
| 6p25.3 | 29 | 6p25.3 | chr6: 1608837-2252425 | 3.01E−17 | 2 | | |
| 21q11.2 | 30 | 21q11.2[T] | chr21: 1-15482604 | 2.34E−14 | 14 | | |
| 9p13.1 | 31 | 9p13.1 | chr9: 38619152-71152237 | 9.75E−14 | 48 | | |
| ZNF132 | 32 | 19q13.43[T] | chr19: 58661582-59128983 | 3.77E−13 | 24 | TRIM28[E], ZNF132 | |
| 5q15 | 33 | 5q15 | chr5: 73236070-114508587 | 8.15E−13 | 156 | APC[K], CHD1[E] | APC = 2.6e−13, RASA1 = 0.0029 |
| MLL3 | 34 | 7q36.1 | chr7: 151817415-152136074 | 9.26E−13 | 1 | MLL3[K, E] | MLL3 = 1.1e−05 |
| 19q13.32 | 35 | 19q13.32 | chr19: 47332686-47763284 | 2.38E−12 | 10 | | |
| 15q12 | 36 | 15q12[T] | chr15: 1-32929863 | 3.40E−11 | 155 | | OTUD7A = 0.027 |
| 12q24.33 | 37 | 12q24.33[T] | chr12: 131692956-133851895 | 1.24E−10 | 27 | | POLE = 3.9e−05, PGAM5 = 0.038 |
| 10q26.3 | 38 | 10q26.3[T] | chr10: 135190263-135534747 | 2.09E−10 | 14 | | |
| 6q21 | 39 | 6q21 | chr6: 86319089-117076132 | 4.56E−10 | 141 | PRDM1[E], HDAC2[E], PRDM13[E] | PRDM1 = 0.00054 |
| PPP2R2A | 40 | 8p21.2 | chr8: 25896447-26250295 | 1.78E−09 | 1 | PPP2R2A | |
| IKZF2 | 41 | 2q34 | chr2: 211542637-214143899 | 3.24E−09 | 4 | IKZF2[K], ERBB4[L] | ERBB4 = 0.00058 |
| CNTN4 | 42 | 3p26.3[T] | chr3: 1-3100786 | 6.44E−09 | 3 | CNTN4[L] | |
| 3p12.2 | 43 | 3p12.2 | chr3: 75363575-86988125 | 1.22E−07 | 12 | ROBO1[L], CADM2[E] | |
| RAD51B | 44 | 14q24.1 | chr14: 68275375-69288431 | 1.38E−07 | 2 | RAD51B[L] | ZFP36L1 = 0.0016 |
| 11q23.1 | 45 | 11q23.1 | chr11: 105849158-117024891 | 5.31E−07 | 84 | ATM[K] | ATM = 1.4e−06, POU2AF1 = 0.082 |
| IMMP2L | 46 | 7q31.1 | chr7: 109599468-111366370 | 5.74E−07 | 2 | IMMP2L[L] | |
| NEGR1 | 47 | 1p31.1 | chr1: 71699756-74522473 | 7.25E−07 | 2 | NEGR1[E] | |
| BRCA1 | 48 | 17q21.31 | chr17: 41178765-41336147 | 7.25E−07 | 2 | BRCA1[K] | BRCA1 = 3.5e−08 |
| 9q34.3 | 49 | 9q34.3 | chr9: 135441810-139646221 | 8.73E−06 | 94 | NOTCH1[K], BRD3[E], GTF3C4[E] | NOTCH1 = 1e−08, RXRA = 2.1e−05, COL5A1 = 0.0022, TSC1 = 0.012 |
| ANKS1B | 50 | 12q23.1 | chr12: 99124001-100431272 | 8.73E−06 | 2 | ANKS1B[L] | |
| DMD | 51 | Xp21.2 | chrX: 30865118-34644819 | 5.15E−05 | 4 | DMD[L] | |
| ZMYND11 | 52 | 10p15.3[T] | chr10: 1-857150 | 7.12E−05 | 4 | ZMYND11[E] | |
| PRKG1 | 53 | 10q11.23 | chr10: 52644085-54061437 | 9.79E−05 | 3 | PRKG1[L] | |
| FOXK2 | 54 | 17q25.3 | chr17: 80443432-80574531 | 0.00019271 | 1 | FOXK2 | |
| AGBL4 | 55 | 1p33 | chr1: 48935280-50514967 | 0.000219 | 2 | AGBL4 | |
| CDKN1B | 56 | 12p13.1 | chr12: 12710990-12966966 | 0.00035777 | 5 | CDKN1B[K] | CDKN1B = 2.2e−06 |
| 14q32.33 | 57 | 14q32.33[T] | chr14: 94381429-107349540 | 0.00074358 | 227 | SETD3[E], TDRD9[E] | AKT1 = 2.1e−13, TRAF3 = 9.7e−05 |
| 14q11.2 | 58 | 14q11.2[T] | chr14: 1-30047530 | 0.0010181 | 162 | PRMT5[E], CHD8[E] | CHD8 = 0.034 |
| 2p25.3 | 59 | 2p25.3[T] | chr2: 1-20072169 | 0.0011137 | 86 | MYCN[K] | MYCN = 0.068 |
| 5q35.3 | 60 | 5q35.3[T] | chr5: 153840473-180915260 | 0.0028515 | 212 | NSD1[E], ODZ2[L] | NPM1 = 3.5e−13, NSD1 = 1.9e−09, ZNF454 = 0.0019, UBLCP1 = 0.03, GABRB2 = 0.07 |
| PTTG1IP | 61 | 21q22.3 | chr21: 46230687-46306160 | 0.012227 | 1 | PTTG1IP | |
| 22q11.1 | 62 | 22q11.1[T] | chr22: 1-17960585 | 0.020332 | 15 | | |
| SMAD4 | 63 | 18q21.2 | chr18: 48472083-48920689 | 0.036866 | 3 | SMAD4[K] | SMAD4 = 6.6e−15 |
| 17p13.3 | 64 | 17p13.3[T] | chr17: 1-1180022 | 0.040814 | 16 | | |
| 4p16.3 | 65 | 4p16.3[T] | chr4: 1-1243876 | 0.056345 | 27 | | |
| 9p21.2 | 66 | 9p21.2 | chr9: 27572512-28982153 | 0.091742 | 3 | | |
| 10q25.1 | 67 | 10q25.1 | chr10: 99340084-113910615 | 0.11879 | 137 | HPSE2[L], SMNDC1[E] | SMC3 = 0.00031, GSTO2 = 0.086 |

TABLE 3-continued

Exemplary genetic variations associated with tumors (Deletion of the gene)

| Peak Name | Rank | Genomic location | Peak region | GISTIC q-value | Gene count | Target(s) | Frequently mutated genes[B] |
|---|---|---|---|---|---|---|---|
| SMYD3 | 68 | 1q44 | chr1: 245282267-247110824 | 0.15417 | 8 | SMYD3[E] | |
| 8p11.21 | 69 | 8p11.21 | chr8: 42883855-47753079 | 0.17382 | 4 | | |
| Xp22.33 | 70 | Xp22.33[T] | chrX: 1-11137490 | 0.21462 | 52 | | MXRA5 = 0.031 |

In some embodiments, the probe sets of the present disclosure may be configured to target known genetic variations associated with tumors. These may include mutations, SNPs, copy number variants (e.g., amplifications, deletions), copy neutral variants (e.g., inversions, translocations), and/or complex combinations of these variants.

Figure 67A:
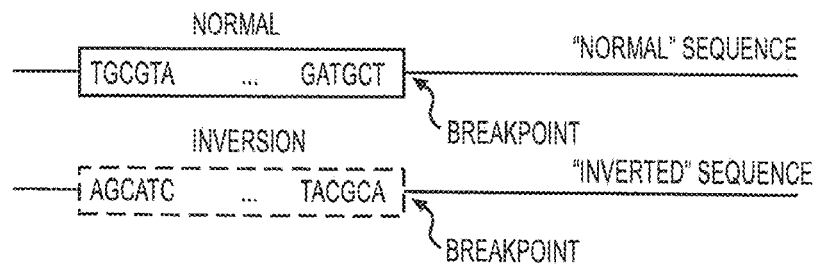
FIGS. 67A, 67B, and 67C depict exemplary probe sets used in methods described herein.
Figure 67B:
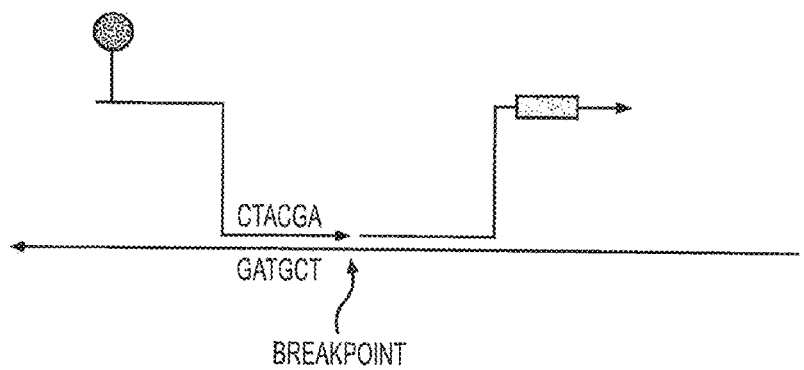
Figure 67C:
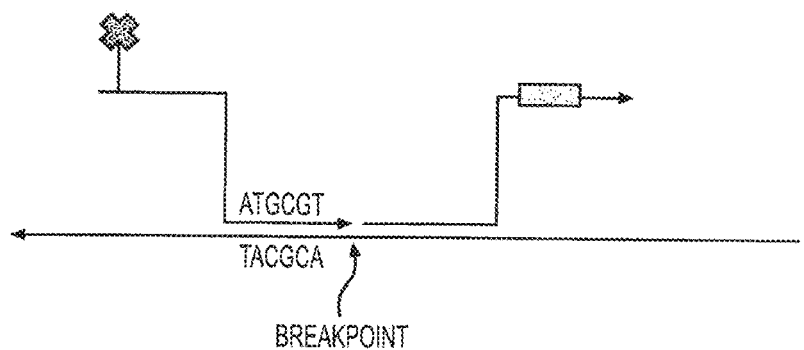

In the method of diagnosing cancer according to some embodiments, inversions that occur at known locations (FIG. 67A) may easily be targeted by designing probes that at least partially overlap the breakpoint in one probe arm. A first probe that binds the "normal" sequence targets non-inverted genomic material (FIG. 67B) and carries a first label type. A second probe that binds the "inverted" target carries a second label type (FIG. 67C). A common right probe arm binds native sequence that is not susceptible to inversion, immediately adjacent the first two probes. This right probe arm further carries a common pull-down tag that localizes the probe products to the same region of an imaging substrate. In this way, the probe pairs may hybridize to the genomic targets, ligate, and be imaged to yield relative counts of the two underlying species.

Figure 68A:
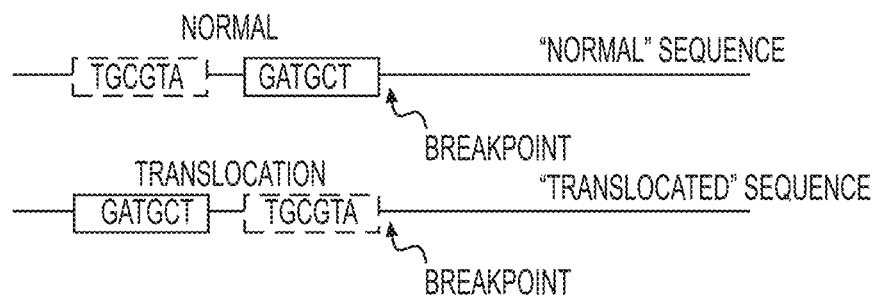
FIGS. 68A, 68B, and 68C depict exemplary probe sets used in methods described herein when translocations that have known breakpoints are assayed.
Figure 68B:
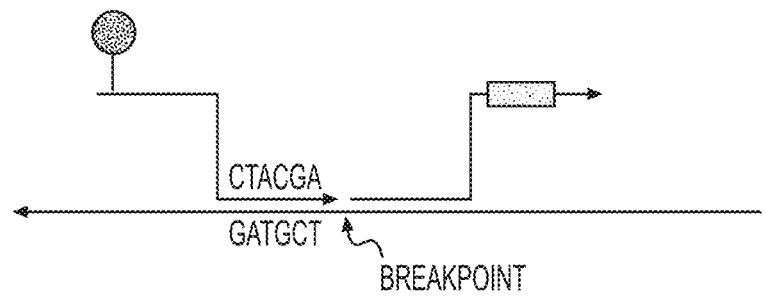
Figure 68C:
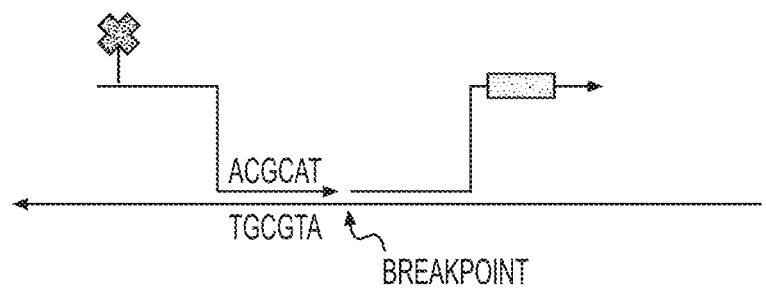

Similarly, translocations that have known breakpoints may also be assayed. FIG. 68A shows two genetic elements that are either in their native order or translocated. Probe arms that at least partially overlap these translocation breakpoints allow differentiation between normal and transposed orders of genetic material. As shown in FIGS. 68B and 68C, by choosing unique labels on the two left arms, the resulting ligated probe products may be distinguished and counted during imaging.

These methods for detecting copy neutral changes (e.g., inversions, translocation) may also be used to detect germline variants in cancer or in other disease or conditions.

Figure 69A:
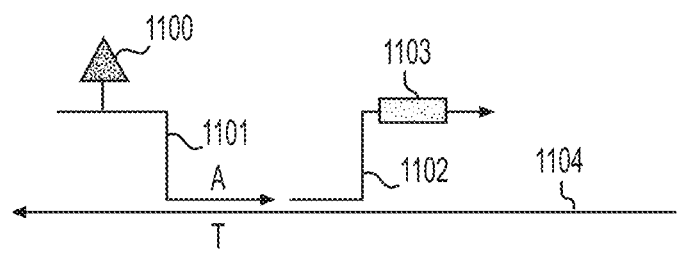
FIGS. 69A, and 69B depict exemplary probe sets used in methods described herein when mutations at SNPs are targeted.
Figure 69B:
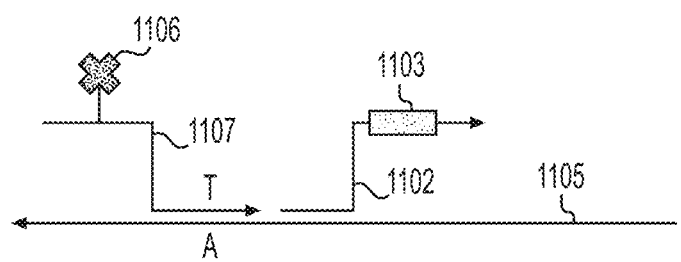
Figure 70:
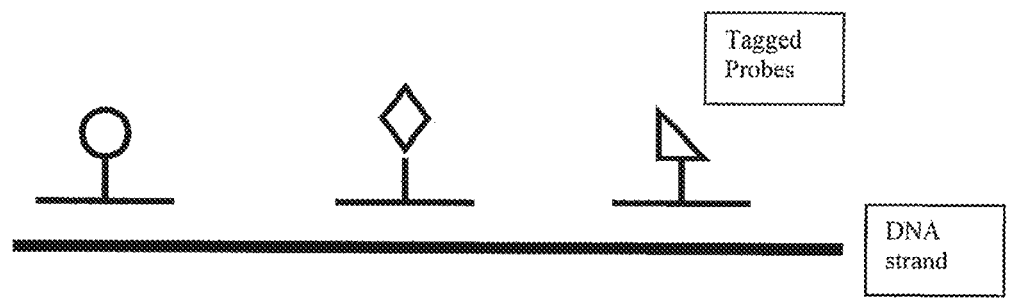
FIG. 70 illustrates encoded probing of single molecule according to some embodiments of the present invention.
Figure 71:
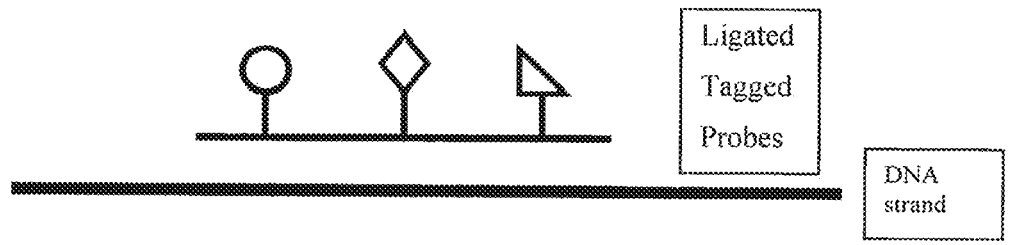
FIG. 71 illustrates complementary strand synthesis by ligation according to some embodiments of the present invention.
Figure 72:
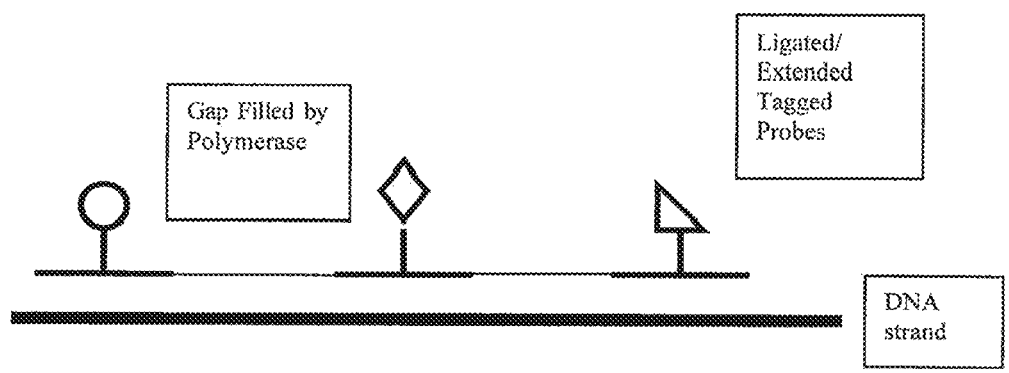
FIG. 72 illustrates gap fill ligation according to some embodiments of the present invention.
Figure 73:
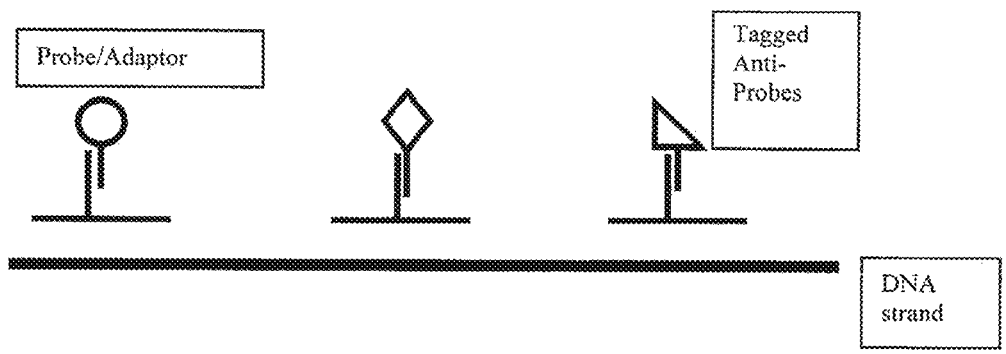
FIG. 73 illustrates the use of secondary anti-probe labels according to some embodiments of the present invention.
Figure 74A:
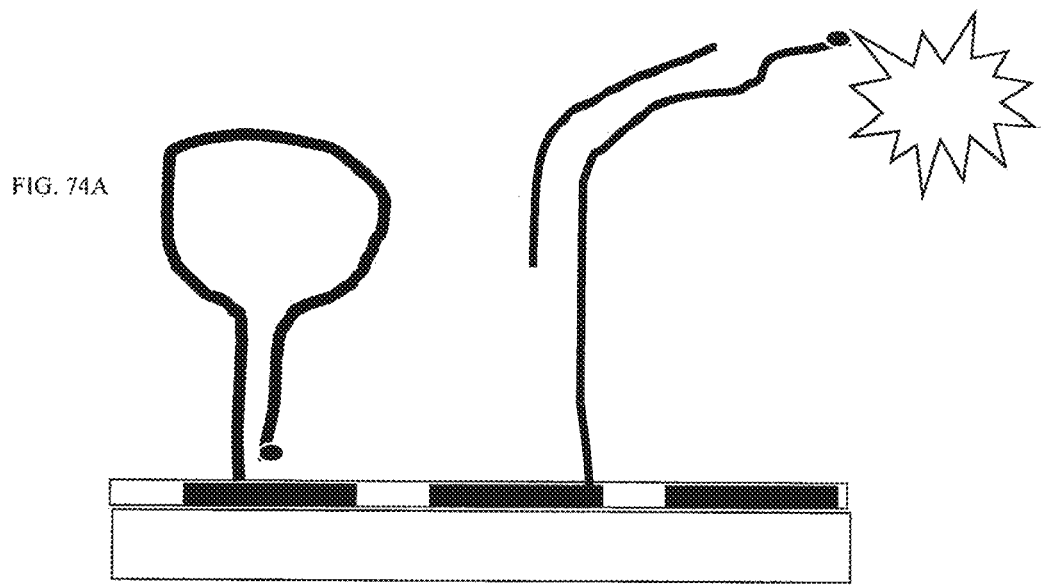
FIG. 74 illustrates a biosensor array according to some embodiments of the present invention.
Figure 74B:
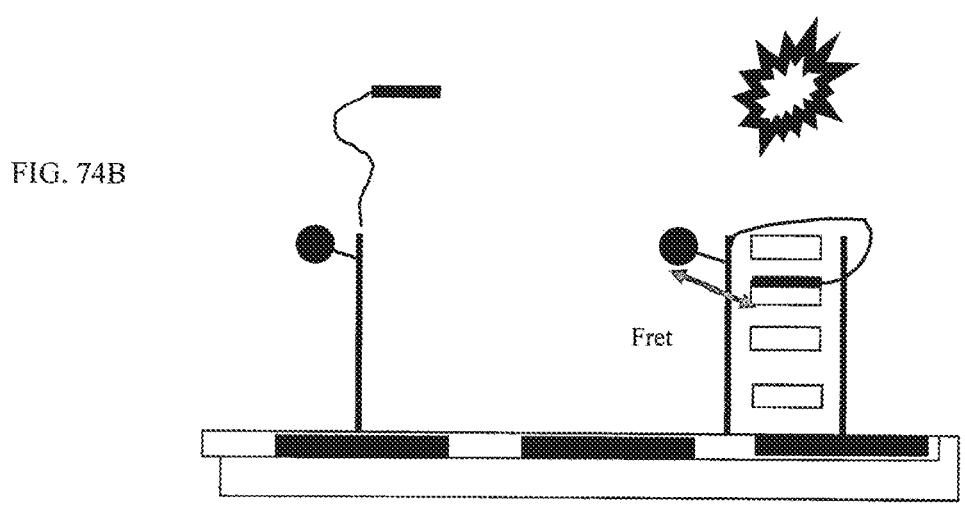
Figure 74C:
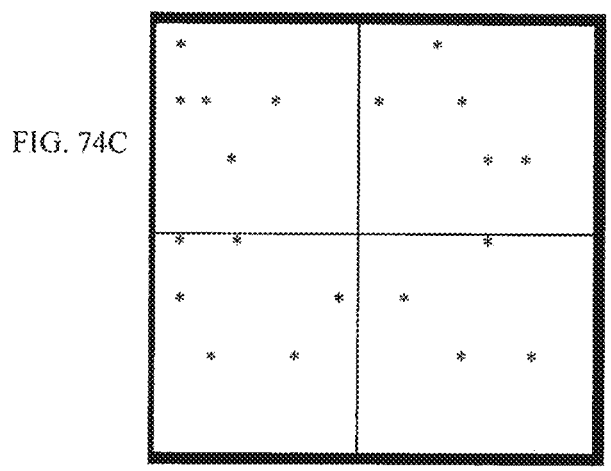
Figure 75A:
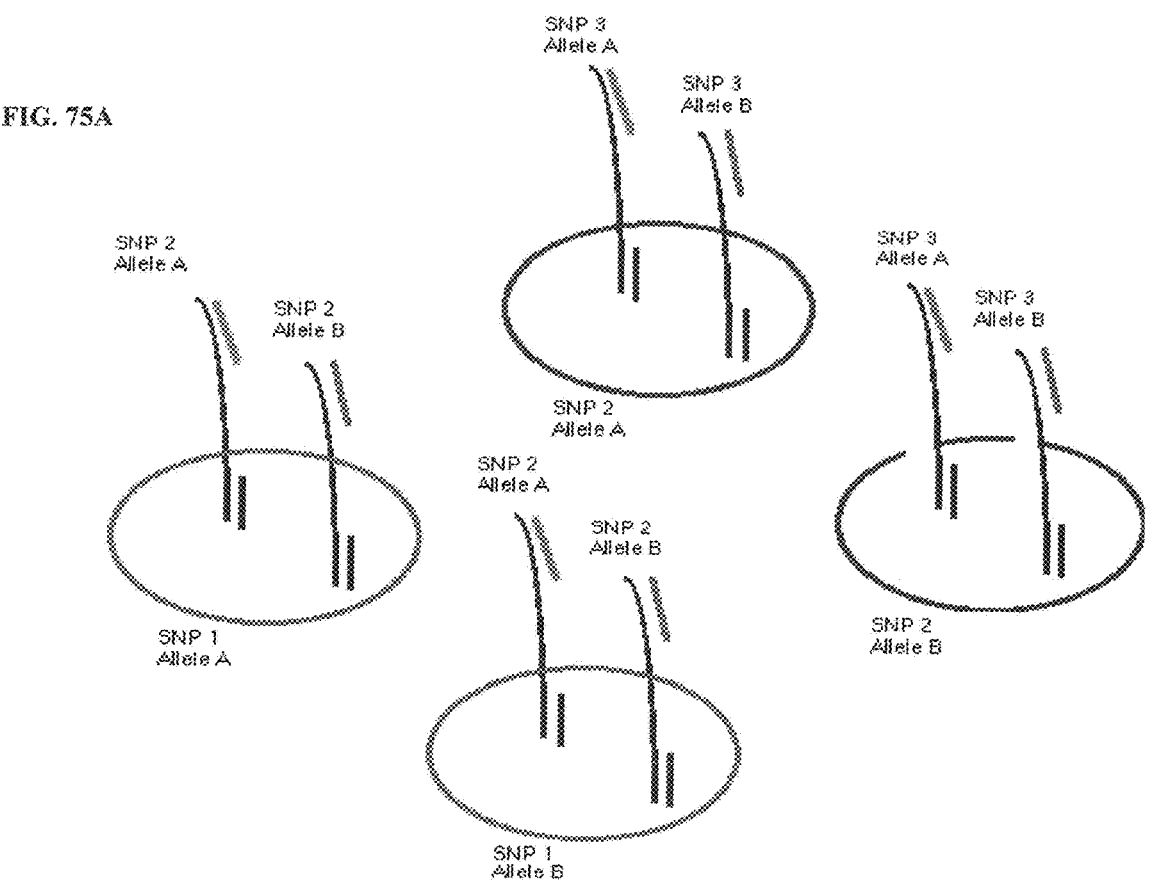
FIG. 75 illustrates SNP detection according to some embodiments of the present invention.
Figure 75B:
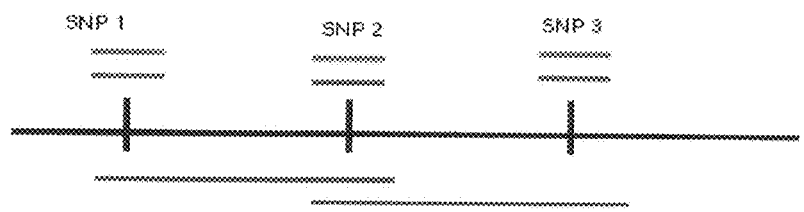
Figure 76A:
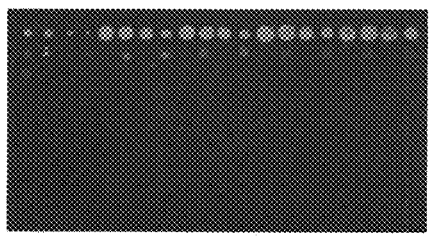
FIG. 76 a. Image of Microarray scan under normal settings according to some embodiments of the present invention. The array carries a dilution series over 12 orders of magnitude concentration from (top to bottom) and a range of oligonucleotide attachment methods from (left to right) for alternative cy3 and cy5 labelled oligonucleotides, b. The same array but with decreased gamma setting, c. A microarray spot from the same array but analysed by Total Internal Reflection Microscopy (TIRF) so that single molecules can be detected (red arrows point to fluorescence from a single molecule), d. Plot of intensity versus time for a single molecule signal, showing blinking and one step photobleaching.
Figure 76B:
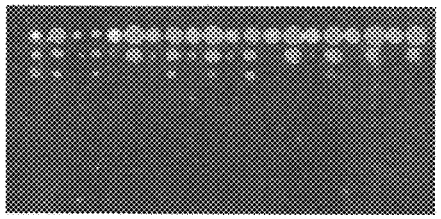
Figure 76D:
Figure 76C:
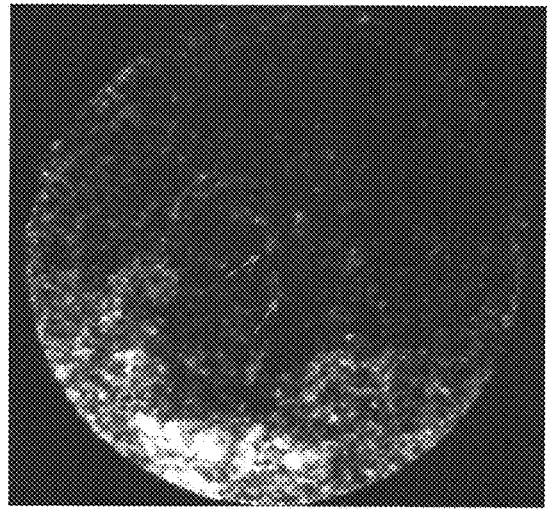
Figure 77:
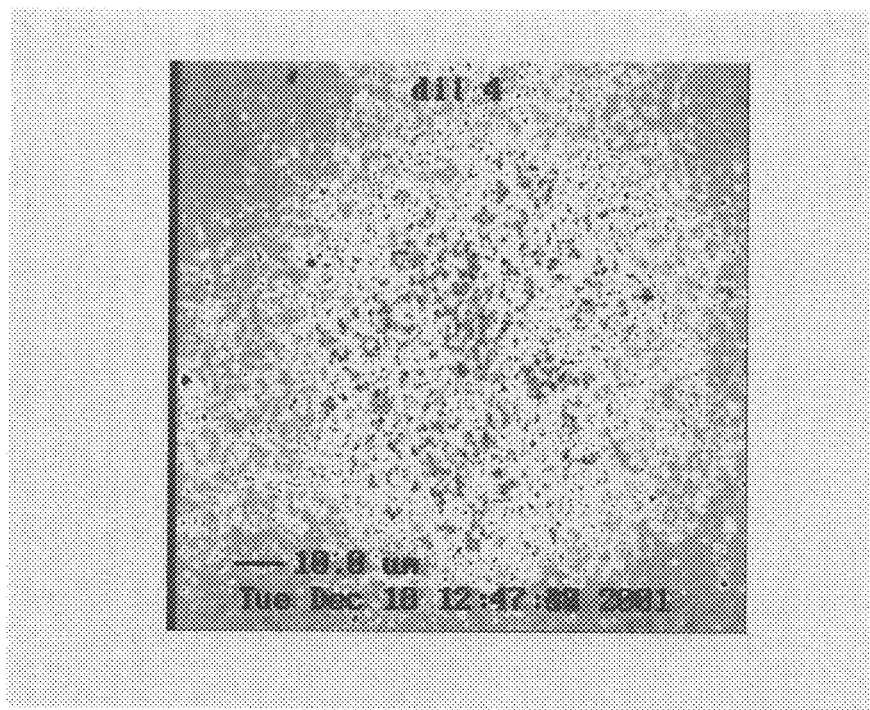
FIG. 77 shows the counting of single molecules by TIRF according to some embodiments of the present invention.
Figure 78A:
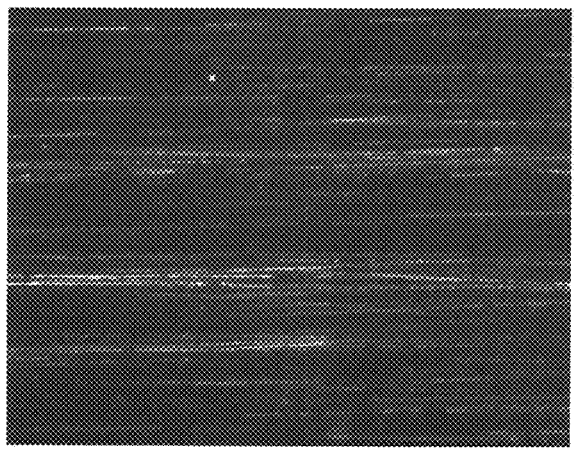
FIG. 78 illustrates: a, Concatemerised lambda phage stretched out on a microscope slide (FOV approx. 250 microns); and b, Sequence repetitively probed on lambda concatemer (arrow) according to some embodiments of the present invention.
Figure 78B:
Figure 79A:
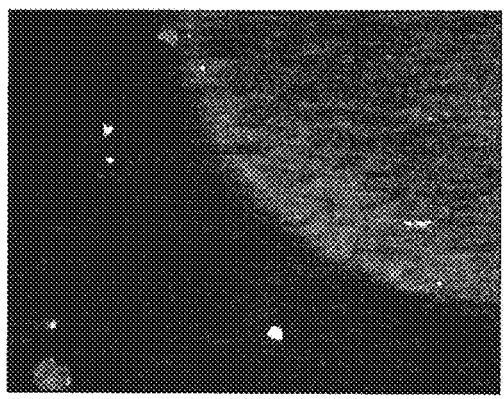
FIG. 79: Spatially addressable combed Lambda DNA spots according to some embodiments of the present invention. 10A: array hybridization and combing of lamda DNA spots with high probe concentration, 100× objective magnification; 10B: array hybridization and combing of lamda DNA spots with low probe concentration, 100× objective magnification; 10C: array hybridization and combing of lamda DNA spots, 100× objective magnification; 10D: array hybridization and combing of lamda DNA spots, 10× objective magnification.
Figure 79B:
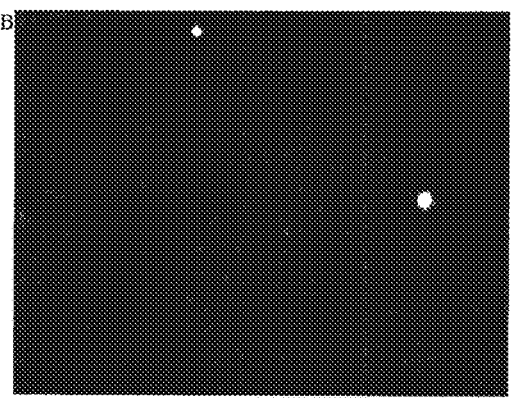
Figure 79C:
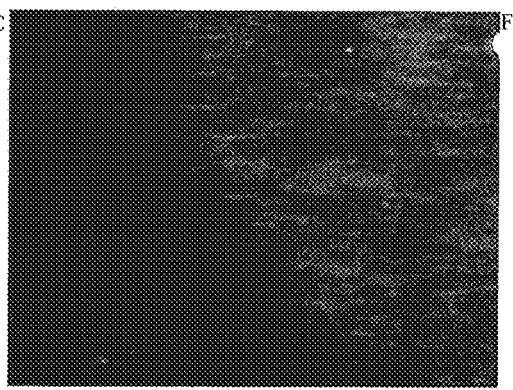
Figure 79D:
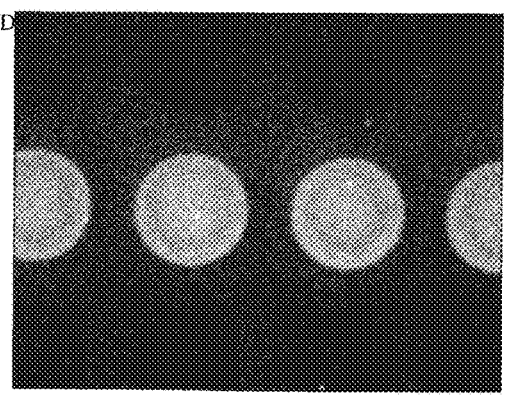

Mutations or SNPs are also implicated in numerous cancers, and are targeted in a similar manner to those that are interrogated in determining fetal fraction in the prenatal diagnostics application. In some embodiments shown in FIGS. 69A and 69B, left probe arms are designed to take advantage of an energetic imbalance caused by one or more mismatched SNPs. This causes one probe arm (1101, carrying one label) to bind more favorably than a second probe arm (1107, carrying a second type of label). Both designs ligate to the same right probe arm (1102) that carries the universal pull-down tag.

A given patient's blood may be probed by one method, or a hybrid of more than one method. Further, in some cases, customizing specific probes for a patient may be valuable. This would involve characterizing tumor features (SNPs, translocations, inversions, etc.) in a sample from the primary tumor (e.g., a biopsy) and creating one or more custom probe sets that is optimized to detect those patient-specific genetic variations in the patient's blood, providing a low-cost, non-invasive method for monitoring. This could have significant value in the case of relapse, where detecting low-level recurrence of a tumor type (identical or related to the original tumor) as early as possible is ideal.

For common disease progression pathways, additional panels may be designed to anticipate and monitor for disease advancement. For example, if mutations tend to accumulate in a given order, probes may be designed to monitor current status and progression "checkpoints," and guide therapy options.

Early detection of cancer: For example, the ALK translocation has been associated with lung cancer. A probe designed to interrogate the ALK translocation may be used to detect tumors of this type via a blood sample. This would be highly advantageous, as the standard method for detecting lung tumors is via a chest x-ray an expensive procedure that may be deleterious to the patient's health and so is not standardly performed.

Detection of recurrence of the primary tumor type: For example, a HER2+ breast tumor is removed by surgery and the patient is in remission. A probe targeting the HER2 gene may be used to monitor for amplifications of the HER2 gene at one or more time points. If these are detected, the patient may have a second HER2+ tumor either at the primary site or elsewhere.

Detection of non-primary tumor types: For example, a HER2+ breast tumor is removed by surgery and the patient is in remission. A probe targeting the EGFR gene may be used to monitor for EGFR+ tumors. If these are detected, the patient may have a second EGFR+ tumor either at the primary site or elsewhere.

Detection of metastasis: For example, the patient has a HER2+ breast tumor. A probe designed to interrogate the ALK translocation may be used to detect tumors of this type via a blood sample. This tumor may not be in the breast and is more likely to be in the lung. If these are detected, the patient may have a metastatic tumor distal to the primary organ.

Determining tumor heterogeneity: Many tumors have multiple clonal populations characterized by different genetic variants. For example, a breast tumor may have one population of cells that are HER2+ and another population of cells that are EGFR+. Using probes designed to target both these variants would allow the identification of this underlying genetic heterogeneity.

Measurement of tumor load: In all the above examples, the quantity of tumor cfDNA may be measured and may be used to determine the size, growth rate, aggressiveness, stage, prognosis, diagnosis and other attributes of the tumor and the patient. Ideally, measurements are made at more than one time point to show changes in the quantity of tumor cfDNA.

Monitoring treatment: For example, a HER2+ breast tumor is treated with Herceptin. A probe targeting the HER2 gene may be used to monitor for quantity of tumor cfDNA, which may be a proxy for the size of the tumor. This may be used to determine if the tumor is changing in size and treatment may be modified to optimize the patient's out-come. This may include changing the dose, stopping treatment, changing to another therapy, combing multiple therapies.

Screening for tumor DNA: There is currently no universal screen for cancer. The present invention offers a way to detect tumors at some or all locations in the body. For example, a panel of probes is developed at a spacing of 100 kb across the genome. This panel may be used as a way to detect genetic variation across the genome. In one example, the panel detects copy number changes of a certain size across the genome. Such copy number changes are associated with tumor cells and so the test detects the presence of tumor cells. Different tumor types may produce different quantities of tumor cfDNA or may have variation in different parts of the genome. As such, the test may be able to identify which organ is affected. Further the quantity of tumor cfDNA measured may indicate the stage or size of the tumor or the location of the tumor. In this way, the test is a whole-genome screen for many or all tumor types.

For all the above tests, in order to mitigate false positives, a threshold may be used to determine the presence or certainty of a tumor. Further, the test may be repeat on multiple sample or at multiple time points to increase the certainty of the results. The results may also be combined with other information or symptoms to provide more information or more certain information on the tumor.

Exemplary probe sets and primers that may be used in the method described herein to measure copy number of nucleic acid regions of interest are listed in Table 4 below. Each of the exemplary probe sets in Table 4 comprises two probes. The first (tagging) probe has a structure including a forward priming site, tag, and homology 1. The second (labeling) probe has structure, including homology 2 and reverse primer site, which is used in labeling. The component sequences of the probes (tag, homology sequence etc.) are also shown.

TABLE 4

Exemplary probes and primers.

| Chromosome | Locus ID | Tagging Probe (Forward Primer + Tag + 5pHom) | Labeling Probe (3'-Hop + Reverse Primer) | Forward primer | Tag | Hom 5p | Hom 3p | Reverse primer |
|---|---|---|---|---|---|---|---|---|
| 18 | 18-1 | GCCCTCATCTTC TTCCCTGCGTTC TCACCACCCTCA CCAAGGAGAAA GTGAGGGCTTCT C (SEQ ID NO: 1) | CGTGCTAATAGTC TCAGGGCTTCCTC CACCGAACGTGT CT (SEQ ID NO: 17) | GCCCTCAT CTTCTTCC CTGC (SEQ ID NO: 33) | GTTCTCA CCACCCT CACCAA (SEQ ID NO: 34) | GGAAGAA GTGAGGG CTTCTC (SEQ ID NO: 35) | CGTGCTA ATAGTCT CAGGGC (SEQ ID NO: 51) | TTCCTCCA CCGAACGT GTCT (SEQ ID NO: 67) |
| 18 | 18-2 | GCCCTCATCTTC TTCCCTGCGTTC TCACCACCCTCA CCAAAAATCAAG GTGACCAGTCC (SEQ ID NO: 2) | CGAGCTTCATTG CTTCATTTCCTC CACCGAACGTGT CT (SEQ ID NO: 18) | GCCCTCAT CTTCTTCC CTGC (SEQ ID NO: 33) | GTTCTCA CCACCCT CACCAA (SEQ ID NO: 34) | AAATCAA GGTGACC AGTCC (SEQ ID NO: 36) | CGACGC TTCATTG CTTCATT (SEQ ID NO: 52) | TTCCTCCA CCGAACGT GTCT (SEQ ID NO: 67) |
| 18 | 18-3 | GCCCTCATCTTC TTCCCTGCGTTC TCACCACCCTCA CCAATCATCTGC CAAGACAGAAG TTC (SEQ ID NO: 3) | CTTGCGCCAAAC AATTGTCCTTCCT CCACCGAACGTG TCT (SEQ ID NO: 19) | GCCCTCAT CTTCTTCC CTGC (SEQ ID NO: 33) | GTTCTCA CCACCCT CACCAA (SEQ ID NO: 34) | TCATCTG CCAAGAC AGAAGTT C (SEQ ID NO: 37) | CTTGCGC CAAACA ATTGTCC (SEQ ID NO: 53) | TTCCTCCA CCGAACGT GTCT (SEQ ID NO: 67) |
| 18 | 18-4 | GCCCTCATCTTC TTCCCTGCGTTC TCACCACCCTCA CCAAGCAGGAG AGTCAAGGTCT G (SEQ ID NO: 4) | GCTGCAGAGTTTG CATTCATTTCCTC CACCGAACGTGT CT (SEQ ID NO: 20) | GCCCTCAT CTTCTTCC CTGC (SEQ ID NO: 33) | GTTCTCA CCACCCT CACCAA (SEQ ID NO: 34) | GCAGGAG AGTCAAA GGTCTG (SEQ ID NO: 38) | GCTGCA GAGTTTG CATTCAT (SEQ ID NO: 54) | TTCCTCCA CCGAACGT GTCT (SEQ ID NO: 67) |
| 18 | 18-5 | GCCCTCATCTTC TTCCCTGCGTTC TCACCACCCTCA CCAAGTTGCCAT GGAGATTGTTGC (SEQ ID NO: 5) | CATACACACAGA CCGAGAGTCTTCC TCCACCGAACGT GTCT (SEQ ID NO: 21) | GC CCTCAT CTTCTTCC CTGC (SEQ ID NO: 33) | GTTCTCA CCACCCT CACCAA (SEQ ID NO: 34) | GTTGC CA TGGAGAT TGTTGC (SEQ ID NO: 39) | CATACA CACAGA CCGAGA GTC (SEQ ID NO: 55) | TTCCTCCA CCGAACGT GTCT (SEQ ID NO: 67) |
| 18 | 18-6 | GCCCTCATCTTC TTCCCTGCGTTC TCACCACCCTCA CCAAGTCAGCTCAG TGATGTCATTGC (SEQ ID NO: 6) | GGATGTCAGCCA GCATAAGTTTCCT CCACCGAACGTG TCT (SEQ ID NO: 22) | GCCCTCAT CTTCTTCC CTGC (SEQ ID NO: 33) | GTTCTCA CCACCCT CACCAA (SEQ ID NO: 34) | CAGCTCA GTGATGT CATTGC (SEQ ID NO: 40) | GGATGT CAGCCA GCATAA GT (SEQ ID NO: 56) | TTCCTCCA CCGAACGT GTCT (SEQ ID NO: 67) |

TABLE 4-continued

Exemplary probes and primers.

| Chromosome | Locus ID | Tagging Probe (Forward Primer + Tag + 5pHom) | Labeling Probe (3'-Hop + Reverse Primer) | Forward primer | Tag | Hom 5p | Hom 3p | Reverse primer |
|---|---|---|---|---|---|---|---|---|
| 18 | 18-7 | GCCCTCATCTTC TTCCCTGCGTTC TCACCACCCTCA CCAACCTTGACC TCTGCTAATGTG G (SEQ ID NO: 7) | GCAAGTGCCAAA CAGTTCTCTTCCT CCACCGAACGTG TCT (SEQ ID NO: 23) | GCCCTCAT CTTCTTCC CTGC (SEQ ID NO: 33) | GTTCTCA CCACCCT CACCAA (SEQ ID NO: 34) | CCTTGAC CTCTGCT AATGTGG (SEQ ID NO: 41) | GCAAGT GCCAAA CAGTTCT C (SEQ ID NO: 57) | TTCCTCCA CCGAACGT GTCT (SEQ ID NO: 67) |
| 18 | 18-8 | GCCCTCATCTTC TTCCCTGCGTTC TCACCACCCTCA CCAACACCTGTC CAACAGCTACAG (SEQ ID NO: 8) | GATTCCAGCACA CTTGAGTCTTTCC TCCACCGAACGT GTCT (SEQ ID NO: 24) | GCCCTCAT CTTCTTCC CTGC (SEQ ID NO: 33) | GTTCTCA CCACCCT CACCAA (SEQ ID NO: 34) | CACCTGT CCAACAG CTACAG (SEQ ID NO: 42) | GATTCCA GCACAC TTGAGTC T (SEQ ID NO: 58) | TTCCTCCA CCGAACGT GTCT (SEQ ID NO: 67) |
| X | X-1 | GCCCTCATCTTC TTCCCTGCGTTC TCACCACCCTCA CCAAAGAATGTA TCTTCAGGCCTG C (SEQ ID NO: 9) | CCGTTGCAGTTT AAATGGCGCCCT ATTGCAAGCCCT TT (SEQ ID NO: 25) | GCCCTCAT CTTCTTCC CTGC (SEQ ID NO: 33) | GTTCTCA CCACCCT CACCAA (SEQ ID NO: 34) | AGAATGT ATCTTCA GGCCTGC (SEQ ID NO: 43) | CCGTTGC AGGTTTA AATGC (SEQ ID NO: 59) | GCCCTATT GCAAGCCC TCTT (SEQ ID NO: 68) |
| X | X-2 | GCCCTCATCTTC TTCCCTGCGTTC TCACCACCCTCA CCAAAGTAATC ACTCTGGGTGGC (SEQ ID NO: 10) | CAAGAGTGCTTTA TGGGCCTGCCCTA TTGCAAGCCCTCT T (SEQ ID NO: 26) | GCCCTCAT CTTCTTCC CTGC (SEQ ID NO: 33) | GTTCTCA CCACCCT CACCAA (SEQ ID NO: 34) | AAGTAAT CACTCTG GGTGGC (SEQ ID NO: 44) | CAAGAG TGCTTTA TGGGCCT (SEQ ID NO: 60) | GCCCTATT GCAAGCCC TCTT (SEQ ID NO: 68) |
| X | X-3 | GCCCTCATCTTC TTCCCTGCGTTC TCACCACCCTCA CCAAGCTCACA GACAACCTTGTG (SEQ ID NO: 11) | GCACTCAAGGAG ATCAGACTGCCC CTATTGCAAGCCC TCTT (SEQ ID NO: 27) | GCCCTCAT CTTCTTCC CTGC (SEQ ID NO: 33) | GTTCTCA CCACCCT CACCAA (SEQ ID NO: 34) | AGCTCAC AGACAAC CTTGTG (SEQ ID NO: 45) | GCACTC AAGGAG ATCAGA CTG (SEQ ID NO: 61) | GCCCTATT GCAAGCCC TCTT (SEQ ID NO: 68) |
| X | X-4 | GCCCTCATCTTC TTCCCTGCGTTC TCACCACCCTCA CCAAGCAATAGA CACCTACAGGCG (SEQ ID NO: 12) | GGCTATCGAACT ACAACCACGCC CTATTGCAAGCCC TCTT (SEQ ID NO: 28) | GCCCTCAT CTTCTTCC CTGC (SEQ ID NO: 33) | GTTCTCA CCACCCT CACCAA (SEQ ID NO: 34) | GCAATAG ACACCTA CAGCG (SEQ ID NO: 46) | GGCTATC GAACTA CAACCA CA (SEQ ID NO: 62) | GCCCTATT GCAAGCCC TCTT (SEQ ID NO: 68) |

TABLE 4-continued

Exemplary probes and primers.

| Chromosome | Locus ID | Tagging Probe (Forward Primer + Tag + 5pHom) | Labeling Probe (3'-Hop + Reverse Primer) | Forward primer | Tag | Hom 5p | Hom 3p | Reverse primer |
|---|---|---|---|---|---|---|---|---|
| X | X-5 | GCCCTCATCTTC TTCCCTGCGTTC TCACCACCCTCA CCAAGGCCACG TCAAAGCCACG (SEQ ID NO: 13) | GTAGCTGTCTGTG GTGTGATCGCCCT ATTGCAAGCCCTC TT (SEQ ID NO: 29) | GCCCTCAT CTTCTTCC CTGC (SEQ ID NO: 33) | GTTCTCA CCACCCT CACCAA (SEQ ID NO: 34) | GCACATT ATCAAAG GCCACG (SEQ ID NO: 47) | GTAGCT GTCTGTG GTGTGAT C (SEQ ID NO: 63) | GCCCTATT GCAAGCCC TCTT (SEQ ID NO: 68) |
| X | X-6 | GCCCTCATCTTC TTCCCTGCGTTC TCACCACCCTCA CCAACAACGACC TAAAGCATGTGC (SEQ ID NO: 14) | CAAGAAACTTCG AGCCTTAGCAGC CCTATTGCAAGCC CTCTT (SEQ ID NO: 30) | GCCCTCAT CTTCTTCC CTGC (SEQ ID NO: 33) | GTTCTCA CCACCCT CACCAA (SEQ ID NO: 34) | CAACGAC CTAAAGC ATGTGC (SEQ ID NO: 48) | CAAGAA ACTTCGA GCCTTAG CA (SEQ ID NO: 64) | GCCCTATT GCAAGCCC TCTT (SEQ ID NO: 68) |
| X | X-7 | GCCCTCATCTTC TTCCCTGCGTTC TCACCACCCTCA CCAAGACATACA TGGCTTTGGCAG (SEQ ID NO: 15) | GTGAACCAGTCC GAGTGAAAGCCC TATTGCAAGCCCT CTT (SEQ ID NO: 31) | GCCCTCAT CTTCTTCC CTGC (SEQ ID NO: 33) | GTTCTCA CCACCCT CACCAA (SEQ ID NO: 34) | GACATAC ATGGCTT TGGCAG (SEQ ID NO: 49) | GTGAAC CAGTCC GAGTGA AA (SEQ ID NO: 65) | GCCCTATT GCAAGCCC TCTT (SEQ ID NO: 68) |
| X | X-8 | GCCCTCATCTTC TTCCCTGCGTTC TCACCACCCTCA CCAAGAGATACT GCCACTTATGCA CG (SEQ ID NO: 16) | GCAAATGATGTTC AGCACCACGCCC TATTGCAAGCCCT CTT (SEQ ID NO: 32) | GCCCTCAT CTTCTTCC CTGC (SEQ ID NO: 33) | GTTCTCA CCACCCT CACCAA (SEQ ID NO: 34) | GAGATAC TGCCACT TATGCAC G (SEQ ID NO: 50) | GCAAAT GATGTTC AGCACC AC (SEQ ID NO: 66) | GCCCTATT GCAAGCCC TCTT (SEQ ID NO: 68) |

Exemplary probe sets and primers that may be used in the method described herein to detect a polymorphism at a SNP site are listed in Table 5 below. Each of the exemplary probe sets in Table 5 comprises three probes, two allele specific probes (that are used for labeling) and a tagging probe. In these examples, the two allele specific probes have homology sequences that are different at one or more nucleotides. The structure of the first allelic probe includes a Forward Primer Site Allele 1 and Homology Allele 1; and the structure of the second allelic probe includes a Forward Primer Site Allele 2 and Homology Allele 2. In practice, labeled primers may be used with different labels on the two primers (so the labels are allele specific). In these examples, there also is a universal 3' probe which includes a homology region (without any SNP), the tagging sequence and a reverse primer site. The component sequences of the probes (tag, homology sequence etc.) are also shown.

In this disclosure, references are made to the accompanying drawings, and specific examples are disclosed below, which form a part of the description and in which are shown specific embodiments in accordance with the described embodiments. Although these embodiments are described in sufficient detail to enable one skilled in the art to practice the described embodiments, it is understood that these examples are not limiting; such that other embodiments may be used, and changes may be made without departing from the spirit and scope of the described embodiments.

TABLE 5

Exemplary probes and primers.

| Chromosome | Labeling Probe-Allele 1 (Forward Primer Allele 1 + Hom 5p Allele 1) | Labeling Probe-Allele 2 (Forward Primer Allele 2 + Hom 5p Allele 2) | Tagging Probe (Hom 3p + Tag + Reverse Primer) | Forward Primer-Allele 1 | Forward Primer-Allele 2 | Hom 5p-Allele 1 | Hom 5p-Allele 2 | Hom 3p | Tag | Reverse Primer |
|---|---|---|---|---|---|---|---|---|---|---|
| chr21 | TTCCTCCACC GAACGTGTCT AGACCAGCAC AACTTACTcg (SEQ ID NO: 69) | GCCCTATTGCA AGCCCTCTTAG ACCAGCACAAC TTACTta (SEQ ID NO: 112) | CACTTGACAA AGTTCTCACG CGCCGAAGTT CTCCGAAGGA TGCCCTCATC TTCTTCCCTGC (SEQ ID NO: 155) | TTCCTC CACCGA ACGTGT CT (SEQ ID NO: 67) | GCCCTAT TGCAAG CCCTCTT (SEQ ID NO: 68) | AGACCA GCACAA CTTACTc g (SEQ ID NO: 198) | AGACC AGCAC AACTT ACTta (SEQ ID NO: 241) | CACTT GACA AAGTT CTCAC GC (SEQ ID NO: 284) | GCCGA AGTTC TCCGA AGGAT CA (SEQ ID NO: 327) | GCCCT CATCT TCTTC CCTGC (SEQ ID NO: 33) |
| chr3 | TTCCTCCACC GAACGTGTCT CCAAATgCAC CTGCCtg (SEQ ID NO: 70) | GCCCTATTGCA AGCCCTCTTCCA AATtCACCTGCC ca (SEQ ID NO: 113) | CATTAGGGAT TAACGGCTTG GGACAGACTG ACGGAGCTTC AGCCCTCATC TTCTTCCCTGC (SEQ ID NO: 156) | TTCCTC CACCGA ACGTGT CT (SEQ ID NO: 67) | GCCCTAT TGCAAG CCCTCTT (SEQ ID NO: 68) | CCAAAT gCACCT GCCtg (SEQ ID NO: 199) | CCAAA TtCACC TGCCca (SEQ ID NO: 242) | CATTA GGGAT TAACG GCTTG G (SEQ ID NO: 285) | GACA GACTG ACGG AGCTT CA (SEQ ID NO: 328) | GCCCT CATCT TCTTC CCTGC (SEQ ID NO: 33) |
| chr13 | TTCCTCCACC GAACGTGTCT AGTTTGGACA AAGGCaATTcg (SEQ ID NO: 71) | GCCCTATTGCA AGCCCTCTTAGT TTGGACAAGG CgATTta (SEQ ID NO: 114) | CACACGTTAA GAAGACTTTC TGCTGACTCT GCCGCACATG ATCGCCCTCA TCTTCTTCCCT GC (SEQ ID NO: 157) | TTCCTC CACCGA ACGTGT CT (SEQ ID NO: 67) | GCCCTAT TGCAAG CCCTCTT (SEQ ID NO: 68) | AGTTTG GACAAA GGCaAT Tcg (SEQ ID NO: 200) | AGTTT GGACA AAGGC gATTta (SEQ ID NO: 243) | CACAC GTTAA GAAG ACTTT CTGC (SEQ ID NO: 286) | TGACT CTGCC GCACA TGATC CA (SEQ ID NO: 329) | GCCCT CATCT TCTTC CCTGC (SEQ ID NO: 33) |
| chr3 | TTCCTCCACC GAACGTGTCT TGAGCTTAGC CAATATCAAg AAGg (SEQ ID NO: 72) | GCCCTATTGCA AGCCCTCTTTGA GCTTAGCCAAT ATCAAcAAGa (SEQ ID NO: 115) | CTAAGTGCCC TCCATGAGAA AGGATCCGAT AGCCCTCATC AGGCCCTCAT CTTCTTCCCTG C (SEQ ID NO: 158) | TTCCTC CACCGA ACGTGT CT (SEQ ID NO: 67) | GCCCTAT TGCAAG CCCTCTT (SEQ ID NO: 68) | TGAGCT TAGCCA ATATCA AgAAGg (SEQ ID NO: 201) | TGAGC TTAGC CAATA TCAAcA AGa (SEQ ID NO: 244) | CTAAG TGCCC TCCAT GAGA AAG (SEQ ID NO: 287) | GATCC GATAG CCCTC TGCAG CA (SEQ ID NO: 330) | GCCCT CATCT TCTTC CCTGC (SEQ ID NO: 33) |

TABLE 5-continued

Exemplary probes and primers.

| Chromo-some | Labeling Probe-Allele 1 (Forward Primer Allele 1 + Hom 5p Allele 1) | Labeling Probe-Allele 2 (Forward Primer Allele 2 + Hom 5p Allele 2) | Tagging Probe (Hom 3p + Tag + Reverse Primer) | Forward Primer-Allele 1 | Forward Primer-Allele 2 | Hom 5p-Allele 1 | Hom 5p-Allele 2 | Hom 3p | Tag | Reverse Primer |
|---|---|---|---|---|---|---|---|---|---|---|
| chr9 | TTCCTCCACC GAACGTGTCT ACGTGAACTT TCCTTGGTAcA c (SEQ ID NO: 73) | GCCCTATTGCA AGCCCTCTTAC GTGAACTTTCCT TGGTAaAt (SEQ ID NO: 116) | GCACAGATTT CCCACACTCT CAACAGGCCT GCTAAACACC GCCCTCATCT TCTTCCCTGC (SEQ ID NO: 159) | TTCCTC CACCGA ACGTGT CT (SEQ ID NO: 67) | GCCCTAT TGCAAG CCCTCTT (SEQ ID NO: 68) | ACGTGA ACTTTC CTTGGT AcAc (SEQ ID NO: 202) | ACGTG AACTT TCCTTG GTAaAt (SEQ ID NO: 245) | GCACA GATTT CCCAC ACTCT (SEQ ID NO: 288) | CAACA GGCCT GCTAA ACACC (SEQ ID NO: 331) | GCCCT CATCT TCTTC CCTGC (SEQ ID NO: 33) |
| chr3 | TTCCTCCACC GAACGTGTCT TGAAGATGTT CTAATACCTT GCcg (SEQ ID NO: 74) | GCCCTATTGCA AGCCCTCTTGA AGATGTTCTAA TACCTTGCta (SEQ ID NO: 117) | CTTACAGGAG GTCTGGCATC AGGTCAACAA CCGAGGGACT CGCCCTCATC TTCTTCCCTGC (SEQ ID NO: 160) | TTCCTC CACCGA ACGTGT CT (SEQ ID NO: 67) | GCCCTAT TGCAAG CCCTCTT (SEQ ID NO: 68) | TGAAGA TGTTCT AATACC TTGCcg (SEQ ID NO: 203) | TGAAG ATGTT CTAAT ACCTT GCta (SEQ ID NO: 246) | CTTAC AGGA GGTCT GGCAT CA (SEQ ID NO: 289) | GGTCA ACAAC CGAG GGACT C (SEQ ID NO: 332) | GCCCT CATCT TCTTC CCTGC (SEQ ID NO: 33) |
| chr17 | TTCCTCCACC GAACGTGTCT CAGTGTGGAG ACtg (SEQ ID NO: 75) | GCCCTATTGCA AGCCCTCTTCA GTGTGGAGACc GAACa (SEQ ID NO: 118) | CCACAATGGA AAGGCAGAGT TGTCATTAAT GCTGGCGGCG CCCTCATCTTC TTCCCTGC (SEQ ID NO: 161) | TTCCTC CACCGA ACGTGT CT (SEQ ID NO: 67) | GCCCTAT TGCAAG CCCTCTT (SEQ ID NO: 68) | CAGTGT GGAGAC tgAAACg (SEQ ID NO: 204) | CAGTG TGGAG ACcGA ACa (SEQ ID NO: 247) | CCACA ATGGA AAGG CAGA G (SEQ ID NO: 290) | TTGTC ATTAA TGCTG GCGGC (SEQ ID NO: 333) | GCCCT CATCT TCTTC CCTGC (SEQ ID NO: 33) |
| chr16 | TTCCTCCACC GAACGTGTCT AGGCAGGGTA ATGTCATGAA aTg (SEQ ID NO: 76) | GCCCTATTGCA AGCCCTCTTAG GCAGGGTAATG TCATGAAgTt (SEQ ID NO: 119) | GCTGTGGCAT AGCTACACTC CGTGACGGT TTGCAACTTT GCCCTCATCT TCTTCCCTGC (SEQ ID NO: 162) | TTCCTC CACCGA ACGTGT CT (SEQ ID NO: 67) | GCCCTAT TGCAAG CCCTCTT (SEQ ID NO: 68) | AGGCAG GGTAAT GTCATG AAaTg (SEQ ID NO: 205) | AGGCA GGGTA GTCTC ATGAA gTt (SEQ ID NO: 248) | GCTGT GGCAT AGCTA CACTC (SEQ ID NO: 291) | CGGTG ACGGT TTGCA ACTTT (SEQ ID NO: 334) | GCCCT CATCT TCTTC CCTGC (SEQ ID NO: 33) |

TABLE 5-continued

Exemplary probes and primers.

| Chromosome | Labeling Probe-Allele 1 (Forward Primer Allele 1 + Hom 5p Allele 1) | Labeling Probe-Allele 2 (Forward Primer Allele 2 + Hom 5p Allele 2) | Tagging Probe (Hom 3p + Tag + Reverse Primer) | Forward Primer-Allele 1 | Forward Primer-Allele 2 | Hom 5p-Allele 1 | Hom 5p-Allele 2 | Hom 3p | Tag | Reverse Primer |
|---|---|---|---|---|---|---|---|---|---|---|
| chr21 | TTCCTCCACC GAACGTGTCT GATTGTCTGG AGcGCTg (SEQ ID NO: 77) | GCCCTATTGCA AGCCCTCTTGAT TGTCTGGAGGGC Tc (SEQ ID NO: 120) | CAGGGTAATT TGTGGGTCTG GTCGGCAGT TAAGGGTCTC GCCCTCATCT TCTTCCCTGC (SEQ ID NO: 163) | TTCCTC CACCGA ACGTGT CT (SEQ ID NO: 67) | GCCCTAT TGCAAG CCCTCTT (SEQ ID NO: 68) | GATTGT CTGGAG cGCTg (SEQ ID NO: 206) | GATTG TCTGG AGGGC Tc (SEQ ID NO: 249) | CAGG GTAAT TTGTG GGTCT G (SEQ ID NO: 292) | GTCCG GCAGT TAAGG GTCTC (SEQ ID NO: 335) | GCCCT CATCT TCTTC CCTGC (SEQ ID NO: 33) |
| chr2 | TTCCTCCACC GAACGTGTCT AGGGAGCAAT AGGCcg (SEQ ID NO: 78) | GCCCTATTGCA AGCCCTCTTAG GGAGCAATAGG Cta (SEQ ID NO: 121) | GGGCTATCCA GAAAGATAAG AATACTCACA AACGACTGCG CAGCCCTCAT CTTCTTCCCTG C (SEQ ID NO: 164) | TTCCTC CACCGA ACGTGT CT (SEQ ID NO: 67) | GCCCTAT TGCAAG CCCTCTT (SEQ ID NO: 68) | AGGGAG CAATAG GCcg (SEQ ID NO: 207) | AGGGA GCAAT AGGCta (SEQ ID NO: 250) | GGGCT ATCCA GAAA GATAA GAA (SEQ ID NO: 293) | TACTC ACAA ACGAC TGCGC A (SEQ ID NO: 336) | GCCCT CATCT TCTTC CCTGC (SEQ ID NO: 33) |
| chr2 | TTCCTCCACC GAACGTGTCT CTGCAGGGTA CAAACg (SEQ ID NO: 79) | GCCCTATTGCA AGCCCTCTTCTG CAGGGTACAAg ACa (SEQ ID NO: 122) | CATAACTGGT GGAGTATTTC ACTCGTATAT GGCCGACTGG AGGGCCCTCA TCTTCTTCCCT GC (SEQ ID NO: 165) | TTCCTC CACCGA ACGTGT CT (SEQ ID NO: 67) | GCCCTAT TGCAAG CCCTCTT (SEQ ID NO: 68) | CTGCAG GGTACA AcACg (SEQ ID NO: 208) | CTGCA GGGTA CAAgA Ca (SEQ ID NO: 251) | CATAA CTGGT GGAGT ATTTC ACT (SEQ ID NO: 294) | CGTAT ATGGC CGACT GGAG G (SEQ ID NO: 337) | GCCCT CATCT TCTTC CCTGC (SEQ ID NO: 33) |
| chr19 | TTCCTCCACC GAACGTGTCT CGTATCTGGG AAGACGGc (SEQ ID NO: 80) | GCCCTATTGCA AGCCCTCTTCGT ATCTGGAAGAt GGg (SEQ ID NO: 123) | CTTCAAGGAA GAAATTCAAC AGGGTAGGGT TTGCGGCGAT AAGGGCCCTC ATCTTCTTCCC TGC (SEQ ID NO: 166) | TTCCTC CACCGA ACGTGT CT (SEQ ID NO: 67) | GCCCTAT TGCAAG CCCTCTT (SEQ ID NO: 68) | CGTATC TGGGAA GAcGGc (SEQ ID NO: 209) | CGTAT CTGGG AAGAtG Gg (SEQ ID NO: 252) | CTTCA AGGA AGAA ATTCA ACAG GG (SEQ ID NO: 295) | TAGGG TTTGC GGCG ATAAG G (SEQ ID NO: 338) | GCCCT CATCT TCTTC CCTGC (SEQ ID NO: 33) |

TABLE 5-continued

Exemplary probes and primers.

| Chromosome | Labeling Probe-Allele 1 (Forward Primer Allele 1 + Hom 5p Allele 1) | Labeling Probe-Allele 2 (Forward Primer Allele 2 + Hom 5p Allele 2) | Tagging Probe (Hom 3p + Tag + Reverse Primer) | Forward Primer-Allele 1 | Forward Primer-Allele 2 | Hom 5p-Allele 1 | Hom 5p-Allele 2 | Hom 3p | Tag | Reverse Primer |
|---|---|---|---|---|---|---|---|---|---|---|
| chr9 | TTCCTCCACC GAACGTGTCT CCTGTAATCC CTTGCAATgc (SEQ ID NO: 81) | GCCCTATTGCA AGCCCTCTTCCT GTAATCCCTTG AATaa (SEQ ID NO: 124) | CATGGATTCA ACACAGCAAA CACCAAGTCA ACCACCCGAG ACGCCCTCAT CTTCTTCCCTG C (SEQ ID NO: 167) | TTCCTC CACCGA ACGTGT CT (SEQ ID NO: 67) | GCCCTAT GCAAG CCCTCTT (SEQ ID NO: 68) | CCTGTA ATCCCT TGCAAT gc (SEQ ID NO: 210) | CCTGT AATCC CTTGC AATaa (SEQ ID NO: 253) | CATGG ATTCA ACACA GCAA ACA (SEQ ID NO: 296) | CCAAG TCAAC CACCC GAGA C (SEQ ID NO: 339) | GCCCT CATCT TCTTC CCTGC (SEQ ID NO: 33) |
| chr16 | TTCCTCCACC GAACGTGTCT GGTCTCAGCA CGGTcTg (SEQ ID NO: 82) | GCCCTATTGCA AGCCCTCTTGGT CTCAGCACGGTc CTt (SEQ ID NO: 125) | CTCTGACCTC CTTCACTCTTA CACTTCCCTG GCCTTCCTTCT TCTTCCCTGC (SEQ ID NO: 168) | TTCCTC CACCGA ACGTGT CT (SEQ ID NO: 67) | GCCCTAT GCAAG CCCTCTT (SEQ ID NO: 68) | GGTCTC AGCACG GTtCTg (SEQ ID NO: 211) | GGTCT CAGCA CGGTcC Tt (SEQ ID NO: 254) | CTCTG ACCTC CTTCA CTCTT AC (SEQ ID NO: 297) | ACTTC CCTGG CCTTC CTTCT (SEQ ID NO: 340) | GCCCT CATCT TCTTC CCTGC (SEQ ID NO: 33) |
| chr9 | TTCCTCCACC GAACGTGTCT GCACTCCCT AcCACAc (SEQ ID NO: 83) | GCCCTATTGCA AGCCCTCTTGC ACCTCCCTAtCA Cat (SEQ ID NO: 126) | GCTTTCATTTG TGCTAAACCT CGCTTGGGTC CTCTCCTGAA CGCCTCCATC TTCTTCCCTGC (SEQ ID NO: 169) | TTCCTC CACCGA ACGTGT CT (SEQ ID NO: 67) | GCCCTAT GCAAG CCCTCTT (SEQ ID NO: 68) | GCACCT CCCTAc CACAc (SEQ ID NO: 212) | GCACC TCCCT AtCACA t (SEQ ID NO: 255) | GCTTT CATTT GTGCT AAACC TC (SEQ ID NO: 298) | GCTTG GGTCC TCTCC TGAAC (SEQ ID NO: 341) | GCCCT CATCT TCTTC CCTGC (SEQ ID NO: 33) |
| chr3 | TTCCTCCACC GAACGTGTCT GCCTCTAGCT TCTAGCTAGAG AGAAGcg (SEQ ID NO: 84) | GCCCTATTGCA AGCCCTCTTGCC TCTAGCTAGAG AGAAGcg (SEQ ID NO: 127) | CATCCCAGAT GCCCTCATAA CGTCCGAACC ACAATGCTGC CCTCACTTCT TCCCTGC (SEQ ID NO: 170) | TTCCTC CACCGA ACGTGT CT (SEQ ID NO: 67) | GCCCTAT GCAAG CCCTCTT (SEQ ID NO: 68) | GCCTCT AGCTAG AGAGAA Gtc (SEQ ID NO: 213) | GCCTC TAGCT AGAGA GAAGcg (SEQ ID NO: 256) | CATCC CAGAT GCCCT CAT (SEQ ID NO: 299) | AACGT CCGAA CCACA ATGCT (SEQ ID NO: 342) | GCCCT CATCT TCTTC CCTGC (SEQ ID NO: 33) |
| chr20 | TTCCTCCACC GAACGTGTCT CTGGCAGTCT AGCCgTTAc (SEQ ID NO: 85) | GCCCTATTGCA AGCCCTCTTCTG GCAGTCTAGCCa TTAt (SEQ ID NO: 128) | GTAGAAATCC CAAGGCAATC AGCTCCTCGC ATCCCAACAGT CGGCCCTTCAT CTTCTTCCCTG C (SEQ ID NO: 171) | TTCCTC CACCGA ACGTGT CT (SEQ ID NO: 67) | GCCCTAT GCAAG CCCTCTT (SEQ ID NO: 68) | CTGGCA GTCTAG CCgTTAc (SEQ ID NO: 214) | CTGGC AGTCT AGCCaT TAt (SEQ ID NO: 257) | GTAGA AATCC CAAG GCAAT CAG (SEQ ID NO: 300) | CTCTC CGCAT CCAAC AGTCG (SEQ ID NO: 343) | GCCCT CATCT TCTTC CCTGC (SEQ ID NO: 33) |

TABLE 5-continued

Exemplary probes and primers.

| Chromo-some | Labeling Probe-Allele 1 (Forward Primer Allele 1 + Hom 5p Allele 1) | Labeling Probe-Allele 2 (Forward Primer Allele 2 + Hom 5p Allele 2) | Tagging Probe (Hom 3p + Tag + Reverse Primer) | Forward Primer-Allele 1 | Forward Primer-Allele 2 | Hom 5p-Allele 1 | Hom 5p-Allele 2 | Hom 3p | Tag | Reverse Primer |
|---|---|---|---|---|---|---|---|---|---|---|
| chrX | TTCCTCCACC GAACGTGTCT TGTCTTAGAA TTTGGCAACTg Gc (SEQ ID NO: 86) | GCCCTATTGCA AGCCCTCTTTGT CTTAGAATTTG GCAACTaGt (SEQ ID NO: 129) | GAACAACTAA CTCCACAGAA CCCCACCGT AGCACTCCTT CTTGCCCTCA TCTTCTTCCCT GC (SEQ ID NO: 172) | TTCCTC CACCGA ACGTGT CT (SEQ ID NO: 67) | GCCCTAT TGCAAG CCCTCTT (SEQ ID NO: 68) | TGTCTT AGAATT TGGCAA CTgGc (SEQ ID NO: 215) | TGTCTT AGAAT TTGGC AACTaG t (SEQ ID NO: 258) | GAAC AACTA ACTCC ACAG AACCC (SEQ ID NO: 301) | CCACC GTAGC ACTCC TTCTT (SEQ ID NO: 344) | GCCCT CATCT TCTTC CCTGC (SEQ ID NO: 33) |
| chr7 | TTCCTCCACC GAACGTGTCT GCAGGAAAGC CTACTGAAc (SEQ ID NO: 87) | GCCCTATTGCA AGCCCTCTGC AGGAAAGCCTAt TGAAt (SEQ ID NO: 130) | GTGCAGAGGA CAGGAAGAAC GGGAGCGTCGG TAGTGTAAAG CCCTCATCTTC TTCCCTGC (SEQ ID NO: 173) | TTCCTC CACCGA ACGTGT CT (SEQ ID NO: 67) | GCCCTAT TGCAAG CCCTCTT (SEQ ID NO: 68) | GCAGGA AAGCCT AcTGAA c (SEQ ID NO: 216) | GCAGG AAAGC CTAtTG AAt (SEQ ID NO: 259) | GTGCA GAGG ACAG GAAG AA (SEQ ID NO: 302) | CGGA GCGTC GGTAG TGTAA A (SEQ ID NO: 345) | GCCCT CATCT TCTTC CCTGC (SEQ ID NO: 33) |
| chr3 | TTCCTCCACC GAACGTGTCT GGGAGCCAGA GAAATgTCc (SEQ ID NO: 88) | GCCCTATTGCA AGCCCTCTGG GAGCCAGAGAA AttTct (SEQ ID NO: 131) | GGTGCTTCAA GACATACACC TTAACAACTC GACGAACCTA CCGGCCCCTCA TCTTCTTCCCT GC (SEQ ID NO: 174) | TTCCTC CACCGA ACGTGT CT (SEQ ID NO: 67) | GCCCTAT TGCAAG CCCTCTT (SEQ ID NO: 68) | GGGAGC CAGAGA AATgTCc (SEQ ID NO: 217) | GGGAG CCAGA GAAAtt Tct (SEQ ID NO: 260) | GGTGC TTCAA GACAT ACACC TTA (SEQ ID NO: 303) | ACAAC TCGAC GAACC TACCG (SEQ ID NO: 346) | GCCCT CATCT TCTTC CCTGC (SEQ ID NO: 33) |
| chr2 | TTCCTCCACC GAACGTGTCT TCCACTTCATt TAg (SEQ ID NO: 89) | GCCCTATTGCA AGCCCTCTTTGT CTCCAGTTCCAC TTCATgTAa (SEQ ID NO: 132) | GGAACCTCTG TGACCTTGGA TGGCCCATCC TTATGTGCTG GCCCTCATCT TCTTCCCTGC (SEQ ID NO: 175) | TTCCTC CACCGA ACGTGT CT (SEQ ID NO: 67) | GCCCTAT TGCAAG CCCTCTT (SEQ ID NO: 68) | TGTCTC CAGTTC CACTTC AttTAg (SEQ ID NO: 218) | TGTCTC CAGTT CCACT TCATgT Aa (SEQ ID NO: 261) | GGAA CCTCT GTGAC CTTGG A (SEQ ID NO: 304) | TGGCC CATCC TTATG TGCTG (SEQ ID NO: 347) | GCCCT CATCT TCTTC CCTGC (SEQ ID NO: 33) |
| chr15 | TTCCTCCACC GAACGTGTCT CCCGTTAATT GCCTAcTcg (SEQ ID NO: 90) | GCCCTATTGCA AGCCCTCTCCC GTTAATTGCCTA tTta (SEQ ID NO: 133) | CCCAGTGGTA CCTTCTGAAG GTCGTTATTG CTCAAGCCCG CCCTCATCTTC TTCCCTGC (SEQ ID NO: 176) | TTCCTC CACCGA ACGTGT CT (SEQ ID NO: 67) | GCCCTAT TGCAAG CCCTCTT (SEQ ID NO: 68) | CCCGTT AATTGC CTAcTcg (SEQ ID NO: 219) | CCCGT TAATT GCCTAt Tta (SEQ ID NO: 262) | CCCAG TGGTA CCTTC TGAA (SEQ ID NO: 305) | GGTCG TTATT GCTCA AGCCC (SEQ ID NO: 348) | GCCCT CATCT TCTTC CCTGC (SEQ ID NO: 33) |

TABLE 5-continued

Exemplary probes and primers.

| Chromo-some | Labeling Probe-Allele 1 (Forward Primer Allele 1 + Hom 5p Allele 1) | Labeling Probe-Allele 2 (Forward Primer Allele 2 + Hom 5p Allele 2) | Tagging Probe (Hom 3p + Tag + Reverse Primer) | Forward Primer-Allele 1 | Forward Primer-Allele 2 | Hom 5p-Allele 1 | Hom 5p-Allele 2 | Hom 3p | Tag | Reverse Primer |
|---|---|---|---|---|---|---|---|---|---|---|
| chr15 | TTCCTCCACC GAACGTGTCT CTCGGTCCCA CTGGaAAg (SEQ ID NO: 91) | GCCCTATTGCA AGCCCTCTTCTC GGTCCACTGGG AAa (SEQ ID NO: 134) | CTTCTGTTGCT TATTTGGGTA ACTTGATTCT GGCCCTCCCA TCGCCCTCAT CTTCTTCCCTG C (SEQ ID NO: 177) | TTCCTC CACCGA ACGTGT CT (SEQ ID NO: 67) | GCCCTAT TGCAAG CCCTCTT (SEQ ID NO: 68) | CTCGGT CCCACT GGaAAg (SEQ ID NO: 220) | CTCGG TCCCA CTGGg AAa (SEQ ID NO: 263) | CTTCT GTTGC TTATT TGGGT AAC (SEQ ID NO: 306) | TTGAT TCTGG CCCTC CCATC (SEQ ID NO: 349) | GCCCT CATCT TCTTC CCTGC (SEQ ID NO: 33) |
| chr2 | TTCCTCCACC GAACGTGTCT ACACCCATGA TTCAGTTACtg (SEQ ID NO: 92) | GCCCTATTGCA AGCCCTCTTAC ACCCATGATTC AGTTACca (SEQ ID NO: 135) | CCCACTGGAT GCTCCCTCCA CGCCGGCTAT TTAGGTGCCC TCATCTTCTTC CCTGC (SEQ ID NO: 178) | TTCCTC CACCGA ACGTGT CT (SEQ ID NO: 67) | GCCCTAT TGCAAG CCCTCTT (SEQ ID NO: 68) | ACACCC ATGATT CAGTTA Ctg (SEQ ID NO: 221) | ACACC CATGA TTCAG TTACca (SEQ ID NO: 264) | CCCAC TGGAT GCCGG CCCTC C (SEQ ID NO: 307) | CTCAC GCCGG CTATT TAGGT (SEQ ID NO: 350) | GCCCT CATCT TCTTC CCTGC (SEQ ID NO: 33) |
| chr9 | TTCCTCCACC GAACGTGTCT GCTAGTATGA ACATCACAgGc (SEQ ID NO: 93) | GCCCTATTGCA AGCCCTCTTAC AGTATGAACAT CACAAgt (SEQ ID NO: 136) | CGGAGAGACG CATCGAAAGG TCTGGGTAGG TGGAGGACGC CCTCATCTTCT CCCTGC (SEQ ID NO: 179) | TTCCTC CACCGA ACGTGT CT (SEQ ID NO: 67) | GCCCTAT TGCAAG CCCTCTT (SEQ ID NO: 68) | GCTAGT ATGAAC ATCACA gGc (SEQ ID NO: 222) | GCTAG TATGA ACATC ACAagt (SEQ ID NO: 265) | CGGA GAGA CGCAT CTGAA (SEQ ID NO: 308) | AGTCT GGGTA GGTGG AGGA C (SEQ ID NO: 351) | GCCCT CATCT TCTTC CCTGC (SEQ ID NO: 33) |
| chr7 | TTCCTCCACC GAACGTGTCT ACAAATGAGT AAGAAGCGAG Tcg (SEQ ID NO: 94) | GCCCTATTGCA AGCCCTCTTAC AAATGAGTAAG AAGCGAGTta (SEQ ID NO: 137) | CAGGATTTCC AGCTTACAGG GCCATGAGC CACATCCAAC TGCCCTCATC TTCTTCCCTGC (SEQ ID NO: 180) | TTCCTC CACCGA ACGTGT CT (SEQ ID NO: 67) | GCCCTAT TGCAAG CCCTCTT (SEQ ID NO: 68) | ACAAAT GAGTAA GAAGCG AGTcg (SEQ ID NO: 223) | ACAAA TGAGT AAGAA GCGAG Tta (SEQ ID NO: 266) | CAGG ATTTC CAGCT TACAG GG (SEQ ID NO: 309) | CGACT GAGCC ACATC CAACT (SEQ ID NO: 352) | GCCCT CATCT TCTTC CCTGC (SEQ ID NO: 33) |
| chr20 | TTCCTCCACC GAACGTGTCT GATAAGGGTT GCTCgCg (SEQ ID NO: 95) | GCCCTATTGCA AGCCCTCTTGAT AAGGGTTGCTC TaCa (SEQ ID NO: 138) | CTTGCAAGAT GTGCCTCTTA GAGCCTCAGC CGGAATTGAA GCCCTCATCT TCTTCCCTGC (SEQ ID NO: 181) | TTCCTC CACCGA ACGTGT CT (SEQ ID NO: 67) | GCCCTAT TGCAAG CCCTCTT (SEQ ID NO: 68) | GATAAG GGTTGC TCTgCg (SEQ ID NO: 224) | GATAA GGGTT GCTCTa Ca (SEQ ID NO: 267) | CTTGC AAGAT GTGCC TCTTA (SEQ ID NO: 310) | GAGCC TCAGC CGGA ATTGA A (SEQ ID NO: 353) | GCCCT CATCT TCTTC CCTGC (SEQ ID NO: 33) |

TABLE 5-continued

Exemplary probes and primers.

| Chromo-some | Labeling Probe-Allele 1 (Forward Primer Allele 1 + Hom 5p Allele 1) | Labeling Probe-Allele 2 (Forward Primer Allele 2 + Hom 5p Allele 2) | Tagging Probe (Hom 3p + Tag + Reverse Primer) | Forward Primer-Allele 1 | Forward Primer-Allele 2 | Hom 5p-Allele 1 | Hom 5p-Allele 2 | Hom 3p | Tag | Reverse Primer |
|---|---|---|---|---|---|---|---|---|---|---|
| chr20 | TTCCTCCACC GAACGTGTCT CCATGCACCA GCTACcc (SEQ ID NO: 96) | GCCCTATTGCA AGCCCTCTTCCA TGCACCAGCTA Cta (SEQ ID NO: 139) | GGGTGGTTTC TCTAAACACA AATTGCCATT CTGCACCAAT GCGCCCTCAT CTTCTTCCCTG C (SEQ ID NO: 182) | TTCCTC CACCGA ACGTGT CT (SEQ ID NO: 67) | GCCCTAT TGCAAG CCCTCTT (SEQ ID NO: 68) | CCATGC ACCAGC TACcc (SEQ ID NO: 225) | CCATG CACCA GCTAct a (SEQ ID NO: 268) | GGGTG GTTTC TCTAA ACACA AA (SEQ ID NO: 311) | TTGCC ATTCT GCACC AATGC (SEQ ID NO: 354) | GCCCT CATCT TCTTC CCTGC (SEQ ID NO: 33) |
| chr1 | TTCCTCCACC GAACGTGTCT AACTGTACCC TACTCCCagc (SEQ ID NO: 97) | GCCCTATTGCA AGCCCTCTTAG CTGTACCCTACT CCCAat (SEQ ID NO: 140) | GCAGGGTATT GAGAGAAGG ATCTATTGGT GTTCGCGGCT GATGCCCTCA TCTTCTTCCCT GC (SEQ ID NO: 183) | TTCCTC CACCGA ACGTGT CT (SEQ ID NO: 67) | GCCCTAT TGCAAG CCCTCTT (SEQ ID NO: 68) | AACTGT ACCCTA CTCCCA gc (SEQ ID NO: 226) | AACTG TACCC TACTC CCAat (SEQ ID NO: 269) | GCAG GGTAT TGAGA GAAG (SEQ ID NO: 312) | TATTG GTGTT CGCGG AGGA (SEQ ID NO: 355) | GCCCT CATCT TCTTC CCTGC (SEQ ID NO: 33) |
| chr2 | TTCCTCCACC GAACGTGTCT AGGACCAAGG GACCAGTTAg (SEQ ID NO: 98) | GCCCTATTGCA AGCCCTCTTAG GACCAAGGAC CAGTTcAc (SEQ ID NO: 141) | GTGCACATTT CTTGATGAAG GGATGGGCGT AACAGGAGGA CTGCCCTCAT CTTCTTCCCTG C (SEQ ID NO: 184) | TTCCTC CACCGA ACGTGT CT (SEQ ID NO: 67) | GCCCTAT TGCAAG CCCTCTT (SEQ ID NO: 68) | AGGACC AAGGGA CCAGTTt Ag (SEQ ID NO: 227) | AGGAC CAAGG GACCA GTTcAc (SEQ ID NO: 270) | GTGCA CATTT CTTGA TGAAG GG (SEQ ID NO: 313) | ATGGG CGTAA CAGG AGGA CT (SEQ ID NO: 356) | GCCCT CATCT TCTTC CCTGC (SEQ ID NO: 33) |
| chr7 | TTCCTCCACC GAACGTGTCT CAGAGTTCCTC CAAGAAATTG cg (SEQ ID NO: 99) | GCCCTATTGCA AGCCCTCTTAG AGTTCCTCCAA GAAATTGta (SEQ ID NO: 142) | GAGCAATGCC TGTTTCATGA GAGGAATGGC CTACCTGCAT CAGCCCTCAT CTTCTTCCCTG C (SEQ ID NO: 185) | TTCCTC CACCGA ACGTGT CT (SEQ ID NO: 67) | GCCCTAT TGCAAG CCCTCTT (SEQ ID NO: 68) | AGAGTT CCTCCA AGAAAT TGcg (SEQ ID NO: 228) | AGAGT TCCTCC AAGAA ATTGta (SEQ ID NO: 271) | GAGC AATGC CTGTT TCATG AGA (SEQ ID NO: 314) | GGAAT GGCCT ACCTG CATCA (SEQ ID NO: 357) | GCCCT CATCT TCTTC CCTGC (SEQ ID NO: 33) |
| chr5 | TTCCTCCACC GAACGTGTCT ACATTATACA GCATGCTGGc TAtc (SEQ ID NO: 100) | GCCCTATTGCA AGCCCTCTTAC ATTATACAGCA TGCTGGtTAga (SEQ ID NO: 143) | GTTAACATTA TACAGCATGG TGGCCCGTT GTTGTCATCG CATCGCCCTC ATCTTCTTCCC TGC (SEQ ID NO: 186) | TTCCTC CACCGA ACGTGT CT (SEQ ID NO: 67) | GCCCTAT TGCAAG CCCTCTT (SEQ ID NO: 68) | ACATTA TACAGC ATGCTG GcTAtc (SEQ ID NO: 229) | ACATT ATACA GCATG CTGGtT Aga (SEQ ID NO: 272) | GTTAA CATTA TACAG CATGG TGGC (SEQ ID NO: 315) | CCCGT TGTTG TCATC GCATC (SEQ ID NO: 358) | GCCCT CATCT TCTTC CCTGC (SEQ ID NO: 33) |

TABLE 5-continued

Exemplary probes and primers.

| Chromo-some | Labeling Probe-Allele 1 (Forward Primer Allele 1 + Hom 5p Allele 1) | Labeling Probe-Allele 2 (Forward Primer Allele 2 + Hom 5p Allele 2) | Tagging Probe (Hom 3p + Tag + Reverse Primer) | Forward Primer-Allele 1 | Forward Primer-Allele 2 | Hom 5p-Allele 1 | Hom 5p-Allele 2 | Hom 3p | Tag | Reverse Primer |
|---|---|---|---|---|---|---|---|---|---|---|
| chr2 | TTCCTCCACC GAACGTGTCT GAGGAGAA AGTGAGgTTT Gc (SEQ ID NO: 101) | GCCCTATTGCA AGCCCTCTTGA GGAAGAAAGTG AGaTTTGt (SEQ ID NO: 144) | GCAGAACATG TCCTGAAGCG TTCGAGTGCT CCCATGAGTG CCCTCATCTTC TTCCCTGC (SEQ ID NO: 187) | TTCCTC CACCGA ACGTGT CT (SEQ ID NO: 67) | GCCCTAT TGCAAG CCCTCTT (SEQ ID NO: 68) | GAGGAA GAAAGT GAGGTT TGc (SEQ ID NO: 230) | GAGGA AGAAA GTGAG aTTTGt (SEQ ID NO: 273) | GCAG AACAT GTCCT GAAG C (SEQ ID NO: 316) | GTTCG ATGCG TCCCA TGAGT (SEQ ID NO: 359) | GCCCT CATCT TCTTC CCTGC (SEQ ID NO: 33) |
| chr15 | TTCCTCCACC GAACGTGTCT CTGAATTATG TGCTTACCAg AGc (SEQ ID NO: 102) | GCCCTATTGCA AGCCCTCTTG AATTATGTGCTT ACCAgGAGt (SEQ ID NO: 145) | CAGCTTGTTC CCAAACCCAT CAACCCGCGT AGATGTTCCT GCCCTCATCT TCTTCCCTGC (SEQ ID NO: 188) | TTCCTC CACCGA ACGTGT CT (SEQ ID NO: 67) | GCCCTAT TGCAAG CCCTCTT (SEQ ID NO: 68) | CTGAAT TATGTG CTTACC AaGAGc (SEQ ID NO: 231) | CTGAA TTATGT GCTTA CCAgG Agt (SEQ ID NO: 274) | CAGCT TGTTC CCAAA CCCAT (SEQ ID NO: 317) | CAACC CGCGT AGATG TTCCT (SEQ ID NO: 360) | GCCCT CATCT TCTTC CCTGC (SEQ ID NO: 33) |
| chr9 | TTCCTCCACC GAACGTGTCT TGGGTTCTGA TAACCTTATC AAgc (SEQ ID NO: 103) | GCCCTATTGCA AGCCCTCTTGG GTTCTGATAAC CTTATCAAct (SEQ ID NO: 146) | CAAAGTGTGG AAGTTGCTTC CGCCAGCTCA AGAGTGTAGC CGCCCTCATC TTCTTCCCTGC (SEQ ID NO: 189) | TTCCTC CACCGA ACGTGT CT (SEQ ID NO: 67) | GCCCTAT TGCAAG CCCTCTT (SEQ ID NO: 68) | TGGGTT CTGATA ACCTTA TCAAgc (SEQ ID NO: 232) | TGGGT TCTGA TAACC TTATC AAct (SEQ ID NO: 275) | CAAA GTGTG AAGTT GCTT CC (SEQ ID NO: 318) | GCCAG CTCAA GAGTG TAGCC (SEQ ID NO: 361) | GCCCT CATCT TCTTC CCTGC (SEQ ID NO: 33) |
| chr2 | TTCCTCCACC GAACGTGTCT GGTTAGTCAA ACATGcTGc (SEQ ID NO: 104) | GCCCTATTGCA AGCCCTCTTGGT TAGTCAAACAT GtTGt (SEQ ID NO: 147) | GGTCGACTTT GTCCATCCTT CTTGATCCTG CGCGATGTGC CCTTCATCTTCT TCCCTGC (SEQ ID NO: 190) | TTCCTC CACCGA ACGTGT CT (SEQ ID NO: 67) | GCCCTAT TGCAAG CCCTCTT (SEQ ID NO: 68) | GGTTAG TCAAAC ATGcTGc (SEQ ID NO: 233) | GGTTA GTCAA ACATGt TGt (SEQ ID NO: 276) | GGTCG ACTTT GTCCA TCC (SEQ ID NO: 319) | TTCTT GATCC TGCGC GATGT (SEQ ID NO: 362) | GCCCT CATCT TCTTC CCTGC (SEQ ID NO: 33) |
| chr17 | TTCCTCCACC GAACGTGTCT GAACTGGCA GAATCAAAtc Ac (SEQ ID NO: 105) | GCCCTATTGCA AGCCCTCTTGA CACTGGCAGAA TCAAAcCAa (SEQ ID NO: 148) | CTCTGTTGCCT GTGGACTCAT CGCAGGCGTT CCCTATACGC CCTCATCTTCT TCCCTGC (SEQ ID NO: 191) | TTCCTC CACCGA ACGTGT CT (SEQ ID NO: 67) | GCCCTAT TGCAAG CCCTCTT (SEQ ID NO: 68) | GACACT GGCAGA ATCAAA tCAc (SEQ ID NO: 234) | GACAC TGGCA GAATC AAAcC Aa (SEQ ID NO: 277) | CTCTG TTGCC TGTGG ACTC (SEQ ID NO: 320) | ATCGC AGGC GTTCC CTATA C (SEQ ID NO: 363) | GCCCT CATCT TCTTC CCTGC (SEQ ID NO: 33) |

TABLE 5-continued

Exemplary probes and primers.

| Chromo-some | Labeling Probe-Allele 1 (Forward Primer Allele 1 + Hom 5p Allele 1) | Labeling Probe-Allele 2 (Forward Primer Allele 2 + Hom 5p Allele 2) | Tagging Probe (Hom 3p + Tag + Reverse Primer) | Forward Primer-Allele 1 | Forward Primer-Allele 2 | Hom 5p-Allele 1 | Hom 5p-Allele 2 | Hom 3p | Tag | Reverse Primer |
|---|---|---|---|---|---|---|---|---|---|---|
| chr6 | TTCCTCCACC GAACGTGTCT AGAGTTACAC CTTTAGCTAA CCAc (SEQ ID NO: 106) | GCCCTATTGCA AGCCCTCTTAG AGTTACACCTTT AGCTAActAg (SEQ ID NO: 149) | CTAACTAGAA TTAGTCTGCC TGCCTATTGG ACCTCCGACC ACGAGCCCTC ATCTTCTTCCC TGC (SEQ ID NO: 192) | TTCCTC CACCGA ACGTGT CT (SEQ ID NO: 67) | GCCCTAT TGCAAG CCCTCTT (SEQ ID NO: 68) | AGAGTT ACACCT TTAGCT AACCAc (SEQ ID NO: 235) | AGAGT TACAC CTTTA GCTAA CtAg (SEQ ID NO: 278) | CTAAC TAGAA TTAGT CTGCC TGCC (SEQ ID NO: 321) | TATTG GACCT CCGAC CACGA (SEQ ID NO: 364) | GCCCT CATCT TCTTC CCTGC (SEQ ID NO: 33) |
| chr7 | TTCCTCCACC GAACGTGTCT CCAGGAGTTC AAGaAGCg (SEQ ID NO: 107) | GCCCTATTGCA AGCCCTCTTCCA GGAGTTCAAGg AGCa (SEQ ID NO: 150) | GTGAGCCATA ATCGTGTCAA GCCACCATTT AGATCCGCCG CCCTCATCTTC TCCCTGC (SEQ ID NO: 193) | TTCCTC CACCGA ACGTGT CT (SEQ ID NO: 67) | GCCCTAT TGCAAG CCCTCTT (SEQ ID NO: 68) | CCAGGA GTTCAA GaAGCg (SEQ ID NO: 236) | CCAGG AGTTC AAGgA GCa (SEQ ID NO: 279) | GTGAG CCATA ATCGT GTCA (SEQ ID NO: 322) | AGCCA CCATT TAGAT CCGCG (SEQ ID NO: 365) | GCCCT CATCT TCTTC CCTGC (SEQ ID NO: 33) |
| chr4 | TTCCTCCACC GAACGTGTCT ACCACTCCTT TCCCaTCTc (SEQ ID NO: 108) | GCCCTATTGCA AGCCCTCTTACC ACTCCTTTCTCC CgTCTt (SEQ ID NO: 151) | GAGAATTAAT GCTCCTTTGC CTGGACCAGT AGAAGTCTGC CCGGCCCTCA TCTTCTTCCCT GC (SEQ ID NO: 194) | TTCCTC CACCGA ACGTGT CT (SEQ ID NO: 67) | GCCCTAT TGCAAG CCCTCTT (SEQ ID NO: 68) | ACCACT CCTTTC TCCCaTC Tc (SEQ ID NO: 237) | ACCAC TCCTTT CTCCCg TCTt (SEQ ID NO: 280) | GAGA ATTAA TGCTC CCTCT CCTG (SEQ ID NO: 323) | GACCA GTAGA AGTCT GCCCG (SEQ ID NO: 366) | GCCCT CATCT TCTTC CCTGC (SEQ ID NO: 33) |
| chr2 | TTCCTCCACC GAACGTGTCT GTCTTATGGG ACAATGGTtG ATAg (SEQ ID NO: 109) | GCCCTATTGCA AGCCCTCTTGTC TATGGGACAA TGGTcGATAt (SEQ ID NO: 152) | GTGGTCTGCT GTTGACCAAT TTCAGAATGG CCGAGCTGTG CCCTCATCTTC TTCCCTGC (SEQ ID NO: 195) | TTCCTC CACCGA ACGTGT CT (SEQ ID NO: 67) | GCCCTAT TGCAAG CCCTCTT (SEQ ID NO: 68) | GTCTTA TGGGAC AATGGT tGATAg (SEQ ID NO: 238) | GTCTT ATGGG ACAAT GGTcG ATAt (SEQ ID NO: 281) | GTGGT CTGCT GTTGA CCAA (SEQ ID NO: 324) | TTTCA GAATG GCTGA GCTGT (SEQ ID NO: 367) | GCCCT CATCT TCTTC CCTGC (SEQ ID NO: 33) |

TABLE 5-continued

Exemplary probes and primers.

| Chromosome | Labeling Probe-Allele 1 (Forward Primer Allele 1 + Hom 5p Allele 1) | Labeling Probe-Allele 2 (Forward Primer Allele 2 + Hom 5p Allele 2) | Tagging Probe (Hom 3p + Tag + Reverse Primer) | Forward Primer-Allele 1 | Forward Primer-Allele 2 | Hom 5p-Allele 1 | Hom 5p-Allele 2 | Hom 3p | Tag | Reverse Primer |
|---|---|---|---|---|---|---|---|---|---|---|
| chr17 | TTCCTCCACC GAACGTGTCT CTACCCTCAA CCCTCGTc (SEQ ID NO: 110) | GCCCTATTGCA AGCCCTCTTCTA CCCTCAACCTC aTt (SEQ ID NO: 153) | GGTTGCAACT GCTGATCTAT AGGTGACCTT CTTGTACGCC GCCCTCATCT TCTTCCCTGC (SEQ ID NO: 196) | TTCCTC CACCGA ACGTGT CT (SEQ ID NO: 67) | GCCCTAT TGCAAG CCCTCTT (SEQ ID NO: 68) | CTACCC TCAACC CTCgTc (SEQ ID NO: 239) | CTACC CTCAA CCCTCa Tt (SEQ ID NO: 282) | GGTTG CAACT GCTGA TCTAT (SEQ ID NO: 325) | AGGTG ACCTT CTTGT ACGCC (SEQ ID NO: 368) | GCCCT CATCT TCTTC CCTGC (SEQ ID NO: 33) |
| chr7 | TTCCTCCACC GAACGTGTCT CCAAGACTGA TCATGCcg (SEQ ID NO: 111) | GCCCTATTGCA AGCCCTCTTCCA AGACTGATCAT GCta (SEQ ID NO: 154) | CTTTCCCAGT CAAGGCAGGG CGCGTCCTTA TTTCCATCGC CCTCATCTTCT TCCCTGC (SEQ ID NO: 197) | TTCCTC CACCGA ACGTGT CT (SEQ ID NO: 67) | GCCCTAT TGCAAG CCCTCTT (SEQ ID NO: 68) | CCAAGA CTGATC ATGCcg (SEQ ID NO: 240) | CCAAG ACTGA TCATG Cta (SEQ ID NO: 283) | CTTTC CCAGT CAAG GCAG (SEQ ID NO: 326) | GGCGC GTCCT TATTT CCATC (SEQ ID NO: 369) | GCCCT CATCT TCTTC CCTGC (SEQ ID NO: 33) |

EXAMPLES

Example 1—Cleaning Substrates

The following procedures are preferably performed in a clean room. The surface of a pure white glass plate/slide (Knittel Glazer, Germany) (which may be polished for flatness) or spectrosil slides is thoroughly cleaned by, for example, sonication in a surfactant solution (2% Micro-90) for 25 minutes, washing in de-ionised water, rinsing thoroughly with milliQ water and immersing in 6:4:1 milliQ $H_2O$:30% $NH_4OH$:30% $H_2O_2$ or in a $H_2SO_4$/$CrO_3$ cleaning solution for 1.5 hr. After cleaning the plate is rinsed and stored in a dust free environment e.g. under milliQ water. The top layer of Mica Substrates are cleaved by covering with scotch tape and rapidly pulling off of the layer.

Example 2—Microscopy

1) TIRF

There are two configurations that can be used with TIRF, the objective method and the Prism method.

The objective method is supported by Olympus Microscopes and application notes are found at the following web site: olympusmicro.com/primer/techniques/fluorescence/tirf/olympusaptirf.html The Prism method below is described in Osborne et al J. Phys. Chem. B, 105 (15), 3120-3126, 2001.

The instrument consists of an inverted optical microscope (Nikon TE200, Japan), two color laser excitation sources, and an Intensified Charge Coupled Device (ICCD) camera (Pentamax, Princeton Instruments, NJ). A mode-locked frequency-doubled Nd:YAG laser (76 MHz Antares 76-s, Coherent) is split into two beams to provide up to 100 mW of 532-nm laser light and a pump dye laser (700 series, Coherent) with output powers in excess of 200 mW at 630 nm (DCM, Lambda Physik). The sample chamber is inverted over a ×100 oil immersion objective lens and a 60 fused silica dispersion prism optically coupled to the back of the slide through a thin film of glycerol. Laser light is focused with a 20-cm focal length lens at the prism such that at the glass/sample interface it subtends an angle of approximately 68° to the normal of the slide and undergoes total internal reflection (TIR). The critical angle for a glass/water interface is 66°. The footprint of the TIR has a 1/e2 diameter of about 300 m. Fluorescence produced by excitation of the sample with the surface-specific evanescent wave is collected by the objective, passed through a dichroic beam splitter (560DRLP, Omega Optics), and filtered before imaging onto the ICCD camera. Images were recorded by using synchronized 532 nm excitation with detection at 580 nm (580DF30, Omega) for TAMRA labeled substrates and 630 nm excitation with detection at 670 nm (670DF40, Omega) for Cy5 labeled probes. Exposure times are set between 250 and 500 ms with the ICCD gain at maximum (1 kV). The laser powers at the prism are adjusted to 40 mW at both laser wavelengths.

2) Confocal Microscopy with Pulsed Laser and Time Resolved Detection

This set up is available as the Lightstation from Atto_tec (Heidelberg).

3) AFM

Images can be obtained by using a Multimode Ma with a nanoscope IV controller and Si cantilever tips (Veeco, Santa Barbara, Calif.). This is placed on an active isolation system (MOD1-M, Halcyonics, Gottingen, Germany). Typical imaging parameters are 60-90 Hz resonant frequency, 0.5-1V oscillation amplitude, 0.3-0.7V setpoint voltage, 1.5-2 Hz scan rate.

4) SNOM

The BioLyser SNOM (Triple-O Potsdam, Germany) can be used for near field optical imaging.

The following CCD set ups can be used I-PentaMAX Gen III; Roper Scientific, Trenton, N.J. USA) or cooled (e.g. Model ST-71 (Santa Barbara Instruments Group, CA, USA); ISIT camera composed of a SIT camera (Hamamatsu), an image intensifier and (VS-1845, Video Scope International, USA) and stored on S-VHS videotape. Video taped images are processed with a digital image processor (Argus-30, Hamamatsu photonics). Gain setting are adjusted depending on camera and brightness of signal.

The movement form one field of view to another can be done by attaching the substrate on a High Precision TST series X-Y translation stage (Newport).

The following oxygen scavenging solution can be used to minimise photobleaching when single molecule analysis is done in solution: Catalase (0.2 mg/ml), Glucose oxidase (0.1 mg/ml), DTT (20 mM), BSA (0.5 mg/ml), Glucose 3 mg/ml. This can be added to the buffer solution that is being used in the experiment.

Example 3—General Scheme for Determining Optimal Spotting Concentration for Making Single Molecule Arrays Where the array is made by spotting, spots of oligonucleotides of different sequence or identity are placed at different spatial locations on a surface.

The first step in the procedure for making a single molecule microarray is to do a dilution series of fluorescent oligonucleotides. This has been done with 13 mers and 25 mers but any appropriate length of oligonucleotide can be chosen. These oligonucleotides may be aminated and preferably Cy3 labeled at the 5' end.

Although this is exemplified for oligonucleotides, this procedure is also appropriate to proteins and chemical spotting.

A 10 uM solution of the oligonucleotide is placed in a first well of the microtitre plate. For a 10 fold dilution, 1 ul is transferred into the next well of the microtitre plate and so on over several orders of magnitude. Twelve orders of magnitude were tested. A 1:1 volume of 2× spotting buffer that is being tested is added to each well. This gives 5 uM concentration in the first well, 500 nM in the second well and so on. The array is then spotted using a microarrayer (Amersham Generation III).

The Dilution series is then analyzed by TIRF microscopy, AFM or by another relevant microscopy system. The morphology of spot is looked at and the distribution of molecules within the spot determined. The spot range with the desired number of resolvable single molecules is chosen. Optionally, a further more focused dilution series is created around the dilution of interest. For example, two 50% dilutions in the range 500 nM to 50 nM can be done.

In a first experiment, a dilution series over 12 orders of magnitude was spotted with 4 buffers to establish the range of dilutions necessary. Subsequently, more focused dilutions series are used. It was found that between 250 nM to 67.5 nM gave resolvable single molecules within an identifiable spot. (If there are too few molecules then it is difficult to know exactly where the spot is but this will not be a problem when spot position and morphology is know to be regular and movement of translation stage or CCD is automated and is not manual). Some spots give a faint ring around the perimeter which can help identify spots.

To achieve a single molecule array, a dilution series of modified and unmodified oligonucleotides was tested a) in several different spotting buffers; b) on three different slide chemistries; c) on slides from several different manufacturers; d) using two different humidities and e) using several different post-spotting protocols. Due to the effects of photobleaching, the amount of pre-exposure to light also influences the number of single-dye labeled single molecules that can be counted.

Slides

It was found that the intrinsic fluorescence from slides from different suppliers varied. We found the slides most appropriate for our low fluorescence needs (determined by TIRF microscopy) to be the commercial slides from Asper Biotech (Tartu, Estonia) coated and cleaned on slides supplied by Knittel Glaser (Germany). These slides not only have a uniform surface coating of silanes but also have very low intrinsic fluorescence. Regular glass slides are float glass and contain some levels of intrinsic fluorescence but specialty pure white glass is more suitable. Spectrosil fused silica slides (TSL group, Tyne and Wear, UK) are also appropriate but are more expensive. Cover glass which is made of borosilicate glass is also of low fluorescence but some spotters cannot spot onto these.

Slide Chemistry

Three different slide chemistries, Epoxysilane, Aminosilane and enhanced aminosilane (3-Aminopropyltrimethoxysilane+1, 4-Phenylenediisothiocyanate) have been tested. Single molecule arrays can be obtained with all three chemistries.

Oligonucleotide Chemistry

Unmodified DNA olignucleotides and oligonucletides that were aminated at the 5' or 3' end were tested. There appears to be no significant difference in morphology or attachment whether the oligos are terminally modified or not. However, only the terminally modified oligos have been tested in hybridization or other assays. Several different sequences of varying lengths that probe TNF alpha promoter have been tested.

Buffers

In total 11 different buffers have been tested. From the study it has emerged that the best general buffer on the epoxysilane slides supplied by Asper Biotech is 50% DMSO and 50% Water. This buffer gives far superior spot morphology than any other buffer that was tested. Spotting humidity affects the morphology. Spotting was tested at 42-43% and 53-55% humidity with both conditions giving useable arrays. However, there is a slight doughnut effect at 43% humidity compared to the almost perfect homogeneity at 55% humidity. QMT2 (Quantifoil, Jena Germany) buffer also give reasonable spots on Asper's Epoxysilane slides.

After spotting the epoxysilane slide is, optionally, placed at 97 degrees C. for 15 minutes before storage at room temperature for 12-24 hours. This is followed by storage at 4 degrees C. overnight or, preferably, longer. The slides are washed before use. Two methods of washing work well. The first is washing 3× in milliQ water at room temperature. The second is washing on the Amersham Slide Processor (ASP). The following wash protocol was used:

| ASP WASH PROTOCOL | |
| --- | --- |
| HEAT | To 25 degrees |
| MIX | Wash 1, (1XSSC/0.2% SDS) 5 or 10 minutes |
| PRIME | Prime with wash 2(0.1XSSC/0.2% SDS) |
| FLUSH | Wash 2 |
| MIX | Wash 2 30 seconds or 1 minute |

| ASP WASH PROTOCOL -continued | |
| --- | --- |
| FLUSH | Wash 3 (Wash (0.1XSSC) |
| MIX | Wash 3 30 seconds or 1 minute |
| PRIME | Prime with was 4 (0.1XSSC) |
| FLUSH | Wash 4 (0.1XSSC) |
| Prime | Prime with Isopropanol |
| Flush | Flush with Isopropanol |
| Flush | Flush with air |
| Airpump | Dry Slide |
| Heat | Turn off Heat |

The best buffers on the enhanced aminosilane (3-Aminopropyltrimethoxysilane+1, 4-Phenylenediisothiocyanate) slides from Asper Biotech are 50% 1.5M Betaine/50% 3×SSC and 10% QMT1spotting buffer (Quantifoil, Jena). In addition, some of the other buffers from Quantifoil (Jena, Germany) performed reasonably well; different concentrations of these buffers may give better morphology. Detailed internal morphology seen with epi was not good. DMSO buffer (Amersham) gave intense "sunspots", i.e. a dot of intense fluorescence, within the spots; it is conceivable that single molecules can be counted in the rest of the spot, ignoring the sunspot. Spotting was tested at 43% and 55% humidity with both conditions giving useable arrays.

For the enhanced aminosilane slides, post-processing involves optional 2 hours at 37 degrees in a humid chamber. Under these conditions, more molecules stick but there is a possibility that spots can come out of line or merge. To avoid this, the spots are arrayed far enough apart to prevent merger. This is followed by overnight (or longer) at 4 degrees C. The slides are then dipped in 1% Ammonia solution for 2-3 minutes. The slides are then washed 3× in milliQ water and then put at 4 degrees C. overnight. There is some degree of bleeding of dye from the spots after hybridization. This may be addressed by more stringent or longer washing.

If the buffers in the microtitre wells dry out, they can be resuspended again in water. However, the betaine buffer did not perform well when this was done.

50% DMSO is the best buffer for aminoslinae slides. After spotting these slides are immediately crosslinked with 300 mJoules on a Stratagene Crosslinker. The arrays are washed in hot water with shaking twice for two minutes and are then dipped five times in 95% ethanol and immediately dried with forced air. Substantially more aminated oligonucleotides stick to the surface with this slide chemistry than with other slide chemistries, even when the slides are not fresh. Therefore less oligonucleotide needs to be spotted to get a particular surface density.

Spotting Pins

Capillary pins from Amersham Biotech optimized for Sodium Thiocyanate buffer or pins optimized for DMSO buffer were used in different spotting runs. Both types of pins enabled single molecule arrays to be constructed. Other preferred spotting methods are the Affymetrix ring and pin system and ink jet printing. Quills can also be used.

Example 4—Hybridization to Single Molecule Arrays

A simple array containing the biallelic probe set for two sequences of TNF alpha promoter were tested. The array probes were designed with the polymorpic base at the centre of a 13mer sequence. One of two oligonucleotides with Cy3 label at the 5'end (or TAMRA label), complementary to one of the two biallelic probes was hybridized to the single molecule array. The array contained a dilution series of the biallelic probe set. It was found that there was more signal from the perfect match than the mismatch. Spots down the dilution series were analyzed, and single molecule counting was done in the spots found to give even and resolvable distribution of single molecule signals. Resolution of molecules at higher dilutions is possible by optimising the set up and by software for deconvolution. BSA, carrier DNA, tRNA, NTPs could be added in the Hybridization mix or a pre-hybridization done to block non-specific binding.

Hybridization cycle for Hybridization of oligonucleotides to 13 mer oligos on array: The Automated Slide Processor from Amersham Pharmacia was used for hybridization:

| ASP HYBRIDIZATION PROTOCOL | |
| --- | --- |
| PRIME | PRIME WITH WASH 1 |
| WAIT | inject probe |
| HEAT | To 25 degrees |
| MIX | Hybridization mixing for 12 hrs or 2 hours |
| FLUSH | Wash 1 (1x SSC/0.2% SDS) |
| HEAT | To 30 degrees C. |
| MIX | Wash 1 5 minutes |
| PRIME | Prime with wash 2(0.1XSSC/0.2% SDS) |
| FLUSH | Wash 2 |
| MIX | Wash 2 30 seconds |
| FLUSH | Wash 3 (Wash (0.1XSSC) |
| MIX | Wash 3 30 seconds |
| PRIME | Prime with was 4 (0.1XSSC) |
| FLUSH | Wash 4 (0.1XSSC) |
| Prime | Prime with Isopropanol |
| Flush | Flush with Isopropanol |
| Flush | Flush with air |
| Airpump | Dry Slide |
| Heat | Turn off Heat |

Alternatively, a manual hybridization set up as known in the art can be used. Briefly, a droplet of hybridization mix is sandwiched between the array substrate and a coverslip. The hybridization performed in a humid chamber (with optional edges sealed with rubber cement). The coverslip is slid off in wash buffer and washes are done preferably with some shaking.

On enhanced aminosliane slides, QMT buffer 1, 1.5M Betaine 3×SSC gave the best results. A faint ring was seen around the spots in 1.5M Betaine 3×SSC. Concentrations between 250 nM and 67.5 nM were appropriate for single molecule counting on relatively fresh slides. These slides should be stored at −70 degrees C. At room temperature the ability to retain probe after spotting wanes badly over a 2 month period.

The results are analyzed by TIRF microscopy. Oxygen scavenging solution was used.

Example 5—Making Single Stranded DNA/RNA, Hybridizing to Primary Array to Make Secondary Array, Probing Secondary Array One method for probing when secondary array is made with single stranded DNA is as follows:
Single strand are made e.g. by Asymmetric (long Range) PCR, magnetic bead methods, selective protection of one strand form exonuclease degradation or by in vitro RNA transcription.
Hybridize single stranded DNA to array
Single stranded DNA may be hybridized at two points within or between microarray elements to enable stretching out (the linker holding one or both of the two array probes should be capable of rotating)
Alternatively single stranded DNA can be hybridized to the array, in 3-6×SSC buffer at room temperature for 25 mers which may be facilitated by enzymatic reactions such as ligation or by a coaxially stacking oligo or staking of several contiguous oligos. Sites that are known to remain accessible to probing under low stringency conditions are chosen for probing (these can be selected on oligonucleotide arrays; see Milner et al, Nat Biotechnol. 1997 June; 15(6):537-41).
After Hybridization of single strand the strand needs to be covalently attached at site of capture and then washed stringently to remove secondary structure
The captured single stranded target can then be stretched out as described by Woolley and Kelly (Nanoletters 2001 1: 345-348) by moving a droplet of fluid across a positively charged surface.
Need to control density of positive charge on the surface by coating with 1 ppm poly-L-lysine. The appropriate concentrations of other surface coatings e.g Aminoslinae need to be determined empirically
Need to maintain the ssDNA at low ionic strength. Use 10 mM Tris, 1,M EDTA pH8 (TE buffer)
Move to move droplet of fluid across the surface at a velocity of Approx. 0.5 mm/s (within range 0.2-1 mm/s). This can be done by fixing the slide/mica onto a TST series translation stage (Newport), placing a droplet of fluid onto this, and translating the fluid with respect to the surface by dipping a stationary glass pipette onto the droplet. The glass pipette attracts the droplet by capillary action and the droplet remains stationary as the slide/mica is moved.
After solution evaporates, rinse the mica with water and dry with compressed air
Or by Michalet et als Dynamic molecular combing procedure as described above
or by the ASP procedure described above.
Optionally the single stranded DNA can be coated with single strand binding protein (Amersham)
Single stranded DNA can be labelled by Acridine dyes.
Stretched out single stranded molecule can be probed with single stranded DNA by hybridization at 5 degrees C. below the Tm of the oligonucleotide probe. It is preferable to use LNA oligonucleotides at low salt concentration, 50 mM NaCl or PNA at 0 or 5 mM NaCl.

Example 6—Ligation Assay on Single Molecule Array

Target preparation is essentially as for SNP typing/resequencing section and target analysis
Mix:
5× ligation buffer*
Solution oligonucleotide 5-10 pmol, labelled with fluorescent dye on 3' and phosphoryalted on 5' end
*Thermus thermophilus* DNA ligase (Tth DNA ligase) 1 U/ul,
Target sample
Add to centre of array
Add coverslip over the top of array area and seal edges with rubber cement
Place at 65° C. for 1 hr.

*5× ligation buffer is composed of 100 mM Tris-HCL pH 8.3, 0.5% Triton X-100, 50 mM MgCl, 250 mM KCl, 5 mM NAD+, 50 mM DTT, 5 mM EDTA In this example different sequences that define the allele of a SNP are placed in adjacent spots in the microarray, by the spotting methods described. The last base of these sequences overlap the variant base in the target. The oligonucleotide on the array are spotted with 5' amination. The 3' end is free for ligation with the 5' phosphorylated solution oligonucleotide. Alternatively the array oligonucleotide can be 3' aminated and 5' phosphorylated The solution oligonucleotide can be phosphorylated and labelled on the 5' end. The solution oligonucleotide is preferably a mixture of every 9mer (Oswel, Southampton, UK).

Example 7—Image Processing, Single Molecule Counting and Error Management

The above can be done using algorithms of any of the type in the detailed description of the invention. In addition below is an example of how to do single molecule counting using simple commercial software.

The objective is to use image analysis to count and determine the confidence in putative signals from single molecules within a microarray spot. The image processing package SigmaScanPro is used to automate single molecule counting and measurement. The procedure described here, or modifications of it, can be used for simple single molecule signal counting or more complex analyses of single molecule information, multi-colour analysis and error management.

The microarray spot image is captured using a low light CCD camera, the I-PentaMAX GenIII or Gen IV (Roper Scientific) and an off-the-shelf frame grabber board. The single molecules are excited by laser in a TIRF configuration. Using a 100× objective and spots of approximately 200 microns in diameter.

The image is spatially calibrated using the Image, Calibrate, Distance and Area menu option. A 2-Point Rescaling calibration is performed using micron units. Single molecule areas will then be reported in square microns.

Increasing the contrast between single molecules and the surrounding region will help identify the single molecules by thresholding. Image contrast is improved by performing a Histogram Stretch from the Image, Intensity menu. This procedure measures the grey levels in the image. The user then "stretches" the range of grey levels with significant magnitude over the entire 255 level intensity range. In this case moving the Old Start line with the mouse to an intensity of 64 will eliminate the effect of the insignificant dark gray levels and improve the contrast.

The single molecules can be identified by thresholding the intensity level to fill in the darkest objects. This is done by selecting Threshold, Intensity Threshold from the Image menu.

Under certain spotting conditions (e.g. 1.5M Betaine 3×SSC onto enhanced Aminosilane slides as well as in 50% DMSO buffer under certain conditions) the spot has a thin but discernibly bright ring round the edge. This can be used to define the area to be processed. This ring can be removed from contributing to the data by using image overlay layer math to intersect the single molecule signals with an overlay plane consisting of the interior of the ring. The overlay is created by filling light pixels in the interior of the spot and selecting out the ring by thresholding. Set the Level to be 180 and the option to select objects that are lighter than this level. Select the Fill Measurement mode (paint bucket icon) and left click in the interior of the plate to fill it. Set the source overlay to red in the Measurements, Settings, Overlays dialog. There are "holes" in the red overlay plane that are not filled since they contain bright pixels from the single molecules. To fill them select Image, Overlay Filters and select the Fill Holes option. Let both the source and destination overlays be red. The red circular overlay plane contains the green bacterial colonies.

The overlay math feature is used to identify the intersection of the red and green overlay planes. From the Image menu select Overlay Math and specify red and green to be the source layers and blue to be the destination layer. Then AND the two layers to obtain the intersection.

The blue pixels overlay the single molecule that can now be counted. Select the blue overlay plane as the source overlay from the Overlays tab in the Measurement Settings dialog. Select Perimeter, Area, Shape Factor, Compactness and Number of Pixels from the Measurements tab in the Measurements Settings dialog. Then measure the single molecule signals by using Measure Objects from the Measurements menu. The single molecule signals can be arbitrarily numbered and the corresponding measured quantities placed into an Excel (Microsoft) spreadsheet A macro is written to perform this for each spot in the array.

The microarray slide is translated relative to the CCD by a TST series X-Y translation stage (Newport) with images taken approximately every 100 micron spacings.

The example given here is for end-point analysis. However, for enhanced error discrimination real time analysis may be desirable, in this case a wider field images can be taken of the whole array by the CCD camera under lower magnification and enhanced by image processing. However, in most cases, a time window after the start of the reaction will have been determined within which the image should be acquired to gate out errors, which may occur early (non specific absorption) and late (mismatch interactions) in the process.

Adobe Photoshop software contains a number of image processing facilities which can be used and more advanced plug-ins are available. The Image Processing Toolkit is available which Plug-in to Photoshops, MicroGrafx Picture Publisher, NIH Image and other programs is available from Quantitative Image Analysis.

Example 8—Derivatization of Glass with Polyethylenimine (PEI)

For AFM analysis the array needs to be spotted onto a derivatised surface that is highly flat. AFM analysis requires a surface flatness of ~1-2 nm or preferably below this. Glass slides, preferably polished can be derivatised with Polyethylenimine which by contrast to reagents such as APTES gives a relatively flat surface coating that is appropriate to AFM analysis. A glass slide is washed with 0.1 N acetic acid, then rinsed with water until the water rinsed from the slide has a pH equal to the pH of the water being used to rinse the slide. The slide is then allowed to dry. To a 95:5 ethanol:water solution is added a sufficient quantity of a 50% w/w solution of trimethoxysilylpropyl-polyethylenimine (600 MW) in 2—to achieve a 2% w/w final concentration. After stirring this 2% solution for five minutes, the glass slide is dipped into the solution, gently agitated for 2 minutes, and then removed. The glass slide is dipped into ethanol in order wash away excess sialylating agent. The glass slide is then air dried. Aminated oligonucleotides are spotted in a 1 M sodium borate pH 8.3 based buffer or 50% DMSO. Mica which can be atomically flat can be coated with PEI in a similar way.

Genomic DNA Labeling Protocol: Developed for microarray-based comparative genomic hybridization.

Genomic DNA can be labeled with a simple random-priming protocol based on Gibco/BRL's Bioprime DNA Labeling kit, though nick translation protocols work too. For example, the BioPrime labeling kit (Gibco/BRL) is a convenient and inexpensive source of random octamers, reaction buffer, and high concentration klenow, though other sources of random primers and high concentration klenow work as well.

1. Add 2 ug DNA of the sample to be labeled to an eppindorf tube.
    Note: For high complexity DNAs (e.g. human genomic DNA), the labeling reaction works more efficiently if the fragment size of the DNA is first reduced. This may be accomplished by restriction enzyme digestion (usually DpnII, though other 4-cutters work as well). After digestion, the DNA should be cleaned up by phenol/chloroform extraction/EtOH precipitation (Qiagen PCR purification kit also works well).
2. Add ddH$_2$O or TE 8.0 to bring the total volume to 21 ul. Then add 20 ul of 2.5× random primer/reaction buffer mix. Boil 5 min, then place on ice.
    2.5× random primer/reaction buffer mix:
    125 mM Tris 6.8
    12.5 mM MgCl$_2$
    25 mM 2-mercaptoethanol
    750 ug/ml random octamers
3. On ice, add 5 ul 10× dNTP mix.
    10× dNTP mix:
    1.2 mM each dATP, dGTP, and dTTP
    0.6 mM dCTP
    10 mM Tris 8.0, 1 mM EDTA
4. Add 3 ul Cy5-dCTP or Cy3-dCTP (Amersham, 1 mM stocks)
    Note: Cy-dCTP and Cy-dUTP work equally well. If using Cy-dUTP, adjust 10× dNTP mix accordingly.
5. Add 1 ul Klenow Fragment.
    Note: High concentration klenow (40-50 units/ul), available through NEB or Gibco/BRL (as part of the BioPrime labeling kit), produces better labeling.
6. Incubate 37 degrees C. for 1 to 2 hours, then stop reaction by adding 5 ul 0.5 M EDTA pH8.0
7. As with RNA probes, the DNA probe may be purified using a microcon 30 filter (Amicon/Millipore):
    Add 450 ul TE 7.4 to the stopped labeling reaction.
    Lay onto microcon 30 filter. Spin ~10 min at 8000 g (10,000 rpm in microcentrifuge).
    Invert and spin 1 min 8000 g to recover purified probe to new tube (~20-40 ul volume).
8. For two-color array hybridizations, combine purified probes (Cy5 and Cy3 labeled probes) in new eppindorf tube. Then add:
    30-50 ug human Cot-1 DNA (Gibco/BRL; 1 mg/ml stock; blocks hybridization to repetitive DNAs if present on array).
    100 ug yeast tRNA (Gibco/BRL; make a 5 mg/ml stock; blocks non-specific DNA hybridization).
    20 ug poly(dA)-poly(dT) (Sigma catalog No. P9764; make a 5 mg/ml stock; blocks hybridization to polyA tails of cDNA array elements).
    450 ul TE 7.4
    Concentrate with a microcon 30 filter as above (8000 g, ~15 min, then check volume every 1 min until appropriate). Collect probe mixture in a volume of 12 ul or less.
9. Adjust volume of probe mixture to 12 ul with ddH$_2$O. Then add 2.55 ul 20×SSC (for a final conc. of 3.4×) and 0.45 ul 10% SDS (for a final conc. of 0.3%).
    Note: The final volume of hybridization is 15 ul. This volume is appropriate for hybridization under a 22 mm2 coverslip. Volumes should be adjusted upwards accordingly for larger arrays/coverslips.
10. Denature hybridization mixture (100° C., 1.5 min), incubate for 30 minutes at 37° C. (Cot-1 preannealing step), then hybridize to the array.
11. Hybridize microarray at 65° C. overnight (16-20 hrs).
    Note, see Human Array Hybridization protocol for details on hybridization.
12. Wash arrays as with mRNA labeling protocol and scan:
    First wash: 2×SSC, 0.03% SDS, 5 min 65° C.
    Second wash: 1×SSC, 5 min RT
    Third wash: 0.2×SSC, 5 min RT
    Note: the first washing step should be performed at 65° C.; this appears to significantly increase the specific to non-specific hybridization signal.

Example 9—Making Spatially Addressable Arrays by AFM Deposition

A spatially addressable array of single molecules by picking up by AFM and deposition, at low conc is made, for example, by making a patterned array of loosely bound molecules, pulling a single molecule of this array and taking and deposition at a specific position on the substrate, of known coordinates. This coordinate can be addressed by light microscopy in single molecule fluorescence or by AFM. Ideally the AFM stage will not be on piezo to minimize drift.

Example 10

The following protocol describes the processing of up to 24 cell-free DNA samples through hybridization-ligation, purification, amplification, microarray target preparation, microarray hybridization and microarray washing.

The following materials were prepared or obtained: Cell-free DNA (cfDNA) in a volume of 20 µL water; Probe Mix: mixture of all Tagging and Labeling probe oligonucleotides at a concentration of 2 nM each; Taq Ligase (40 U/µL); Magnetic Beads: MyOne Streptavidin C1 Dynabeads; Bead Binding and Washing Buffer, 1× and 2× concentrations; Forward amplification primer, 5' phosphate modified; Reverse amplification primer, labeled; AmpliTaq Gold Enzyme (5 U/µL); dNTP Mix; Lambda Exonuclease (5 U/µL); Hybridization Buffer, 1.25×; Hybridization control oligonucleotides; Microarray Wash Buffer A; Microarray Wash Buffer B; Microarray Wash Buffer C.

Hybridization-Ligation Reaction:

The cfDNA samples (20 µL) were added to wells A3-H3 of a 96-well reaction plate. The following reagents were added to each cfDNA sample for a total reaction volume of 50 µL, and mixed by pipetting up and down 5-8 times.

| Component | Volume |
|---|---|
| H$_2$O | 19.33 µL |
| Probe Mix | 5 µL |

-continued

| Component | Volume |
|---|---|
| 10X Taq Ligase Buffer | 5 µL |
| Taq Ligase | 0.67 µL |

The plate was placed in a thermal cycler and ligate using the following cycling profile: (i) 95° C. for 5 minutes; (ii) 95° C. for 30 seconds; (iii) 45° C. for 25 minutes; (iv) Repeat steps b to c 4 times; and (v) 4° C. hold.

Hybridization-ligation Product Purification:

Wash Dynabeads: a vial of Dynabeads was vortexted at highest setting for 30 seconds. 260 µL beads were transferred to a 1.5 mL tube. 900 µL of 2× Bead Binding and Washing Buffer and mix beads were mixed by pipetting up and down 5-8 times. The tube was placed on a magnetic stand for 1 min, and the supernatant was discarded. The tube from the magnetic stand was removed and resuspended the washed magnetic beads in 900 µL of 2× Bead Binding and Washing Buffer by pipetting up and down 5-8 times. The tube was placed on the magnetic stand for 1 min and discard the supernatant. The tube was removed from the magnetic stand and add 1,230 µL of 2× Bead Binding and Washing Buffer. The beads were resuspended by pipetting up and down 5-8 times.

Immobilize HL Products: 50 µL of washed beads was transferred to each hybridization-ligation reaction product in the 96-well reaction plate and mix by pipetting up and down 8 times, was incubated for 15 min at room temperature, mixed on a plate magnet twice during the incubation time. The beads were separated with on a plate magnet for 3 min and then remove and discard the supernatant. The plate was removed from the plate magnet, 200 µL 1× Bead Binding and Washing Buffer were added, and the beads were resuspended by pipetting up and down 5-8 times. The plate was placed on the plate magnet for 1 min, and the supernatant was discarded. The plate was removed from the plate magnet, 180 µL 1×SSC was added, and the beads were resuspended by pipetting up and down 5-8 times. The plate was placed on the plate magnet for 1 min, and the supernatant was discarded.

Purify Hyb-Ligation Products: 50 µL of freshly prepared 0.15 M NaOH was added to each well and, the beads were resuspended by pipetting up and down 5-8 times, and incubated at room temperature for 10 minutes. The plate was placed on the plate magnet for 2 minutes and then was removed, and the supernatant was discarded. The plate was removed from the plate magnet, 200 µL of freshly prepared 0.1 M NaOH was added, and the beads were resuspended by pipetting up and down 5-8 times. The plate was placed on the plate magnet for 1 min, and the supernatant was discarded. The plate was removed from the plate magnet, and 180 µL 0.1 M NaOH was added, and the beads were resuspended by pipetting up and down 5-8 times. The plate was placed on the plate magnet for 1 min, and the supernatant was discarded. The plate was removed from the plate magnet, 200 µL of 1× Binding and Wash Buffer were added, and the beads were resuspended by pipetting up and down 5-8 times. Place the plate on the plate magnet for 1 min and discard the supernatant. Remove the plate from the plate magnet, add 180 µL TE, and the beads were resuspended by pipetting up and down 5-8 times. The plate was placed on the plate magnet for 1 min, and the supernatant was discarded. 20 µL water was added to each well and the beads were resuspended by pipetting up and down 5-8 times. The plate was sealed and store at 4° C. until used in subsequent steps.

Amplification:

The following reagents were added to each hybridization-ligation reaction product in the 96-well reaction plate for a total reaction volume of 50 µL.

| Component | Volume |
|---|---|
| H$_2$O | 17.25 µL |
| Forward Primer, 10 µM | 2.5 µL |
| Reverse Primer, 10 µM | 2.5 µL |
| 4 mM dNTP Mix (L/N 052114) | 2.5 µL |
| 10X AmpliTaq Gold Buffer | 5 µL |
| AmpliTaq Gold Enzyme | 0.25 µL |

The plate was placed in a thermal cycler, and the probes were ligated using the following cycling profile: (i) 95° C. for 5 minutes; (ii) 95° C. for 30 seconds; (iii) 45° C. for 25 minutes; (iv) Repeat steps b to c 4 times; and (v) 4° C. hold.

Hybridization-ligation Product Purification: the reagents were mixed by pipetting up and down 5-8 times. The plate was placed in a thermal cycler, and the probes were amplified using the following cycling profile: (i) 95° C. for 5 minutes; (ii) 95° C. for 30 seconds; (iii) 54° C. for 30 seconds; (iv) 72° C. for 60 seconds, (v) Repeat steps b to d 29 times; (vi) 72° C. for 5 minutes; (vii) Repeat steps b to c 4 times; and (v) 4° C. hold.

Microarray Target Preparation (single strand digestion): the following reagents were added to each amplified reaction product in the 96-well reaction plate for a total reaction volume of 60 µL.

| Component | Volume |
|---|---|
| H2O | 3 µL |
| 10X Lambda Exonuclease Buffer | 6 µL |
| Lambda Exonuclease Enzyme | 1 µL |

The reagents were mixed by pipetting up and down 5-8 times. The plate was placed in a thermal cycler, and the probes were digested using the following cycling profile: (i) 37° C. for 60 minutes; (ii) 80° C. for 30 minutes; (iii) 4° C. hold. The plate was placed in Speed-vac and dry down samples using medium heat setting for about 60 minutes or until all liquid has evaporated. Samples were stored at 4° C. in the dark until used in subsequent steps.

Microarray hybridization: the following reagents were added to each dried Microarray Target in the 96-well reaction plate for a total reaction volume of 20 µL.

| Component | Volume |
|---|---|
| H$_2$O | 3 µL |
| 1.25X Hybridization Buffer | 16 µL |
| Hybridization control oligonucleotides | 1 µL |

The reagents were mixed by pipetting up and down 10-20 times to be resuspended and were spun briefly to bring contents to the bottoms of the plate wells. The plate was placed in a thermal cycler, and the probes were denatured using the following cycling profile: (i) 70° C. for 3 minutes; (ii) 42° C. hold. The barcode of the microarray to be used was recorded for each sample in the Tracking Sheet. A hybridization chamber containing a Lifter Slip for each microarray to be processed is prepared. For each sample, 15 µL of Microarray Target was added to the center of a Lifter Slip in a hybridization chamber, and the appropriate microarray was immediately placed onto the target fluid by placing the top edge down onto the lifter slip and slowly letting it fall down flat. The hybridization chambers were closed and incubated them at 42° C. for 60 minutes. The hybridization chambers were opened, and each microarray was removed from the Lifter Slips and placed into a rack immersed in Microarray Wash Buffer A. Once all the microarrays were in the rack, the rack was stirred at 650 rpm for 5 minutes. The rack of microarrays was removed from Microarray Wash Buffer A, excess liquid on a clean room wipe was tapped off, and the rack were quickly placed into Microarray Wash Buffer B. The rack was stirred at 650 rpm for 5 minutes. The rack of microarrays was removed from Microarray Wash Buffer B, excess liquid was tapped off on a clean room wipe, and the rack was quickly placed into Microarray Wash Buffer C. The rack was stirred at 650 rpm for 5 minutes. Immediately upon completion of the 5 minute wash in Microarray Wash Buffer C, the rack of microarrays was slowly removed from the buffer. This took 5-10 seconds to maximize the sheeting of the wash buffer from the cover slip surface. Excess liquid was tapped off on a clean room wipe. A vacuum aspirator was used to remove any remaining buffer droplets present on either surface of each microarray. The microarrays were stored in a slide rack under nitrogen and in the dark until the microarrays were analyzed.

The invention claimed is:

1. A method of producing a molecular array, the method comprising:
   (i) hybridizing first and second probe sets to first and second nucleic acid regions of interest in target nucleic acid sequences, respectively, in a genetic sample from a human, wherein nucleotide sequences of the first and second nucleic acid regions of interest are different, wherein the first probe set comprises a first labeling probe comprising a first priming sequence, and a first tagging probe comprising an affinity tag and a second priming sequence, wherein the first labeling probe hybridizes adjacent to the first tagging probe on the first nucleic acid region of interest, wherein the affinity tag comprises a nucleotide sequence complementary to a capture probe immobilized to a location on a substrate, and wherein the nucleotide sequence of the affinity tag does not hybridize to the first or second nucleic acid regions of interest, and
   the second probe set comprises a second labeling probe comprising a third priming sequence, and a second tagging probe comprising the affinity tag and the second priming sequence, wherein the second labeling probe hybridizes adjacent to the second tagging probe on the second nucleic acid region of interest;
   (ii) ligating the first labeling probe to the first tagging probe thereby providing a first ligated probe set, and ligating the second labeling probe to the second tagging probe, thereby providing a second ligated probe set;
   (iii) amplifying the first and the second ligated probe sets to form first and second amplified ligated probe sets, respectively, wherein (a) the first ligated probe set is amplified using:
  a first primer that comprises a first label and that hybridizes to the first priming sequence or complement thereof, and
  a second primer that hybridizes to the second priming sequence or complement thereof,
  wherein the first amplified ligated probe set comprises a first plurality of identical single-stranded amplicons of the first ligated probe set, each comprising the first label and the affinity tag, and
(b) the second ligated probe set is amplified using:
  a third primer that comprises a second label and that hybridizes to the third priming sequence or complement thereof, and
  the second primer of (a),
  wherein the second amplified ligated probe set comprises a second plurality of identical single-stranded amplicons of the second ligated probe set, each comprising the second label and the affinity tag, and wherein the first and second labels are different; and
(iv) immobilizing the first and second plurality of identical single-stranded amplicons to the location on the substrate by hybridizing the nucleotide sequence of the affinity tag to the capture probe immobilized on the substrate at a density wherein individual labeled molecules of the single-stranded amplicons optically resolvable at the location by digital imaging, thereby producing the molecular array comprising the first and second plurality of identical single-stranded amplicons immobilized to the location on the substrate.

2. The method according to claim 1, wherein the human is a pregnant female.

3. The method according to claim 1, wherein the genetic sample is obtained from a source selected from the group consisting of whole blood, serum, plasma, urine, saliva, sweat, fecal matter, and tears.

4. The method according to claim 1, wherein the genetic sample comprises cell free DNA.

5. The method according to claim 1, wherein each of the immobilized single-stranded amplicons of the first and second ligated probe sets are separated by a distance of at least 250 nm on the substrate.

6. The method according to claim 1, wherein the first and the second labels are fluorescent dyes.

7. The method according to claim 1, wherein the array further comprises a plurality of locations on the substrate, each of the plurality of locations comprising immobilized single-stranded amplicons different than the plurality of identical single-stranded amplicons of the first and second ligated probe sets.

8. The method according to claim 7, wherein each of the plurality of locations on the substrate comprise wells or raised regions.

9. The method according to claim 1, wherein the substrate comprises a material selected from the group consisting of glass, quartz, silicon wafers, mica, ceramics, organic polymers, plastics, polystyrene and polymethacrylate.

10. The method according to claim 1, wherein the target nucleic acid sequences are human genomic sequences.

* * * * *

SEQUENCE LISTING

```
<160> NUMBER OF SEQ ID NOS: 369

<210> SEQ ID NO 1
<211> LENGTH: 60
<212> TYPE: DNA
<213> ORGANISM: Artificial Sequence
<220> FEATURE:
<223> OTHER INFORMATION: Synthetic sequence

<400> SEQUENCE: 1
gccctcatct tcttccctgc gttctcacca ccctcaccaa ggaagaagtg agggcttctc    60

<210> SEQ ID NO 2
<211> LENGTH: 60
<212> TYPE: DNA
<213> ORGANISM: Artificial Sequence
<220> FEATURE:
<223> OTHER INFORMATION: Synthetic sequence

<400> SEQUENCE: 2
gccctcatct tcttccctgc gttctcacca ccctcaccaa aaatcaaggt gaccagctcc    60

<210> SEQ ID NO 3
<211> LENGTH: 62
<212> TYPE: DNA
<213> ORGANISM: Artificial Sequence
<220> FEATURE:
<223> OTHER INFORMATION: Synthetic sequence

<400> SEQUENCE: 3
gccctcatct tcttccctgc gttctcacca ccctcaccaa tcatctgcca agacagaagt    60
tc                                                                   62

<210> SEQ ID NO 4
<211> LENGTH: 60
<212> TYPE: DNA
<213> ORGANISM: Artificial Sequence
<220> FEATURE:
<223> OTHER INFORMATION: Synthetic sequence

<400> SEQUENCE: 4
gccctcatct tcttccctgc gttctcacca ccctcaccaa gcaggagagt caaaggtctg    60

<210> SEQ ID NO 5
<211> LENGTH: 60
<212> TYPE: DNA
<213> ORGANISM: Artificial Sequence
<220> FEATURE:
<223> OTHER INFORMATION: Synthetic sequence
```

<400> SEQUENCE: 5
gccctcatct tcttccctgc gttctcacca ccctcaccaa gttgccatgg agattgttgc    60

<210> SEQ ID NO 6
<211> LENGTH: 60
<212> TYPE: DNA
<213> ORGANISM: Artificial Sequence
<220> FEATURE:
<223> OTHER INFORMATION: Synthetic sequence

<400> SEQUENCE: 6
gccctcatct tcttccctgc gttctcacca ccctcaccaa cagctcagtg atgtcattgc    60

<210> SEQ ID NO 7
<211> LENGTH: 61
<212> TYPE: DNA
<213> ORGANISM: Artificial Sequence
<220> FEATURE:
<223> OTHER INFORMATION: Synthetic sequence

<400> SEQUENCE: 7
gccctcatct tcttccctgc gttctcacca ccctcaccaa ccttgacctc tgctaatgtg    60
g                                                                   61

<210> SEQ ID NO 8
<211> LENGTH: 60
<212> TYPE: DNA
<213> ORGANISM: Artificial Sequence
<220> FEATURE:
<223> OTHER INFORMATION: Synthetic sequence

<400> SEQUENCE: 8
gccctcatct tcttccctgc gttctcacca ccctcaccaa cacctgtcca acagctacag    60

<210> SEQ ID NO 9
<211> LENGTH: 61
<212> TYPE: DNA
<213> ORGANISM: Artificial Sequence
<220> FEATURE:
<223> OTHER INFORMATION: Synthetic sequence

<400> SEQUENCE: 9
gccctcatct tcttccctgc gttctcacca ccctcaccaa agaatgtatc ttcaggcctg    60
c                                                                   61

<210> SEQ ID NO 10
<211> LENGTH: 60
<212> TYPE: DNA
<213> ORGANISM: Artificial Sequence
<220> FEATURE:
<223> OTHER INFORMATION: Synthetic sequence

<400> SEQUENCE: 10
gccctcatct tcttccctgc gttctcacca ccctcaccaa aagtaatcac tctgggtggc    60

<210> SEQ ID NO 11
<211> LENGTH: 60
<212> TYPE: DNA
<213> ORGANISM: Artificial Sequence
<220> FEATURE:
<223> OTHER INFORMATION: Synthetic sequence

<400> SEQUENCE: 11
gccctcatct tcttccctgc gttctcacca ccctcaccaa agctcacaga caaccttgtg    60

```
<210> SEQ ID NO 12
<211> LENGTH: 60
<212> TYPE: DNA
<213> ORGANISM: Artificial Sequence
<220> FEATURE:
<223> OTHER INFORMATION: Synthetic sequence

<400> SEQUENCE: 12
gccctcatct tcttccctgc gttctcacca ccctcaccaa gcaatagaca cctacaggcg    60

<210> SEQ ID NO 13
<211> LENGTH: 60
<212> TYPE: DNA
<213> ORGANISM: Artificial Sequence
<220> FEATURE:
<223> OTHER INFORMATION: Synthetic sequence

<400> SEQUENCE: 13
gccctcatct tcttccctgc gttctcacca ccctcaccaa gcacattatc aaaggccacg    60

<210> SEQ ID NO 14
<211> LENGTH: 60
<212> TYPE: DNA
<213> ORGANISM: Artificial Sequence
<220> FEATURE:
<223> OTHER INFORMATION: Synthetic sequence

<400> SEQUENCE: 14
gccctcatct tcttccctgc gttctcacca ccctcaccaa caacgaccta aagcatgtgc    60

<210> SEQ ID NO 15
<211> LENGTH: 60
<212> TYPE: DNA
<213> ORGANISM: Artificial Sequence
<220> FEATURE:
<223> OTHER INFORMATION: Synthetic sequence

<400> SEQUENCE: 15
gccctcatct tcttccctgc gttctcacca ccctcaccaa gacatacatg gctttggcag    60

<210> SEQ ID NO 16
<211> LENGTH: 62
<212> TYPE: DNA
<213> ORGANISM: Artificial Sequence
<220> FEATURE:
<223> OTHER INFORMATION: Synthetic sequence

<400> SEQUENCE: 16
gccctcatct tcttccctgc gttctcacca ccctcaccaa gagatactgc cacttatgca    60
cg                                                                  62

<210> SEQ ID NO 17
<211> LENGTH: 40
<212> TYPE: DNA
<213> ORGANISM: Artificial Sequence
<220> FEATURE:
<223> OTHER INFORMATION: Synthetic sequence

<400> SEQUENCE: 17
cgtgctaata gtctcagggc ttcctccacc gaacgtgtct                          40

<210> SEQ ID NO 18
<211> LENGTH: 40
<212> TYPE: DNA
<213> ORGANISM: Artificial Sequence
```

<220> FEATURE:
<223> OTHER INFORMATION: Synthetic sequence

<400> SEQUENCE: 18
cgacgcttca ttgcttcatt ttcctccacc gaacgtgtct        40

<210> SEQ ID NO 19
<211> LENGTH: 40
<212> TYPE: DNA
<213> ORGANISM: Artificial Sequence
<220> FEATURE:
<223> OTHER INFORMATION: Synthetic sequence

<400> SEQUENCE: 19
cttgcgccaa acaattgtcc ttcctccacc gaacgtgtct        40

<210> SEQ ID NO 20
<211> LENGTH: 40
<212> TYPE: DNA
<213> ORGANISM: Artificial Sequence
<220> FEATURE:
<223> OTHER INFORMATION: Synthetic sequence

<400> SEQUENCE: 20
gctgcagagt ttgcattcat ttcctccacc gaacgtgtct        40

<210> SEQ ID NO 21
<211> LENGTH: 41
<212> TYPE: DNA
<213> ORGANISM: Artificial Sequence
<220> FEATURE:
<223> OTHER INFORMATION: Synthetic sequence

<400> SEQUENCE: 21
catacacaca gaccgagagt cttcctccac cgaacgtgtc t       41

<210> SEQ ID NO 22
<211> LENGTH: 40
<212> TYPE: DNA
<213> ORGANISM: Artificial Sequence
<220> FEATURE:
<223> OTHER INFORMATION: Synthetic sequence

<400> SEQUENCE: 22
ggatgtcagc cagcataagt ttcctccacc gaacgtgtct        40

<210> SEQ ID NO 23
<211> LENGTH: 40
<212> TYPE: DNA
<213> ORGANISM: Artificial Sequence
<220> FEATURE:
<223> OTHER INFORMATION: Synthetic sequence

<400> SEQUENCE: 23
gcaagtgcca aacagttctc ttcctccacc gaacgtgtct        40

<210> SEQ ID NO 24
<211> LENGTH: 41
<212> TYPE: DNA
<213> ORGANISM: Artificial Sequence
<220> FEATURE:
<223> OTHER INFORMATION: Synthetic sequence

<400> SEQUENCE: 24
gattccagca cacttgagtc tttcctccac cgaacgtgtc t       41

```
<210> SEQ ID NO 25
<211> LENGTH: 40
<212> TYPE: DNA
<213> ORGANISM: Artificial Sequence
<220> FEATURE:
<223> OTHER INFORMATION: Synthetic sequence

<400> SEQUENCE: 25
ccgttgcagg tttaaatggc gccctattgc aagccctctt                              40

<210> SEQ ID NO 26
<211> LENGTH: 40
<212> TYPE: DNA
<213> ORGANISM: Artificial Sequence
<220> FEATURE:
<223> OTHER INFORMATION: Synthetic sequence

<400> SEQUENCE: 26
caagagtgct ttatgggcct gccctattgc aagccctctt                              40

<210> SEQ ID NO 27
<211> LENGTH: 41
<212> TYPE: DNA
<213> ORGANISM: Artificial Sequence
<220> FEATURE:
<223> OTHER INFORMATION: Synthetic sequence

<400> SEQUENCE: 27
gcactcaagg agatcagact ggccctattg caagccctct t                            41

<210> SEQ ID NO 28
<211> LENGTH: 41
<212> TYPE: DNA
<213> ORGANISM: Artificial Sequence
<220> FEATURE:
<223> OTHER INFORMATION: Synthetic sequence

<400> SEQUENCE: 28
ggctatcgaa ctacaaccac agccctattg caagccctct t                            41

<210> SEQ ID NO 29
<211> LENGTH: 41
<212> TYPE: DNA
<213> ORGANISM: Artificial Sequence
<220> FEATURE:
<223> OTHER INFORMATION: Synthetic sequence

<400> SEQUENCE: 29
gtagctgtct gtggtgtgat cgccctattg caagccctct t                            41

<210> SEQ ID NO 30
<211> LENGTH: 42
<212> TYPE: DNA
<213> ORGANISM: Artificial Sequence
<220> FEATURE:
<223> OTHER INFORMATION: Synthetic sequence

<400> SEQUENCE: 30
caagaaactt cgagccttag cagccctatt gcaagccctc tt                           42

<210> SEQ ID NO 31
<211> LENGTH: 40
<212> TYPE: DNA
<213> ORGANISM: Artificial Sequence
<220> FEATURE:
<223> OTHER INFORMATION: Synthetic sequence
```

<400> SEQUENCE: 31
gtgaaccagt ccgagtgaaa gccctattgc aagccctctt                40

<210> SEQ ID NO 32
<211> LENGTH: 41
<212> TYPE: DNA
<213> ORGANISM: Artificial Sequence
<220> FEATURE:
<223> OTHER INFORMATION: Synthetic sequence

<400> SEQUENCE: 32
gcaaatgatg ttcagcacca cgccctattg caagccctct t              41

<210> SEQ ID NO 33
<211> LENGTH: 20
<212> TYPE: DNA
<213> ORGANISM: Artificial Sequence
<220> FEATURE:
<223> OTHER INFORMATION: Synthetic sequence

<400> SEQUENCE: 33
gccctcatct tcttccctgc                                      20

<210> SEQ ID NO 34
<211> LENGTH: 20
<212> TYPE: DNA
<213> ORGANISM: Artificial Sequence
<220> FEATURE:
<223> OTHER INFORMATION: Synthetic sequence

<400> SEQUENCE: 34
gttctcacca ccctcaccaa                                      20

<210> SEQ ID NO 35
<211> LENGTH: 20
<212> TYPE: DNA
<213> ORGANISM: Artificial Sequence
<220> FEATURE:
<223> OTHER INFORMATION: Synthetic sequence

<400> SEQUENCE: 35
ggaagaagtg agggcttctc                                      20

<210> SEQ ID NO 36
<211> LENGTH: 20
<212> TYPE: DNA
<213> ORGANISM: Artificial Sequence
<220> FEATURE:
<223> OTHER INFORMATION: Synthetic sequence

<400> SEQUENCE: 36
aaatcaaggt gaccagctcc                                      20

<210> SEQ ID NO 37
<211> LENGTH: 22
<212> TYPE: DNA
<213> ORGANISM: Artificial Sequence
<220> FEATURE:
<223> OTHER INFORMATION: Synthetic sequence

<400> SEQUENCE: 37
tcatctgcca agacagaagt tc                                   22

```
<210> SEQ ID NO 38
<211> LENGTH: 20
<212> TYPE: DNA
<213> ORGANISM: Artificial Sequence
<220> FEATURE:
<223> OTHER INFORMATION: Synthetic sequence

<400> SEQUENCE: 38
gcaggagagt caaaggtctg                                              20

<210> SEQ ID NO 39
<211> LENGTH: 20
<212> TYPE: DNA
<213> ORGANISM: Artificial Sequence
<220> FEATURE:
<223> OTHER INFORMATION: Synthetic sequence

<400> SEQUENCE: 39
gttgccatgg agattgttgc                                              20

<210> SEQ ID NO 40
<211> LENGTH: 20
<212> TYPE: DNA
<213> ORGANISM: Artificial Sequence
<220> FEATURE:
<223> OTHER INFORMATION: Synthetic sequence

<400> SEQUENCE: 40
cagctcagtg atgtcattgc                                              20

<210> SEQ ID NO 41
<211> LENGTH: 21
<212> TYPE: DNA
<213> ORGANISM: Artificial Sequence
<220> FEATURE:
<223> OTHER INFORMATION: Synthetic sequence

<400> SEQUENCE: 41
ccttgacctc tgctaatgtg g                                            21

<210> SEQ ID NO 42
<211> LENGTH: 20
<212> TYPE: DNA
<213> ORGANISM: Artificial Sequence
<220> FEATURE:
<223> OTHER INFORMATION: Synthetic sequence

<400> SEQUENCE: 42
cacctgtcca acagctacag                                              20

<210> SEQ ID NO 43
<211> LENGTH: 21
<212> TYPE: DNA
<213> ORGANISM: Artificial Sequence
<220> FEATURE:
<223> OTHER INFORMATION: Synthetic sequence

<400> SEQUENCE: 43
agaatgtatc ttcaggcctg c                                            21

<210> SEQ ID NO 44
<211> LENGTH: 20
<212> TYPE: DNA
<213> ORGANISM: Artificial Sequence
<220> FEATURE:
<223> OTHER INFORMATION: Synthetic sequence
```

<400> SEQUENCE: 44
aagtaatcac tctgggtggc                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic sequence

<400> SEQUENCE: 45
agctcacaga caaccttgtg                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic sequence

<400> SEQUENCE: 46
gcaatagaca cctacaggcg                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic sequence

<400> SEQUENCE: 47
gcacattatc aaaggccacg                                              20

<210> SEQ ID NO 48
<211> LENGTH: 20
<212> TYPE: DNA
<213> ORGANISM: Artificial Sequence
<220> FEATURE:
<223> OTHER INFORMATION: Synthetic sequence

<400> SEQUENCE: 48
caacgaccta aagcatgtgc                                              20

<210> SEQ ID NO 49
<211> LENGTH: 20
<212> TYPE: DNA
<213> ORGANISM: Artificial Sequence
<220> FEATURE:
<223> OTHER INFORMATION: Synthetic sequence

<400> SEQUENCE: 49
gacatacatg gctttggcag                                              20

<210> SEQ ID NO 50
<211> LENGTH: 22
<212> TYPE: DNA
<213> ORGANISM: Artificial Sequence
<220> FEATURE:
<223> OTHER INFORMATION: Synthetic sequence

<400> SEQUENCE: 50
gagatactgc cacttatgca cg                                           22

```
<210> SEQ ID NO 51
<211> LENGTH: 20
<212> TYPE: DNA
<213> ORGANISM: Artificial Sequence
<220> FEATURE:
<223> OTHER INFORMATION: Synthetic sequence

<400> SEQUENCE: 51
cgtgctaata gtctcagggc                                          20

<210> SEQ ID NO 52
<211> LENGTH: 20
<212> TYPE: DNA
<213> ORGANISM: Artificial Sequence
<220> FEATURE:
<223> OTHER INFORMATION: Synthetic sequence

<400> SEQUENCE: 52
cgacgcttca ttgcttcatt                                          20

<210> SEQ ID NO 53
<211> LENGTH: 20
<212> TYPE: DNA
<213> ORGANISM: Artificial Sequence
<220> FEATURE:
<223> OTHER INFORMATION: Synthetic sequence

<400> SEQUENCE: 53
cttgcgccaa acaattgtcc                                          20

<210> SEQ ID NO 54
<211> LENGTH: 20
<212> TYPE: DNA
<213> ORGANISM: Artificial Sequence
<220> FEATURE:
<223> OTHER INFORMATION: Synthetic sequence

<400> SEQUENCE: 54
gctgcagagt ttgcattcat                                          20

<210> SEQ ID NO 55
<211> LENGTH: 21
<212> TYPE: DNA
<213> ORGANISM: Artificial Sequence
<220> FEATURE:
<223> OTHER INFORMATION: Synthetic sequence

<400> SEQUENCE: 55
catacacaca gaccgagagt c                                        21

<210> SEQ ID NO 56
<211> LENGTH: 20
<212> TYPE: DNA
<213> ORGANISM: Artificial Sequence
<220> FEATURE:
<223> OTHER INFORMATION: Synthetic sequence

<400> SEQUENCE: 56
ggatgtcagc cagcataagt                                          20

<210> SEQ ID NO 57
<211> LENGTH: 20
<212> TYPE: DNA
<213> ORGANISM: Artificial Sequence
<220> FEATURE:
<223> OTHER INFORMATION: Synthetic sequence
```

<400> SEQUENCE: 57
gcaagtgcca aacagttctc                                                       20

<210> SEQ ID NO 58
<211> LENGTH: 21
<212> TYPE: DNA
<213> ORGANISM: Artificial Sequence
<220> FEATURE:
<223> OTHER INFORMATION: Synthetic sequence

<400> SEQUENCE: 58
gattccagca cacttgagtc t                                                     21

<210> SEQ ID NO 59
<211> LENGTH: 20
<212> TYPE: DNA
<213> ORGANISM: Artificial Sequence
<220> FEATURE:
<223> OTHER INFORMATION: Synthetic sequence

<400> SEQUENCE: 59
ccgttgcagg tttaaatggc                                                       20

<210> SEQ ID NO 60
<211> LENGTH: 20
<212> TYPE: DNA
<213> ORGANISM: Artificial Sequence
<220> FEATURE:
<223> OTHER INFORMATION: Synthetic sequence

<400> SEQUENCE: 60
caagagtgct ttatgggcct                                                       20

<210> SEQ ID NO 61
<211> LENGTH: 21
<212> TYPE: DNA
<213> ORGANISM: Artificial Sequence
<220> FEATURE:
<223> OTHER INFORMATION: Synthetic sequence

<400> SEQUENCE: 61
gcactcaagg agatcagact g                                                     21

<210> SEQ ID NO 62
<211> LENGTH: 21
<212> TYPE: DNA
<213> ORGANISM: Artificial Sequence
<220> FEATURE:
<223> OTHER INFORMATION: Synthetic sequence

<400> SEQUENCE: 62
ggctatcgaa ctacaaccac a                                                     21

<210> SEQ ID NO 63
<211> LENGTH: 21
<212> TYPE: DNA
<213> ORGANISM: Artificial Sequence
<220> FEATURE:
<223> OTHER INFORMATION: Synthetic sequence

<400> SEQUENCE: 63
gtagctgtct gtggtgtgat c                                                     21

```
<210> SEQ ID NO 64
<211> LENGTH: 22
<212> TYPE: DNA
<213> ORGANISM: Artificial Sequence
<220> FEATURE:
<223> OTHER INFORMATION: Synthetic sequence

<400> SEQUENCE: 64
caagaaactt cgagccttag ca                                              22

<210> SEQ ID NO 65
<211> LENGTH: 20
<212> TYPE: DNA
<213> ORGANISM: Artificial Sequence
<220> FEATURE:
<223> OTHER INFORMATION: Synthetic sequence

<400> SEQUENCE: 65
gtgaaccagt ccgagtgaaa                                                 20

<210> SEQ ID NO 66
<211> LENGTH: 21
<212> TYPE: DNA
<213> ORGANISM: Artificial Sequence
<220> FEATURE:
<223> OTHER INFORMATION: Synthetic sequence

<400> SEQUENCE: 66
gcaaatgatg ttcagcacca c                                               21

<210> SEQ ID NO 67
<211> LENGTH: 20
<212> TYPE: DNA
<213> ORGANISM: Artificial Sequence
<220> FEATURE:
<223> OTHER INFORMATION: Synthetic sequence

<400> SEQUENCE: 67
ttcctccacc gaacgtgtct                                                 20

<210> SEQ ID NO 68
<211> LENGTH: 20
<212> TYPE: DNA
<213> ORGANISM: Artificial Sequence
<220> FEATURE:
<223> OTHER INFORMATION: Synthetic sequence

<400> SEQUENCE: 68
gccctattgc aagccctctt                                                 20

<210> SEQ ID NO 69
<211> LENGTH: 40
<212> TYPE: DNA
<213> ORGANISM: Artificial Sequence
<220> FEATURE:
<223> OTHER INFORMATION: Synthetic sequence

<400> SEQUENCE: 69
ttcctccacc gaacgtgtct agaccagcac aacttactcg                           40

<210> SEQ ID NO 70
<211> LENGTH: 37
<212> TYPE: DNA
<213> ORGANISM: Artificial Sequence
<220> FEATURE:
<223> OTHER INFORMATION: Synthetic sequence
```

<400> SEQUENCE: 70
ttcctccacc gaacgtgtct ccaaatgcac ctgcctg                                37

<210> SEQ ID NO 71
<211> LENGTH: 41
<212> TYPE: DNA
<213> ORGANISM: Artificial Sequence
<220> FEATURE:
<223> OTHER INFORMATION: Synthetic sequence

<400> SEQUENCE: 71
ttcctccacc gaacgtgtct agtttggaca aaggcaattc g                           41

<210> SEQ ID NO 72
<211> LENGTH: 44
<212> TYPE: DNA
<213> ORGANISM: Artificial Sequence
<220> FEATURE:
<223> OTHER INFORMATION: Synthetic sequence

<400> SEQUENCE: 72
ttcctccacc gaacgtgtct tgagcttagc caatatcaag aagg                        44

<210> SEQ ID NO 73
<211> LENGTH: 42
<212> TYPE: DNA
<213> ORGANISM: Artificial Sequence
<220> FEATURE:
<223> OTHER INFORMATION: Synthetic sequence

<400> SEQUENCE: 73
ttcctccacc gaacgtgtct acgtgaactt tccttggtac ac                          42

<210> SEQ ID NO 74
<211> LENGTH: 44
<212> TYPE: DNA
<213> ORGANISM: Artificial Sequence
<220> FEATURE:
<223> OTHER INFORMATION: Synthetic sequence

<400> SEQUENCE: 74
ttcctccacc gaacgtgtct tgaagatgtt ctaataccct gccg                        44

<210> SEQ ID NO 75
<211> LENGTH: 38
<212> TYPE: DNA
<213> ORGANISM: Artificial Sequence
<220> FEATURE:
<223> OTHER INFORMATION: Synthetic sequence

<400> SEQUENCE: 75
ttcctccacc gaacgtgtct cagtgtggag actgaacg                               38

<210> SEQ ID NO 76
<211> LENGTH: 43
<212> TYPE: DNA
<213> ORGANISM: Artificial Sequence
<220> FEATURE:
<223> OTHER INFORMATION: Synthetic sequence

<400> SEQUENCE: 76
ttcctccacc gaacgtgtct aggcagggta atgtcatgaa atg                         43

<210> SEQ ID NO 77
<211> LENGTH: 37
<212> TYPE: DNA
<213> ORGANISM: Artificial Sequence
<220> FEATURE:
<223> OTHER INFORMATION: Synthetic sequence

<400> SEQUENCE: 77
ttcctccacc gaacgtgtct gattgtctgg agcgctg        37

<210> SEQ ID NO 78
<211> LENGTH: 36
<212> TYPE: DNA
<213> ORGANISM: Artificial Sequence
<220> FEATURE:
<223> OTHER INFORMATION: Synthetic sequence

<400> SEQUENCE: 78
ttcctccacc gaacgtgtct agggagcaat aggccg        36

<210> SEQ ID NO 79
<211> LENGTH: 37
<212> TYPE: DNA
<213> ORGANISM: Artificial Sequence
<220> FEATURE:
<223> OTHER INFORMATION: Synthetic sequence

<400> SEQUENCE: 79
ttcctccacc gaacgtgtct ctgcagggta caacacg        37

<210> SEQ ID NO 80
<211> LENGTH: 38
<212> TYPE: DNA
<213> ORGANISM: Artificial Sequence
<220> FEATURE:
<223> OTHER INFORMATION: Synthetic sequence

<400> SEQUENCE: 80
ttcctccacc gaacgtgtct cgtatctggg aagacggc        38

<210> SEQ ID NO 81
<211> LENGTH: 40
<212> TYPE: DNA
<213> ORGANISM: Artificial Sequence
<220> FEATURE:
<223> OTHER INFORMATION: Synthetic sequence

<400> SEQUENCE: 81
ttcctccacc gaacgtgtct cctgtaatcc cttgcaatgc        40

<210> SEQ ID NO 82
<211> LENGTH: 38
<212> TYPE: DNA
<213> ORGANISM: Artificial Sequence
<220> FEATURE:
<223> OTHER INFORMATION: Synthetic sequence

<400> SEQUENCE: 82
ttcctccacc gaacgtgtct ggtctcagca cggttctg        38

<210> SEQ ID NO 83
<211> LENGTH: 37
<212> TYPE: DNA
<213> ORGANISM: Artificial Sequence
<220> FEATURE:
<223> OTHER INFORMATION: Synthetic sequence

```
<400> SEQUENCE: 83
ttcctccacc gaacgtgtct gcacctccct accacac                              37

<210> SEQ ID NO 84
<211> LENGTH: 41
<212> TYPE: DNA
<213> ORGANISM: Artificial Sequence
<220> FEATURE:
<223> OTHER INFORMATION: Synthetic sequence

<400> SEQUENCE: 84
ttcctccacc gaacgtgtct gcctctagct agagagaagt c                         41

<210> SEQ ID NO 85
<211> LENGTH: 39
<212> TYPE: DNA
<213> ORGANISM: Artificial Sequence
<220> FEATURE:
<223> OTHER INFORMATION: Synthetic sequence

<400> SEQUENCE: 85
ttcctccacc gaacgtgtct ctggcagtct agccgttac                            39

<210> SEQ ID NO 86
<211> LENGTH: 43
<212> TYPE: DNA
<213> ORGANISM: Artificial Sequence
<220> FEATURE:
<223> OTHER INFORMATION: Synthetic sequence

<400> SEQUENCE: 86
ttcctccacc gaacgtgtct tgtcttagaa tttggcaact ggc                       43

<210> SEQ ID NO 87
<211> LENGTH: 39
<212> TYPE: DNA
<213> ORGANISM: Artificial Sequence
<220> FEATURE:
<223> OTHER INFORMATION: Synthetic sequence

<400> SEQUENCE: 87
ttcctccacc gaacgtgtct gcaggaaagc ctactgaac                            39

<210> SEQ ID NO 88
<211> LENGTH: 39
<212> TYPE: DNA
<213> ORGANISM: Artificial Sequence
<220> FEATURE:
<223> OTHER INFORMATION: Synthetic sequence

<400> SEQUENCE: 88
ttcctccacc gaacgtgtct gggagccaga gaaatgtcc                            39

<210> SEQ ID NO 89
<211> LENGTH: 44
<212> TYPE: DNA
<213> ORGANISM: Artificial Sequence
<220> FEATURE:
<223> OTHER INFORMATION: Synthetic sequence

<400> SEQUENCE: 89
ttcctccacc gaacgtgtct tgtctccagt tccacttcat ttag                      44
```

```
<210> SEQ ID NO 90
<211> LENGTH: 39
<212> TYPE: DNA
<213> ORGANISM: Artificial Sequence
<220> FEATURE:
<223> OTHER INFORMATION: Synthetic sequence

<400> SEQUENCE: 90
ttcctccacc gaacgtgtct cccgttaatt gcctactcg                              39

<210> SEQ ID NO 91
<211> LENGTH: 38
<212> TYPE: DNA
<213> ORGANISM: Artificial Sequence
<220> FEATURE:
<223> OTHER INFORMATION: Synthetic sequence

<400> SEQUENCE: 91
ttcctccacc gaacgtgtct ctcggtccca ctggaaag                               38

<210> SEQ ID NO 92
<211> LENGTH: 41
<212> TYPE: DNA
<213> ORGANISM: Artificial Sequence
<220> FEATURE:
<223> OTHER INFORMATION: Synthetic sequence

<400> SEQUENCE: 92
ttcctccacc gaacgtgtct acacccatga ttcagttact g                           41

<210> SEQ ID NO 93
<211> LENGTH: 41
<212> TYPE: DNA
<213> ORGANISM: Artificial Sequence
<220> FEATURE:
<223> OTHER INFORMATION: Synthetic sequence

<400> SEQUENCE: 93
ttcctccacc gaacgtgtct gctagtatga acatcacagg c                           41

<210> SEQ ID NO 94
<211> LENGTH: 43
<212> TYPE: DNA
<213> ORGANISM: Artificial Sequence
<220> FEATURE:
<223> OTHER INFORMATION: Synthetic sequence

<400> SEQUENCE: 94
ttcctccacc gaacgtgtct acaaatgagt aagaagcgag tcg                         43

<210> SEQ ID NO 95
<211> LENGTH: 38
<212> TYPE: DNA
<213> ORGANISM: Artificial Sequence
<220> FEATURE:
<223> OTHER INFORMATION: Synthetic sequence

<400> SEQUENCE: 95
ttcctccacc gaacgtgtct gataagggtt gctctgcg                               38

<210> SEQ ID NO 96
<211> LENGTH: 37
<212> TYPE: DNA
<213> ORGANISM: Artificial Sequence
<220> FEATURE:
<223> OTHER INFORMATION: Synthetic sequence
```

```
<400> SEQUENCE: 96
ttcctccacc gaacgtgtct ccatgcacca gctaccc                              37

<210> SEQ ID NO 97
<211> LENGTH: 40
<212> TYPE: DNA
<213> ORGANISM: Artificial Sequence
<220> FEATURE:
<223> OTHER INFORMATION: Synthetic sequence

<400> SEQUENCE: 97
ttcctccacc gaacgtgtct aactgtaccc tactcccagc                           40

<210> SEQ ID NO 98
<211> LENGTH: 41
<212> TYPE: DNA
<213> ORGANISM: Artificial Sequence
<220> FEATURE:
<223> OTHER INFORMATION: Synthetic sequence

<400> SEQUENCE: 98
ttcctccacc gaacgtgtct aggaccaagg gaccagttta g                         41

<210> SEQ ID NO 99
<211> LENGTH: 42
<212> TYPE: DNA
<213> ORGANISM: Artificial Sequence
<220> FEATURE:
<223> OTHER INFORMATION: Synthetic sequence

<400> SEQUENCE: 99
ttcctccacc gaacgtgtct agagttcctc caagaaattg cg                        42

<210> SEQ ID NO 100
<211> LENGTH: 44
<212> TYPE: DNA
<213> ORGANISM: Artificial Sequence
<220> FEATURE:
<223> OTHER INFORMATION: Synthetic sequence

<400> SEQUENCE: 100
ttcctccacc gaacgtgtct acattataca gcatgctggc tatc                      44

<210> SEQ ID NO 101
<211> LENGTH: 41
<212> TYPE: DNA
<213> ORGANISM: Artificial Sequence
<220> FEATURE:
<223> OTHER INFORMATION: Synthetic sequence

<400> SEQUENCE: 101
ttcctccacc gaacgtgtct gaggaagaaa gtgaggtttg c                         41

<210> SEQ ID NO 102
<211> LENGTH: 44
<212> TYPE: DNA
<213> ORGANISM: Artificial Sequence
<220> FEATURE:
<223> OTHER INFORMATION: Synthetic sequence

<400> SEQUENCE: 102
ttcctccacc gaacgtgtct ctgaattatg tgcttaccaa gagc                      44
```

<210> SEQ ID NO 103
<211> LENGTH: 44
<212> TYPE: DNA
<213> ORGANISM: Artificial Sequence
<220> FEATURE:
<223> OTHER INFORMATION: Synthetic sequence

<400> SEQUENCE: 103
ttcctccacc gaacgtgtct tgggttctga taaccttatc aagc                44

<210> SEQ ID NO 104
<211> LENGTH: 39
<212> TYPE: DNA
<213> ORGANISM: Artificial Sequence
<220> FEATURE:
<223> OTHER INFORMATION: Synthetic sequence

<400> SEQUENCE: 104
ttcctccacc gaacgtgtct ggttagtcaa acatgctgc                      39

<210> SEQ ID NO 105
<211> LENGTH: 42
<212> TYPE: DNA
<213> ORGANISM: Artificial Sequence
<220> FEATURE:
<223> OTHER INFORMATION: Synthetic sequence

<400> SEQUENCE: 105
ttcctccacc gaacgtgtct gacactggca gaatcaaatc ac                  42

<210> SEQ ID NO 106
<211> LENGTH: 44
<212> TYPE: DNA
<213> ORGANISM: Artificial Sequence
<220> FEATURE:
<223> OTHER INFORMATION: Synthetic sequence

<400> SEQUENCE: 106
ttcctccacc gaacgtgtct agagttacac ctttagctaa ccac                44

<210> SEQ ID NO 107
<211> LENGTH: 38
<212> TYPE: DNA
<213> ORGANISM: Artificial Sequence
<220> FEATURE:
<223> OTHER INFORMATION: Synthetic sequence

<400> SEQUENCE: 107
ttcctccacc gaacgtgtct ccaggagttc aagaagcg                       38

<210> SEQ ID NO 108
<211> LENGTH: 41
<212> TYPE: DNA
<213> ORGANISM: Artificial Sequence
<220> FEATURE:
<223> OTHER INFORMATION: Synthetic sequence

<400> SEQUENCE: 108
ttcctccacc gaacgtgtct accactcctt tctcccatct c                   41

<210> SEQ ID NO 109
<211> LENGTH: 44
<212> TYPE: DNA
<213> ORGANISM: Artificial Sequence
<220> FEATURE:
<223> OTHER INFORMATION: Synthetic sequence

<400> SEQUENCE: 109
ttcctccacc gaacgtgtct gtcttatggg acaatggttg atag        44

<210> SEQ ID NO 110
<211> LENGTH: 38
<212> TYPE: DNA
<213> ORGANISM: Artificial Sequence
<220> FEATURE:
<223> OTHER INFORMATION: Synthetic sequence

<400> SEQUENCE: 110
ttcctccacc gaacgtgtct ctaccctcaa ccctcgtc              38

<210> SEQ ID NO 111
<211> LENGTH: 38
<212> TYPE: DNA
<213> ORGANISM: Artificial Sequence
<220> FEATURE:
<223> OTHER INFORMATION: Synthetic sequence

<400> SEQUENCE: 111
ttcctccacc gaacgtgtct ccaagactga tcatgccg              38

<210> SEQ ID NO 112
<211> LENGTH: 40
<212> TYPE: DNA
<213> ORGANISM: Artificial Sequence
<220> FEATURE:
<223> OTHER INFORMATION: Synthetic sequence

<400> SEQUENCE: 112
gccctattgc aagccctctt agaccagcac aacttactta            40

<210> SEQ ID NO 113
<211> LENGTH: 37
<212> TYPE: DNA
<213> ORGANISM: Artificial Sequence
<220> FEATURE:
<223> OTHER INFORMATION: Synthetic sequence

<400> SEQUENCE: 113
gccctattgc aagccctctt ccaaattcac ctgccca               37

<210> SEQ ID NO 114
<211> LENGTH: 41
<212> TYPE: DNA
<213> ORGANISM: Artificial Sequence
<220> FEATURE:
<223> OTHER INFORMATION: Synthetic sequence

<400> SEQUENCE: 114
gccctattgc aagccctctt agtttggaca aaggcgattt a          41

<210> SEQ ID NO 115
<211> LENGTH: 44
<212> TYPE: DNA
<213> ORGANISM: Artificial Sequence
<220> FEATURE:
<223> OTHER INFORMATION: Synthetic sequence

<400> SEQUENCE: 115
gccctattgc aagccctctt tgagcttagc caatatcaac aaga       44

```
<210> SEQ ID NO 116
<211> LENGTH: 42
<212> TYPE: DNA
<213> ORGANISM: Artificial Sequence
<220> FEATURE:
<223> OTHER INFORMATION: Synthetic sequence

<400> SEQUENCE: 116
gccctattgc aagccctctt acgtgaactt tccttggtaa at               42

<210> SEQ ID NO 117
<211> LENGTH: 44
<212> TYPE: DNA
<213> ORGANISM: Artificial Sequence
<220> FEATURE:
<223> OTHER INFORMATION: Synthetic sequence

<400> SEQUENCE: 117
gccctattgc aagccctctt tgaagatgtt ctaatacctt gcta             44

<210> SEQ ID NO 118
<211> LENGTH: 38
<212> TYPE: DNA
<213> ORGANISM: Artificial Sequence
<220> FEATURE:
<223> OTHER INFORMATION: Synthetic sequence

<400> SEQUENCE: 118
gccctattgc aagccctctt cagtgtggag accgaaca                    38

<210> SEQ ID NO 119
<211> LENGTH: 43
<212> TYPE: DNA
<213> ORGANISM: Artificial Sequence
<220> FEATURE:
<223> OTHER INFORMATION: Synthetic sequence

<400> SEQUENCE: 119
gccctattgc aagccctctt aggcagggta atgtcatgaa gtt              43

<210> SEQ ID NO 120
<211> LENGTH: 37
<212> TYPE: DNA
<213> ORGANISM: Artificial Sequence
<220> FEATURE:
<223> OTHER INFORMATION: Synthetic sequence

<400> SEQUENCE: 120
gccctattgc aagccctctt gattgtctgg agggctc                     37

<210> SEQ ID NO 121
<211> LENGTH: 36
<212> TYPE: DNA
<213> ORGANISM: Artificial Sequence
<220> FEATURE:
<223> OTHER INFORMATION: Synthetic sequence

<400> SEQUENCE: 121
gccctattgc aagccctctt agggagcaat aggcta                      36

<210> SEQ ID NO 122
<211> LENGTH: 37
<212> TYPE: DNA
<213> ORGANISM: Artificial Sequence
<220> FEATURE:
<223> OTHER INFORMATION: Synthetic sequence
```

<400> SEQUENCE: 122
gccctattgc aagccctctt ctgcagggta caagaca                                    37

<210> SEQ ID NO 123
<211> LENGTH: 38
<212> TYPE: DNA
<213> ORGANISM: Artificial Sequence
<220> FEATURE:
<223> OTHER INFORMATION: Synthetic sequence

<400> SEQUENCE: 123
gccctattgc aagccctctt cgtatctggg aagatggg                                   38

<210> SEQ ID NO 124
<211> LENGTH: 40
<212> TYPE: DNA
<213> ORGANISM: Artificial Sequence
<220> FEATURE:
<223> OTHER INFORMATION: Synthetic sequence

<400> SEQUENCE: 124
gccctattgc aagccctctt cctgtaatcc cttgcaataa                                 40

<210> SEQ ID NO 125
<211> LENGTH: 38
<212> TYPE: DNA
<213> ORGANISM: Artificial Sequence
<220> FEATURE:
<223> OTHER INFORMATION: Synthetic sequence

<400> SEQUENCE: 125
gccctattgc aagccctctt ggtctcagca cggtcctt                                   38

<210> SEQ ID NO 126
<211> LENGTH: 37
<212> TYPE: DNA
<213> ORGANISM: Artificial Sequence
<220> FEATURE:
<223> OTHER INFORMATION: Synthetic sequence

<400> SEQUENCE: 126
gccctattgc aagccctctt gcacctccct atcacat                                    37

<210> SEQ ID NO 127
<211> LENGTH: 41
<212> TYPE: DNA
<213> ORGANISM: Artificial Sequence
<220> FEATURE:
<223> OTHER INFORMATION: Synthetic sequence

<400> SEQUENCE: 127
gccctattgc aagccctctt gcctctagct agagagaagc g                               41

<210> SEQ ID NO 128
<211> LENGTH: 39
<212> TYPE: DNA
<213> ORGANISM: Artificial Sequence
<220> FEATURE:
<223> OTHER INFORMATION: Synthetic sequence

<400> SEQUENCE: 128
gccctattgc aagccctctt ctggcagtct agccattat                                  39

```
<210> SEQ ID NO 129
<211> LENGTH: 43
<212> TYPE: DNA
<213> ORGANISM: Artificial Sequence
<220> FEATURE:
<223> OTHER INFORMATION: Synthetic sequence

<400> SEQUENCE: 129
gccctattgc aagccctctt tgtcttagaa tttggcaact agt              43

<210> SEQ ID NO 130
<211> LENGTH: 39
<212> TYPE: DNA
<213> ORGANISM: Artificial Sequence
<220> FEATURE:
<223> OTHER INFORMATION: Synthetic sequence

<400> SEQUENCE: 130
gccctattgc aagccctctt gcaggaaagc ctattgaat                   39

<210> SEQ ID NO 131
<211> LENGTH: 39
<212> TYPE: DNA
<213> ORGANISM: Artificial Sequence
<220> FEATURE:
<223> OTHER INFORMATION: Synthetic sequence

<400> SEQUENCE: 131
gccctattgc aagccctctt gggagccaga gaaatttct                   39

<210> SEQ ID NO 132
<211> LENGTH: 44
<212> TYPE: DNA
<213> ORGANISM: Artificial Sequence
<220> FEATURE:
<223> OTHER INFORMATION: Synthetic sequence

<400> SEQUENCE: 132
gccctattgc aagccctctt tgtctccagt tccacttcat gtaa             44

<210> SEQ ID NO 133
<211> LENGTH: 39
<212> TYPE: DNA
<213> ORGANISM: Artificial Sequence
<220> FEATURE:
<223> OTHER INFORMATION: Synthetic sequence

<400> SEQUENCE: 133
gccctattgc aagccctctt cccgttaatt gcctattta                   39

<210> SEQ ID NO 134
<211> LENGTH: 38
<212> TYPE: DNA
<213> ORGANISM: Artificial Sequence
<220> FEATURE:
<223> OTHER INFORMATION: Synthetic sequence

<400> SEQUENCE: 134
gccctattgc aagccctctt ctcggtccca ctgggaaa                    38

<210> SEQ ID NO 135
<211> LENGTH: 41
<212> TYPE: DNA
<213> ORGANISM: Artificial Sequence
<220> FEATURE:
<223> OTHER INFORMATION: Synthetic sequence
```

<400> SEQUENCE: 135
gccctattgc aagccctctt acacccatga ttcagttacc a         41

<210> SEQ ID NO 136
<211> LENGTH: 41
<212> TYPE: DNA
<213> ORGANISM: Artificial Sequence
<220> FEATURE:
<223> OTHER INFORMATION: Synthetic sequence

<400> SEQUENCE: 136
gccctattgc aagccctctt gctagtatga acatcacaag t         41

<210> SEQ ID NO 137
<211> LENGTH: 43
<212> TYPE: DNA
<213> ORGANISM: Artificial Sequence
<220> FEATURE:
<223> OTHER INFORMATION: Synthetic sequence

<400> SEQUENCE: 137
gccctattgc aagccctctt acaaatgagt aagaagcgag tta       43

<210> SEQ ID NO 138
<211> LENGTH: 38
<212> TYPE: DNA
<213> ORGANISM: Artificial Sequence
<220> FEATURE:
<223> OTHER INFORMATION: Synthetic sequence

<400> SEQUENCE: 138
gccctattgc aagccctctt gataagggtt gctctaca             38

<210> SEQ ID NO 139
<211> LENGTH: 37
<212> TYPE: DNA
<213> ORGANISM: Artificial Sequence
<220> FEATURE:
<223> OTHER INFORMATION: Synthetic sequence

<400> SEQUENCE: 139
gccctattgc aagccctctt ccatgcacca gctacta              37

<210> SEQ ID NO 140
<211> LENGTH: 40
<212> TYPE: DNA
<213> ORGANISM: Artificial Sequence
<220> FEATURE:
<223> OTHER INFORMATION: Synthetic sequence

<400> SEQUENCE: 140
gccctattgc aagccctctt aactgtaccc tactcccaat           40

<210> SEQ ID NO 141
<211> LENGTH: 41
<212> TYPE: DNA
<213> ORGANISM: Artificial Sequence
<220> FEATURE:
<223> OTHER INFORMATION: Synthetic sequence

<400> SEQUENCE: 141
gccctattgc aagccctctt aggaccaagg gaccagttca c         41

<210> SEQ ID NO 142
<211> LENGTH: 42
<212> TYPE: DNA
<213> ORGANISM: Artificial Sequence
<220> FEATURE:
<223> OTHER INFORMATION: Synthetic sequence

<400> SEQUENCE: 142
gccctattgc aagccctctt agagttcctc caagaaattg ta        42

<210> SEQ ID NO 143
<211> LENGTH: 44
<212> TYPE: DNA
<213> ORGANISM: Artificial Sequence
<220> FEATURE:
<223> OTHER INFORMATION: Synthetic sequence

<400> SEQUENCE: 143
gccctattgc aagccctctt acattataca gcatgctggt taga      44

<210> SEQ ID NO 144
<211> LENGTH: 41
<212> TYPE: DNA
<213> ORGANISM: Artificial Sequence
<220> FEATURE:
<223> OTHER INFORMATION: Synthetic sequence

<400> SEQUENCE: 144
gccctattgc aagccctctt gaggaagaaa gtgagatttg t          41

<210> SEQ ID NO 145
<211> LENGTH: 44
<212> TYPE: DNA
<213> ORGANISM: Artificial Sequence
<220> FEATURE:
<223> OTHER INFORMATION: Synthetic sequence

<400> SEQUENCE: 145
gccctattgc aagccctctt ctgaattatg tgcttaccag gagt      44

<210> SEQ ID NO 146
<211> LENGTH: 44
<212> TYPE: DNA
<213> ORGANISM: Artificial Sequence
<220> FEATURE:
<223> OTHER INFORMATION: Synthetic sequence

<400> SEQUENCE: 146
gccctattgc aagccctctt tgggttctga taaccttatc aact      44

<210> SEQ ID NO 147
<211> LENGTH: 39
<212> TYPE: DNA
<213> ORGANISM: Artificial Sequence
<220> FEATURE:
<223> OTHER INFORMATION: Synthetic sequence

<400> SEQUENCE: 147
gccctattgc aagccctctt ggttagtcaa acatgttgt            39

<210> SEQ ID NO 148
<211> LENGTH: 42
<212> TYPE: DNA
<213> ORGANISM: Artificial Sequence
<220> FEATURE:
<223> OTHER INFORMATION: Synthetic sequence

```
<400> SEQUENCE: 148
gccctattgc aagccctctt gacactggca gaatcaaacc aa                          42

<210> SEQ ID NO 149
<211> LENGTH: 44
<212> TYPE: DNA
<213> ORGANISM: Artificial Sequence
<220> FEATURE:
<223> OTHER INFORMATION: Synthetic sequence

<400> SEQUENCE: 149
gccctattgc aagccctctt agagttacac ctttagctaa ctag                       44

<210> SEQ ID NO 150
<211> LENGTH: 38
<212> TYPE: DNA
<213> ORGANISM: Artificial Sequence
<220> FEATURE:
<223> OTHER INFORMATION: Synthetic sequence

<400> SEQUENCE: 150
gccctattgc aagccctctt ccaggagttc aaggagca                              38

<210> SEQ ID NO 151
<211> LENGTH: 41
<212> TYPE: DNA
<213> ORGANISM: Artificial Sequence
<220> FEATURE:
<223> OTHER INFORMATION: Synthetic sequence

<400> SEQUENCE: 151
gccctattgc aagccctctt accactcctt tctcccgtct t                          41

<210> SEQ ID NO 152
<211> LENGTH: 44
<212> TYPE: DNA
<213> ORGANISM: Artificial Sequence
<220> FEATURE:
<223> OTHER INFORMATION: Synthetic sequence

<400> SEQUENCE: 152
gccctattgc aagccctctt gtcttatggg acaatggtcg atat                       44

<210> SEQ ID NO 153
<211> LENGTH: 38
<212> TYPE: DNA
<213> ORGANISM: Artificial Sequence
<220> FEATURE:
<223> OTHER INFORMATION: Synthetic sequence

<400> SEQUENCE: 153
gccctattgc aagccctctt ctaccctcaa ccctcatt                              38

<210> SEQ ID NO 154
<211> LENGTH: 38
<212> TYPE: DNA
<213> ORGANISM: Artificial Sequence
<220> FEATURE:
<223> OTHER INFORMATION: Synthetic sequence

<400> SEQUENCE: 154
gccctattgc aagccctctt ccaagactga tcatgcta                              38
```

```
<210> SEQ ID NO 155
<211> LENGTH: 61
<212> TYPE: DNA
<213> ORGANISM: Artificial Sequence
<220> FEATURE:
<223> OTHER INFORMATION: Synthetic sequence

<400> SEQUENCE: 155
cacttgacaa agttctcacg cgccgaagtt ctccgaagga tgccctcatc ttcttccctg      60
c                                                                     61

<210> SEQ ID NO 156
<211> LENGTH: 61
<212> TYPE: DNA
<213> ORGANISM: Artificial Sequence
<220> FEATURE:
<223> OTHER INFORMATION: Synthetic sequence

<400> SEQUENCE: 156
cattagggat taacggcttg ggacagactg acggagcttc agccctcatc ttcttccctg      60
c                                                                     61

<210> SEQ ID NO 157
<211> LENGTH: 63
<212> TYPE: DNA
<213> ORGANISM: Artificial Sequence
<220> FEATURE:
<223> OTHER INFORMATION: Synthetic sequence

<400> SEQUENCE: 157
cacacgttaa gaagactttc tgctgactct gccgcacatg atcgccctca tcttcttccc      60
tgc                                                                   63

<210> SEQ ID NO 158
<211> LENGTH: 62
<212> TYPE: DNA
<213> ORGANISM: Artificial Sequence
<220> FEATURE:
<223> OTHER INFORMATION: Synthetic sequence

<400> SEQUENCE: 158
ctaagtgccc tccatgagaa aggatccgat agccctctgc aggccctcat cttcttccct      60
gc                                                                    62

<210> SEQ ID NO 159
<211> LENGTH: 60
<212> TYPE: DNA
<213> ORGANISM: Artificial Sequence
<220> FEATURE:
<223> OTHER INFORMATION: Synthetic sequence

<400> SEQUENCE: 159
gcacagattt cccacactct caacaggcct gctaaacacc gccctcatct tcttccctgc      60

<210> SEQ ID NO 160
<211> LENGTH: 61
<212> TYPE: DNA
<213> ORGANISM: Artificial Sequence
<220> FEATURE:
<223> OTHER INFORMATION: Synthetic sequence
```

<400> SEQUENCE: 160
cttacaggag gtctggcatc aggtcaacaa ccgagggact cgccctcatc ttcttccctg        60
c                                                                       61

<210> SEQ ID NO 161
<211> LENGTH: 59
<212> TYPE: DNA
<213> ORGANISM: Artificial Sequence
<220> FEATURE:
<223> OTHER INFORMATION: Synthetic sequence

<400> SEQUENCE: 161
ccacaatgag aaggcagagt tgtcattaat gctggcggcg ccctcatctt cttccctgc         59

<210> SEQ ID NO 162
<211> LENGTH: 60
<212> TYPE: DNA
<213> ORGANISM: Artificial Sequence
<220> FEATURE:
<223> OTHER INFORMATION: Synthetic sequence

<400> SEQUENCE: 162
gctgtggcat agctacactc cggtgacggt ttgcaacttt gccctcatct tcttccctgc        60

<210> SEQ ID NO 163
<211> LENGTH: 60
<212> TYPE: DNA
<213> ORGANISM: Artificial Sequence
<220> FEATURE:
<223> OTHER INFORMATION: Synthetic sequence

<400> SEQUENCE: 163
cagggtaatt tgtgggtctg gtccggcagt taagggtctc gccctcatct tcttccctgc        60

<210> SEQ ID NO 164
<211> LENGTH: 62
<212> TYPE: DNA
<213> ORGANISM: Artificial Sequence
<220> FEATURE:
<223> OTHER INFORMATION: Synthetic sequence

<400> SEQUENCE: 164
gggctatcca gaaagataag aatactcaca aacgactgcg cagccctcat cttcttccct        60
gc                                                                      62

<210> SEQ ID NO 165
<211> LENGTH: 63
<212> TYPE: DNA
<213> ORGANISM: Artificial Sequence
<220> FEATURE:
<223> OTHER INFORMATION: Synthetic sequence

<400> SEQUENCE: 165
cataactggt ggagtatttc actcgtatat ggccgactgg agggccctca tcttcttccc        60
tgc                                                                     63

<210> SEQ ID NO 166
<211> LENGTH: 64
<212> TYPE: DNA
<213> ORGANISM: Artificial Sequence
<220> FEATURE:
<223> OTHER INFORMATION: Synthetic sequence

```
<400> SEQUENCE: 166
cttcaaggaa gaaattcaac agggtagggt ttgcggcgat aagggccctc atcttcttcc    60
ctgc                                                                 64

<210> SEQ ID NO 167
<211> LENGTH: 62
<212> TYPE: DNA
<213> ORGANISM: Artificial Sequence
<220> FEATURE:
<223> OTHER INFORMATION: Synthetic sequence

<400> SEQUENCE: 167
catggattca acacagcaaa caccaagtca accacccgag acgccctcat cttcttccct    60
gc                                                                   62

<210> SEQ ID NO 168
<211> LENGTH: 62
<212> TYPE: DNA
<213> ORGANISM: Artificial Sequence
<220> FEATURE:
<223> OTHER INFORMATION: Synthetic sequence

<400> SEQUENCE: 168
ctctgacctc cttcactctt acacttccct ggccttcctt ctgccctcat cttcttccct    60
gc                                                                   62

<210> SEQ ID NO 169
<211> LENGTH: 62
<212> TYPE: DNA
<213> ORGANISM: Artificial Sequence
<220> FEATURE:
<223> OTHER INFORMATION: Synthetic sequence

<400> SEQUENCE: 169
gctttcattt gtgctaaacc tcgcttgggt cctctcctga acgccctcat cttcttccct    60
gc                                                                   62

<210> SEQ ID NO 170
<211> LENGTH: 58
<212> TYPE: DNA
<213> ORGANISM: Artificial Sequence
<220> FEATURE:
<223> OTHER INFORMATION: Synthetic sequence

<400> SEQUENCE: 170
catcccagat gccctcataa cgtccgaacc acaatgctgc cctcatcttc ttccctgc      58

<210> SEQ ID NO 171
<211> LENGTH: 62
<212> TYPE: DNA
<213> ORGANISM: Artificial Sequence
<220> FEATURE:
<223> OTHER INFORMATION: Synthetic sequence

<400> SEQUENCE: 171
gtagaaatcc caaggcaatc agctcctcgc atccaacagt cggccctcat cttcttccct    60
gc                                                                   62

<210> SEQ ID NO 172
<211> LENGTH: 63
<212> TYPE: DNA
<213> ORGANISM: Artificial Sequence
```

<220> FEATURE:
<223> OTHER INFORMATION: Synthetic sequence

<400> SEQUENCE: 172
gaacaactaa ctccacagaa cccccaccgt agcactcctt cttgccctca tcttcttccc    60
tgc                                                                  63

<210> SEQ ID NO 173
<211> LENGTH: 59
<212> TYPE: DNA
<213> ORGANISM: Artificial Sequence
<220> FEATURE:
<223> OTHER INFORMATION: Synthetic sequence

<400> SEQUENCE: 173
gtgcagagga caggaagaac ggagcgtcgg tagtgtaaag ccctcatctt cttccctgc     59

<210> SEQ ID NO 174
<211> LENGTH: 63
<212> TYPE: DNA
<213> ORGANISM: Artificial Sequence
<220> FEATURE:
<223> OTHER INFORMATION: Synthetic sequence

<400> SEQUENCE: 174
ggtgcttcaa gacatacacc ttaacaactc gacgaaccta ccggccctca tcttcttccc    60
tgc                                                                  63

<210> SEQ ID NO 175
<211> LENGTH: 60
<212> TYPE: DNA
<213> ORGANISM: Artificial Sequence
<220> FEATURE:
<223> OTHER INFORMATION: Synthetic sequence

<400> SEQUENCE: 175
ggaacctctg tgaccttgga tggcccatcc ttatgtgctg gccctcatct tcttccctgc    60

<210> SEQ ID NO 176
<211> LENGTH: 59
<212> TYPE: DNA
<213> ORGANISM: Artificial Sequence
<220> FEATURE:
<223> OTHER INFORMATION: Synthetic sequence

<400> SEQUENCE: 176
cccagtggta ccttctgaag gtcgttattg ctcaagcccg ccctcatctt cttccctgc     59

<210> SEQ ID NO 177
<211> LENGTH: 63
<212> TYPE: DNA
<213> ORGANISM: Artificial Sequence
<220> FEATURE:
<223> OTHER INFORMATION: Synthetic sequence

<400> SEQUENCE: 177
cttctgttgc ttatttgggt aacttgattc tggccctccc atcgccctca tcttcttccc    60
tgc                                                                  63

<210> SEQ ID NO 178
<211> LENGTH: 56
<212> TYPE: DNA
<213> ORGANISM: Artificial Sequence

```
<220> FEATURE:
<223> OTHER INFORMATION: Synthetic sequence

<400> SEQUENCE: 178
cccactggat gcctccctca cgccggctat ttaggtgccc tcatcttctt ccctgc      56

<210> SEQ ID NO 179
<211> LENGTH: 58
<212> TYPE: DNA
<213> ORGANISM: Artificial Sequence
<220> FEATURE:
<223> OTHER INFORMATION: Synthetic sequence

<400> SEQUENCE: 179
cggagagacg catctgaaag tctgggtagg tggaggacgc cctcatcttc ttccctgc    58

<210> SEQ ID NO 180
<211> LENGTH: 61
<212> TYPE: DNA
<213> ORGANISM: Artificial Sequence
<220> FEATURE:
<223> OTHER INFORMATION: Synthetic sequence

<400> SEQUENCE: 180
caggatttcc agcttacagg gcgactgagc cacatccaac tgccctcatc ttcttccctg   60
c                                                                  61

<210> SEQ ID NO 181
<211> LENGTH: 60
<212> TYPE: DNA
<213> ORGANISM: Artificial Sequence
<220> FEATURE:
<223> OTHER INFORMATION: Synthetic sequence

<400> SEQUENCE: 181
cttgcaagat gtgcctctta gagcctcagc cggaattgaa gccctcatct tcttccctgc   60

<210> SEQ ID NO 182
<211> LENGTH: 62
<212> TYPE: DNA
<213> ORGANISM: Artificial Sequence
<220> FEATURE:
<223> OTHER INFORMATION: Synthetic sequence

<400> SEQUENCE: 182
gggtggtttc tctaaacaca aattgccatt ctgcaccaat gcgccctcat cttcttccct   60
gc                                                                  62

<210> SEQ ID NO 183
<211> LENGTH: 62
<212> TYPE: DNA
<213> ORGANISM: Artificial Sequence
<220> FEATURE:
<223> OTHER INFORMATION: Synthetic sequence

<400> SEQUENCE: 183
gcagggtatt gagagaagga tctattggtg ttcgcggctg atgccctcat cttcttccct   60
gc                                                                  62

<210> SEQ ID NO 184
<211> LENGTH: 62
<212> TYPE: DNA
<213> ORGANISM: Artificial Sequence
```

```
<220> FEATURE:
<223> OTHER INFORMATION: Synthetic sequence

<400> SEQUENCE: 184
gtgcacattt cttgatgaag ggatgggcgt aacaggagga ctgccctcat cttcttccct    60
gc                                                                  62

<210> SEQ ID NO 185
<211> LENGTH: 62
<212> TYPE: DNA
<213> ORGANISM: Artificial Sequence
<220> FEATURE:
<223> OTHER INFORMATION: Synthetic sequence

<400> SEQUENCE: 185
gagcaatgcc tgtttcatga gaggaatggc ctacctgcat cagccctcat cttcttccct    60
gc                                                                  62

<210> SEQ ID NO 186
<211> LENGTH: 64
<212> TYPE: DNA
<213> ORGANISM: Artificial Sequence
<220> FEATURE:
<223> OTHER INFORMATION: Synthetic sequence

<400> SEQUENCE: 186
gttaacatta tacagcatgg tggccccgtt gttgtcatcg catcgccctc atcttcttcc    60
ctgc                                                                64

<210> SEQ ID NO 187
<211> LENGTH: 59
<212> TYPE: DNA
<213> ORGANISM: Artificial Sequence
<220> FEATURE:
<223> OTHER INFORMATION: Synthetic sequence

<400> SEQUENCE: 187
gcagaacatg tcctgaagcg ttcgatgcgt cccatgagtg ccctcatctt cttccctgc     59

<210> SEQ ID NO 188
<211> LENGTH: 60
<212> TYPE: DNA
<213> ORGANISM: Artificial Sequence
<220> FEATURE:
<223> OTHER INFORMATION: Synthetic sequence

<400> SEQUENCE: 188
cagcttgttc ccaaacccat caacccgcgt agatgttcct gccctcatct tcttccctgc    60

<210> SEQ ID NO 189
<211> LENGTH: 61
<212> TYPE: DNA
<213> ORGANISM: Artificial Sequence
<220> FEATURE:
<223> OTHER INFORMATION: Synthetic sequence

<400> SEQUENCE: 189
caaagtgtgg aagttgcttc cgccagctca agagtgtagc cgccctcatc ttcttccctg    60
c                                                                   61
```

<210> SEQ ID NO 190
<211> LENGTH: 58
<212> TYPE: DNA
<213> ORGANISM: Artificial Sequence
<220> FEATURE:
<223> OTHER INFORMATION: Synthetic sequence

<400> SEQUENCE: 190
ggtcgacttt gtccatcctt cttgatcctg cgcgatgtgc cctcatcttc ttccctgc          58

<210> SEQ ID NO 191
<211> LENGTH: 59
<212> TYPE: DNA
<213> ORGANISM: Artificial Sequence
<220> FEATURE:
<223> OTHER INFORMATION: Synthetic sequence

<400> SEQUENCE: 191
ctctgttgcc tgtggactca tcgcaggcgt tccctatacg ccctcatctt cttccctgc         59

<210> SEQ ID NO 192
<211> LENGTH: 64
<212> TYPE: DNA
<213> ORGANISM: Artificial Sequence
<220> FEATURE:
<223> OTHER INFORMATION: Synthetic sequence

<400> SEQUENCE: 192
ctaactagaa ttagtctgcc tgcctattgg acctccgacc acgagccctc atcttcttcc         60
ctgc                                                                     64

<210> SEQ ID NO 193
<211> LENGTH: 59
<212> TYPE: DNA
<213> ORGANISM: Artificial Sequence
<220> FEATURE:
<223> OTHER INFORMATION: Synthetic sequence

<400> SEQUENCE: 193
gtgagccata atcgtgtcaa gccaccattt agatccgcgg ccctcatctt cttccctgc         59

<210> SEQ ID NO 194
<211> LENGTH: 63
<212> TYPE: DNA
<213> ORGANISM: Artificial Sequence
<220> FEATURE:
<223> OTHER INFORMATION: Synthetic sequence

<400> SEQUENCE: 194
gagaattaat gctccctctc ctggaccagt agaagtctgc ccggccctca tcttcttccc         60
tgc                                                                      63

<210> SEQ ID NO 195
<211> LENGTH: 59
<212> TYPE: DNA
<213> ORGANISM: Artificial Sequence
<220> FEATURE:
<223> OTHER INFORMATION: Synthetic sequence

<400> SEQUENCE: 195
gtggtctgct gttgaccaat ttcagaatgg ccgagctgtg ccctcatctt cttccctgc         59

```
<210> SEQ ID NO 196
<211> LENGTH: 60
<212> TYPE: DNA
<213> ORGANISM: Artificial Sequence
<220> FEATURE:
<223> OTHER INFORMATION: Synthetic sequence

<400> SEQUENCE: 196
ggttgcaact gctgatctat aggtgacctt cttgtacgcc gccctcatct tcttccctgc    60

<210> SEQ ID NO 197
<211> LENGTH: 58
<212> TYPE: DNA
<213> ORGANISM: Artificial Sequence
<220> FEATURE:
<223> OTHER INFORMATION: Synthetic sequence

<400> SEQUENCE: 197
ctttcccagt caaggcaggg cgcgtcctta tttccatcgc cctcatcttc ttccctgc      58

<210> SEQ ID NO 198
<211> LENGTH: 20
<212> TYPE: DNA
<213> ORGANISM: Artificial Sequence
<220> FEATURE:
<223> OTHER INFORMATION: Synthetic sequence

<400> SEQUENCE: 198
agaccagcac aacttactcg                                                20

<210> SEQ ID NO 199
<211> LENGTH: 17
<212> TYPE: DNA
<213> ORGANISM: Artificial Sequence
<220> FEATURE:
<223> OTHER INFORMATION: Synthetic sequence

<400> SEQUENCE: 199
ccaaatgcac ctgcctg                                                   17

<210> SEQ ID NO 200
<211> LENGTH: 21
<212> TYPE: DNA
<213> ORGANISM: Artificial Sequence
<220> FEATURE:
<223> OTHER INFORMATION: Synthetic sequence

<400> SEQUENCE: 200
agtttggaca aaggcaattc g                                              21

<210> SEQ ID NO 201
<211> LENGTH: 24
<212> TYPE: DNA
<213> ORGANISM: Artificial Sequence
<220> FEATURE:
<223> OTHER INFORMATION: Synthetic sequence

<400> SEQUENCE: 201
tgagcttagc caatatcaag aagg                                           24

<210> SEQ ID NO 202
<211> LENGTH: 22
<212> TYPE: DNA
<213> ORGANISM: Artificial Sequence
<220> FEATURE:
<223> OTHER INFORMATION: Synthetic sequence
```

<400> SEQUENCE: 202
acgtgaactt tccttggtac ac                                       22

<210> SEQ ID NO 203
<211> LENGTH: 24
<212> TYPE: DNA
<213> ORGANISM: Artificial Sequence
<220> FEATURE:
<223> OTHER INFORMATION: Synthetic sequence

<400> SEQUENCE: 203
tgaagatgtt ctaatacctt gccg                                     24

<210> SEQ ID NO 204
<211> LENGTH: 18
<212> TYPE: DNA
<213> ORGANISM: Artificial Sequence
<220> FEATURE:
<223> OTHER INFORMATION: Synthetic sequence

<400> SEQUENCE: 204
cagtgtggag actgaacg                                            18

<210> SEQ ID NO 205
<211> LENGTH: 23
<212> TYPE: DNA
<213> ORGANISM: Artificial Sequence
<220> FEATURE:
<223> OTHER INFORMATION: Synthetic sequence

<400> SEQUENCE: 205
aggcagggta atgtcatgaa atg                                      23

<210> SEQ ID NO 206
<211> LENGTH: 17
<212> TYPE: DNA
<213> ORGANISM: Artificial Sequence
<220> FEATURE:
<223> OTHER INFORMATION: Synthetic sequence

<400> SEQUENCE: 206
gattgtctgg agcgctg                                             17

<210> SEQ ID NO 207
<211> LENGTH: 16
<212> TYPE: DNA
<213> ORGANISM: Artificial Sequence
<220> FEATURE:
<223> OTHER INFORMATION: Synthetic sequence

<400> SEQUENCE: 207
agggagcaat aggccg                                              16

<210> SEQ ID NO 208
<211> LENGTH: 17
<212> TYPE: DNA
<213> ORGANISM: Artificial Sequence
<220> FEATURE:
<223> OTHER INFORMATION: Synthetic sequence

<400> SEQUENCE: 208
ctgcagggta caacacg                                             17

```
<210> SEQ ID NO 209
<211> LENGTH: 18
<212> TYPE: DNA
<213> ORGANISM: Artificial Sequence
<220> FEATURE:
<223> OTHER INFORMATION: Synthetic sequence

<400> SEQUENCE: 209
cgtatctggg aagacggc                                                 18

<210> SEQ ID NO 210
<211> LENGTH: 20
<212> TYPE: DNA
<213> ORGANISM: Artificial Sequence
<220> FEATURE:
<223> OTHER INFORMATION: Synthetic sequence

<400> SEQUENCE: 210
cctgtaatcc cttgcaatgc                                               20

<210> SEQ ID NO 211
<211> LENGTH: 18
<212> TYPE: DNA
<213> ORGANISM: Artificial Sequence
<220> FEATURE:
<223> OTHER INFORMATION: Synthetic sequence

<400> SEQUENCE: 211
ggtctcagca cggttctg                                                 18

<210> SEQ ID NO 212
<211> LENGTH: 17
<212> TYPE: DNA
<213> ORGANISM: Artificial Sequence
<220> FEATURE:
<223> OTHER INFORMATION: Synthetic sequence

<400> SEQUENCE: 212
gcacctccct accacac                                                  17

<210> SEQ ID NO 213
<211> LENGTH: 21
<212> TYPE: DNA
<213> ORGANISM: Artificial Sequence
<220> FEATURE:
<223> OTHER INFORMATION: Synthetic sequence

<400> SEQUENCE: 213
gcctctagct agagagaagt c                                             21

<210> SEQ ID NO 214
<211> LENGTH: 19
<212> TYPE: DNA
<213> ORGANISM: Artificial Sequence
<220> FEATURE:
<223> OTHER INFORMATION: Synthetic sequence

<400> SEQUENCE: 214
ctggcagtct agccgttac                                                19

<210> SEQ ID NO 215
<211> LENGTH: 23
<212> TYPE: DNA
<213> ORGANISM: Artificial Sequence
<220> FEATURE:
<223> OTHER INFORMATION: Synthetic sequence
```

```
<400> SEQUENCE: 215
tgtcttagaa tttggcaact ggc                                    23

<210> SEQ ID NO 216
<211> LENGTH: 19
<212> TYPE: DNA
<213> ORGANISM: Artificial Sequence
<220> FEATURE:
<223> OTHER INFORMATION: Synthetic sequence

<400> SEQUENCE: 216
gcaggaaagc ctactgaac                                         19

<210> SEQ ID NO 217
<211> LENGTH: 19
<212> TYPE: DNA
<213> ORGANISM: Artificial Sequence
<220> FEATURE:
<223> OTHER INFORMATION: Synthetic sequence

<400> SEQUENCE: 217
gggagccaga gaaatgtcc                                         19

<210> SEQ ID NO 218
<211> LENGTH: 24
<212> TYPE: DNA
<213> ORGANISM: Artificial Sequence
<220> FEATURE:
<223> OTHER INFORMATION: Synthetic sequence

<400> SEQUENCE: 218
tgtctccagt tccacttcat ttag                                   24

<210> SEQ ID NO 219
<211> LENGTH: 19
<212> TYPE: DNA
<213> ORGANISM: Artificial Sequence
<220> FEATURE:
<223> OTHER INFORMATION: Synthetic sequence

<400> SEQUENCE: 219
cccgttaatt gcctactcg                                         19

<210> SEQ ID NO 220
<211> LENGTH: 18
<212> TYPE: DNA
<213> ORGANISM: Artificial Sequence
<220> FEATURE:
<223> OTHER INFORMATION: Synthetic sequence

<400> SEQUENCE: 220
ctcggtccca ctggaaag                                          18

<210> SEQ ID NO 221
<211> LENGTH: 21
<212> TYPE: DNA
<213> ORGANISM: Artificial Sequence
<220> FEATURE:
<223> OTHER INFORMATION: Synthetic sequence

<400> SEQUENCE: 221
acacccatga ttcagttact g                                      21
```

```
<210> SEQ ID NO 222
<211> LENGTH: 21
<212> TYPE: DNA
<213> ORGANISM: Artificial Sequence
<220> FEATURE:
<223> OTHER INFORMATION: Synthetic sequence

<400> SEQUENCE: 222
gctagtatga acatcacagg c                                              21

<210> SEQ ID NO 223
<211> LENGTH: 23
<212> TYPE: DNA
<213> ORGANISM: Artificial Sequence
<220> FEATURE:
<223> OTHER INFORMATION: Synthetic sequence

<400> SEQUENCE: 223
acaaatgagt aagaagcgag tcg                                            23

<210> SEQ ID NO 224
<211> LENGTH: 18
<212> TYPE: DNA
<213> ORGANISM: Artificial Sequence
<220> FEATURE:
<223> OTHER INFORMATION: Synthetic sequence

<400> SEQUENCE: 224
gataagggtt gctctgcg                                                  18

<210> SEQ ID NO 225
<211> LENGTH: 17
<212> TYPE: DNA
<213> ORGANISM: Artificial Sequence
<220> FEATURE:
<223> OTHER INFORMATION: Synthetic sequence

<400> SEQUENCE: 225
ccatgcacca gctaccc                                                   17

<210> SEQ ID NO 226
<211> LENGTH: 20
<212> TYPE: DNA
<213> ORGANISM: Artificial Sequence
<220> FEATURE:
<223> OTHER INFORMATION: Synthetic sequence

<400> SEQUENCE: 226
aactgtaccc tactcccagc                                                20

<210> SEQ ID NO 227
<211> LENGTH: 21
<212> TYPE: DNA
<213> ORGANISM: Artificial Sequence
<220> FEATURE:
<223> OTHER INFORMATION: Synthetic sequence

<400> SEQUENCE: 227
aggaccaagg gaccagttta g                                              21

<210> SEQ ID NO 228
<211> LENGTH: 22
<212> TYPE: DNA
<213> ORGANISM: Artificial Sequence
<220> FEATURE:
<223> OTHER INFORMATION: Synthetic sequence
```

<400> SEQUENCE: 228
agagttcctc caagaaattg cg                                      22

<210> SEQ ID NO 229
<211> LENGTH: 24
<212> TYPE: DNA
<213> ORGANISM: Artificial Sequence
<220> FEATURE:
<223> OTHER INFORMATION: Synthetic sequence

<400> SEQUENCE: 229
acattataca gcatgctggc tatc                                    24

<210> SEQ ID NO 230
<211> LENGTH: 21
<212> TYPE: DNA
<213> ORGANISM: Artificial Sequence
<220> FEATURE:
<223> OTHER INFORMATION: Synthetic sequence

<400> SEQUENCE: 230
gaggaagaaa gtgaggtttg c                                       21

<210> SEQ ID NO 231
<211> LENGTH: 24
<212> TYPE: DNA
<213> ORGANISM: Artificial Sequence
<220> FEATURE:
<223> OTHER INFORMATION: Synthetic sequence

<400> SEQUENCE: 231
ctgaattatg tgcttaccaa gagc                                    24

<210> SEQ ID NO 232
<211> LENGTH: 24
<212> TYPE: DNA
<213> ORGANISM: Artificial Sequence
<220> FEATURE:
<223> OTHER INFORMATION: Synthetic sequence

<400> SEQUENCE: 232
tgggttctga taaccttatc aagc                                    24

<210> SEQ ID NO 233
<211> LENGTH: 19
<212> TYPE: DNA
<213> ORGANISM: Artificial Sequence
<220> FEATURE:
<223> OTHER INFORMATION: Synthetic sequence

<400> SEQUENCE: 233
ggttagtcaa acatgctgc                                          19

<210> SEQ ID NO 234
<211> LENGTH: 22
<212> TYPE: DNA
<213> ORGANISM: Artificial Sequence
<220> FEATURE:
<223> OTHER INFORMATION: Synthetic sequence

<400> SEQUENCE: 234
gacactggca gaatcaaatc ac                                      22

```
<210> SEQ ID NO 235
<211> LENGTH: 24
<212> TYPE: DNA
<213> ORGANISM: Artificial Sequence
<220> FEATURE:
<223> OTHER INFORMATION: Synthetic sequence

<400> SEQUENCE: 235
agagttacac ctttagctaa ccac                                          24

<210> SEQ ID NO 236
<211> LENGTH: 18
<212> TYPE: DNA
<213> ORGANISM: Artificial Sequence
<220> FEATURE:
<223> OTHER INFORMATION: Synthetic sequence

<400> SEQUENCE: 236
ccaggagttc aagaagcg                                                 18

<210> SEQ ID NO 237
<211> LENGTH: 21
<212> TYPE: DNA
<213> ORGANISM: Artificial Sequence
<220> FEATURE:
<223> OTHER INFORMATION: Synthetic sequence

<400> SEQUENCE: 237
accactcctt tctcccatct c                                             21

<210> SEQ ID NO 238
<211> LENGTH: 24
<212> TYPE: DNA
<213> ORGANISM: Artificial Sequence
<220> FEATURE:
<223> OTHER INFORMATION: Synthetic sequence

<400> SEQUENCE: 238
gtcttatggg acaatggttg atag                                          24

<210> SEQ ID NO 239
<211> LENGTH: 18
<212> TYPE: DNA
<213> ORGANISM: Artificial Sequence
<220> FEATURE:
<223> OTHER INFORMATION: Synthetic sequence

<400> SEQUENCE: 239
ctaccctcaa ccctcgtc                                                 18

<210> SEQ ID NO 240
<211> LENGTH: 18
<212> TYPE: DNA
<213> ORGANISM: Artificial Sequence
<220> FEATURE:
<223> OTHER INFORMATION: Synthetic sequence

<400> SEQUENCE: 240
ccaagactga tcatgccg                                                 18

<210> SEQ ID NO 241
<211> LENGTH: 20
<212> TYPE: DNA
<213> ORGANISM: Artificial Sequence
<220> FEATURE:
<223> OTHER INFORMATION: Synthetic sequence
```

```
<400> SEQUENCE: 241
agaccagcac aacttactta                                              20

<210> SEQ ID NO 242
<211> LENGTH: 17
<212> TYPE: DNA
<213> ORGANISM: Artificial Sequence
<220> FEATURE:
<223> OTHER INFORMATION: Synthetic sequence

<400> SEQUENCE: 242
ccaaattcac ctgccca                                                 17

<210> SEQ ID NO 243
<211> LENGTH: 21
<212> TYPE: DNA
<213> ORGANISM: Artificial Sequence
<220> FEATURE:
<223> OTHER INFORMATION: Synthetic sequence

<400> SEQUENCE: 243
agtttggaca aaggcgattt a                                            21

<210> SEQ ID NO 244
<211> LENGTH: 24
<212> TYPE: DNA
<213> ORGANISM: Artificial Sequence
<220> FEATURE:
<223> OTHER INFORMATION: Synthetic sequence

<400> SEQUENCE: 244
tgagcttagc caatatcaac aaga                                         24

<210> SEQ ID NO 245
<211> LENGTH: 22
<212> TYPE: DNA
<213> ORGANISM: Artificial Sequence
<220> FEATURE:
<223> OTHER INFORMATION: Synthetic sequence

<400> SEQUENCE: 245
acgtgaactt tccttggtaa at                                           22

<210> SEQ ID NO 246
<211> LENGTH: 24
<212> TYPE: DNA
<213> ORGANISM: Artificial Sequence
<220> FEATURE:
<223> OTHER INFORMATION: Synthetic sequence

<400> SEQUENCE: 246
tgaagatgtt ctaatacctt gcta                                         24

<210> SEQ ID NO 247
<211> LENGTH: 18
<212> TYPE: DNA
<213> ORGANISM: Artificial Sequence
<220> FEATURE:
<223> OTHER INFORMATION: Synthetic sequence

<400> SEQUENCE: 247
cagtgtggag accgaaca                                                18
```

```
<210> SEQ ID NO 248
<211> LENGTH: 23
<212> TYPE: DNA
<213> ORGANISM: Artificial Sequence
<220> FEATURE:
<223> OTHER INFORMATION: Synthetic sequence

<400> SEQUENCE: 248
aggcagggta atgtcatgaa gtt                                             23

<210> SEQ ID NO 249
<211> LENGTH: 17
<212> TYPE: DNA
<213> ORGANISM: Artificial Sequence
<220> FEATURE:
<223> OTHER INFORMATION: Synthetic sequence

<400> SEQUENCE: 249
gattgtctgg agggctc                                                    17

<210> SEQ ID NO 250
<211> LENGTH: 16
<212> TYPE: DNA
<213> ORGANISM: Artificial Sequence
<220> FEATURE:
<223> OTHER INFORMATION: Synthetic sequence

<400> SEQUENCE: 250
agggagcaat aggcta                                                     16

<210> SEQ ID NO 251
<211> LENGTH: 17
<212> TYPE: DNA
<213> ORGANISM: Artificial Sequence
<220> FEATURE:
<223> OTHER INFORMATION: Synthetic sequence

<400> SEQUENCE: 251
ctgcagggta caagaca                                                    17

<210> SEQ ID NO 252
<211> LENGTH: 18
<212> TYPE: DNA
<213> ORGANISM: Artificial Sequence
<220> FEATURE:
<223> OTHER INFORMATION: Synthetic sequence

<400> SEQUENCE: 252
cgtatctggg aagatggg                                                   18

<210> SEQ ID NO 253
<211> LENGTH: 20
<212> TYPE: DNA
<213> ORGANISM: Artificial Sequence
<220> FEATURE:
<223> OTHER INFORMATION: Synthetic sequence

<400> SEQUENCE: 253
cctgtaatcc cttgcaataa                                                 20

<210> SEQ ID NO 254
<211> LENGTH: 18
<212> TYPE: DNA
<213> ORGANISM: Artificial Sequence
<220> FEATURE:
<223> OTHER INFORMATION: Synthetic sequence
```

```
<400> SEQUENCE: 254
ggtctcagca cggtcctt                                                    18

<210> SEQ ID NO 255
<211> LENGTH: 17
<212> TYPE: DNA
<213> ORGANISM: Artificial Sequence
<220> FEATURE:
<223> OTHER INFORMATION: Synthetic sequence

<400> SEQUENCE: 255
gcacctccct atcacat                                                     17

<210> SEQ ID NO 256
<211> LENGTH: 21
<212> TYPE: DNA
<213> ORGANISM: Artificial Sequence
<220> FEATURE:
<223> OTHER INFORMATION: Synthetic sequence

<400> SEQUENCE: 256
gcctctagct agagagaagc g                                                21

<210> SEQ ID NO 257
<211> LENGTH: 19
<212> TYPE: DNA
<213> ORGANISM: Artificial Sequence
<220> FEATURE:
<223> OTHER INFORMATION: Synthetic sequence

<400> SEQUENCE: 257
ctggcagtct agccattat                                                   19

<210> SEQ ID NO 258
<211> LENGTH: 23
<212> TYPE: DNA
<213> ORGANISM: Artificial Sequence
<220> FEATURE:
<223> OTHER INFORMATION: Synthetic sequence

<400> SEQUENCE: 258
tgtcttagaa tttggcaact agt                                              23

<210> SEQ ID NO 259
<211> LENGTH: 19
<212> TYPE: DNA
<213> ORGANISM: Artificial Sequence
<220> FEATURE:
<223> OTHER INFORMATION: Synthetic sequence

<400> SEQUENCE: 259
gcaggaaagc ctattgaat                                                   19

<210> SEQ ID NO 260
<211> LENGTH: 19
<212> TYPE: DNA
<213> ORGANISM: Artificial Sequence
<220> FEATURE:
<223> OTHER INFORMATION: Synthetic sequence

<400> SEQUENCE: 260
gggagccaga gaaatttct                                                   19
```

-continued

```
<210> SEQ ID NO 261
<211> LENGTH: 24
<212> TYPE: DNA
<213> ORGANISM: Artificial Sequence
<220> FEATURE:
<223> OTHER INFORMATION: Synthetic sequence

<400> SEQUENCE: 261
tgtctccagt tccacttcat gtaa                                          24

<210> SEQ ID NO 262
<211> LENGTH: 19
<212> TYPE: DNA
<213> ORGANISM: Artificial Sequence
<220> FEATURE:
<223> OTHER INFORMATION: Synthetic sequence

<400> SEQUENCE: 262
cccgttaatt gcctattta                                                19

<210> SEQ ID NO 263
<211> LENGTH: 18
<212> TYPE: DNA
<213> ORGANISM: Artificial Sequence
<220> FEATURE:
<223> OTHER INFORMATION: Synthetic sequence

<400> SEQUENCE: 263
ctcggtccca ctgggaaa                                                 18

<210> SEQ ID NO 264
<211> LENGTH: 21
<212> TYPE: DNA
<213> ORGANISM: Artificial Sequence
<220> FEATURE:
<223> OTHER INFORMATION: Synthetic sequence

<400> SEQUENCE: 264
acacccatga ttcagttacc a                                             21

<210> SEQ ID NO 265
<211> LENGTH: 21
<212> TYPE: DNA
<213> ORGANISM: Artificial Sequence
<220> FEATURE:
<223> OTHER INFORMATION: Synthetic sequence

<400> SEQUENCE: 265
gctagtatga acatcacaag t                                             21

<210> SEQ ID NO 266
<211> LENGTH: 23
<212> TYPE: DNA
<213> ORGANISM: Artificial Sequence
<220> FEATURE:
<223> OTHER INFORMATION: Synthetic sequence

<400> SEQUENCE: 266
acaaatgagt aagaagcgag tta                                           23

<210> SEQ ID NO 267
<211> LENGTH: 18
<212> TYPE: DNA
<213> ORGANISM: Artificial Sequence
<220> FEATURE:
<223> OTHER INFORMATION: Synthetic sequence
```

<400> SEQUENCE: 267
gataagggtt gctctaca                                                 18

<210> SEQ ID NO 268
<211> LENGTH: 17
<212> TYPE: DNA
<213> ORGANISM: Artificial Sequence
<220> FEATURE:
<223> OTHER INFORMATION: Synthetic sequence

<400> SEQUENCE: 268
ccatgcacca gctacta                                                  17

<210> SEQ ID NO 269
<211> LENGTH: 20
<212> TYPE: DNA
<213> ORGANISM: Artificial Sequence
<220> FEATURE:
<223> OTHER INFORMATION: Synthetic sequence

<400> SEQUENCE: 269
aactgtaccc tactcccaat                                               20

<210> SEQ ID NO 270
<211> LENGTH: 21
<212> TYPE: DNA
<213> ORGANISM: Artificial Sequence
<220> FEATURE:
<223> OTHER INFORMATION: Synthetic sequence

<400> SEQUENCE: 270
aggaccaagg gaccagttca c                                             21

<210> SEQ ID NO 271
<211> LENGTH: 22
<212> TYPE: DNA
<213> ORGANISM: Artificial Sequence
<220> FEATURE:
<223> OTHER INFORMATION: Synthetic sequence

<400> SEQUENCE: 271
agagttcctc caagaaattg ta                                            22

<210> SEQ ID NO 272
<211> LENGTH: 24
<212> TYPE: DNA
<213> ORGANISM: Artificial Sequence
<220> FEATURE:
<223> OTHER INFORMATION: Synthetic sequence

<400> SEQUENCE: 272
acattataca gcatgctggt taga                                          24

<210> SEQ ID NO 273
<211> LENGTH: 21
<212> TYPE: DNA
<213> ORGANISM: Artificial Sequence
<220> FEATURE:
<223> OTHER INFORMATION: Synthetic sequence

<400> SEQUENCE: 273
gaggaagaaa gtgagatttg t                                             21

```
<210> SEQ ID NO 274
<211> LENGTH: 24
<212> TYPE: DNA
<213> ORGANISM: Artificial Sequence
<220> FEATURE:
<223> OTHER INFORMATION: Synthetic sequence

<400> SEQUENCE: 274
ctgaattatg tgcttaccag gagt                                          24

<210> SEQ ID NO 275
<211> LENGTH: 24
<212> TYPE: DNA
<213> ORGANISM: Artificial Sequence
<220> FEATURE:
<223> OTHER INFORMATION: Synthetic sequence

<400> SEQUENCE: 275
tgggttctga taaccttatc aact                                          24

<210> SEQ ID NO 276
<211> LENGTH: 19
<212> TYPE: DNA
<213> ORGANISM: Artificial Sequence
<220> FEATURE:
<223> OTHER INFORMATION: Synthetic sequence

<400> SEQUENCE: 276
ggttagtcaa acatgttgt                                                19

<210> SEQ ID NO 277
<211> LENGTH: 22
<212> TYPE: DNA
<213> ORGANISM: Artificial Sequence
<220> FEATURE:
<223> OTHER INFORMATION: Synthetic sequence

<400> SEQUENCE: 277
gacactggca gaatcaaacc aa                                            22

<210> SEQ ID NO 278
<211> LENGTH: 24
<212> TYPE: DNA
<213> ORGANISM: Artificial Sequence
<220> FEATURE:
<223> OTHER INFORMATION: Synthetic sequence

<400> SEQUENCE: 278
agagttacac ctttagctaa ctag                                          24

<210> SEQ ID NO 279
<211> LENGTH: 18
<212> TYPE: DNA
<213> ORGANISM: Artificial Sequence
<220> FEATURE:
<223> OTHER INFORMATION: Synthetic sequence

<400> SEQUENCE: 279
ccaggagttc aaggagca                                                 18

<210> SEQ ID NO 280
<211> LENGTH: 21
<212> TYPE: DNA
<213> ORGANISM: Artificial Sequence
<220> FEATURE:
<223> OTHER INFORMATION: Synthetic sequence
```

<400> SEQUENCE: 280
accactcctt tctcccgtct t                                           21

<210> SEQ ID NO 281
<211> LENGTH: 24
<212> TYPE: DNA
<213> ORGANISM: Artificial Sequence
<220> FEATURE:
<223> OTHER INFORMATION: Synthetic sequence

<400> SEQUENCE: 281
gtcttatggg acaatggtcg atat                                        24

<210> SEQ ID NO 282
<211> LENGTH: 18
<212> TYPE: DNA
<213> ORGANISM: Artificial Sequence
<220> FEATURE:
<223> OTHER INFORMATION: Synthetic sequence

<400> SEQUENCE: 282
ctaccctcaa ccctcatt                                               18

<210> SEQ ID NO 283
<211> LENGTH: 18
<212> TYPE: DNA
<213> ORGANISM: Artificial Sequence
<220> FEATURE:
<223> OTHER INFORMATION: Synthetic sequence

<400> SEQUENCE: 283
ccaagactga tcatgcta                                               18

<210> SEQ ID NO 284
<211> LENGTH: 21
<212> TYPE: DNA
<213> ORGANISM: Artificial Sequence
<220> FEATURE:
<223> OTHER INFORMATION: Synthetic sequence

<400> SEQUENCE: 284
cacttgacaa agttctcacg c                                           21

<210> SEQ ID NO 285
<211> LENGTH: 21
<212> TYPE: DNA
<213> ORGANISM: Artificial Sequence
<220> FEATURE:
<223> OTHER INFORMATION: Synthetic sequence

<400> SEQUENCE: 285
cattagggat taacggcttg g                                           21

<210> SEQ ID NO 286
<211> LENGTH: 23
<212> TYPE: DNA
<213> ORGANISM: Artificial Sequence
<220> FEATURE:
<223> OTHER INFORMATION: Synthetic sequence

<400> SEQUENCE: 286
cacacgttaa gaagactttc tgc                                         23

-continued

```
<210> SEQ ID NO 287
<211> LENGTH: 22
<212> TYPE: DNA
<213> ORGANISM: Artificial Sequence
<220> FEATURE:
<223> OTHER INFORMATION: Synthetic sequence

<400> SEQUENCE: 287
ctaagtgccc tccatgagaa ag                                              22

<210> SEQ ID NO 288
<211> LENGTH: 20
<212> TYPE: DNA
<213> ORGANISM: Artificial Sequence
<220> FEATURE:
<223> OTHER INFORMATION: Synthetic sequence

<400> SEQUENCE: 288
gcacagattt cccacactct                                                 20

<210> SEQ ID NO 289
<211> LENGTH: 21
<212> TYPE: DNA
<213> ORGANISM: Artificial Sequence
<220> FEATURE:
<223> OTHER INFORMATION: Synthetic sequence

<400> SEQUENCE: 289
cttacaggag gtctggcatc a                                               21

<210> SEQ ID NO 290
<211> LENGTH: 19
<212> TYPE: DNA
<213> ORGANISM: Artificial Sequence
<220> FEATURE:
<223> OTHER INFORMATION: Synthetic sequence

<400> SEQUENCE: 290
ccacaatgag aaggcagag                                                  19

<210> SEQ ID NO 291
<211> LENGTH: 20
<212> TYPE: DNA
<213> ORGANISM: Artificial Sequence
<220> FEATURE:
<223> OTHER INFORMATION: Synthetic sequence

<400> SEQUENCE: 291
gctgtggcat agctacactc                                                 20

<210> SEQ ID NO 292
<211> LENGTH: 20
<212> TYPE: DNA
<213> ORGANISM: Artificial Sequence
<220> FEATURE:
<223> OTHER INFORMATION: Synthetic sequence

<400> SEQUENCE: 292
cagggtaatt tgtgggtctg                                                 20

<210> SEQ ID NO 293
<211> LENGTH: 22
<212> TYPE: DNA
<213> ORGANISM: Artificial Sequence
<220> FEATURE:
<223> OTHER INFORMATION: Synthetic sequence
```

```
<400> SEQUENCE: 293
gggctatcca gaaagataag aa                                              22

<210> SEQ ID NO 294
<211> LENGTH: 23
<212> TYPE: DNA
<213> ORGANISM: Artificial Sequence
<220> FEATURE:
<223> OTHER INFORMATION: Synthetic sequence

<400> SEQUENCE: 294
cataactggt ggagtatttc act                                             23

<210> SEQ ID NO 295
<211> LENGTH: 24
<212> TYPE: DNA
<213> ORGANISM: Artificial Sequence
<220> FEATURE:
<223> OTHER INFORMATION: Synthetic sequence

<400> SEQUENCE: 295
cttcaaggaa gaaattcaac aggg                                            24

<210> SEQ ID NO 296
<211> LENGTH: 22
<212> TYPE: DNA
<213> ORGANISM: Artificial Sequence
<220> FEATURE:
<223> OTHER INFORMATION: Synthetic sequence

<400> SEQUENCE: 296
catggattca acacagcaaa ca                                              22

<210> SEQ ID NO 297
<211> LENGTH: 22
<212> TYPE: DNA
<213> ORGANISM: Artificial Sequence
<220> FEATURE:
<223> OTHER INFORMATION: Synthetic sequence

<400> SEQUENCE: 297
ctctgacctc cttcactctt ac                                              22

<210> SEQ ID NO 298
<211> LENGTH: 22
<212> TYPE: DNA
<213> ORGANISM: Artificial Sequence
<220> FEATURE:
<223> OTHER INFORMATION: Synthetic sequence

<400> SEQUENCE: 298
gctttcattt gtgctaaacc tc                                              22

<210> SEQ ID NO 299
<211> LENGTH: 18
<212> TYPE: DNA
<213> ORGANISM: Artificial Sequence
<220> FEATURE:
<223> OTHER INFORMATION: Synthetic sequence

<400> SEQUENCE: 299
catcccagat gccctcat                                                   18
```

-continued

```
<210> SEQ ID NO 300
<211> LENGTH: 22
<212> TYPE: DNA
<213> ORGANISM: Artificial Sequence
<220> FEATURE:
<223> OTHER INFORMATION: Synthetic sequence

<400> SEQUENCE: 300
gtagaaatcc caaggcaatc ag                                              22

<210> SEQ ID NO 301
<211> LENGTH: 23
<212> TYPE: DNA
<213> ORGANISM: Artificial Sequence
<220> FEATURE:
<223> OTHER INFORMATION: Synthetic sequence

<400> SEQUENCE: 301
gaacaactaa ctccacagaa ccc                                             23

<210> SEQ ID NO 302
<211> LENGTH: 19
<212> TYPE: DNA
<213> ORGANISM: Artificial Sequence
<220> FEATURE:
<223> OTHER INFORMATION: Synthetic sequence

<400> SEQUENCE: 302
gtgcagagga caggaagaa                                                  19

<210> SEQ ID NO 303
<211> LENGTH: 23
<212> TYPE: DNA
<213> ORGANISM: Artificial Sequence
<220> FEATURE:
<223> OTHER INFORMATION: Synthetic sequence

<400> SEQUENCE: 303
ggtgcttcaa gacatacacc tta                                             23

<210> SEQ ID NO 304
<211> LENGTH: 20
<212> TYPE: DNA
<213> ORGANISM: Artificial Sequence
<220> FEATURE:
<223> OTHER INFORMATION: Synthetic sequence

<400> SEQUENCE: 304
ggaacctctg tgaccttgga                                                 20

<210> SEQ ID NO 305
<211> LENGTH: 19
<212> TYPE: DNA
<213> ORGANISM: Artificial Sequence
<220> FEATURE:
<223> OTHER INFORMATION: Synthetic sequence

<400> SEQUENCE: 305
cccagtggta ccttctgaa                                                  19

<210> SEQ ID NO 306
<211> LENGTH: 23
<212> TYPE: DNA
<213> ORGANISM: Artificial Sequence
<220> FEATURE:
<223> OTHER INFORMATION: Synthetic sequence
```

<400> SEQUENCE: 306
cttctgttgc ttatttgggt aac								23

<210> SEQ ID NO 307
<211> LENGTH: 16
<212> TYPE: DNA
<213> ORGANISM: Artificial Sequence
<220> FEATURE:
<223> OTHER INFORMATION: Synthetic sequence

<400> SEQUENCE: 307
cccactggat gcctcc								16

<210> SEQ ID NO 308
<211> LENGTH: 18
<212> TYPE: DNA
<213> ORGANISM: Artificial Sequence
<220> FEATURE:
<223> OTHER INFORMATION: Synthetic sequence

<400> SEQUENCE: 308
cggagagacg catctgaa								18

<210> SEQ ID NO 309
<211> LENGTH: 21
<212> TYPE: DNA
<213> ORGANISM: Artificial Sequence
<220> FEATURE:
<223> OTHER INFORMATION: Synthetic sequence

<400> SEQUENCE: 309
caggatttcc agcttacagg g								21

<210> SEQ ID NO 310
<211> LENGTH: 20
<212> TYPE: DNA
<213> ORGANISM: Artificial Sequence
<220> FEATURE:
<223> OTHER INFORMATION: Synthetic sequence

<400> SEQUENCE: 310
cttgcaagat gtgcctctta								20

<210> SEQ ID NO 311
<211> LENGTH: 22
<212> TYPE: DNA
<213> ORGANISM: Artificial Sequence
<220> FEATURE:
<223> OTHER INFORMATION: Synthetic sequence

<400> SEQUENCE: 311
gggtggtttc tctaaacaca aa								22

<210> SEQ ID NO 312
<211> LENGTH: 22
<212> TYPE: DNA
<213> ORGANISM: Artificial Sequence
<220> FEATURE:
<223> OTHER INFORMATION: Synthetic sequence

<400> SEQUENCE: 312
gcagggtatt gagagaagga tc								22

```
<210> SEQ ID NO 313
<211> LENGTH: 22
<212> TYPE: DNA
<213> ORGANISM: Artificial Sequence
<220> FEATURE:
<223> OTHER INFORMATION: Synthetic sequence

<400> SEQUENCE: 313
gtgcacattt cttgatgaag gg                                              22

<210> SEQ ID NO 314
<211> LENGTH: 22
<212> TYPE: DNA
<213> ORGANISM: Artificial Sequence
<220> FEATURE:
<223> OTHER INFORMATION: Synthetic sequence

<400> SEQUENCE: 314
gagcaatgcc tgtttcatga ga                                              22

<210> SEQ ID NO 315
<211> LENGTH: 24
<212> TYPE: DNA
<213> ORGANISM: Artificial Sequence
<220> FEATURE:
<223> OTHER INFORMATION: Synthetic sequence

<400> SEQUENCE: 315
gttaacatta tacagcatgg tggc                                            24

<210> SEQ ID NO 316
<211> LENGTH: 19
<212> TYPE: DNA
<213> ORGANISM: Artificial Sequence
<220> FEATURE:
<223> OTHER INFORMATION: Synthetic sequence

<400> SEQUENCE: 316
gcagaacatg tcctgaagc                                                  19

<210> SEQ ID NO 317
<211> LENGTH: 20
<212> TYPE: DNA
<213> ORGANISM: Artificial Sequence
<220> FEATURE:
<223> OTHER INFORMATION: Synthetic sequence

<400> SEQUENCE: 317
cagcttgttc ccaaacccat                                                 20

<210> SEQ ID NO 318
<211> LENGTH: 21
<212> TYPE: DNA
<213> ORGANISM: Artificial Sequence
<220> FEATURE:
<223> OTHER INFORMATION: Synthetic sequence

<400> SEQUENCE: 318
caaagtgtgg aagttgcttc c                                               21

<210> SEQ ID NO 319
<211> LENGTH: 18
<212> TYPE: DNA
<213> ORGANISM: Artificial Sequence
<220> FEATURE:
<223> OTHER INFORMATION: Synthetic sequence
```

<400> SEQUENCE: 319
ggtcgacttt gtccatcc                                                        18

<210> SEQ ID NO 320
<211> LENGTH: 19
<212> TYPE: DNA
<213> ORGANISM: Artificial Sequence
<220> FEATURE:
<223> OTHER INFORMATION: Synthetic sequence

<400> SEQUENCE: 320
ctctgttgcc tgtggactc                                                       19

<210> SEQ ID NO 321
<211> LENGTH: 24
<212> TYPE: DNA
<213> ORGANISM: Artificial Sequence
<220> FEATURE:
<223> OTHER INFORMATION: Synthetic sequence

<400> SEQUENCE: 321
ctaactagaa ttagtctgcc tgcc                                                 24

<210> SEQ ID NO 322
<211> LENGTH: 19
<212> TYPE: DNA
<213> ORGANISM: Artificial Sequence
<220> FEATURE:
<223> OTHER INFORMATION: Synthetic sequence

<400> SEQUENCE: 322
gtgagccata atcgtgtca                                                       19

<210> SEQ ID NO 323
<211> LENGTH: 23
<212> TYPE: DNA
<213> ORGANISM: Artificial Sequence
<220> FEATURE:
<223> OTHER INFORMATION: Synthetic sequence

<400> SEQUENCE: 323
gagaattaat gctccctctc ctg                                                  23

<210> SEQ ID NO 324
<211> LENGTH: 19
<212> TYPE: DNA
<213> ORGANISM: Artificial Sequence
<220> FEATURE:
<223> OTHER INFORMATION: Synthetic sequence

<400> SEQUENCE: 324
gtggtctgct gttgaccaa                                                       19

<210> SEQ ID NO 325
<211> LENGTH: 20
<212> TYPE: DNA
<213> ORGANISM: Artificial Sequence
<220> FEATURE:
<223> OTHER INFORMATION: Synthetic sequence

<400> SEQUENCE: 325
ggttgcaact gctgatctat                                                      20

```
<210> SEQ ID NO 326
<211> LENGTH: 18
<212> TYPE: DNA
<213> ORGANISM: Artificial Sequence
<220> FEATURE:
<223> OTHER INFORMATION: Synthetic sequence

<400> SEQUENCE: 326
ctttcccagt caaggcag                                                 18

<210> SEQ ID NO 327
<211> LENGTH: 20
<212> TYPE: DNA
<213> ORGANISM: Artificial Sequence
<220> FEATURE:
<223> OTHER INFORMATION: Synthetic sequence

<400> SEQUENCE: 327
gccgaagttc tccgaaggat                                               20

<210> SEQ ID NO 328
<211> LENGTH: 20
<212> TYPE: DNA
<213> ORGANISM: Artificial Sequence
<220> FEATURE:
<223> OTHER INFORMATION: Synthetic sequence

<400> SEQUENCE: 328
gacagactga cggagcttca                                               20

<210> SEQ ID NO 329
<211> LENGTH: 20
<212> TYPE: DNA
<213> ORGANISM: Artificial Sequence
<220> FEATURE:
<223> OTHER INFORMATION: Synthetic sequence

<400> SEQUENCE: 329
tgactctgcc gcacatgatc                                               20

<210> SEQ ID NO 330
<211> LENGTH: 20
<212> TYPE: DNA
<213> ORGANISM: Artificial Sequence
<220> FEATURE:
<223> OTHER INFORMATION: Synthetic sequence

<400> SEQUENCE: 330
gatccgatag ccctctgcag                                               20

<210> SEQ ID NO 331
<211> LENGTH: 20
<212> TYPE: DNA
<213> ORGANISM: Artificial Sequence
<220> FEATURE:
<223> OTHER INFORMATION: Synthetic sequence

<400> SEQUENCE: 331
caacaggcct gctaaacacc                                               20

<210> SEQ ID NO 332
<211> LENGTH: 20
<212> TYPE: DNA
<213> ORGANISM: Artificial Sequence
<220> FEATURE:
<223> OTHER INFORMATION: Synthetic sequence
```

<400> SEQUENCE: 332
ggtcaacaac cgagggactc					20

<210> SEQ ID NO 333
<211> LENGTH: 20
<212> TYPE: DNA
<213> ORGANISM: Artificial Sequence
<220> FEATURE:
<223> OTHER INFORMATION: Synthetic sequence

<400> SEQUENCE: 333
ttgtcattaa tgctggcggc					20

<210> SEQ ID NO 334
<211> LENGTH: 20
<212> TYPE: DNA
<213> ORGANISM: Artificial Sequence
<220> FEATURE:
<223> OTHER INFORMATION: Synthetic sequence

<400> SEQUENCE: 334
cggtgacggt ttgcaacttt					20

<210> SEQ ID NO 335
<211> LENGTH: 20
<212> TYPE: DNA
<213> ORGANISM: Artificial Sequence
<220> FEATURE:
<223> OTHER INFORMATION: Synthetic sequence

<400> SEQUENCE: 335
gtccggcagt taagggtctc					20

<210> SEQ ID NO 336
<211> LENGTH: 20
<212> TYPE: DNA
<213> ORGANISM: Artificial Sequence
<220> FEATURE:
<223> OTHER INFORMATION: Synthetic sequence

<400> SEQUENCE: 336
tactcacaaa cgactgcgca					20

<210> SEQ ID NO 337
<211> LENGTH: 20
<212> TYPE: DNA
<213> ORGANISM: Artificial Sequence
<220> FEATURE:
<223> OTHER INFORMATION: Synthetic sequence

<400> SEQUENCE: 337
cgtatatggc cgactggagg					20

<210> SEQ ID NO 338
<211> LENGTH: 20
<212> TYPE: DNA
<213> ORGANISM: Artificial Sequence
<220> FEATURE:
<223> OTHER INFORMATION: Synthetic sequence

<400> SEQUENCE: 338
tagggtttgc ggcgataagg					20

-continued

```
<210> SEQ ID NO 339
<211> LENGTH: 20
<212> TYPE: DNA
<213> ORGANISM: Artificial Sequence
<220> FEATURE:
<223> OTHER INFORMATION: Synthetic sequence

<400> SEQUENCE: 339
ccaagtcaac cacccgagac                                              20

<210> SEQ ID NO 340
<211> LENGTH: 20
<212> TYPE: DNA
<213> ORGANISM: Artificial Sequence
<220> FEATURE:
<223> OTHER INFORMATION: Synthetic sequence

<400> SEQUENCE: 340
acttccctgg ccttccttct                                              20

<210> SEQ ID NO 341
<211> LENGTH: 20
<212> TYPE: DNA
<213> ORGANISM: Artificial Sequence
<220> FEATURE:
<223> OTHER INFORMATION: Synthetic sequence

<400> SEQUENCE: 341
gcttgggtcc tctcctgaac                                              20

<210> SEQ ID NO 342
<211> LENGTH: 20
<212> TYPE: DNA
<213> ORGANISM: Artificial Sequence
<220> FEATURE:
<223> OTHER INFORMATION: Synthetic sequence

<400> SEQUENCE: 342
aacgtccgaa ccacaatgct                                              20

<210> SEQ ID NO 343
<211> LENGTH: 20
<212> TYPE: DNA
<213> ORGANISM: Artificial Sequence
<220> FEATURE:
<223> OTHER INFORMATION: Synthetic sequence

<400> SEQUENCE: 343
ctcctcgcat ccaacagtcg                                              20

<210> SEQ ID NO 344
<211> LENGTH: 20
<212> TYPE: DNA
<213> ORGANISM: Artificial Sequence
<220> FEATURE:
<223> OTHER INFORMATION: Synthetic sequence

<400> SEQUENCE: 344
ccaccgtagc actccttctt                                              20

<210> SEQ ID NO 345
<211> LENGTH: 20
<212> TYPE: DNA
<213> ORGANISM: Artificial Sequence
<220> FEATURE:
<223> OTHER INFORMATION: Synthetic sequence
```

<400> SEQUENCE: 345
cggagcgtcg gtagtgtaaa                                                    20

<210> SEQ ID NO 346
<211> LENGTH: 20
<212> TYPE: DNA
<213> ORGANISM: Artificial Sequence
<220> FEATURE:
<223> OTHER INFORMATION: Synthetic sequence

<400> SEQUENCE: 346
acaactcgac gaacctaccg                                                    20

<210> SEQ ID NO 347
<211> LENGTH: 20
<212> TYPE: DNA
<213> ORGANISM: Artificial Sequence
<220> FEATURE:
<223> OTHER INFORMATION: Synthetic sequence

<400> SEQUENCE: 347
tggcccatcc ttatgtgctg                                                    20

<210> SEQ ID NO 348
<211> LENGTH: 20
<212> TYPE: DNA
<213> ORGANISM: Artificial Sequence
<220> FEATURE:
<223> OTHER INFORMATION: Synthetic sequence

<400> SEQUENCE: 348
ggtcgttatt gctcaagccc                                                    20

<210> SEQ ID NO 349
<211> LENGTH: 20
<212> TYPE: DNA
<213> ORGANISM: Artificial Sequence
<220> FEATURE:
<223> OTHER INFORMATION: Synthetic sequence

<400> SEQUENCE: 349
ttgattctgg ccctcccatc                                                    20

<210> SEQ ID NO 350
<211> LENGTH: 20
<212> TYPE: DNA
<213> ORGANISM: Artificial Sequence
<220> FEATURE:
<223> OTHER INFORMATION: Synthetic sequence

<400> SEQUENCE: 350
ctcacgccgg ctatttaggt                                                    20

<210> SEQ ID NO 351
<211> LENGTH: 20
<212> TYPE: DNA
<213> ORGANISM: Artificial Sequence
<220> FEATURE:
<223> OTHER INFORMATION: Synthetic sequence

<400> SEQUENCE: 351
agtctgggta ggtggaggac                                                    20

```
<210> SEQ ID NO 352
<211> LENGTH: 20
<212> TYPE: DNA
<213> ORGANISM: Artificial Sequence
<220> FEATURE:
<223> OTHER INFORMATION: Synthetic sequence

<400> SEQUENCE: 352
cgactgagcc acatccaact                                               20

<210> SEQ ID NO 353
<211> LENGTH: 20
<212> TYPE: DNA
<213> ORGANISM: Artificial Sequence
<220> FEATURE:
<223> OTHER INFORMATION: Synthetic sequence

<400> SEQUENCE: 353
gagcctcagc cggaattgaa                                               20

<210> SEQ ID NO 354
<211> LENGTH: 20
<212> TYPE: DNA
<213> ORGANISM: Artificial Sequence
<220> FEATURE:
<223> OTHER INFORMATION: Synthetic sequence

<400> SEQUENCE: 354
ttgccattct gcaccaatgc                                               20

<210> SEQ ID NO 355
<211> LENGTH: 20
<212> TYPE: DNA
<213> ORGANISM: Artificial Sequence
<220> FEATURE:
<223> OTHER INFORMATION: Synthetic sequence

<400> SEQUENCE: 355
tattggtgtt cgcggctgat                                               20

<210> SEQ ID NO 356
<211> LENGTH: 20
<212> TYPE: DNA
<213> ORGANISM: Artificial Sequence
<220> FEATURE:
<223> OTHER INFORMATION: Synthetic sequence

<400> SEQUENCE: 356
atgggcgtaa caggaggact                                               20

<210> SEQ ID NO 357
<211> LENGTH: 20
<212> TYPE: DNA
<213> ORGANISM: Artificial Sequence
<220> FEATURE:
<223> OTHER INFORMATION: Synthetic sequence

<400> SEQUENCE: 357
ggaatggcct acctgcatca                                               20

<210> SEQ ID NO 358
<211> LENGTH: 20
<212> TYPE: DNA
<213> ORGANISM: Artificial Sequence
<220> FEATURE:
<223> OTHER INFORMATION: Synthetic sequence
```

<400> SEQUENCE: 358
cccgttgttg tcatcgcatc                                              20

<210> SEQ ID NO 359
<211> LENGTH: 20
<212> TYPE: DNA
<213> ORGANISM: Artificial Sequence
<220> FEATURE:
<223> OTHER INFORMATION: Synthetic sequence

<400> SEQUENCE: 359
gttcgatgcg tcccatgagt                                              20

<210> SEQ ID NO 360
<211> LENGTH: 20
<212> TYPE: DNA
<213> ORGANISM: Artificial Sequence
<220> FEATURE:
<223> OTHER INFORMATION: Synthetic sequence

<400> SEQUENCE: 360
caacccgcgt agatgttcct                                              20

<210> SEQ ID NO 361
<211> LENGTH: 20
<212> TYPE: DNA
<213> ORGANISM: Artificial Sequence
<220> FEATURE:
<223> OTHER INFORMATION: Synthetic sequence

<400> SEQUENCE: 361
gccagctcaa gagtgtagcc                                              20

<210> SEQ ID NO 362
<211> LENGTH: 20
<212> TYPE: DNA
<213> ORGANISM: Artificial Sequence
<220> FEATURE:
<223> OTHER INFORMATION: Synthetic sequence

<400> SEQUENCE: 362
ttcttgatcc tgcgcgatgt                                              20

<210> SEQ ID NO 363
<211> LENGTH: 20
<212> TYPE: DNA
<213> ORGANISM: Artificial Sequence
<220> FEATURE:
<223> OTHER INFORMATION: Synthetic sequence

<400> SEQUENCE: 363
atcgcaggcg ttccctatac                                              20

<210> SEQ ID NO 364
<211> LENGTH: 20
<212> TYPE: DNA
<213> ORGANISM: Artificial Sequence
<220> FEATURE:
<223> OTHER INFORMATION: Synthetic sequence

<400> SEQUENCE: 364
tattggacct ccgaccacga                                              20

```
<210> SEQ ID NO 365
<211> LENGTH: 20
<212> TYPE: DNA
<213> ORGANISM: Artificial Sequence
<220> FEATURE:
<223> OTHER INFORMATION: Synthetic sequence

<400> SEQUENCE: 365
agccaccatt tagatccgcg                                              20

<210> SEQ ID NO 366
<211> LENGTH: 20
<212> TYPE: DNA
<213> ORGANISM: Artificial Sequence
<220> FEATURE:
<223> OTHER INFORMATION: Synthetic sequence

<400> SEQUENCE: 366
gaccagtaga agtctgcccg                                              20

<210> SEQ ID NO 367
<211> LENGTH: 20
<212> TYPE: DNA
<213> ORGANISM: Artificial Sequence
<220> FEATURE:
<223> OTHER INFORMATION: Synthetic sequence

<400> SEQUENCE: 367
tttcagaatg gccgagctgt                                              20

<210> SEQ ID NO 368
<211> LENGTH: 20
<212> TYPE: DNA
<213> ORGANISM: Artificial Sequence
<220> FEATURE:
<223> OTHER INFORMATION: Synthetic sequence

<400> SEQUENCE: 368
aggtgacctt cttgtacgcc                                              20

<210> SEQ ID NO 369
<211> LENGTH: 20
<212> TYPE: DNA
<213> ORGANISM: Artificial Sequence
<220> FEATURE:
<223> OTHER INFORMATION: Synthetic sequence

<400> SEQUENCE: 369
ggcgcgtcct tatttccatc                                              20
```